(12) United States Patent
Winkler et al.

(10) Patent No.: US 11,858,925 B2
(45) Date of Patent: Jan. 2, 2024

(54) GAS41 INHIBITORS AND METHODS OF USE THEREOF

(71) Applicant: The Regents of the University of Michigan, Ann Arbor, MI (US)

(72) Inventors: Alyssa Winkler, Ann Arbor, MI (US); Brian Linhares, Ann Arbor, MI (US); Dymytrii Listunov, Ann Arbor, MI (US); Jolanta Grembecka, Ann Arbor, MI (US); Tomasz Cierpicki, Ann Arbor, MI (US); EunGi Kim, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 35 days.

(21) Appl. No.: 17/159,916

(22) Filed: Jan. 27, 2021

(65) Prior Publication Data
US 2022/0017509 A1    Jan. 20, 2022

Related U.S. Application Data

(60) Provisional application No. 63/050,303, filed on Jul. 10, 2020.

(51) Int. Cl.
| | | |
|---|---|---|
| *C07D 417/14* | (2006.01) | |
| *C07D 495/04* | (2006.01) | |
| *C07D 409/14* | (2006.01) | |
| *C07D 487/10* | (2006.01) | |
| *C07D 409/06* | (2006.01) | |
| *A61P 35/00* | (2006.01) | |
| *A61K 47/55* | (2017.01) | |

(52) U.S. Cl.
CPC ............ *C07D 417/14* (2013.01); *A61K 47/55* (2017.08); *A61P 35/00* (2018.01); *C07D 409/06* (2013.01); *C07D 409/14* (2013.01); *C07D 487/10* (2013.01); *C07D 495/04* (2013.01)

(58) Field of Classification Search
CPC .. C07D 417/14; C07D 409/06; C07D 409/14; C07D 487/10; C07D 495/04
See application file for complete search history.

(56) References Cited

U.S. PATENT DOCUMENTS

| | | | |
|---|---|---|---|
| 3,598,122 A | 8/1971 | Zaffaroni | |
| 3,598,123 A | 8/1971 | Zaffaroni | |
| 3,710,795 A | 1/1973 | Higuchi et al. | |
| 3,731,683 A | 5/1973 | Zaffaroni | |
| 3,742,951 A | 7/1973 | Zaffaroni | |
| 3,814,097 A | 6/1974 | Ganderton et al. | |
| 3,921,636 A | 11/1975 | Zaffaroni | |
| 3,972,995 A | 8/1976 | Tsuk et al. | |
| 3,993,072 A | 11/1976 | Zaffaroni | |
| 3,993,073 A | 11/1976 | Zaffaroni | |
| 3,996,934 A | 12/1976 | Zaffaroni | |
| 4,031,894 A | 6/1977 | Urquhart et al. | |
| 4,060,084 A | 11/1977 | Kumar et al. | |
| 4,069,307 A | 1/1978 | Higuchi et al. | |
| 4,077,407 A | 3/1978 | Theeuwes et al. | |
| 4,151,273 A | 4/1979 | Riegelman et al. | |
| 4,201,211 A | 5/1980 | Chandrasekaran et al. | |
| 4,229,447 A | 10/1980 | Porter | |
| 4,230,105 A | 10/1980 | Harwood | |
| 4,292,299 A | 9/1981 | Suzuki et al. | |
| 4,292,303 A | 9/1981 | Keith et al. | |
| 4,343,789 A | 8/1982 | Kawata et al. | |
| 4,476,116 A | 10/1984 | Anik | |
| 4,596,795 A | 6/1986 | Pitha | |
| 4,755,386 A | 7/1988 | Hsiao et al. | |
| 5,033,252 A | 7/1991 | Carter | |
| 5,052,558 A | 10/1991 | Carter | |
| 5,116,817 A | 5/1992 | Anik | |
| 5,281,420 A | 1/1994 | Kelm et al. | |
| 5,323,907 A | 6/1994 | Kalvelage | |
| 5,336,168 A | 8/1994 | Sibalis | |
| 5,340,591 A | 8/1994 | Nakano et al. | |
| 5,456,923 A | 10/1995 | Nakamichi et al. | |
| 5,665,378 A | 9/1997 | Davis et al. | |
| 5,700,485 A | 12/1997 | Berde et al. | |
| 5,723,269 A | 3/1998 | Akagi et al. | |
| 5,739,136 A | 4/1998 | Ellinwood, Jr. et al. | |
| 5,837,280 A | 11/1998 | Kenealy et al. | |
| 5,858,401 A | 1/1999 | Bhalani et al. | |
| 5,861,510 A | 1/1999 | Piscopio et al. | |
| 5,863,949 A | 1/1999 | Robinson et al. | |
| 5,869,090 A | 2/1999 | Rosenbaum | |
| 6,083,518 A | 7/2000 | Lindahl | |
| 6,136,826 A | 10/2000 | Fujioka et al. | |
| 6,214,872 B1 | 4/2001 | Robinson | |
| 6,391,452 B1 | 5/2002 | Antonsen et al. | |
| 6,667,048 B1 | 12/2003 | Lambert et al. | |
| 6,923,983 B2 | 8/2005 | Morgan et al. | |
| 6,929,801 B2 | 8/2005 | Klose et al. | |
| 6,946,144 B1 | 9/2005 | Jordan | |
| 6,960,563 B2 | 11/2005 | Egbaria et al. | |
| 7,030,242 B2 | 4/2006 | Noe et al. | |
| 2004/0013734 A1 | 1/2004 | Babcock et al. | |
| 2019/0077767 A1 | 3/2019 | Tanaka et al. | |

FOREIGN PATENT DOCUMENTS

| | | |
|---|---|---|
| EP | 0606046 | 7/1994 |
| EP | 0780386 | 6/1997 |
| EP | 0818442 | 1/1998 |
| EP | 0931788 | 7/1999 |
| EP | 1004578 | 5/2000 |
| EP | 1262193 | 12/2002 |
| EP | 1746999 | 11/2011 |
| EP | 2534153 | 9/2016 |

(Continued)

OTHER PUBLICATIONS

Registry No. 85032-63-9, File Registry on STN, Nov. 16, 1984.*

(Continued)

*Primary Examiner* — Rebecca L Anderson
(74) *Attorney, Agent, or Firm* — Casimir Jones, S.C.; Anne M. Reynolds

(57) ABSTRACT

Provided herein are small molecules that bind to GAS41 and inhibit GAS41 activity, and methods of use thereof for the treatment of cancer.

15 Claims, 5 Drawing Sheets

(56) References Cited

FOREIGN PATENT DOCUMENTS

| WO | WO 90/05719 | 5/1990 |
|---|---|---|
| WO | WO 96/27583 | 9/1996 |
| WO | WO 96/33172 | 10/1996 |
| WO | WO 98/03516 | 1/1998 |
| WO | WO 98/07697 | 2/1998 |
| WO | WO 98/30566 | 7/1998 |
| WO | WO 98/33768 | 8/1998 |
| WO | WO 98/34915 | 8/1998 |
| WO | WO 98/34918 | 8/1998 |
| WO | WO 99/07675 | 2/1999 |
| WO | WO 99/29667 | 6/1999 |
| WO | WO 99/52889 | 10/1999 |
| WO | WO 99/52910 | 10/1999 |
| WO | WO 00/71510 | 11/2000 |
| WO | WO 00/74681 | 12/2000 |
| WO | WO 2005/107758 | 11/2005 |
| WO | WO 2007/022258 | 2/2007 |

OTHER PUBLICATIONS

Registry No. 1343723-72-7, File Registry on STN, Nov. 11, 2011.*
Registry No. 1404113-01-4, File Registry on STN, Nov. 16, 2012.*
Registry No. 1584887-00-2, File Registry on STN, Apr. 15, 2014.*
Casagrande et al. Bioorganic & Medicinal Chemistry 20 (2012) 5965-5979.*
Registry No. 927072-39-7, File Registry on STN, Mar. 18, 2007.*
Registry No. 2412403-83-7, File Registry on STN, Mar. 22, 2020.*
Registry No. 1061204-86-1, File Registry on STN, Oct. 14, 2008.*
Registry No. 1061236-48-3, File Registry on STN, Oct. 14, 2008.*
Registry No. 2435409-54-2, File Registry on STN, Jun. 26, 2020.*
International Search Report and Written Opinion for PCT/US21/15263, dated Jun. 9, 2021. 10 pages.
Allis et al., The molecular hallmarks of epigenetic control. Nat Rev Genet. Aug. 2016;17(8):487-500.
Barretina et al., Subtype-specific genomic alteratSubtype-specific genomic alterations define new targets for soft-tissue sarcoma therapy. Nat Genet. Aug. 2010;42(8):715-21.
Cho et al., GAS41 Recognizes Diacetylated Histone H3 through a Bivalent Binding Mode. ACS Chem Biol. Sep. 21, 2018;13(9):2739-2746.
Cho. Recent Advances in Oral Prodrug Discovery. Annual Reports in Medicinal Chemistry, 2006, vol. 41, 395-407.
Fischer et al., Cloning of a novel transcription factor-like gene amplified in human glioma including astrocytoma grade I. Hum Mol Genet. Oct. 1997;6(11):1817-22.
Fischer et al., Twelve amplified and expressed genes localized in a single domain in glioma. Hum Genet. Nov. 1996;98(5):625-8.
Hsu et al., Recognition of histone acetylation by the GAS41 YEATS domain promotes H2A.Z deposition in non-small cell lung cancer. Genes Dev. Jan. 1, 2018;32(1):58-69.
Italiano et al., HMGA2 is the partner of MDM2 in well-differentiated and dedifferentiated liposarcomas whereas CDK4 belongs to a distinct inconsistent amplicon. Int J Cancer. May 15, 2008;122(10):2233-41.
Kiuchi et al., Overexpression of YEATS4 contributes to malignant outcomes in gastric carcinoma. Am J Cancer Res. Dec. 1, 2018;8(12):2436-2452.
Miller et al., Histone deacetylase inhibitors. J Med Chem. Nov. 20, 2003;46(24):5097-116.
Pikor et al., YEATS4 is a novel oncogene amplified in non-small cell lung cancer that regulates the p53 pathway. Cancer Res. Dec. 15, 2013;73(24):7301-12.
PUBCHEM-SID: 145415845 Deposit Date: Oct. 18, 2012. Retrieved from the internet Aug. 12, 2022. pp. 1-6.
PUBCHEM-SID: 168945146 Deposit Date: Dec. 2, 2013. Retrieved from the internet Aug. 12, 2022. pp. 1-7.
Rooseboom et al., Enzyme-catalyzed activation of anticancer prodrugs. Pharmacol Rev. Mar. 2004;56(1):53-102.
Tao et al., Knockdown of YEATS4 inhibits colorectal cancer cell proliferation and induces apoptosis. Am J Transl Res. Mar. 15, 2015;7(3):616-23.

* cited by examiner

A.

B.

GAS41 INHIBITORS AND METHODS OF USE THEREOF

CROSS-REFERENCE TO RELATED APPLICATIONS

This application claims priority to U.S. Provisional Patent Application No. 63/050,303, filed on Jul. 10, 2020, the entire contents of which are fully incorporated herein by reference.

STATEMENT REGARDING FEDERALLY SPONSORED RESEARCH

This invention was made with government support under CA240514 awarded by the National Institutes of Health. The government has certain rights in the invention.

FIELD

Provided herein are small molecules that bind to GAS41 and inhibit GAS41 activity, and methods of use thereof for the treatment of cancer.

BACKGROUND

Proteins recognizing post-transcriptional modifications in histone proteins play a key role in transcriptional regulation (Allis et al. *Nat. Rev. Genet.* 17, 487-500 (2016)). The YEATS domain containing proteins belong to a relatively newly-discovered family of epigenetic reader proteins and include four human paralogs: ENL, YEATS2, AF9 and GAS41. Biochemical studies have revealed that YEATS domains bind to chromatin by recognizing histones with acetylated or crotonylated lysine side chains.

GAS41 (Glioma amplified sequence 41) is an emerging oncogene that is overexpressed and implicated in multiple cancers. Amplifications of GAS41 have been identified in brain cancer patients, including 23% of glioblastomas and 80% of astrocytomas (Fischer et al., *Hum. Genet.* 98, 625-628 (1996); Fischer et al. *Hum. Mol. Genet.* 6, 1817-1822 (1997)). GAS41 is also frequently amplified in sarcomas (Italiano et al. *Int. J. Cancer* 122, 2233-2241 (2008); Barretina et al. *Nat. Genet.* 42, 715-721 (2010)), colorectal (Tao et al. *Am. J. Transl. Res.* 7, 616-623 (2015)), lung (Pikor et al. *Cancer Res* 73, 7301-7312 (2013); Hsu et al. *Genes Dev* 32, 58-69 (2018)), and gastric cancers (Kiuchi et al. *Am J Cancer Res* 8, 2436-2452 (2018)). For example, analysis of lung cancer samples identified amplification and overexpression of the GAS41 gene in 20% of non-small cell lung cancer cells when compared to the matched normal tissues (Pikor 2013). Overexpression of GAS41 was also detected in NSCLC but not in "normal" lung epithelial and fibroblast cell lines (Hsu 2018). Knockdown of GAS41 in a panel of NSCLC cell lines with GAS41 amplification strongly impaired cell growth and formation of colonies (Pikor 2013; Hsu 2018). Furthermore, GAS41 binds to promoter regions of actively transcribed genes enriched in H3K27ac, suggesting that recognition of acetylated H3 is necessary for chromatin binding and its oncogenic activity (Hsu et al. *Genes Dev* 32, 58-69 (2018)).

SUMMARY

Provided herein are small molecules that bind to GAS41 and inhibit GAS41 activity, and methods of use thereof for the treatment of cancer.

In one aspect, the disclosure provides a compound of formula (I):

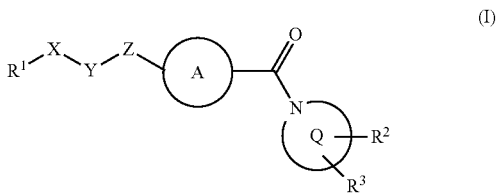

or a pharmaceutically acceptable salt thereof, wherein:
$R^1$ is selected from heterocyclyl, heterocyclylalkyl, heteroaryl, heteroarylalkyl, aryl, arylalkyl, cycloalkyl, cycloalkylalkyl, alkyl, alkenyl, alkynyl, hydroxy, alkoxy, thioalkyl, halogen, haloalkyl, carboxy, acyl, amido, cyano, sulfonyl, and hydrogen;
X is —C(O)—, —C(S)—, —CH$_2$—, or —SO$_2$—, or is absent;
Y is —NR$^a$— or —O—;
$R^a$ is selected from hydrogen, alkyl, haloalkyl, heteroalkyl, cycloalkyl, hydroxyalkyl, and aminoalkyl, or $R^a$ is taken together with the nitrogen atom to which it is attached to form a fused ring with A, or $R^a$ and $R^1$ together with the atoms to which they are attached together form an optionally substituted heterocyclic ring;
Z is absent or is —CR$^b$R$^c$—;
$R^b$ and $R^c$ are each independently selected from hydrogen and alkyl;
A is a five-membered heteroaryl;
Q is a four-, five-, or six-membered heterocyclyl;
$R^2$ is selected from hydrogen, halo, alkyl, amino, and hydroxy;
$R^3$ is selected from hydrogen, halo, —OR$^d$, —NR$^e$R$^f$, aryl, arylalkyl, heteroaryl, heteroarylalkyl, heterocyclyl, heterocyclylalkyl, and a group of formula:

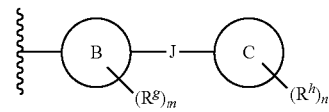

wherein B is aryl or heteroaryl; J is absent or is —CH$_2$—, —O—, —S—, or —NH—; C is selected from aryl, heteroaryl, and heterocyclyl; m is 0, 1, 2, 3, or 4; n is 0, 1, 2, 3, 4, or 5; and R$^g$ and R$^h$ are each independently selected from alkyl, alkenyl, alkynyl, halo, haloalkyl, amino, alkylamino, dialkylamino, aminoalkyl, alkylaminoalkyl, dialkylaminoalkyl, amido, amidoalkyl, sulfonamido, sulfonamidoalkyl, urea, ureaalkyl, thiourea, thioureaalkyl, hydroxy, hydroxyalkyl, alkoxy, alkoxyalkyl, haloalkoxy, thioalkyl, acyl, carboxy, nitro, oxo, aryl, arylalkyl, heteroaryl, heteroarylalkyl, heterocyclyl, heterocyclylalkyl, cycloalkyl, and cycloalkylalkyl;
or $R^2$ and $R^3$ are taken together with the carbon atom(s) to which they are attached to form a ring selected from aryl, heteroaryl, cycloalkyl, and heterocycle; or $R^2$ and $R^3$ are taken together with the carbon atom to which they are attached to form an alkenyl group; and
$R^d$, $R^e$, and $R^f$ are each independently selected from hydrogen, alkyl, haloalkyl, hydroxyalkyl, aminoalkyl, carboxyalkyl, heteroalkyl, aryl, arylalkyl, heteroaryl, heteroarylalkyl;

wherein each alkyl, alkenyl, alkynyl, aryl, arylalkyl, heteroalkyl, heteroaryl, heteroarylalkyl, cycloalkyl, heterocyclyl, and heterocyclylalkyl is independently optionally substituted with 1, 2, 3, 4, or 5 substituents, with the proviso that when Z is —$CR^bR^c$—, $R^1$ is not cycloalkyl.

In some embodiments, $R^1$ is selected from heterocyclyl, alkyl, and aryl. In some embodiments, $R^1$ is a monocyclic heterocyclyl having 1 or 2 heteroatoms independently selected from N, O, and S. In some embodiments, $R^1$ is pyrrolidinyl.

In some embodiments, X is —C(O)—. In some embodiments, Y is —$NR^a$—, and $R^a$ is hydrogen. In some embodiments, Z is absent.

In some embodiments, A is a five-membered heteroaryl having 1, 2, or 3 heteroatoms independently selected from N, O, and S. In some embodiments, A is selected from thiophene and thiazole. In some embodiments, A is thiophene.

In some embodiments, Q is selected from azetidine, pyrrolidine, and piperidine. In some embodiments, Q is azetidine.

In some embodiments, $R^2$ is hydrogen.

In some embodiments, $R^3$ is a group of formula

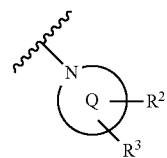

In some embodiments, B is a 5-membered monocyclic heteroaryl having 1 or 2 heteroatoms independently selected from N and S; J is absent; C is selected from aryl, heteroaryl, and heterocyclyl; m is 0 or 1; n is 0, 1, 2, or 3; $R^g$ is $C_1$-$C_6$ alkyl; and each $R^h$ is independently selected from alkyl, halo, haloalkyl, amino, aminoalkyl, amido, amidoalkyl, sulfonamido, sulfonamidoalkyl, acyl, aryl, arylalkyl, heteroaryl, heteroarylalkyl, heterocyclyl, heterocyclylalkyl, cycloalkyl, and cycloalkylalkyl.

In some embodiments, the group

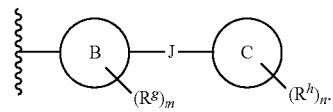

a formula selected from:

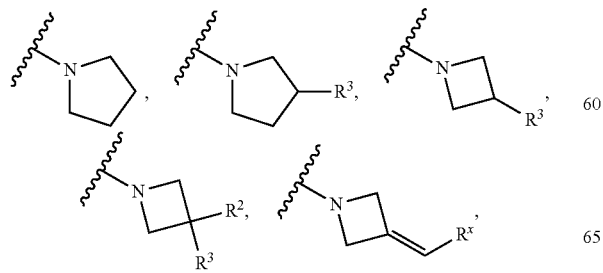

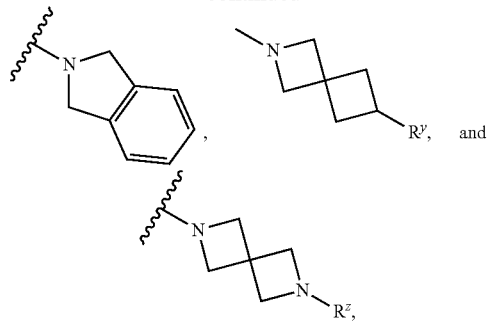

wherein $R^x$, $R^y$, and $R^z$ are substituents that are each independently selected from —$OR^v$, aryl, and heteroaryl, wherein $R^v$ is selected from $C_1$-$C_6$ alkyl, aryl and heteroaryl.

In some embodiments, compound has formula (Ia):

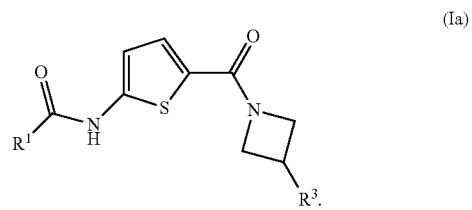

(Ia)

In some embodiments, the compound has formula (Ib):

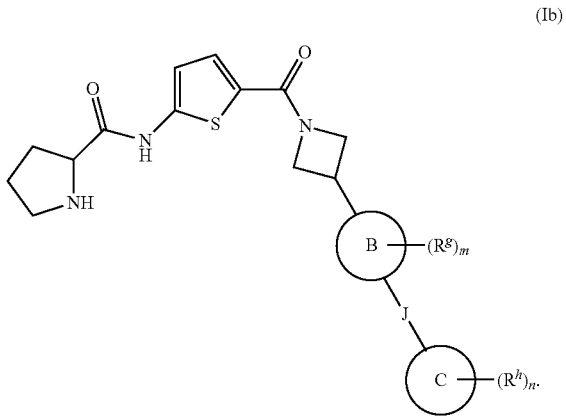

(Ib)

In some embodiments, the compound has formula (Ic):

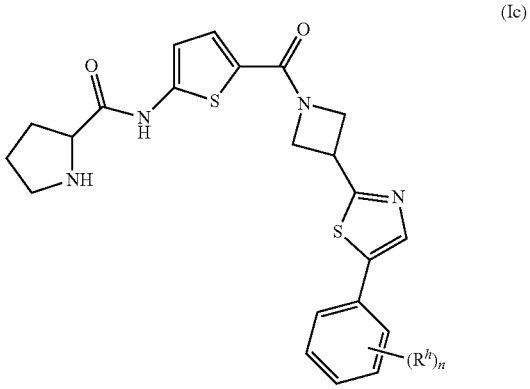

(Ic)

wherein:

n is 0, 1, 2 or 3; and each $R^h$ is independently selected from $C_1$-$C_6$ alkyl, halo, halo-$C_1$-$C_6$-alkyl, amino, amino-$C_1$-$C_6$-alkyl, hydroxy, hydroxy-$C_1$-$C_6$-alkyl, $C_1$-$C_6$ alkoxy, amido, amido-$C_1$-$C_6$-alkyl, acyl, aryl, aryl-$C_1$-$C_6$-alkyl, heteroaryl, heteroaryl-$C_1$-$C_6$-alkyl, heterocyclyl, heterocyclyl-$C_1$-$C_6$-alkyl, cycloalkyl, and cycloalkyl-$C_1$-$C_6$-alkyl.

In some embodiments, at least one $R^h$ has formula —$(CH_2)_rC(O)NR^iR^j$ or —$(CH_2)_sNR^kC(O)R^m$, wherein:

r and s are each independently selected from 0, 1, and 2;

$R^i$ and $R^k$ are each independently selected from hydrogen and $C_1$-$C_6$ alkyl;

$R^j$ is selected from $C_1$-$C_6$-alkyl, aryl, aryl-$C_1$-$C_6$-alkyl, heteroaryl, heteroaryl-$C_1$-$C_6$-alkyl, heterocyclyl, heterocyclyl-$C_1$-$C_6$-alkyl, cycloalkyl, and cycloalkyl-$C_1$-$C_6$-alkyl;

$R^m$ is selected from $C_1$-$C_6$-alkyl, aryl, aryl-$C_1$-$C_6$-alkyl, heteroaryl, heteroaryl-$C_1$-$C_6$-alkyl, heterocyclyl, heterocyclyl-$C_1$-$C_6$-alkyl, cycloalkyl, and cycloalkyl-$C_1$-$C_6$-alkyl, amino, $C_1$-$C_6$-alkylamino, arylamino, and aryl-$C_1$-$C_6$-alkylamino;

wherein each alkyl, aryl, heteroaryl, heterocyclyl, and cycloalkyl is independently unsubstituted or substituted with 1 or 2 substituents independently selected from halo, $C_1$-$C_6$-alkyl, $C_1$-$C_6$-alkoxy, hydroxy, amino and oxo.

In some embodiments, the compound is selected from the group consisting of compounds shown in Table 1, or a pharmaceutically acceptable salt thereof.

In another aspect, the disclosure provides a compound of formula (IIa):

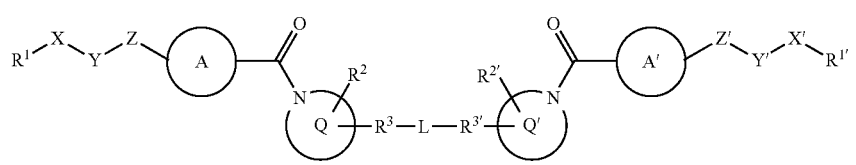

(IIa)

or a pharmaceutically acceptable salt thereof, wherein:

$R^1$ and $R^{1'}$ are each independently selected from heterocyclyl, heterocyclylalkyl, heteroaryl, heteroarylalkyl, aryl, arylalkyl, cycloalkyl, cycloalkylalkyl, alkyl, alkenyl, alkynyl, hydroxy, alkoxy, thioalkyl, halogen, haloalkyl, carboxy, acyl, amido, cyano, sulfonyl, and hydrogen;

X and X' are each independently absent or selected from —C(O)—, —C(S)—, —$CH_2$—, and —$SO_2$—;

Y and Y' are each independently —$NR^a$— or —O—;

$R^a$ is selected from hydrogen, alkyl, haloalkyl, heteroalkyl, cycloalkyl, hydroxyalkyl, and aminoalkyl, or $R^a$ is taken together with the nitrogen atom to which it is attached to form a fused ring with A, or $R^a$ and $R^1$ together with the atoms to which they are attached together form an optionally substituted heterocyclic ring;

Z and Z' are each independently absent or —$CR^bR^c$—;

$R^b$ and $R^c$ are each independently selected from hydrogen and alkyl;

A and A' are each independently a five-membered heteroaryl ring;

Q and Q' are each independently a four-, five-, or six-membered heterocycle;

$R^2$ and $R^{2'}$ are each independently selected from hydrogen, halo, alkyl, amino, and hydroxy;

$R^3$ and $R^{3'}$ are each independently selected from aryl, heteroaryl, cycloalkyl, heterocyclyl, and a group of formula:

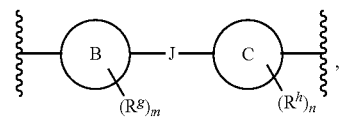

wherein B is aryl or heteroaryl; J is absent or is —$CH_2$—, —O—, —S—, or —NH—; C is selected from aryl, heteroaryl, and heterocyclyl; m is 0, 1, 2, 3, or 4; n is 0, 1, 2, 3, or 4; and $R^g$ and $R^h$ are each independently selected from alkyl, alkenyl, alkynyl, halo, haloalkyl, amino, alkylamino, dialkylamino, aminoalkyl, alkylaminoalkyl, dialkylaminoalkyl, amido, amidoalkyl, sulfonamido, sulfonamidoalkyl, urea, ureaalkyl, thiourea, thioureaalkyl, hydroxy, hydroxyalkyl, alkoxy, alkoxyalkyl, haloalkoxy, thioalkyl, acyl, carboxy, nitro, oxo, aryl, arylalkyl, heteroaryl, heteroarylalkyl, heterocyclyl, heterocyclylalkyl, cycloalkyl, and cycloalkylalkyl;

$R^d$, $R^e$, and $R^f$ are each independently selected from hydrogen, alkyl, haloalkyl, hydroxyalkyl, aminoalkyl, carboxyalkyl, heteroalkyl, aryl, arylalkyl, and heteroaryl; and L is a linker;

wherein each alkyl, alkenyl, alkynyl, aryl, arylalkyl, heteroalkyl, heteroaryl, heteroarylalkyl, cycloalkyl, heterocyclyl, and heterocyclylalkyl is independently optionally substituted with 1, 2, 3, 4, or 5 substituents.

In some embodiments, $R^1$ and $R^{1'}$ are the same, $R^2$ and $R^{2'}$ are the same, $R^3$ and $R^{3'}$ are the same, X and X' are the same, Y and Y' are the same, Z and Z' are the same, A and A' are the same, and Q and Q' are the same. In some embodiments, $R^1$ and $R^{1'}$ are each a 4- or 5-membered monocyclic heterocyclyl. In some embodiments, $R^1$ and $R^{1'}$ are pyrrolidine.

In some embodiments, X and X' are —C(O)—. In some embodiments, Y and Y' are —$NR^a$—, and $R^a$ is hydrogen. In some embodiments, Z and Z' are each absent.

In some embodiments, A and A' are thiophene or thiazole.

In some embodiments, Q and Q' are selected from azetidine and pyrrolidine.

In some embodiments, $R^2$ and $R^{2'}$ are hydrogen.

In some embodiments, $R^3$ and $R^{3'}$ are selected from aryl, heteroaryl, and a group of formula:

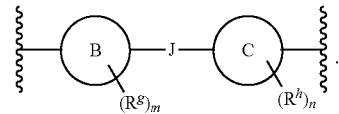

In some embodiments, $R^3$ and $R^{3'}$ are each a group of formula:

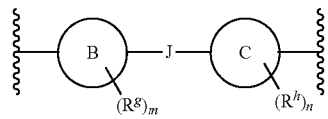

wherein B is a 5-membered monocyclic heteroaryl having 1 or 2 heteroatoms independently selected from N, S or O; J is absent; C is selected from aryl, heteroaryl, and heterocyclyl; m is 0 or 1; $R^g$ is $C_1$-$C_6$ alkyl; n is 0, 1, or 2; and each $R^h$ is independently selected from $C_1$-$C_6$ alkyl, halo, $C_1$-$C_6$ haloalkyl, amino, amino-$C_1$-$C_6$-alkyl, amido-$C_1$-$C_6$-alkyl, and heterocyclyl.

In some embodiments, L is a linker comprising one or more groups independently selected from methylene (—$CH_2$—), vinylene (—CH=CH—), acetylene (—C≡C—), ether (—O—), amine (—NH—), alkylamine (—NR—, wherein R is an optionally substituted $C_1$-$C_6$ alkyl group), amide (—C(O)NH—), ester (—C(O)O—), carbamate (—OC(O)NH—), sulfonamide (—S(O)$_2$NH—), phenylene (—$C_6H_4$—), heteroarylene, heterocyclylene, and any combination thereof. In some embodiments, L is selected from:

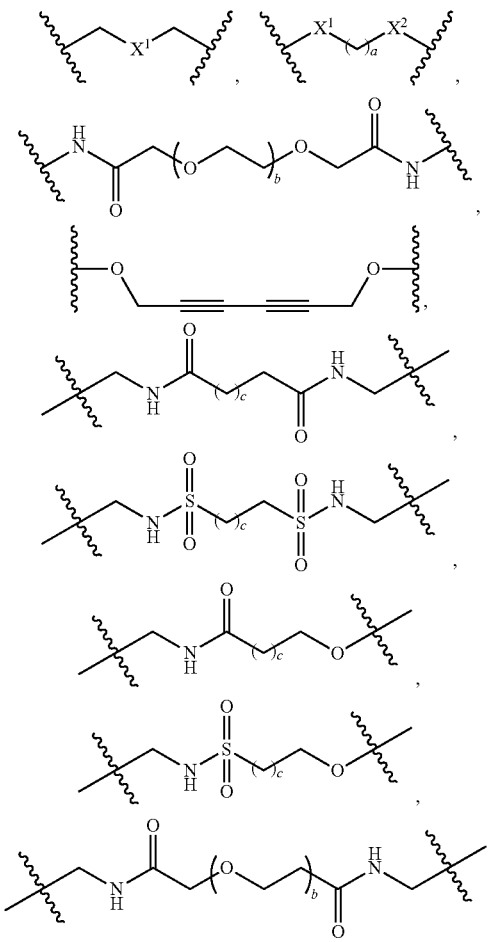

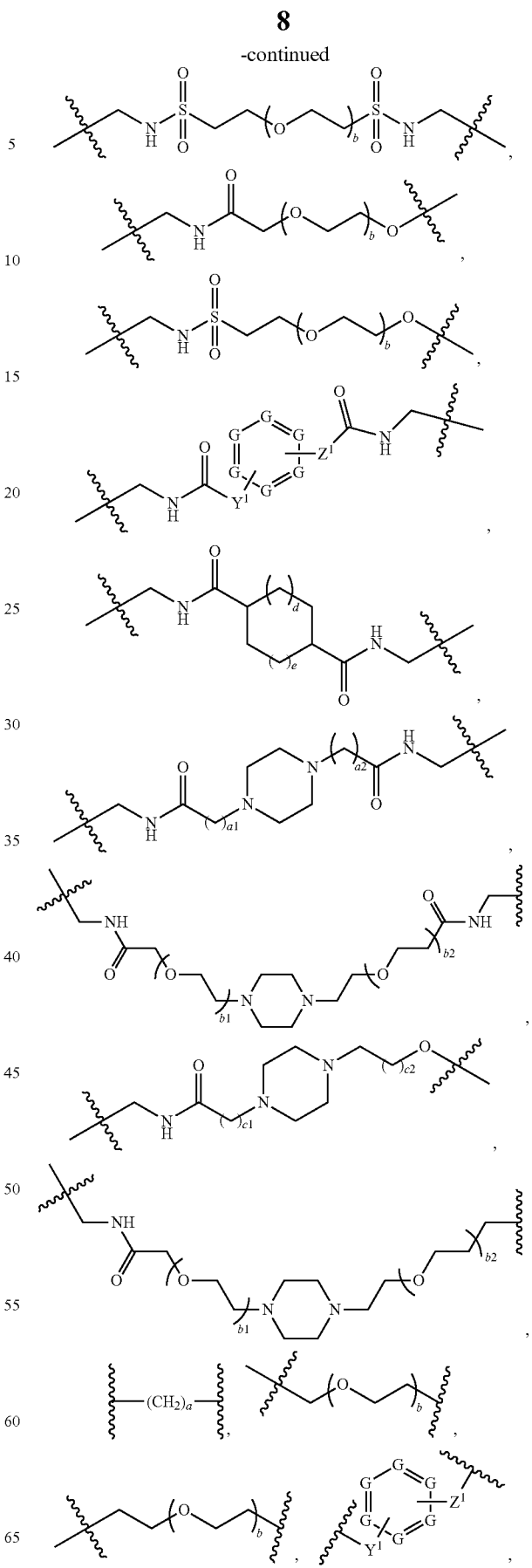

-continued

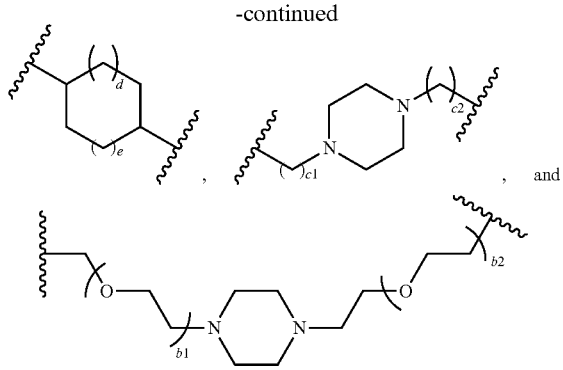

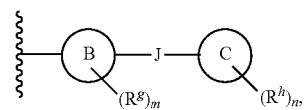

wherein B is aryl or heteroaryl; J is absent or is —CH$_2$—, —O—, —S—, or —NH—; C is selected from aryl, heteroaryl, and heterocyclyl; m is 0, 1, 2, 3, or 4; n is 0, 1, 2, 3, or 4; and R$^g$ and R$^h$ are each independently selected from alkyl, alkenyl, alkynyl, halo, haloalkyl, amino, alkylamino, dialkylamino, aminoalkyl, alkylaminoalkyl, dialkylaminoalkyl, amido, amidoalkyl, sulfonamido, sulfonamidoalkyl, urea, ureaalkyl, thiourea, thioureaalkyl, hydroxy, hydroxyalkyl, alkoxy, alkoxyalkyl, haloalkoxy, thioalkyl, acyl, carboxy, nitro, oxo, aryl, arylalkyl, heteroaryl, heteroarylalkyl, heterocyclyl, heterocyclylalkyl, cycloalkyl, and cycloalkylalkyl;

wherein a, a1, and a2 are each independently selected from 1, 2, 3, 4, 5, 6, 7, 8, 9, 10, 11, and 12; b, b1, and b2 are each independently selected from 0, 1, 2, 3, 4, 5, and 6; c, c1, and c2 are each independently selected from 0, 1, 2, 3, 4, 5, 6, 7, 8, 9, 10, 11, and 12; d and e are each independently selected form 0, 1, and 2; each G is independently selected from CH and N; X$^1$ and X$^2$ are each independently O or —NR$^x$, wherein R$^x$ is hydrogen or optionally substituted alkyl; and Y$^1$ and Z$^1$ are each independently selected from —CH$_2$—, —NH—, and —O—.

In some embodiments, the compound is selected from the group consisting of compounds shown in Table 2, or a pharmaceutically acceptable salt thereof.

In another aspect, the disclosure provides a compound of formula (IIb):

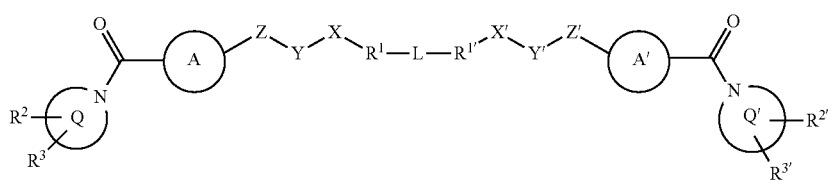

(IIb)

or a pharmaceutically acceptable salt thereof, wherein:

R$^1$ and R$^{1'}$ are each independently selected from heterocyclyl, heterocyclylalkyl, heteroaryl, heteroarylalkyl, aryl, arylalkyl, cycloalkyl, cycloalkylalkyl, alkyl, alkenyl, and alkynyl;

X and X' are each independently absent or selected from —C(O)—, —C(S)—, —CH$_2$—, and —SO$_2$—;

Y and Y' are each independently selected from —NR$^a$— or —O—;

R$^a$ is selected from hydrogen, alkyl, haloalkyl, heteroalkyl, cycloalkyl, hydroxyalkyl, and aminoalkyl, or R$^a$ is taken together with the nitrogen atom to which it is attached to form a fused ring with A;

Z and Z' are each independently absent or —CR$^b$R$^c$—;

R$^b$ and R$^c$ are each independently selected from hydrogen and alkyl;

A and A' are each independently a five-membered heteroaryl ring;

Q and Q' are each independently a four-, five-, or six-membered heterocyclyl;

R$^2$ and R$^{2'}$ are each independently selected from hydrogen, halo, alkyl, amino, and hydroxy;

R$^3$ and R$^{3'}$ are each independently selected from hydrogen, halo, —OR$^d$, —NR$^e$R$^f$, aryl, arylalkyl, heteroaryl, heteroarylalkyl, heterocyclyl, and heterocyclylalkyl, and a group of formula:

or R$^2$ and R$^3$ are taken together with the carbon atom(s) to which they are attached to form a ring selected from aryl, heteroaryl, cycloalkyl, and heterocycle; or R$^2$ and R$^3$ are taken together with the carbon atom to which they are attached to form an alkenyl group;

R$^d$, R$^e$, and R$^f$ are each independently selected from hydrogen, alkyl, haloalkyl, hydroxyalkyl, aminoalkyl, carboxyalkyl, heteroalkyl, aryl, arylalkyl, and heteroaryl; and L is a linker;

wherein each alkyl, alkenyl, alkynyl, aryl, arylalkyl, heteroalkyl, heteroaryl, heteroarylalkyl, cycloalkyl, heterocyclyl, and heterocyclylalkyl is independently optionally substituted with 1, 2, 3, 4, or 5 substituents.

In some embodiments, R$^1$ and R$^{1'}$ are the same, R$^2$ and R$^{2'}$ are the same, R$^3$ and R$^{3'}$ are the same, X and X' are the same, Y and Y' are the same, Z and Z' are the same, A and A' are the same, and Q and Q' are the same. In some embodiments, R$^1$ and R$^{1'}$ are each a 4- or 5-membered monocyclic heterocyclyl. In some embodiments, R$^1$ and R$^{1'}$ are pyrrolidine.

In some embodiments, X and X' are —C(O)—. In some embodiments, Y and Y' are —NR$^a$—, and R$^a$ is hydrogen. In some embodiments, Z and Z' are each absent.

In some embodiments, A and A' are thiophene or thiazole.

In some embodiments, Q and Q' are selected from azetidine and pyrrolidine.

In some embodiments, R$^2$ and R$^{2'}$ are hydrogen.

In some embodiments, R$^3$ and R$^{3'}$ are selected from hydrogen, aryl, heteroaryl, and a group of formula:

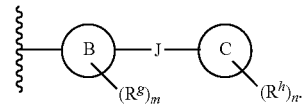

In some embodiments, R$^3$ and R$^{3'}$ are selected from a monocyclic and bicyclic heteroaryl having 1, 2, or 3 heteroatoms independently selected from N and S.

In some embodiments, $R^3$ and $R^{3'}$ are each a group of formula:

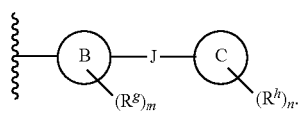

wherein B is a 5-membered monocyclic heteroaryl having 1 or 2 heteroatoms independently selected from N and S; J is absent; C is selected from aryl, heteroaryl, and heterocyclyl; m is 0 or 1; $R^g$ is $C_1$-$C_6$ alkyl; n is 0, 1, or 2; and each $R^h$ is independently selected from $C_1$-$C_6$ alkyl, halo, $C_1$-$C_6$ haloalkyl, amino, amino-$C_1$-$C_6$-alkyl, amido-$C_1$-$C_6$-alkyl, and heterocyclyl.

In some embodiments, L is a linker comprising one or more groups independently selected from methylene (—$CH_2$—), vinylene (—CH=CH—), acetylene (—C≡C—), ether (—O—), amine (—NH—), alkylamine (—NR—, wherein R is an optionally substituted $C_1$-$C_6$ alkyl group), amide (—C(O)NH—), ester (—C(O)O—), carbamate (—OC(O)NH—), sulfonamide (—S(O)$_2$NH—), phenylene (—$C_6H_4$—), heteroarylene, heterocyclylene, and any combination thereof. In some embodiments, L is selected from:

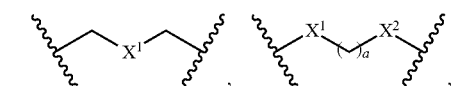

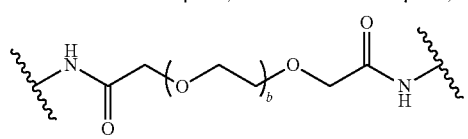

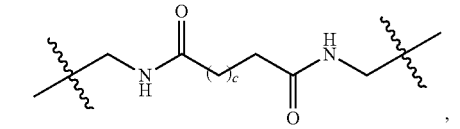

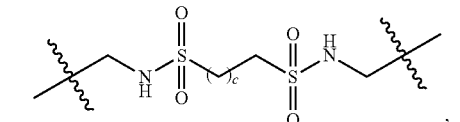

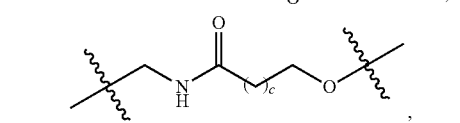

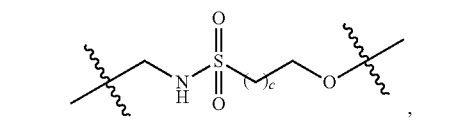

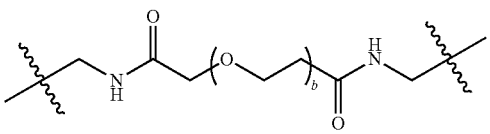

-continued

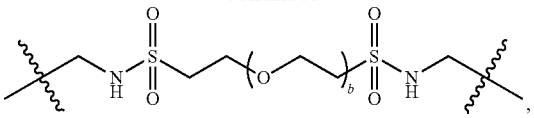

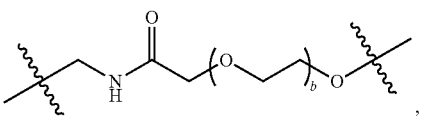

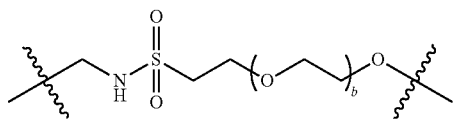

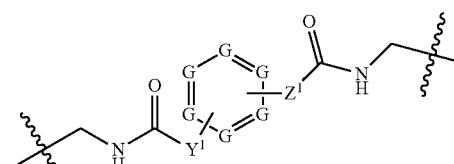

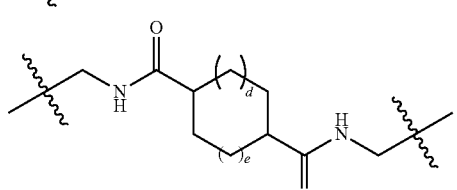

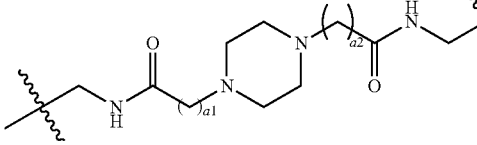

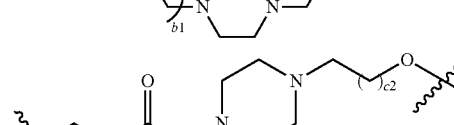

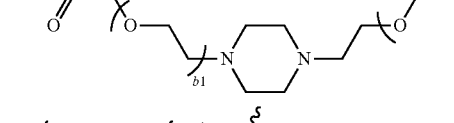

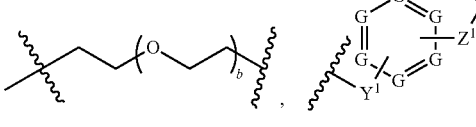

-continued

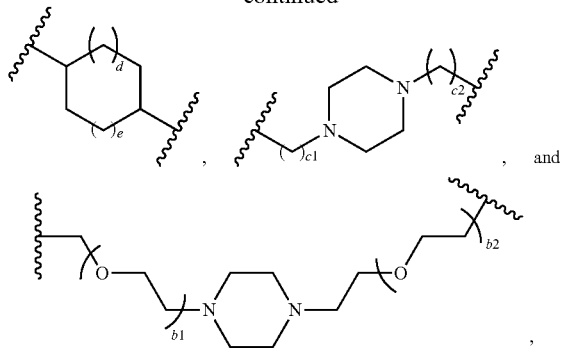

wherein a, a1, and a2 are each independently selected from 1, 2, 3, 4, 5, 6, 7, 8, 9, 10, 11, and 12; b, b1, and b2 are each independently selected from 0, 1, 2, 3, 4, 5, and 6; c, c1, and c2 are each independently selected from 0, 1, 2, 3, 4, 5, 6, 7, 8, 9, 10, 11, and 12; d and e are each independently selected form 0, 1, and 2; each G is independently selected from CH and N; $X^1$ and $X^2$ are each independently O or —$NR^x$, wherein $R^x$ is hydrogen or optionally substituted alkyl; and $Y^1$ and $Z^1$ are each independently selected from —CH$_2$—, —NH—, and —O—.

In some embodiments, the compound is selected from the group consisting of compounds shown in Table 2, or a pharmaceutically acceptable salt thereof.

In another aspect, the disclosure provides a compound of formula (IIc):

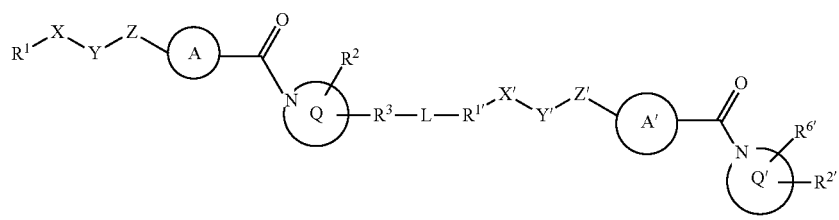

(IIc)

or a pharmaceutically acceptable salt thereof, wherein:
$R^1$ is selected from heterocyclyl, heterocyclylalkyl, heteroaryl, heteroarylalkyl, aryl, arylalkyl, cycloalkyl, cycloalkylalkyl, alkyl, alkenyl, alkynyl, hydroxy, alkoxy, thioalkyl, halogen, haloalkyl, carboxy, acyl, amido, cyano, sulfonyl, and hydrogen;
$R^{1'}$ is selected from heterocyclyl, heterocyclylalkyl, heteroaryl, heteroarylalkyl, aryl, arylalkyl, cycloalkyl, cycloalkylalkyl, alkyl, alkenyl, and alkynyl;
X and X' are each independently absent or selected from —C(O)—, —C(S)—, —CH$_2$—, and —SO$_2$—;
Y and Y' are each independently selected from —$NR^a$— or —O—;
$R^a$ is selected from hydrogen, alkyl, haloalkyl, heteroalkyl, cycloalkyl, hydroxyalkyl, and aminoalkyl, or $R^a$ is taken together with the nitrogen atom to which it is attached to form a fused ring with A, or $R^a$ and $R^1$ together with the atoms to which they are attached together form an optionally substituted heterocyclic ring;
Z and Z' are each independently absent or —$CR^bR^c$—;
$R^b$ and $R^c$ are each independently selected from hydrogen and alkyl;

A and A' are each independently a five-membered heteroaryl ring;
Q and Q' are each independently a four-, five-, or six-membered heterocycle;
$R^2$ and $R^{2'}$ are each independently selected from hydrogen, halo, alkyl, amino, and hydroxy;
$R^3$ is selected from aryl, heteroaryl, heterocyclyl, and a group of formula:

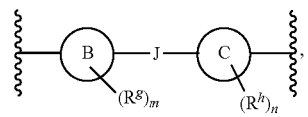

wherein B is aryl or heteroaryl; J is absent or is —CH$_2$—, —O—, —S—, or —NH—; C is selected from aryl, heteroaryl, and heterocyclyl; m is 0, 1, 2, 3, or 4; n is 0, 1, 2, 3, or 4; and $R^g$ and $R^h$ are each independently selected from alkyl, alkenyl, alkynyl, halo, haloalkyl, amino, alkylamino, dialkylamino, aminoalkyl, alkylaminoalkyl, dialkylaminoalkyl, amido, amidoalkyl, sulfonamido, sulfonamidoalkyl, urea, ureaalkyl, thiourea, thioureaalkyl, hydroxy, hydroxyalkyl, alkoxy, alkoxyalkyl, haloalkoxy, thioalkyl, acyl, carboxy, nitro, oxo, aryl, arylalkyl, heteroaryl, heteroarylalkyl, heterocyclyl, heterocyclylalkyl, cycloalkyl, and cycloalkylalkyl;
$R^{3'}$ is selected from hydrogen, halo, —$OR^{d'}$, —$NR^{e'}R^{f'}$, aryl, arylalkyl, heteroaryl, heteroarylalkyl, heterocyclyl, and heterocyclylalkyl, and a group of formula:

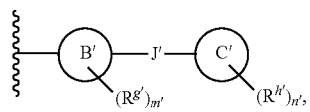

wherein B' is aryl or heteroaryl; J' is absent or is —CH$_2$—, —O—, —S—, or —NH—; C' is selected from aryl, heteroaryl, and heterocyclyl; m' is 0, 1, 2, 3, or 4; n' is 0, 1, 2, 3, or 4; and $R^{g'}$ and $R^{h'}$ are each independently selected from alkyl, alkenyl, alkynyl, halo, haloalkyl, amino, alkylamino, dialkylamino, aminoalkyl, alkylaminoalkyl, dialkylaminoalkyl, amido, amidoalkyl, sulfonamido, sulfonamidoalkyl, urea, ureaalkyl, thiourea, thioureaalkyl, hydroxy, hydroxyalkyl, alkoxy, alkoxyalkyl, haloalkoxy, thioalkyl, acyl, carboxy, nitro, oxo, aryl, arylalkyl, heteroaryl, heteroarylalkyl, heterocyclyl, heterocyclylalkyl, cycloalkyl, and cycloalkylalkyl;
$R^{d'}$, $R^{e'}$, and $R^{f'}$ are each independently selected from hydrogen, alkyl, haloalkyl, hydroxyalkyl, aminoalkyl, carboxyalkyl, heteroalkyl, aryl, arylalkyl, and heteroaryl; and L is a linker;

wherein each alkyl, alkenyl, alkynyl, aryl, arylalkyl, heteroalkyl, heteroaryl, heteroarylalkyl, cycloalkyl, heterocyclyl, and heterocyclylalkyl is independently optionally substituted with 1, 2, 3, 4, or 5 substituents.

In some embodiments, $R^1$ and $R^{1'}$ are the same, $R^2$ and $R^{2'}$ are the same, $R^3$ and $R^{3'}$ are the same, X and X' are the same, Y and Y' are the same, Z and Z' are the same, A and A' are the same, and Q and Q' are the same. In some embodiments, $R^1$ and $R^{2'}$ are each a 4- or 5-membered monocyclic heterocyclyl. In some embodiments, $R^1$ and $R^{1'}$ are pyrrolidine.

In some embodiments, X and X' are —C(O)—. In some embodiments, Y and Y' are —$NR^a$—, and $R^a$ is hydrogen. In some embodiments, Z and Z' are each absent.

In some embodiments, A and A' are thiophene.

In some embodiments, Q and Q' are selected from azetidine and pyrrolidine.

In some embodiments, $R^2$ and $R^{2'}$ are hydrogen.

In some embodiments, $R^3$ is selected from aryl, heteroaryl, and a group of formula:

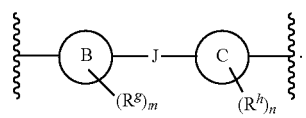

In some embodiments, $R^3$ is a group of formula:

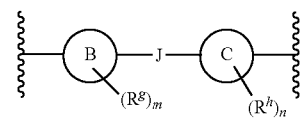

wherein B is a 5-membered monocyclic heteroaryl having 1 or 2 heteroatoms independently selected from N and S; J is absent; C is selected from aryl, heteroaryl, and heterocyclyl; m is 0 or 1; $R^g$ is $C_1$-$C_6$ alkyl; n is 0, 1, or 2; and each $R^h$ is independently selected from $C_1$-$C_6$ alkyl, halo, $C_1$-$C_6$ haloalkyl, amino, amino-$C_1$-$C_6$-alkyl, amido-$C_1$-$C_6$-alkyl, and heterocyclyl.

In some embodiments, $R^{3'}$ is selected from hydrogen, aryl, heteroaryl, and a group of formula:

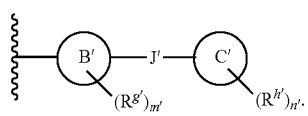

In some embodiments, $R^{3'}$ is selected from a monocyclic and bicyclic heteroaryl having 1, 2, or 3 heteroatoms independently selected from N and S.

In some embodiments, $R^{3'}$ is a group of formula:

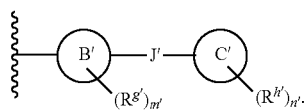

wherein B' is a 5-membered monocyclic heteroaryl having 1 or 2 heteroatoms independently selected from N and S; J' is absent; C' is selected from aryl, heteroaryl, and heterocyclyl; m' is 0 or 1; $R^{g'}$ is $C_1$-$C_6$ alkyl; n' is 0, 1, or 2; and each $R^{h'}$ is independently selected from $C_1$-$C_6$ alkyl, halo, $C_1$-$C_6$ haloalkyl, amino, amino-$C_1$-$C_6$-alkyl, amido-$C_1$-$C_6$-alkyl, and heterocyclyl.

In some embodiments, L is a linker comprising one or more groups independently selected from methylene (—$CH_2$—), vinylene (—CH=CH—), acetylene (—C≡C—), ether (—O—), amine (—NH—), alkylamine (—NR—, wherein R is an optionally substituted $C_1$-$C_6$ alkyl group), amide (—C(O)NH—), ester (—C(O)O—), carbamate (—OC(O)NH—), sulfonamide (—S(O)$_2$NH—), phenylene (—$C_6H_4$—), heteroarylene, heterocyclylene, and any combination thereof. In some embodiments, L is selected from:

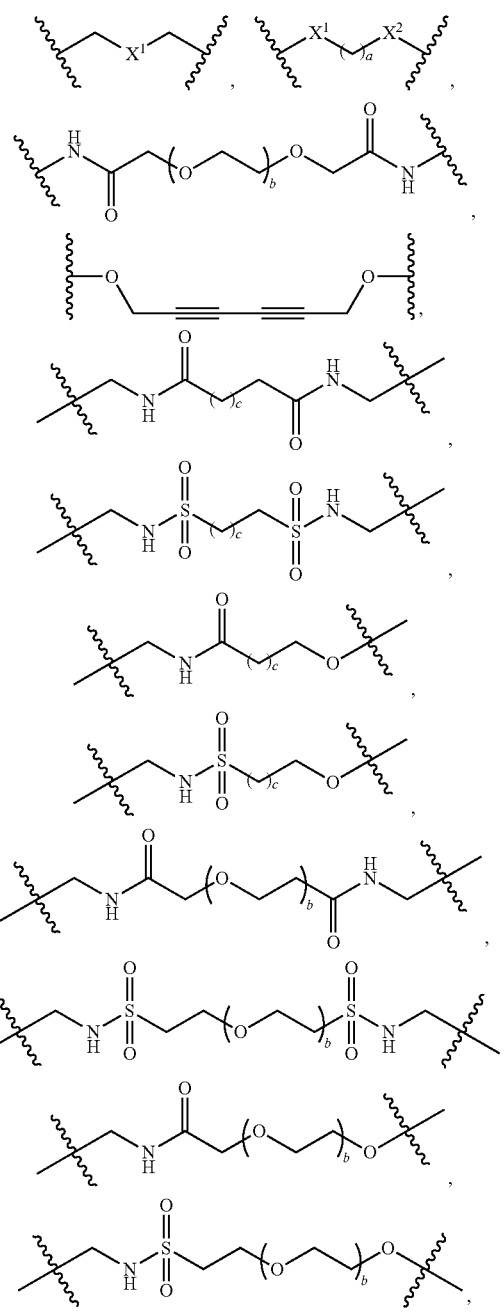

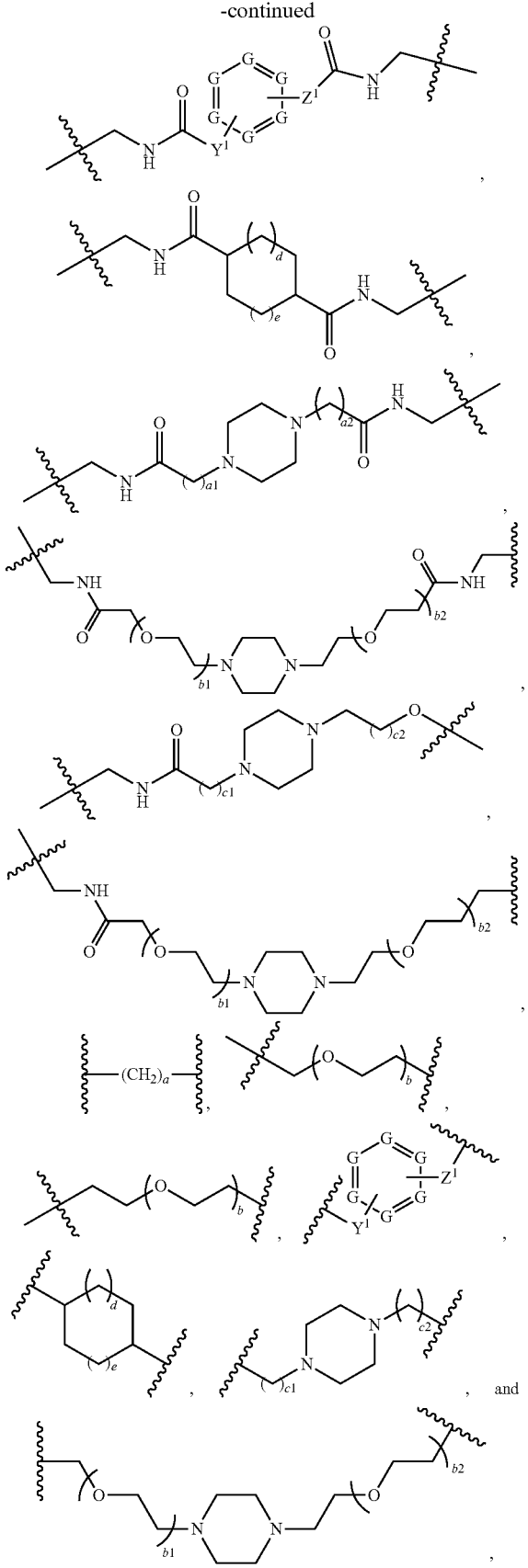

wherein a, a1, and a2 are each independently selected from 1, 2, 3, 4, 5, 6, 7, 8, 9, 10, 11, and 12; b, b1, and b2 are each independently selected from 0, 1, 2, 3, 4, 5, and 6; c, c1, and c2 are each independently selected from 0, 1, 2, 3, 4, 5, 6, 7, 8, 9, 10, 11, and 12; d and e are each independently selected form 0, 1, and 2; each G is independently selected from CH and N; $X^1$ and $X^2$ are each independently O or —$NR^x$, wherein $R^x$ is hydrogen or optionally substituted alkyl; and $Y^1$ and $Z^1$ are each independently selected from —$CH_2$—, —NH—, and —O—.

In one aspect, the disclosure provides a pharmaceutical composition comprising a compound disclosed herein (e.g., a compound of formula (I), (IIa), (IIb), or (IIc)), or a pharmaceutically acceptable salt thereof, and a pharmaceutically acceptable carrier. In some embodiments, the pharmaceutical composition is formulated for oral administration. In some embodiments, the pharmaceutical composition is formulated for parenteral administration.

In one aspect, the disclosure provides a method of inhibiting GAS41 activity in a sample, comprising contacting the sample with an effective amount of a compound disclosed herein (e.g., a compound of formula (I), (IIa), (IIb), or (IIc)) or a pharmaceutically acceptable salt thereof, or a pharmaceutical composition disclosed herein (e.g., a pharmaceutical composition comprising a compound of formula (I), (IIa), (IIb), or (IIc) or a pharmaceutically acceptable salt thereof).

In one aspect, the disclosure provides a method of reducing proliferation of cancer cells in a sample, comprising contacting the sample with an effective amount of a compound disclosed herein (e.g., a compound of formula (I), (IIa), (IIb), or (IIc)) or a pharmaceutically acceptable salt thereof, or a pharmaceutical composition disclosed herein (e.g., a pharmaceutical composition comprising a compound of formula (I), (IIa), (IIb), or (IIc) or a pharmaceutically acceptable salt thereof). In some embodiments, the cancer cells are selected from brain cancer (e.g., glioblastoma or astrocytoma), sarcoma, colorectal cancer, lung cancer (e.g., non-small cell lung cancer), and gastric cancer cells.

In one aspect, the disclosure provides a method of treating cancer in a subject in need thereof, comprising administering to the subject a therapeutically effective amount of a compound disclosed herein (e.g., a compound of formula (I), (IIa), (IIb), or (IIc)) or a pharmaceutically acceptable salt thereof, or a pharmaceutical composition disclosed herein (e.g., a pharmaceutical composition comprising a compound of formula (I), (IIa), (IIb), or (IIc) or a pharmaceutically acceptable salt thereof). In some embodiments, the cancer is selected from brain cancer (e.g., glioblastoma or astrocytoma), sarcoma, colorectal cancer, lung cancer (e.g., non-small cell lung cancer), and gastric cancer. In some embodiments, the method further comprises administering an additional chemotherapeutic agent to the subject. In some embodiments, the subject is a human.

In one aspect, the disclosure provides a use of compound disclosed herein (e.g., a compound of formula (I), (IIa), (IIb), or (IIc)) or a pharmaceutically acceptable salt thereof, or a pharmaceutical composition disclosed herein (e.g., a pharmaceutical composition comprising a compound of formula (I), (IIa), (IIb), or (IIc) or a pharmaceutically acceptable salt thereof), for the treatment of cancer.

DEFINITIONS

Figure 1:
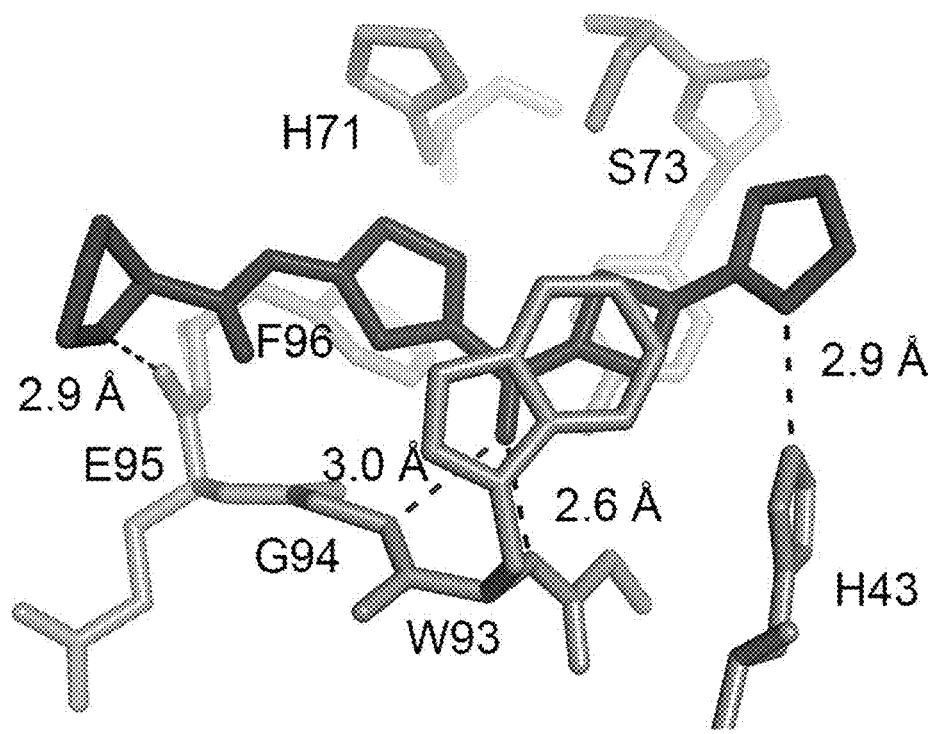
FIG. 1 shows the crystal structure of a compound disclosed herein (Compound 85) in complex with the GAS41 YEATS domain.

Although any methods and materials similar or equivalent to those described herein can be used in the practice or testing of embodiments described herein, some preferred methods, compositions, devices, and materials are described herein. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the embodiments described herein.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the embodiments described herein, the following definitions apply.

As used herein and in the appended claims, the singular forms "a", "an" and "the" include plural reference unless the context clearly dictates otherwise. Thus, for example, reference to "a GAS41 inhibitor" is a reference to one or more GAS41 inhibitors, and so forth.

As used herein, the term "comprise" and linguistic variations thereof denote the presence of recited feature(s), element(s), method step(s), etc. without the exclusion of the presence of additional feature(s), element(s), method step(s), etc. Conversely, the term "consisting of" and linguistic variations thereof, denotes the presence of recited feature(s), element(s), method step(s), etc. and excludes any unrecited feature(s), element(s), method step(s), etc., except for ordinarily-associated impurities. The phrase "consisting essentially of" denotes the recited feature(s), element(s), method step(s), etc. and any additional feature(s), element(s), method step(s), etc. that do not materially affect the basic nature of the composition, system, or method. Many embodiments herein are described using open "comprising" language. Such embodiments encompass multiple closed "consisting of" and/or "consisting essentially of" embodiments, which may alternatively be claimed or described using such language.

All chemical names of substituents should be interpreted in light of IUPAC and/or the modified nomenclature and with reference to the chemical structures depicted and/or described herein. For compounds described herein, groups and substituents thereof may be selected in accordance with permitted valence of the atoms and the substituents, and such that the selections and substitutions result in a stable compound, e.g., a compound that does not spontaneously undergo transformation such as by rearrangement, cyclization, elimination, etc.

In accordance with a convention used in the art, the group:

is used in structural formulae herein to depict the bond that is the point of attachment of the moiety or substituent to the core or backbone structure.

As used herein, the term "subject" broadly refers to any animal, including but not limited to, human and non-human animals (e.g., dogs, cats, cows, horses, sheep, poultry, fish, crustaceans, etc.). As used herein, the term "patient" typically refers to a subject that is being treated for a disease or condition.

As used herein, the term "subject at risk for cancer" refers to a subject with one or more risk factors for developing cancer. Risk factors may include, but are not limited to, gender, age, genetic predisposition, environmental exposures, infections, and previous incidents of diseases, lifestyle, etc.

As used herein, the term "effective amount" refers to the amount of a compound or composition sufficient to effect beneficial or desired results. An effective amount can be administered in one or more administrations, applications or dosages and is not intended to be limited to a particular formulation or administration route.

As used herein, the terms "administration" and "administering" refer to the act of giving a drug, prodrug, or other agent, or therapeutic treatment to a subject or in vivo, in vitro, or ex vivo cells, tissues, and organs. Exemplary routes of administration to the human body can be through space under the arachnoid membrane of the brain or spinal cord (intrathecal), the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the terms "co-administration" and "co-administering" refer to the administration of at least two agent(s) (e.g., a GAS41 inhibitor and one or more additional therapeutics) or therapies to a subject. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s), and/or when co-administration of two or more agents results in sensitization of a subject to beneficial effects of one of the agents via co-administration of the other agent.

As used herein, the term "pharmaceutical composition" refers to the combination of an active agent with a carrier, inert or active, making the composition especially suitable for therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintegrants (e.g., potato starch or sodium starch glycolate), and the like. The compositions also can include stabilizers and preservatives. For examples of carriers, stabilizers and adjuvants, see, e.g., Martin, Remington's Pharmaceutical Sciences, 15th Ed., Mack Publ. Co., Easton, Pa. (1975), incorporated herein by reference in its entirety.

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NR_4^+$, wherein each R is independently $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NR_4^+$ (wherein each R is independently a $C_{1-4}$ alkyl group), and the like.

For therapeutic use, salts of the compounds herein are contemplated as being pharmaceutically acceptable. However, salts of acids and bases that are non-pharmaceutically acceptable may also find use, for example, in the preparation or purification of a pharmaceutically acceptable compound.

As used herein, the term "instructions for administering said compound to a subject," and grammatical equivalents thereof, includes instructions for using the compositions contained in a kit for the treatment of conditions (e.g., providing dosing, route of administration, decision trees for treating physicians for correlating patient-specific characteristics with therapeutic courses of action).

"Amino" refers to a —$NH_2$ moiety.

"Carbonyl" refers to a moiety of formula —C(=O)—.

"Carboxy" or "carboxyl" refers to the —$CO_2H$ moiety.

"Cyano" refers to the —CN moiety.

"Hydroxy" or "hydroxyl" refers to the —OH moiety.

"Imino" refers to the =NH moiety. Unless stated otherwise specifically in the specification, an imino group is optionally substituted.

"Nitro" refers to the —$NO_2$ moiety.

"Oxo" refers to the =O moiety.

"Thioxo" refers to the =S moiety.

"Acyl" refers to the group —C(=O)R, where R is selected from the group consisting of alkyl, alkenyl, alkynyl, aryl, arylalkyl, cycloalkyl, cycloalkylalkyl, heteroaryl, heteroarylalkyl, heterocyclyl, heterocyclylalkyl, and heteroalkyl. Unless stated otherwise specifically in the specification, an acyl group is optionally substituted.

"Alkyl" refers to a straight or branched saturated hydrocarbon chain having from 1 to thirty carbon atoms, for example from 1 to 16 carbon atoms ($C_1$-$C_{16}$ alkyl), 1 to 12 carbon atoms ($C_1$-$C_{12}$ alkyl), 1 to 8 carbon atoms ($C_1$-$C_8$ alkyl), 1 to 6 carbon atoms ($C_1$-$C_6$ alkyl), or 1 to 4 carbon atoms ($C_1$-$C_4$ alkyl), e.g., methyl, ethyl, n-propyl, iso-propyl, n-butyl, sec-butyl, iso-butyl, tert-butyl, n-pentyl, iso-pentyl, neopentyl, n-hexyl, 3-methylhexyl, 2,2-dimethylpentyl, 2,3-dimethylpentyl, n-heptyl, n-octyl, n-nonyl, n-decyl, n-undecyl, and n-dodecyl, and the like. Unless stated otherwise specifically in the specification, an alkyl group is optionally substituted.

"Alkenyl" refers to a straight or branched refers to a straight or branched hydrocarbon chain containing from 2 to 30 carbon atoms, for example from 2 to 16 carbon atoms ($C_2$-$C_{16}$ alkenyl), 2 to 12 carbon atoms ($C_2$-$C_{12}$ alkenyl), 2 to 8 carbon atoms ($C_2$-$C_8$ alkenyl), 2 to 6 carbon atoms ($C_2$-$C_6$ alkenyl), or 2 to 4 carbon atoms ($C_2$-$C_4$ alkenyl), and containing at least one carbon-carbon double bond. Representative examples of alkenyl include, but are not limited to, ethenyl, 2-propenyl, 2-methyl-2-propenyl, 3-butenyl, 4-pentenyl, 1,4-pentadienyl, 5-hexenyl, 2-heptenyl, 2-methyl-1-heptenyl, and 3-decenyl. Unless stated otherwise specifically in the specification, an alkenyl group is optionally substituted.

"Alkynyl" refers to a straight or branched hydrocarbon chain containing from 2 to 30 carbon atoms, for example from 2 to 16 carbon atoms ($C_2$-$C_{16}$ alkynyl), 2 to 12 carbon atoms ($C_2$-$C_{12}$ alkynyl), 2 to 8 carbon atoms ($C_2$-$C_8$ alkynyl), 2 to 6 carbon atoms ($C_2$-$C_6$ alkynyl), or 2 to 4 carbon atoms ($C_2$-$C_4$ alkynyl), and containing at least one carbon-carbon triple bond. Representative examples of alkynyl include, but are not limited to, ethynyl, propynyl, butynyl, pentynyl, and hexynyl. Unless stated otherwise specifically in the specification, an alkynyl group is optionally substituted.

"Alkylene" refers to a divalent group derived from a straight or branched chain hydrocarbon of 1 to 30 carbon atoms ($C_1$-$C_{30}$ alkylene), for example, of 1 to 6 carbon atoms ($C_1$-$C_6$ alkylene). Representative examples of alkylene include, but are not limited to, —$CH_2$—, —$CH_2CH_2$—, —CH($CH_3$)—, —$CH_2CH_2CH_2$—, —$CH_2CH(CH_3)$—, —$CH_2CH_2CH_2CH_2$—, —$CH_2CH(CH_3)CH_2$—, —CH₂CH₂CH(CH₃)—, —CH₂CH₂CH₂CH₂CH₂—, —CH₂CH(CH₃)CH₂CH₂—, —CH(CH₃)CH₂CH₂CH₂—, —CH₂CH₂CH₂CH₂CH₂CH₂—, —CH₂CH₂CH(CH₃)CH₂CH₂—, —CH₂CH(CH₃)CH₂CH₂CH₂—, and —CH(CH₃)CH₂CH₂CH₂CH₂—. Unless stated otherwise specifically in the specification, an alkylene group is optionally substituted.

"Alkoxy" refers to a moiety of the formula —OR where R is an alkyl group as defined herein, e.g., an alkyl group containing 1 to 12 carbon atoms. Representative examples of alkoxy include, but are not limited to, methoxy, ethoxy, propoxy, 2-propoxy, butoxy and tert-butoxy. Unless stated otherwise specifically in the specification, an alkoxy group is optionally substituted.

"Alkenyloxy" refers to a moiety of the formula —OR where R is an alkenyl group as defined herein, e.g., an alkenyl group containing 2 to 12 carbon atoms. Unless stated otherwise specifically in the specification, an alkenyloxy group is optionally substituted.

"Alkynyloxy" refers to a moiety of the formula —OR where R is an alkynyl group as defined herein, e.g., an alkynyl group containing 2 to 12 carbon atoms. Unless stated otherwise specifically in the specification, an alkynyloxy group is optionally substituted.

"Alkylamino" refers to a moiety of the formula —NHR where R is an alkyl group as defined herein. Unless stated otherwise specifically in the specification, an alkylamino or dialkylamino group is optionally substituted.

"Alkylaminoalkyl" refers to an alkyl moiety comprising at least one alkylamino substituent. Unless stated otherwise specifically in the specification, an alkylaminoalkyl group is optionally substituted.

"Amide" or "amido" refers to a moiety with formula —C(=O)NRR' or —NRC(=O)R', where R and R' are each independently selected from the group consisting of hydrogen, alkyl, aryl, arylalkyl, cycloalkyl, cycloalkylalkyl, heteroaryl (bonded through a ring carbon), heteroarylalkyl, heterocyclyl, and heterocyclylalkyl. When the amido moiety is —C(=O)NRR', R and R' may optionally be taken together with the nitrogen to which they are attached to form a 4-, 5-, 6-, or 7-membered ring. Unless stated otherwise specifically in the specification, an amido group is optionally substituted.

"Amidoalkyl" refers to an alkyl moiety, as defined herein, in which at least one hydrogen atom is replaced with an amido group, as defined herein. Unless stated otherwise specifically in the specification, an amidoalkyl group is optionally substituted.

"Aminoalkyl" refers to an alkyl moiety, as defined herein, in which at least one hydrogen atom is replaced with an amino group, as defined herein. The amino group can be substituted on a tertiary, secondary or primary carbon. Unless stated otherwise specifically in the specification, an aminoalkyl group is optionally substituted.

"Aryl" refers to an aromatic carbocyclic ring system having a single ring (monocyclic) or multiple rings (bicyclic or tricyclic) including fused ring systems, and zero heteroatoms. As used herein, aryl contains 6-20 carbon atoms ($C_6$-$C_{20}$ aryl), 6 to 14 ring carbon atoms ($C_6$-$C_{14}$ aryl), 6 to 12 ring carbon atoms ($C_6$-$C_{12}$ aryl), or 6 to 10 ring carbon atoms ($C_6$-$C_{10}$ aryl). Representative examples of aryl groups include, but are not limited to, phenyl, naphthyl, anthracenyl, and phenanthrenyl. Unless stated otherwise specifically in the specification, the term "aryl" is meant to include aryl groups that are optionally substituted.

"Arylalkyl" refers to an alkyl group, as defined herein, wherein at least one hydrogen atom is replaced with an aryl group, as defined herein. Exemplary arylalkyl groups include, but are not limited to, benzyl and phenethyl. Unless stated otherwise specifically in the specification, the term "arylalkyl" is meant to include groups that are optionally substituted on the aryl moiety and/or on the alkyl moiety.

"Arylene" refers to a divalent aryl group (e.g., phenylene). Unless stated specifically otherwise, an arylene is optionally substituted.

"Aryloxy" refers to an —O-aryl moiety. Unless stated otherwise specifically in the specification, an aryloxy is optionally substituted.

"Arylamino" refers to a —NR$_a$-aryl moiety, where R$_a$ is H or alkyl. Unless stated otherwise specifically in the specification, an arylamino is optionally substituted.

"Cycloalkyl" refers to a saturated carbocyclic ring system containing three to ten carbon atoms per ring. The cycloalkyl may be monocyclic, bicyclic, tricyclic, bridged, fused, and/or spirocyclic. Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, bicyclo[2.2.1]heptanyl, bicyclo[3.2.1]octanyl, and bicyclo[5.2.0]nonanyl. Unless stated otherwise specifically in the specification, the term "cycloalkyl" is meant to include cycloalkyl groups that are optionally substituted.

"Cycloalkenyl" refers to a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl, and cycloheptenyl. Unless stated otherwise specifically in the specification, the term "cycloalkenyl" is meant to include cycloalkenyl groups that are optionally substituted.

"Cycloalkylalkyl" refers to an alkyl group, as defined herein, wherein at least one hydrogen atom is replaced with a cycloalkyl group, as defined herein. Unless stated otherwise specifically in the specification, the term "cycloalkylalkyl" is meant to include groups that are optionally substituted on the cycloalkyl moiety and/or on the alkyl moiety.

"Cycloalkylalkylamino" refers to a cycloalkylalkyl-NR$_a$— moiety, where R$_a$ is H or alkyl and where the cycloalkylalkyl moiety is attached via a carbon atom to nitrogen, wherein the nitrogen functions as a linker to attach the moiety to the remainder of the molecule. Unless stated otherwise specifically in the specification, a cycloalkylalkylamino is optionally substituted.

"Cycloalkylalkyloxy" refers to a —O-cycloalkylalkyl moiety, where the cycloalkylalkyl moiety is attached via a carbon atom to oxygen, wherein the oxygen functions as a linker to attach the moiety to the remainder of the molecule. Unless stated otherwise specifically in the specification, a cycloalkylalkyloxy is optionally substituted.

"Cycloalkylamino" refers to a —NR$_a$-cycloalkyl moiety, where R$_a$ is H or alkyl. Unless stated otherwise specifically in the specification, a cycloalkylamino is optionally substituted.

"Cycloalkyloxy" refers to an —O-cycloalkyl moiety. Unless stated otherwise specifically in the specification, a cycloalkyloxy is optionally substituted.

"Dialkylamino" refers to a moiety of the formula —NRR where R and R' are each independently an alkyl group as defined herein. Unless stated otherwise specifically in the specification, an alkylamino or dialkylamino group is optionally substituted.

"Dialkylaminoalkyl" refers to an alkyl moiety comprising at least one dialkylamino substituent. Unless stated otherwise specifically in the specification, an alkylaminoalkyl group is optionally substituted.

"Halo" or "halogen" refers to fluoro, chloro, bromo, or iodo.

"Haloalkyl" refers to an alkyl group, as defined herein, that is substituted by one or more halo atoms, as defined herein, e.g., trifluoromethyl, difluoromethyl, fluoromethyl, trichloromethyl, —CH$_2$CF$_3$, —CH$_2$CHF$_2$, —CH$_2$CH$_2$F, —CHFCF$_3$, —CHFCHF$_2$, —CHFCH$_2$F, —CHFCH$_3$, —CF$_2$CF$_3$, —CF$_2$CHF$_2$, —CF$_2$CH$_2$F, —CF$_2$CH$_3$, —CH$_2$CF$_2$CH$_3$, —CH$_2$CHFCH$_3$, 3-bromo-2-fluoropropyl, 1,2-dibromoethyl, and the like. Unless stated otherwise specifically in the specification, a haloalkyl group is optionally substituted.

"Haloalkoxy" refers to an alkoxy group, as defined herein, that is substituted with one or more halo atoms, as defined herein.

As used herein, the term "heteroatom" or "ring heteroatom" is meant to include any element other than carbon or hydrogen. Suitable heteroatoms are oxygen (O), nitrogen (N), sulfur (S), and phosphorus (P).

"Heteroalkyl" means an alkyl group, as defined herein, in which one or more of the carbon atoms (and any associated hydrogen atoms) are each independently replaced with a heteroatom group such as —NR—, —O—, —S—, —S(O)—, —S(O)$_2$—, and the like, where R is H, alkyl, aryl, cycloalkyl, heteroalkyl, heteroaryl or heterocyclyl, each of which may be optionally substituted. By way of example, 1, 2 or 3 carbon atoms may be independently replaced with the same or different heteroatomic group. Examples of heteroalkyl groups include, but are not limited to, —OCH$_3$, —CH$_2$OCH$_3$, —SCH$_3$, —CH$_2$SCH$_3$, —NRCH$_3$, and —CH$_2$NRCH$_3$, where R is hydrogen, alkyl, aryl, arylalkyl, heteroalkyl, or heteroaryl, each of which may be optionally substituted. Heteroalkyl also includes groups in which a carbon atom of the alkyl is oxidized (i.e., is —C(O)—).

"Heteroalkylene" refers to an alkylene group, as defined herein, in which one or more of the carbon atoms (and any associated hydrogen atoms) are each independently replaced with a heteroatom group such as —NR—, —O—, —S—, —S(O)—, —S(O)$_2$—, and the like, where R is H, alkyl, aryl, cycloalkyl, heteroalkyl, heteroaryl or heterocyclyl, each of which may be optionally substituted. By way of example, 1, 2 or 3 carbon atoms may be independently replaced with the same or different heteroatomic group. Heteroalkylene also includes groups in which a carbon atom of the alkyl is oxidized (i.e., is —C(O)—). Examples of heteroalkylene groups include, but are not limited to, —CH$_2$—O—CH$_2$—, —CH$_2$—S—CH$_2$—, —CH$_2$—NR—CH$_2$—, —CH$_2$—NH—C(O)—CH$_2$—, and the like, as well as polyethylene oxide chains, polypropylene oxide chains, and polyethyleneimine chains.

"Heteroaryl" refers to an aromatic group having a single ring (monocyclic) or multiple rings (bicyclic or tricyclic), having one or more ring heteroatoms independently selected from O, N, and S. The aromatic monocyclic rings are five- or six-membered rings containing at least one heteroatom independently selected from O, N, and S (e.g. 1, 2, 3, or 4 heteroatoms independently selected from O, N, and S). The five-membered aromatic monocyclic rings have two double bonds, and the six-membered aromatic monocyclic rings have three double bonds. The bicyclic heteroaryl groups are exemplified by a monocyclic heteroaryl ring appended fused to a monocyclic aryl group, as defined herein, or a monocyclic heteroaryl group, as defined herein. The tricyclic heteroaryl groups are exemplified by a monocyclic heteroaryl ring fused to two rings independently selected from a monocyclic aryl group, as defined herein, and a monocyclic heteroaryl group as defined herein. Representative examples of monocyclic heteroaryl include, but are not limited to, pyridinyl (including pyridin-2-yl, pyridin-3-yl, pyridin-4-yl), pyrimidinyl, pyrazinyl, pyridazinyl, pyrrolyl, benzopyrazolyl, 1,2,3-triazolyl, 1,3,4-thiadiazolyl, 1,2,4-thiadiazolyl, 1,3,4-oxadiazolyl, 1,2,4-oxadiazolyl, imidazolyl, thiazolyl, isothiazolyl, thienyl, furanyl, oxazolyl, isoxazolyl, 1,2,4-triazinyl, and 1,3,5-triazinyl. Representative examples of bicyclic heteroaryl include, but are not limited to, benzimidazolyl, benzodioxolyl, benzofuranyl, benzooxadiazolyl, benzopyrazolyl, benzothiazolyl, benzothienyl, benzotriazolyl, benzoxadiazolyl, benzoxazolyl, chromenyl, imidazopyridine, imidazothiazolyl, indazolyl, indolyl, isobenzofuranyl, isoindolyl, isoquinolinyl, naphthyridinyl, purinyl, pyridoimidazolyl, quinazolinyl, quinolinyl, quinoxalinyl, thiazolopyridinyl, thiazolopyrimidinyl, thienopyrrolyl, and thienothienyl. Representative examples of tricyclic heteroaryl include, but are not limited to, dibenzofuranyl and dibenzothienyl. The monocyclic, bicyclic, and tricyclic heteroaryls are connected to the parent molecular moiety through any carbon atom or any nitrogen atom contained within the rings. Unless stated otherwise specifically in the specification, a heteroaryl group is optionally substituted.

"Heteroarylalkyl" refers to an alkyl group, as defined herein, wherein at least one hydrogen atom is replaced with a heteroaryl group, as defined herein. Unless stated otherwise specifically in the specification, a heteroarylalkyl group is optionally substituted.

"Heteroarylalkylamino" refers to a heteroarylalkyl-NR$_a$— moiety, where R$_a$ is H or alkyl. Unless stated otherwise specifically in the specification, an heteroarylalkylamino is optionally substituted.

"Heteroarylalkyloxy" refers to an heteroarylalkyl-O— moiety. Unless stated otherwise specifically in the specification, a heteroarylalkyloxy is optionally substituted.

"Heteroarylamino" refers to a —NR$_a$-heteroaryl moiety, where R$_a$ is H or alkyl. Unless stated otherwise specifically in the specification, a heteroarylamino is optionally substituted.

"Heteroaryloxy" refers to an —O-heteroaryl moiety. Unless stated otherwise specifically in the specification, an heteroaryloxy is optionally substituted.

"Heteroarylene" refers to a divalent heteroaryl group. Unless stated specifically otherwise, a heteroarylene is optionally substituted.

"Heterocycle" or "heterocyclic" refers to a saturated or partially unsaturated non-aromatic cyclic group having one or more ring heteroatoms independently selected from O, N, and S. means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from O, N, and S. The three- or four-membered ring contains zero or one double bond, and one heteroatom selected from O, N, and S. The five-membered ring contains zero or one double bond and one, two or three heteroatoms selected from O, N and S. The six-membered ring contains zero, one, or two double bonds and one, two, or three heteroatoms selected from O, N, and S. The seven- and eight-membered rings contains zero, one, two, or three double bonds and one, two, or three heteroatoms selected from O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings. Unless stated otherwise specifically in the specification, a heterocyclyl group is optionally substituted.

"Heterocyclylalkyl" refers to an alkyl group, as defined herein, wherein at least one hydrogen atom is replaced with a heterocyclyl group, as defined herein. Unless stated otherwise specifically in the specification, a heterocyclylalkyl group is optionally substituted.

"Heterocyclylalkylamino" refers to a heterocyclylalkyl-NR$_a$— moiety, where R$_a$ is H or alkyl and where the heterocyclylalkyl moiety is attached via a carbon atom to nitrogen, wherein the nitrogen functions as a linker to attach the moiety to the remainder of the molecule. Unless stated otherwise specifically in the specification, a heterocyclylalkylamino is optionally substituted.

"Heterocyclylalkyloxy" refers to a —O-heterocycloalkyl moiety, where the heterocyclylalkyl moiety is attached via a carbon atom to oxygen, wherein the oxygen functions as a linker to attach the moiety to the remainder of the molecule. Unless stated otherwise specifically in the specification, a heterocyclylalkyloxy is optionally substituted.

"Heterocyclylamino" refers to a —NR$_a$-heterocyclyl moiety, where R$_a$ is H or alkyl and where the heterocyclyl moiety is attached via a carbon atom to nitrogen, wherein the nitrogen functions as a linker to attach the moiety to the remainder of the molecule. Unless stated otherwise specifically in the specification, a heterocyclylamino is optionally substituted.

"Heterocyclyloxy" refers to an —O-heterocyclyl moiety, where the heterocyclyl moiety is attached via a carbon atom to oxygen, wherein the oxygen functions as a linker to attach the moiety to the remainder of the molecule. Unless stated otherwise specifically in the specification, a heterocyclyloxy is optionally substituted.

"Hydroxyalkyl" refers to an alkyl group comprising at least one hydroxyl substituent. The —OH substituent may be on a primary, secondary, or tertiary carbon. Unless stated otherwise specifically in the specification, a hydroxyalkyl group is optionally substituted.

"Sulfonamido" refers to a moiety of the formula —SO$_2$NRR', wherein where R and R' are each independently selected from the group consisting of hydrogen, alkyl, alkenyl, alkynyl, aryl, arylalkyl, cycloalkyl, cycloalkylalkyl, heteroaryl, heteroarylalkyl, heterocyclyl, heterocyclylalkyl, and heteroalkyl. R and R' may optionally be taken together with the nitrogen to which they are attached to form a 4-, 5-, 6-, or 7-membered ring. Unless stated otherwise specifically in the specification, a sulfonamido group is optionally substituted.

"Sulfonamidoalkyl" refers to an alkyl group, as defined herein, wherein at least one hydrogen atom is replaced with a sulfonamido group, as defined herein. Unless stated otherwise specifically in the specification, a sulfonamidoalkyl group is optionally substituted.

"Thioalkyl" refers to a moiety of the formula —SR where R is an alkyl moiety as defined herein containing one to twelve carbon atoms. Unless stated otherwise specifically in the specification, a thioalkyl group is optionally substituted.

"Thiourea" refers to a moiety of the formula —NH—C(S)—NHR where R is selected from hydrogen, alkyl, aryl, arylalkyl, heteroaryl, heteroarylalkyl, cycloalkyl, cycloalkylalkyl, heterocyclyl, and heterocyclylalkyl, each of which may be optionally substituted.

"Thioureaalkyl" refers to an alkyl group, as defined herein, wherein at least one hydrogen atom is replaced with a thiourea group, as defined herein. Unless stated otherwise specifically in the specification, a thioureaalkyl group is optionally substituted.

"Urea" refers to a moiety of the formula —NH—C(O)—NHR where R is selected from hydrogen, alkyl, aryl, arylalkyl, heteroaryl, heteroarylalkyl, cycloalkyl, cycloalkylalkyl, heterocyclyl, and heterocyclylalkyl, each of which may be optionally substituted.

"Ureaalkyl" refers to an alkyl group, as defined herein, wherein at least one hydrogen atom is replaced with a urea group, as defined herein. Unless stated otherwise specifically in the specification, a ureaalkyl group is optionally substituted.

The term "substituted" used herein refers to replacement of at least one hydrogen atom with any of the above groups (e.g., amino, carboxy, hydroxy, imino, acyl, alkyl, alkoxy, alkylamino, alkylaminoalkyl, amido, aminoalkyl, aminocarbonyl, aryl, arylalkyl, arylalkylamino, arylalkyloxy, arylamino, aryloxy, carboxyalkyl, cyano, cyanoalkyl, cycloalkyl, cycloalkyl, cycloalkylamino, cycloalkylalkyloxy, cycloalkylamino, cycloalkyloxy, halo, haloalkyl, heteroatom, heteroalkyl, heteroaryl, heteroarylalkyl, heteroarylalkylamino, heteroarylalkyloxy, heteroarylamino, heteroaryloxy, heterobicycloalkyl, heterocyclyl, heterocyclylalkyl, heterocyclylalkylamino, heterocyclylalkyloxy, heterocyclylamino, heterocyclyloxy, hydroxyalkyl, thioalkyl, alkylene, alkylenecarbonyl, alkenylene, alkenylenecarbonyl, arylene, heteroalkylene, heteroalkylenecarbonyl, heteroarylene, heteroarylenecarbonyl, heterocyclylalkylene, and/or heterocyclylalkylenecarbonyl), wherein the at least one hydrogen atom is replaced by a bond to a non-hydrogen atom such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups such as alkyl sulfone groups, sulfonyl groups such as sulfonamide groups and sulfonylalkyl groups such as sulfonylmethane, and sulfoxide groups such as alkyl sulfoxide groups; a nitrogen atom in groups such as amino, amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; a phosphorus atom in groups such as dialkylphosphine oxide groups; and other heteroatoms in various other groups. "Substituted" also means any of the above groups in which one or more hydrogen atoms are replaced by a higher-order bond (e.g., a double- or triple-bond) to a carbon atom or a heteroatom such as oxygen in oxo, carbonyl, carboxyl, and ester groups; and nitrogen in groups such as imines, oximes, hydrazones, and nitriles. "Substituted" includes any of the above groups in which one or more hydrogen atoms are replaced with —NR$_g$R$_h$, —NR$_g$C(=O)R$_h$, —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, —SO$_2$NR$_g$R$_h$, —C(=O)R$_g$, —C(=O)OR$_g$, —C(=O)NR$_g$R$_h$, —CH$_2$SO$_2$R$_g$, or —CH$_2$SO$_2$NR$_g$R$_h$, where R$_g$ and R$_h$ are independently hydrogen, alkyl, alkoxy, alkylamino, thioalkyl, aryl, arylalkyl, cycloalkyl, cycloalkylalkyl, haloalkyl, heteroalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, carbonyl, carboxy, cyano, hydroxyl, imino, nitro, oxo, thioxo, acyl, alkyl, alkoxy, alkylamino, alkylaminoalkyl, amide, aminoalkyl, aminocarbonyl, aryl, arylalkyl, arylalkylamino, arylalkyloxy, arylamino, aryloxy, bicycloalkyl, carboxyalkyl, cyanoalkyl, cycloalkyl, cycloalkylalkyl, cycloalkylamino, cycloalkyloxy, cycloalkylamino, cycloalkyloxy, halo, haloalkyl, heteroatom, heteroalkyl, heteroaryl, heteroarylalkyl, heteroarylalkylamino, heteroarylalkyloxy, heteroarylamino, heteroaryloxy, heterobicycloalkyl, heterocyclyl, heterocyclylalkyl, heterocyclylalkylamino, heterocyclylalkyloxy, heterocyclylamino, heterocyclyloxy, hydroxyalkyl, N-heteroaryl, N-heterocyclyl, thioalkyl, alkylene, alkylenecarbonyl, alkenylene, alkenylenecarbonyl, arylene, heteroalkylene, heteroalkylenecarbonyl, heteroarylene, heteroarylenecarbonyl, heterocyclylalkylene, heterocyclylalkylenecarbonyl, methylidene, trimethylsilanyl, dialkylphosphine oxide, —OR, —SR, —OC(O)—R, —N(R)$_2$, —C(O)R, —C(O)OR, —C(O)N(R)$_2$, —N(R)C(O)OR, —N(R)C(O)R, —N(R)S(O)$_t$R (where t is 1 or 2), —S(O)$_t$OR (where t is 1 or 2), —S(O)$_t$N(R)$_2$ (where t is 1 or 2), —PO(R)$_2$, or —PO(OR)$_2$ group, where each R is independently hydrogen, alkyl, haloalkyl, cycloalkyl, cycloalkylalkyl, aryl, arylalkyl, heterocyclyl, heterocyclylalkyl, heteroaryl or heteroarylalkyl group. In addition, each of the foregoing substituents is optionally substituted with one or more of the above substituents.

The term "optionally substituted," as used herein, means that the referenced group (e.g., alkyl, cycloalkyl, etc.) may or may not be substituted with one or more substituents.

DETAILED DESCRIPTION

Provided herein are small molecules that bind to GAS41 and inhibit GAS41 activity, and methods of use thereof for the treatment of cancer.

Proteins recognizing post-transcriptional modifications in histone proteins play a key role in transcriptional regulation (Allis 2016). The YEATS domain containing proteins belong to a family of epigenetic reader proteins and include four human paralogs: ENL, YEATS2, AF9 and GAS41. Biochemical studies have revealed that YEATS domains bind to chromatin by recognizing histones with acetylated or crotonylated lysine side chains.

Previous studies reported molecular details of GAS41 YEATS-mediated histone acetyl- or crotonyl-lysine recognition events (Cho et al. *ACS Chem. Biol.* 13, 2739-2746 (2018)). GAS41 YEATS demonstrates site-specific recognition of acetylated- and crotonylated-histone H3 peptides, albeit with modest mid μM affinities (id.). Structural analysis revealed that acylated lysine binds in a channel on GAS41 YEATS domain that may constitute a site for targeting with small molecule inhibitors. Compounds disclosed herein are shown to be low and sub-μM GAS41 YEATS domain inhibitors. GAS41 is dimeric in cells and can recognize di-acylated histone peptides with enhanced affinity via bivalent binding mode. Accordingly, some of the compounds disclosed herein are dimeric GAS41 inhibitors that exhibit enhanced potency and demonstrate activity in non-small cell lung cancer (NSCLC) cells.

In some embodiments, the compounds described herein find use in the treatment or prevention of cancer (e.g., brain cancer, sarcoma, colorectal cancer, lung cancer, or gastric cancer) and/or the alleviation of symptoms associated therewith. In some embodiments, provided herein are pharmaceutical compositions comprising a compound described and/or within the scope herein. In some embodiments, pharmaceutical compositions comprising a compound described and/or within the scope herein are administered to a subject to treat cancer (e.g., brain cancer, sarcoma, colorectal cancer, lung cancer, or gastric cancer).

Provided herein are compounds of formula (I):

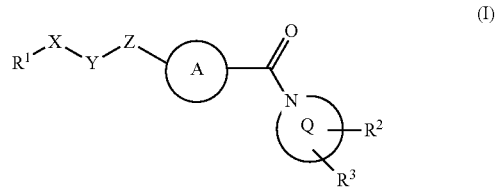

or a pharmaceutically acceptable salt thereof, wherein:
R$^1$ is selected from heterocyclyl, heterocyclylalkyl, heteroaryl, heteroarylalkyl, aryl, arylalkyl, cycloalkyl, cycloalkylalkyl, alkyl, alkenyl, alkynyl, hydroxy, alkoxy, thioalkyl, halogen, haloalkyl, carboxy, acyl, amido, cyano, sulfonyl, and hydrogen;
X is —C(O)—, —C(S)—, —CH$_2$—, or —SO$_2$—, or is absent;
Y is —NR$^a$— or —O—;
R$^a$ is selected from hydrogen, alkyl, haloalkyl, heteroalkyl, cycloalkyl, hydroxyalkyl, and aminoalkyl, or R$^a$ is taken together with the nitrogen atom to which it is attached to form a fused ring with A, or R$^a$ and R$^1$ together with the atoms to which they are attached together form an optionally substituted heterocyclic ring;
Z is absent or is —CR$^b$R$^c$—;
R$^b$ and R$^c$ are each independently selected from hydrogen and alkyl;
A is a five-membered heteroaryl;
Q is a four-, five-, or six-membered heterocyclyl;
R$^2$ is selected from hydrogen, halo, alkyl, amino, and hydroxy;
R$^3$ is selected from hydrogen, halo, —OR$^d$, —NR$^e$R$^f$, aryl, arylalkyl, heteroaryl, heteroarylalkyl, heterocyclyl, heterocyclylalkyl, and a group of formula:

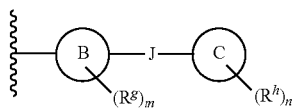

wherein B is aryl or heteroaryl; J is absent or is —CH$_2$—, —O—, —S—, or —NH—; C is selected from aryl, heteroaryl, and heterocyclyl; m is 0, 1, 2, 3, or 4; n is 0, 1, 2, 3, 4, or 5; and R$^g$ and R$^h$ are each independently selected from alkyl, alkenyl, alkynyl, halo, haloalkyl, amino, alkylamino, dialkylamino, aminoalkyl, alkylaminoalkyl, dialkylaminoalkyl, amido, amidoalkyl, sulfonamido, sulfonamidoalkyl, urea, ureaalkyl, thiourea, thioureaalkyl, hydroxy, hydroxyalkyl, alkoxy, alkoxyalkyl, haloalkoxy, thioalkyl, acyl, carboxy, nitro, oxo, aryl, arylalkyl, heteroaryl, heteroarylalkyl, heterocyclyl, heterocyclylalkyl, cycloalkyl, and cycloalkylalkyl;

or R$^2$ and R$^3$ are taken together with the carbon atom(s) to which they are attached to form a ring selected from aryl, heteroaryl, cycloalkyl, and heterocycle; or R$^2$ and R$^3$ are taken together with the carbon atom to which they are attached to form an alkenyl group; and R$^d$, R$^e$, and R$^f$ are each independently selected from hydrogen, alkyl, haloalkyl, hydroxyalkyl, aminoalkyl, carboxyalkyl, heteroalkyl, aryl, arylalkyl, heteroaryl, heteroarylalkyl;

wherein each alkyl, alkenyl, alkynyl, aryl, arylalkyl, heteroalkyl, heteroaryl, heteroarylalkyl, cycloalkyl, heterocyclyl, and heterocyclylalkyl is independently optionally substituted with 1, 2, 3, 4, or 5 substituents, with the proviso that when Z is —CR$^b$R$^c$—, R$^1$ is not cycloalkyl.

In some embodiments, provided herein are compounds of formula (I):

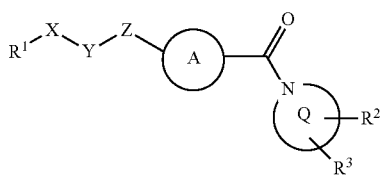

or a pharmaceutically acceptable salt thereof, wherein:
R$^1$ is selected from heterocyclyl, heterocyclylalkyl, heteroaryl, heteroarylalkyl, aryl, arylalkyl, cycloalkyl, cycloalkylalkyl, alkyl, alkenyl, alkynyl, hydroxy, alkoxy, thioalkyl, halogen, haloalkyl, carboxy, acyl, amido, cyano, sulfonyl, and hydrogen;

X is —C(O)—, —C(S)—, —CH$_2$—, or —SO$_2$—, or is absent;
Y is —NR$^a$— or —O—;
R$^a$ is selected from hydrogen, alkyl, haloalkyl, heteroalkyl, cycloalkyl, hydroxyalkyl, and aminoalkyl, or R$^a$ is taken together with the nitrogen atom to which it is attached to form a fused ring with A;
Z is absent or is —CR$^b$R$^c$—;
R$^b$ and R$^c$ are each independently selected from hydrogen and alkyl;
A is a five-membered heteroaryl;
Q is a four-, five-, or six-membered heterocyclyl;
R$^2$ is selected from hydrogen, halo, alkyl, amino, and hydroxy;
R$^3$ is selected from hydrogen, halo, —OR$^d$, —NR$^e$R$^f$, aryl, arylalkyl, heteroaryl, heteroarylalkyl, heterocyclyl, heterocyclylalkyl, and a group of formula:

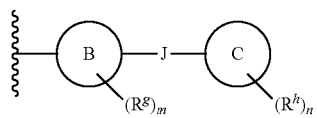

wherein B is aryl or heteroaryl; J is absent or is —CH$_2$—, —O—, —S—, or —NH—; C is selected from aryl, heteroaryl, and heterocyclyl; m is 0, 1, 2, 3, or 4; n is 0, 1, 2, 3, 4, or 5; and R$^g$ and R$^h$ are each independently selected from alkyl, alkenyl, alkynyl, halo, haloalkyl, amino, alkylamino, dialkylamino, aminoalkyl, alkylaminoalkyl, dialkylaminoalkyl, amido, amidoalkyl, sulfonamido, sulfonamidoalkyl, urea, ureaalkyl, thiourea, thioureaalkyl, hydroxy, hydroxyalkyl, alkoxy, alkoxyalkyl, haloalkoxy, thioalkyl, acyl, carboxy, nitro, oxo, aryl, arylalkyl, heteroaryl, heteroarylalkyl, heterocyclyl, heterocyclylalkyl, cycloalkyl, and cycloalkylalkyl;

or R$^2$ and R$^3$ are taken together with the carbon atom(s) to which they are attached to form a ring selected from aryl, heteroaryl, cycloalkyl, and heterocycle; or R$^2$ and R$^3$ are taken together with the carbon atom to which they are attached to form an alkenyl group; and R$^d$, R$^e$, and R$^f$ are each independently selected from hydrogen, alkyl, haloalkyl, hydroxyalkyl, aminoalkyl, carboxyalkyl, heteroalkyl, aryl, arylalkyl, heteroaryl, heteroarylalkyl;

wherein each alkyl, alkenyl, alkynyl, aryl, arylalkyl, heteroalkyl, heteroaryl, heteroarylalkyl, cycloalkyl, heterocyclyl, and heterocyclylalkyl is independently optionally substituted with 1, 2, 3, 4, or 5 substituents, with the proviso that when Z is —CR$^b$R$^c$—, R$^1$ is not cycloalkyl.

In some embodiments, R$^1$ is selected from heterocyclyl, heterocyclylalkyl, heteroaryl, heteroarylalkyl, aryl, arylalkyl, cycloalkyl, cycloalkylalkyl, and alkyl. In some embodiments, R$^1$ is selected from heterocyclyl, heterocyclylalkyl, heteroaryl, heteroarylalkyl, aryl, arylalkyl, cycloalkyl, cycloalkylalkyl, and C$_1$-C$_6$ alkyl. In some embodiments, R$^1$ is selected from heterocyclyl, aryl, arylalkyl, heteroarylalkyl, and C$_1$-C$_6$ alkyl. In some embodiments, R$^1$ is selected from heterocyclyl (e.g., a monocyclic or bicyclic heterocyclyl having 1 or 2 heteroatoms independently selected from N, O, and S), aryl (e.g., phenyl), arylalkyl (e.g., phenethyl), heteroarylalkyl (e.g., wherein the heteroaryl is a monocyclic heteroaryl having 1 or 2 nitrogen atoms), and C$_1$-C$_4$ alkyl (e.g., methyl, ethyl, or n-propyl). In some embodiments, R$^1$ is a monocyclic heterocyclyl having 1 or 2 heteroatoms independently selected from N, O, and S. In some embodiments, $R^1$ is a monocyclic heterocyclyl having 1 or 2 nitrogen atoms. In some embodiments, $R^1$ is pyrrolidinyl. $R^1$ may be unsubstituted or substituted with 1, 2, 3, 4, or 5 substituents. For example, in some embodiments, $R^1$ is unsubstituted or substituted with 1 or 2 substituents independently selected from $C_1$-$C_6$ alkyl, $C_1$-$C_6$ alkoxy, halo, hydroxy, amino, amino-$C_1$-$C_6$-alkyl, aryloxy, alkynyloxy, and methylidene. In some embodiments, $R^1$ is unsubstituted. In some embodiments, $R^1$ is unsubstituted pyrrolidinyl.

In some embodiments, $R^1$ is selected from:

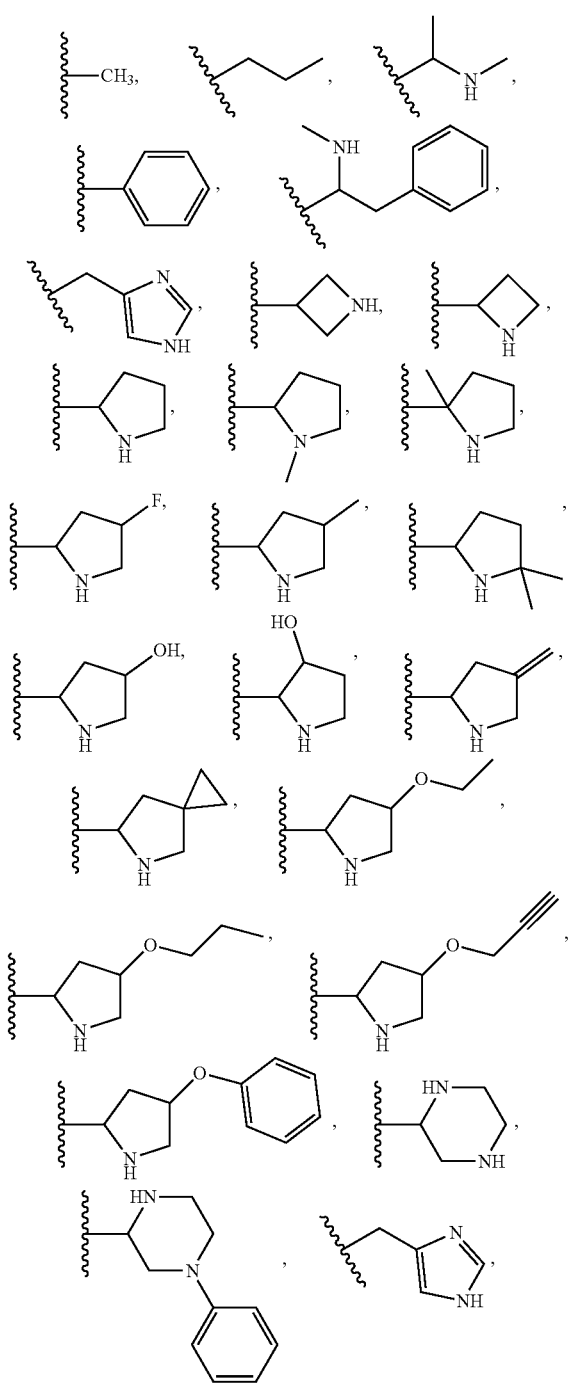

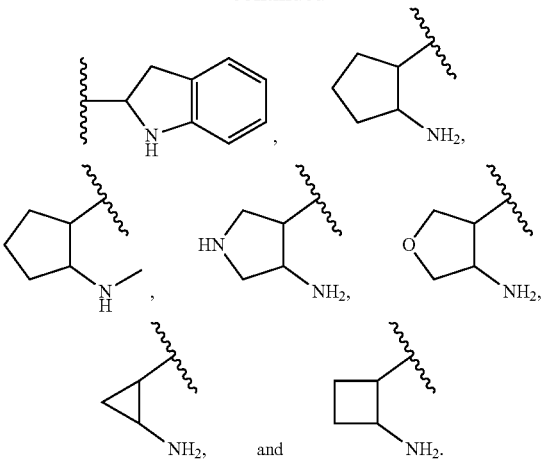

In some embodiments, $R^1$ is:

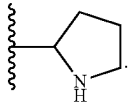

In some embodiments, X is selected from —C(O)—, —CH$_2$—, and —SO$_2$—, or is absent. In some embodiments, X is selected from —C(O)—, —CH$_2$—, and —SO$_2$—. In some embodiments, X is selected from —C(O)— and —CH$_2$—. In some embodiments, X is —C(O)—.

In some embodiments, Y is —NR$^a$—. In some embodiments, Y is —NR$^a$—, and R$^a$ is selected from hydrogen and $C_1$-$C_6$ alkyl. In some embodiments, Y is —NR$^a$—, and R$^a$ is selected from hydrogen, methyl, and ethyl. In some embodiments, Y is —NR$^a$—, and R$^a$ is hydrogen. In some embodiments, Y is O. In some embodiments, Y is —NR$^a$— wherein R$^a$ is taken together with the nitrogen atom to which it is attached to form a fused ring with A (e.g., a five-membered or six-membered ring fused with ring A). In some embodiments, Y is —NRa- wherein R$^a$ is taken together with the nitrogen atom to which it is attached to form a fused ring with $R^1$ (e.g., a bicyclic ring system, such as a 1,7-diazaspiro[4.4]nonane ring system), which ring is optionally substituted (e.g., with an oxo group).

In some embodiments, Z is absent, or is selected from —CH$_2$—, —CH(CH$_3$)—, and —C(CH$_3$)$_2$—. In some embodiments, Z is absent or is —CH$_2$—. In some embodiments, Z is absent.

In some embodiments, A is a five-membered heteroaryl having 1, 2, or 3 heteroatoms independently selected from N, O, and S. In some embodiments, A is a five-membered heteroaryl having 1 or 2 heteroatoms independently selected from N, O, and S. In some embodiments, A is a five-membered heteroaryl having 1 or 2 heteroatoms independently selected from N and S. In some embodiments, A is selected from thiophene and thiazole. In some embodiments, A is thiophene. In some embodiments, A has formula:

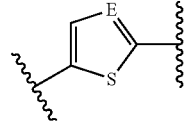

wherein E is selected from N and CH. In some embodiments, E is CH. In some embodiments, E is N. In some embodiments, A has formula:

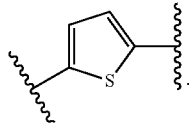 [SMILES: *c1ccc(*)s1]

In some embodiments, Q is a four-, five-, or six-membered heterocyclyl having one nitrogen atom (i.e. the nitrogen atom indicated in formula (I)), wherein the heterocyclyl is optionally substituted. In some embodiments, Q is selected from azetidinyl, pyrrolidinyl, and piperidinyl. In some embodiments, Q is selected from azetidinyl and pyrrolidinyl. In some embodiments, Q is azetidinyl. In some embodiments, Q is pyrrolidinyl.

In some embodiments, $R^2$ is selected from hydrogen, halo, amino, and hydroxy. In some embodiments, $R^2$ is selected from hydrogen, halo, and hydroxy. In some embodiments, $R^2$ is hydrogen.

In some embodiments, $R^3$ is selected from hydrogen, —$OR^d$, —$NR^eR^f$, aryl, arylalkyl, heteroaryl, heteroarylalkyl, heterocyclyl, heterocyclylalkyl, and a group of formula:

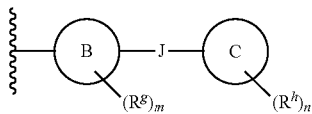

wherein $R^d$ is selected from $C_1$-$C_6$ alkyl, $C_1$-$C_6$ haloalkyl, phenyl, benzyl, and heteroaryl; $R^e$ is hydrogen; and $R^f$ is selected from hydrogen, $C_1$-$C_6$ alkyl, and heteroaryl; B is a monocyclic heteroaryl; J is absent; C is selected from aryl, heteroaryl, and heterocyclyl; m is 0 or 1; n is 0, 1, 2, or 3; and $R^g$ and $R^h$ are each independently selected from alkyl, alkenyl, alkynyl, halo, haloalkyl, amino, alkylamino, dialkylamino, aminoalkyl, alkylaminoalkyl, dialkylaminoalkyl, amido, amidoalkyl, sulfonamido, sulfonamidoalkyl, urea, ureaalkyl, thiourea, thioureaalkyl, hydroxy, hydroxyalkyl, alkoxy, alkoxyalkyl, haloalkoxy, thioalkyl, acyl, carboxy, nitro, oxo, aryl, arylalkyl, heteroaryl, heteroarylalkyl, heterocyclyl, heterocyclylalkyl, cycloalkyl, and cycloalkylalkyl.

In some embodiments, $R^3$ is selected from hydrogen, —$OR^d$, —$NR^eR^f$, phenyl, benzyl, heteroaryl, heteroarylalkyl, and heterocyclyl; wherein $R^d$ is selected from $C_1$-$C_6$ alkyl, $C_1$-$C_6$ haloalkyl, phenyl, benzyl, and heteroaryl; $R^e$ is hydrogen; and $R^f$ is selected from hydrogen, $C_1$-$C_6$ alkyl, and heteroaryl.

In some embodiments, $R^3$ is selected from hydrogen, —$OR^d$, —$NR^eR^f$, phenyl, benzyl, heteroaryl, heteroarylalkyl, and heterocyclyl; wherein $R^d$ is selected from $C_1$-$C_6$ alkyl, $C_1$-$C_6$ haloalkyl, phenyl, benzyl, and heteroaryl; $R^e$ is hydrogen; and $R^f$ is selected from hydrogen, $C_1$-$C_6$ alkyl, and heteroaryl; wherein each heteroaryl is independently a monocyclic or bicyclic heteroaryl having 1 or 2 heteroatoms independently selected from N, S, and O, and wherein each heterocyclyl is independently a monocyclic or bicyclic heterocyclyl having 1 or 2 heteroatoms independently selected from N, S, and O.

In some embodiments, $R^3$ is a group of formula:

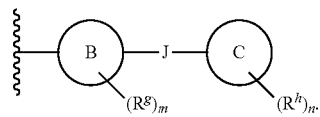

In some embodiments, $R^3$ is a group of formula:

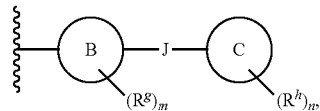

wherein B is a 5-membered monocyclic heteroaryl having 1 or 2 heteroatoms independently selected from N and S; J is absent; C is selected from aryl, heteroaryl, and heterocyclyl; m is 0 or 1; n is 0, 1, 2, or 3; $R^g$ is $C_1$-$C_6$ alkyl; and each $R^h$ is independently selected from alkyl, alkenyl, alkynyl, halo, haloalkyl, amino, alkylamino, dialkylamino, aminoalkyl, alkylaminoalkyl, dialkylaminoalkyl, amido, amidoalkyl, sulfonamido, sulfonamidoalkyl, urea, ureaalkyl, thiourea, thioureaalkyl, hydroxy, hydroxyalkyl, alkoxy, alkoxyalkyl, haloalkoxy, thioalkyl, acyl, carboxy, nitro, oxo, aryl, arylalkyl, heteroaryl, heteroarylalkyl, heterocyclyl, heterocyclylalkyl, cycloalkyl, and cycloalkylalkyl. In some embodiments, B is thiazole or thiophene. In some embodiments, m is 0. In some embodiments, J is absent. In some embodiments, C is selected from phenyl and a monocyclic heteroaryl having 1 or 2 nitrogen atoms. In some embodiments, C is selected from phenyl and pyridyl.

In some embodiments, at least one $R^h$ is amido or amidoalkyl having formula —$(CH_2)_rC(O)NR^iR^j$ or —$(CH_2)_s$ $NR^kC(O)R^m$, wherein:
  r and s are each independently selected from 0, 1, and 2;
  $R^i$ and $R^k$ are each independently selected from hydrogen and $C_1$-$C_6$ alkyl;
  $R^j$ is selected from $C_1$-$C_6$-alkyl, aryl, aryl-$C_1$-$C_6$-alkyl, heteroaryl, heteroaryl-$C_1$-$C_6$-alkyl, heterocyclyl, heterocyclyl-$C_1$-$C_6$-alkyl, cycloalkyl, and cycloalkyl-$C_1$-$C_6$-alkyl;
  $R^m$ is selected from $C_1$-$C_6$-alkyl, aryl, aryl-$C_1$-$C_6$-alkyl, heteroaryl, heteroaryl-$C_1$-$C_6$-alkyl, heterocyclyl, heterocyclyl-$C_1$-$C_6$-alkyl, cycloalkyl, and cycloalkyl-$C_1$-$C_6$-alkyl, amino, $C_1$-$C_6$-alkylamino, arylamino, and aryl-$C_1$-$C_6$-alkylamino;
  wherein each alkyl, aryl, heteroaryl, heterocyclyl, and cycloalkyl is independently unsubstituted or substituted with 1 or 2 substituents independently selected from halo, $C_1$-$C_6$-alkyl, $C_1$-$C_6$-alkoxy, hydroxy, amino and oxo.

In some embodiments, $R^2$ and $R^3$, together with the carbon atom(s) to which they are attached, form a ring selected from aryl, heteroaryl, cycloalkyl, and heterocycle, any of which can be optionally substituted (e.g., with 1, 2, or 3 substituents independently selected from alkyl, halo, amino, alkylamino, dialkylamino, alkoxy, aryl, arylalkyl, heteroaryl, heteroarylalkyl, heterocyclyl, heterocyclylalkyl, aminoalkyl, and amidoalkyl).

In some embodiments, $R^2$ and $R^3$ are substituted on adjacent carbon atoms of ring Q, and are taken together with the carbon atoms to which they are attached to form a phenyl ring that is fused to ring Q, wherein the phenyl ring is optionally substituted. In some embodiments, the phenyl ring is unsubstituted.

In some embodiments, R² and R³ are substituted on the same carbon atom of ring Q, and are taken together with the carbon atom to which they are attached to form a spiro ring, which is optionally substituted. In some embodiments, R² and R³ are substituted on the same carbon atom of ring Q, and are taken together with the carbon atom to which they are attached to form a 4-membered spiro ring selected from cyclobutyl and azetidinyl, each of which is optionally substituted with one substituent selected from —OR' and heteroaryl, wherein R' is selected from C₁-C₆ alkyl, aryl and heteroaryl. In some embodiments, the spiro ring is substituted with one substituent selected from —OR', wherein R' is selected from methyl, phenyl, and a monocyclic 5- or 6-membered heteroaryl having 1 or 2 heteroatoms independently selected from N and S (e.g., pyridyl). In some embodiments, the spiro ring is substituted with a monocyclic 5- or 6-membered heteroaryl having 1 or 2 heteroatoms independently selected from N and S (e.g., pyridyl or thiazolyl).

In some embodiments, R² and R³ are substituted on the same carbon atom of ring Q, and are taken together with the carbon atom to which they are attached to form an alkenyl group (e.g., a methylidene group or a substituted version thereof).

In some embodiments, the group

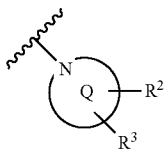

has a formula selected from:

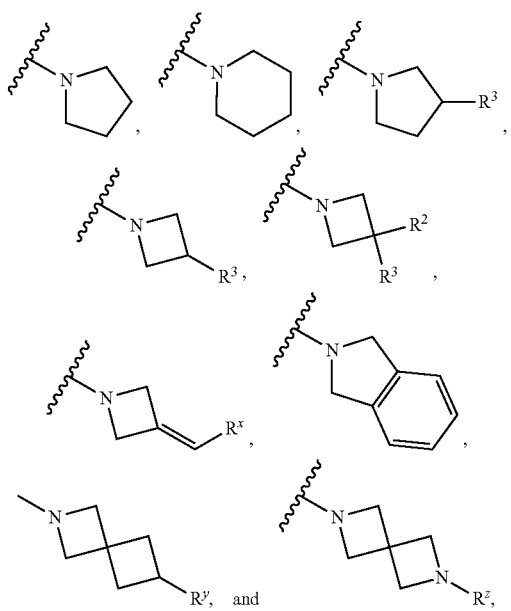

wherein R$^x$, R$^y$, and R$^z$ are substituents that are each independently selected from —OR$^v$, aryl, and heteroaryl, wherein R$^v$ is selected from C₁-C₆ alkyl, aryl and heteroaryl. In some embodiments, R$^x$, R$^y$, and R$^z$ are independently selected from —OR$^v$, phenyl, and a monocyclic 5- or 6-membered heteroaryl having 1 or 2 heteroatoms independently selected from N and S (e.g., pyridyl or thiazolyl), wherein R$^v$ is selected from C₁-C₆ alkyl (e.g., methyl), aryl (e.g., phenyl), and a monocyclic 5- or 6-membered heteroaryl having 1 or 2 heteroatoms independently selected from N and S (e.g., pyridyl or thiazolyl). In some embodiments, R$^x$ is aryl (e.g., phenyl). In some embodiments, R$^y$ is selected from —OR$^v$ and a monocyclic 5- or 6-membered heteroaryl having 1 or 2 heteroatoms independently selected from N and S (e.g., pyridyl or thiazolyl), wherein R$^v$ is selected from C₁-C₆ alkyl (e.g., methyl), aryl (e.g., phenyl), and a monocyclic 5- or 6-membered heteroaryl having 1 or 2 heteroatoms independently selected from N and S (e.g., pyridyl or thiazolyl). In some embodiments, R$^z$ is a monocyclic 5- or 6-membered heteroaryl having 1 or 2 heteroatoms independently selected from N and S, such as a monocyclic 6-membered heteroaryl (e.g., pyridyl).

In some embodiments, the group

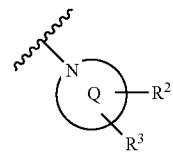

has the formula:

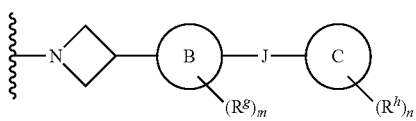

wherein B, J, C, R$^g$, R$^h$, m, and n are as defined herein. In some embodiments, the group

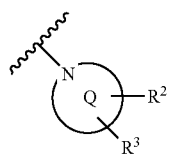

has the formula:

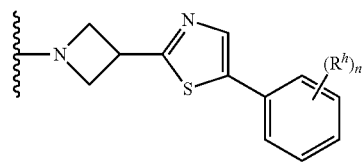

wherein R$^h$ and n are as defined herein. For example, in some embodiments, n is 0, 1, 2 or 3; and each R$^h$ is independently selected from C₁-C₆ alkyl, halo, halo-C₁-C₆-alkyl, amino, amino-C₁-C₆-alkyl, hydroxy, hydroxy-C₁-C₆-alkyl, C₁-C₆ alkoxy, amido, amido-C₁-C₆-alkyl, acyl, aryl, aryl-C₁-C₆-alkyl, heteroaryl, heteroaryl-C₁-C₆-alkyl, heterocyclyl, heterocyclyl-C₁-C₆-alkyl, cycloalkyl, and cycloalkyl-$C_1$-$C_6$-alkyl. In some embodiments, at least one $R^h$ has formula —$(CH_2)_rC(O)NR^iR^j$ or —$(CH_2)_sNR^kC(O)R^m$, wherein:

r and s are each independently selected from 0, 1, and 2;

$R^i$ and $R^k$ are each independently selected from hydrogen and $C_1$-$C_6$ alkyl;

$R^j$ is selected from $C_1$-$C_6$-alkyl, aryl, aryl-$C_1$-$C_6$-alkyl, heteroaryl, heteroaryl-$C_1$-$C_6$-alkyl, heterocyclyl, heterocyclyl-$C_1$-$C_6$-alkyl, cycloalkyl, and cycloalkyl-$C_1$-$C_6$-alkyl;

$R^m$ is selected from $C_1$-$C_6$-alkyl, aryl, aryl-$C_1$-$C_6$-alkyl, heteroaryl, heteroaryl-$C_1$-$C_6$-alkyl, heterocyclyl, heterocyclyl-$C_1$-$C_6$-alkyl, cycloalkyl, and cycloalkyl-$C_1$-$C_6$-alkyl, amino, $C_1$-$C_6$-alkylamino, arylamino, aryl-$C_1$-$C_6$-alkylamino;

wherein each alkyl, aryl, heteroaryl, heterocyclyl, and cycloalkyl is independently unsubstituted or substituted with 1 or 2 substituents independently selected from halo, $C_1$-$C_6$-alkyl, $C_1$-$C_6$-alkoxy, hydroxy, amino and oxo.

In some embodiments, the group

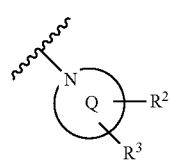

is selected from:

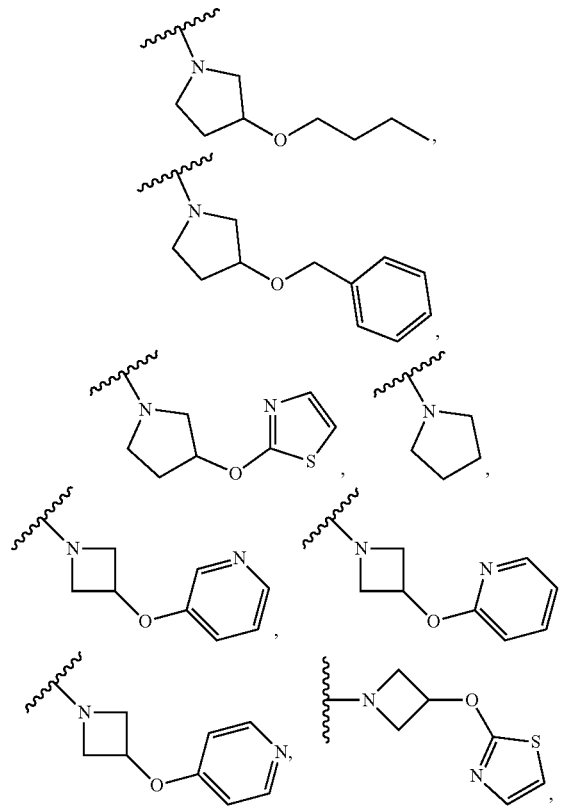

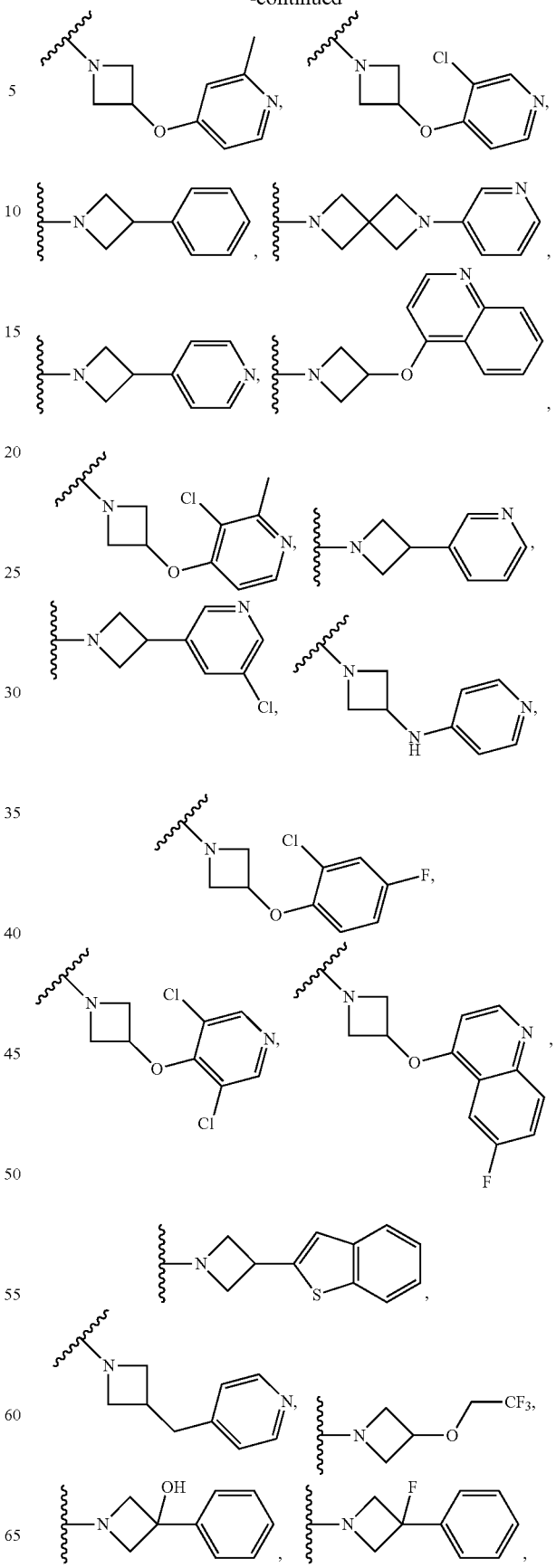

-continued
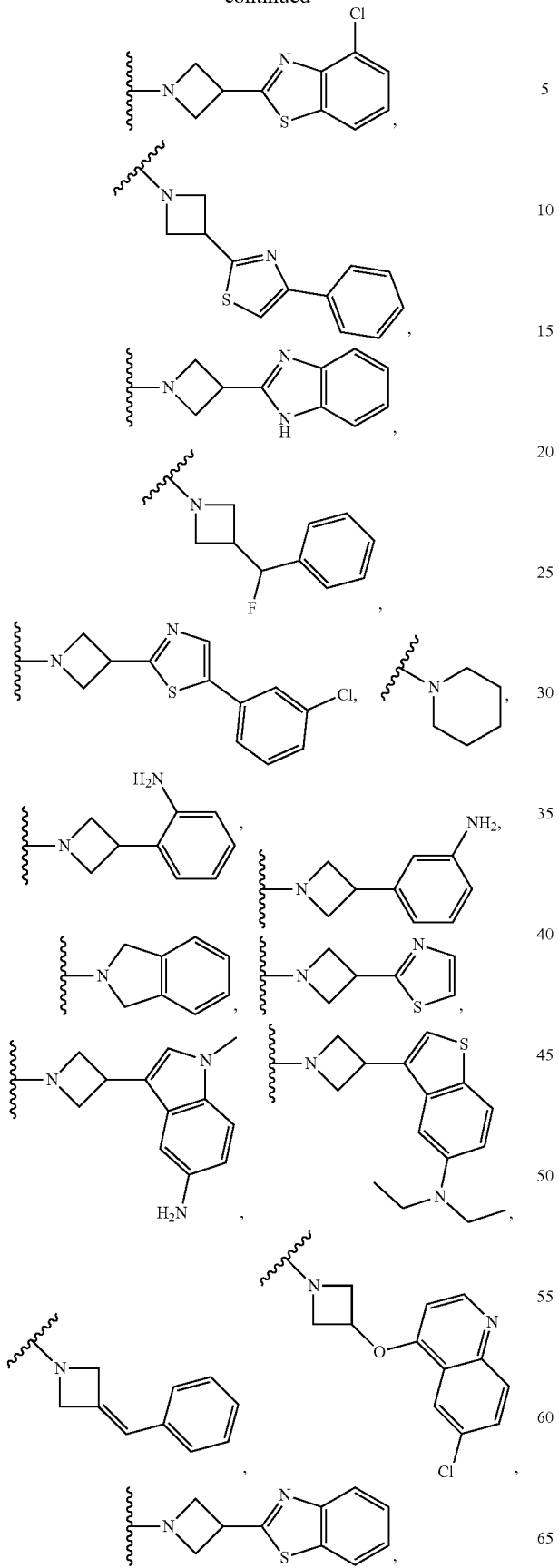
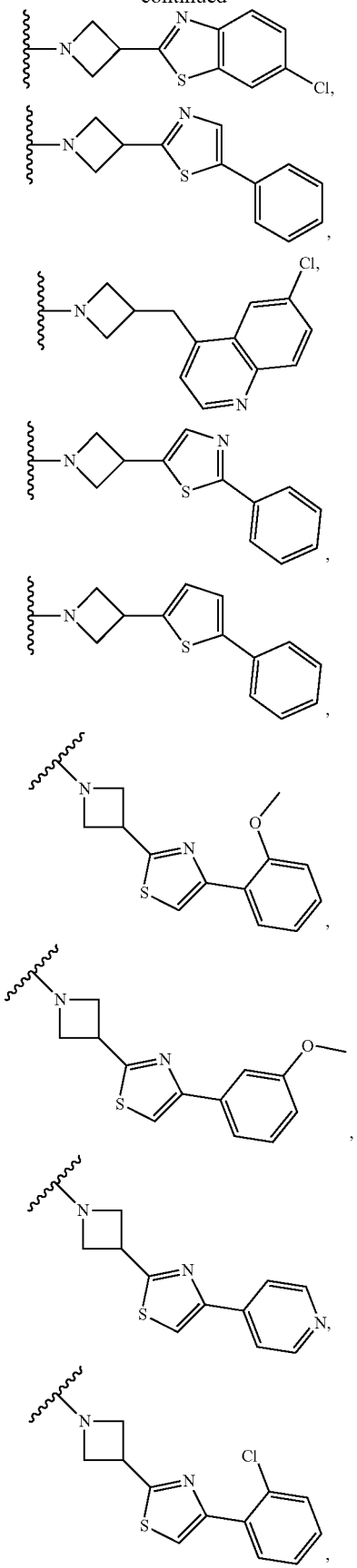

-continued
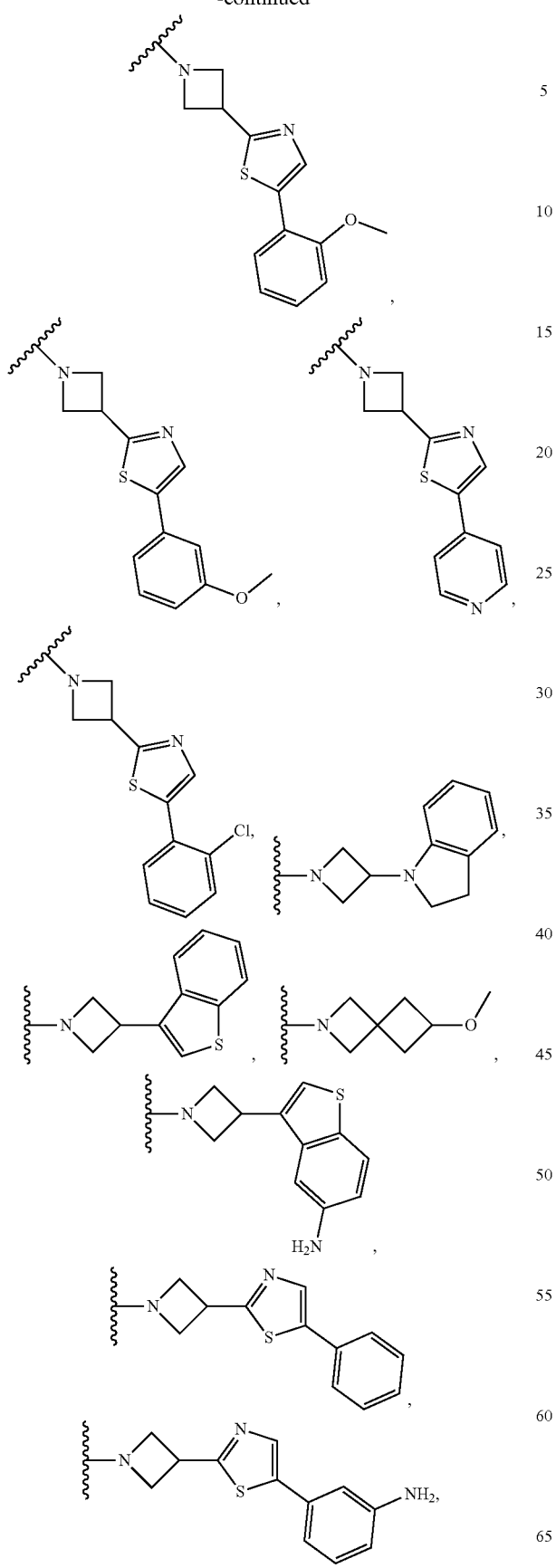
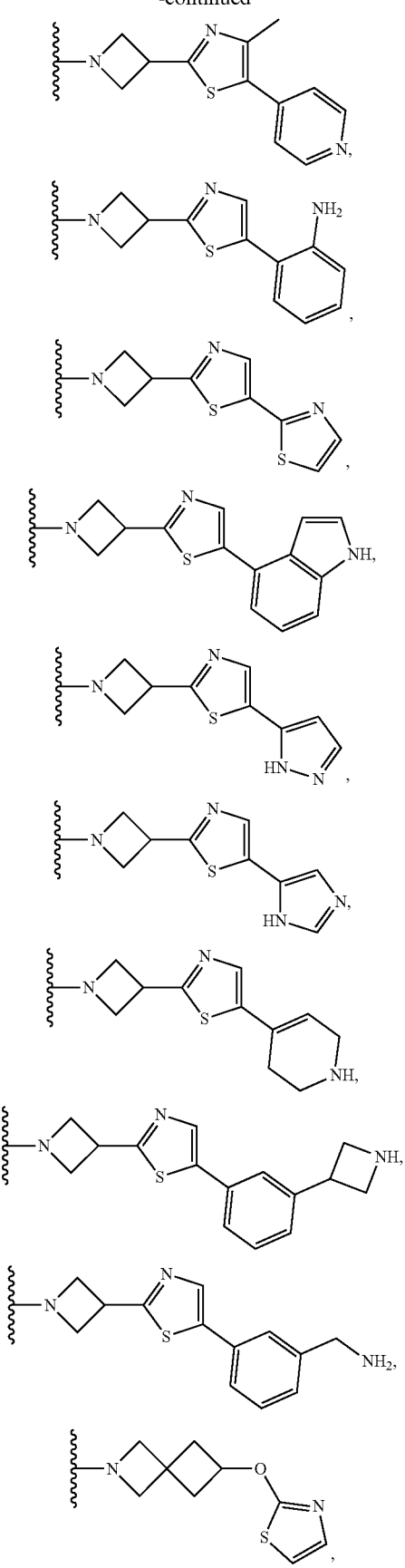

-continued
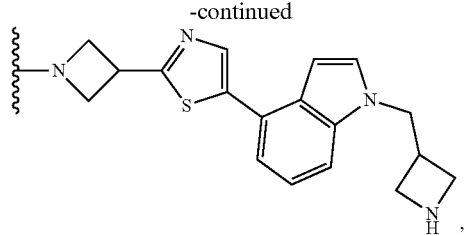,
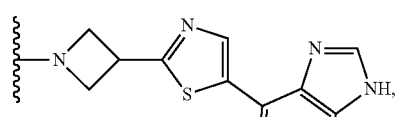,
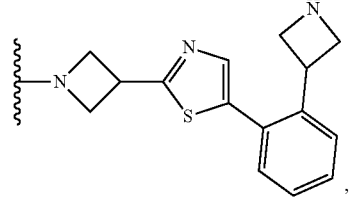,
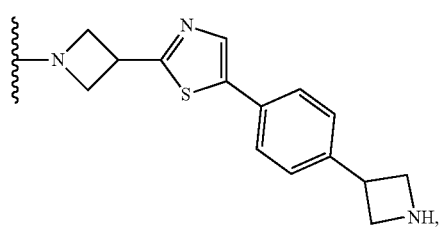,
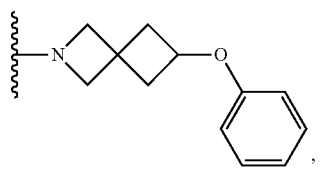,
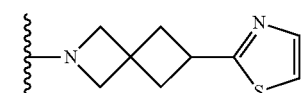,
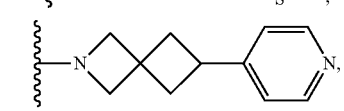,
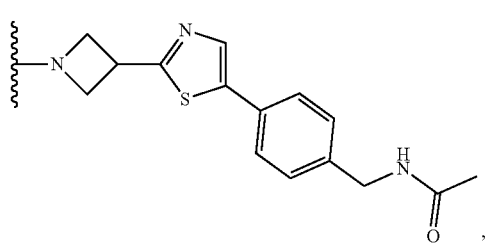,
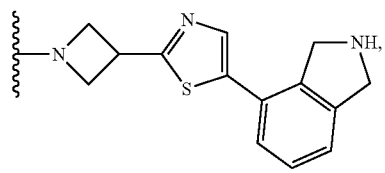
-continued
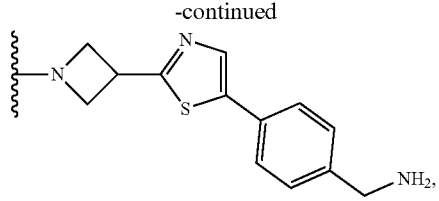,
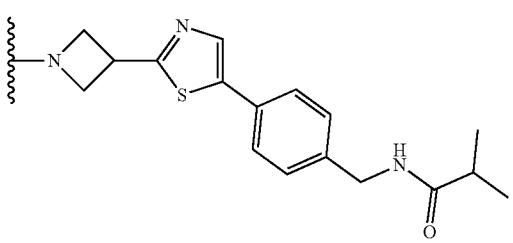,
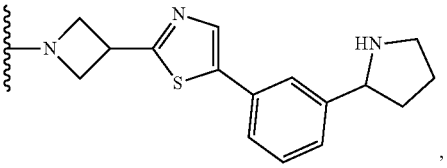,
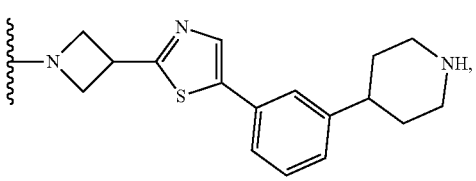,
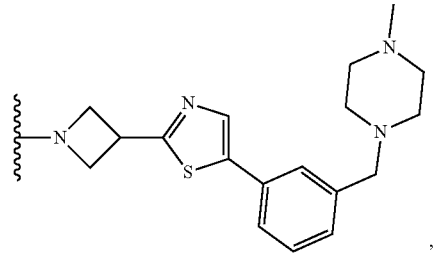,
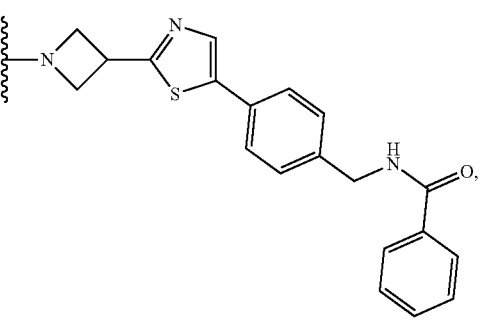,
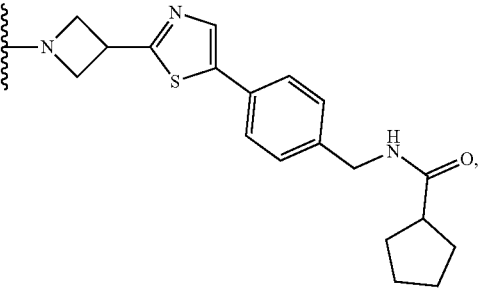,

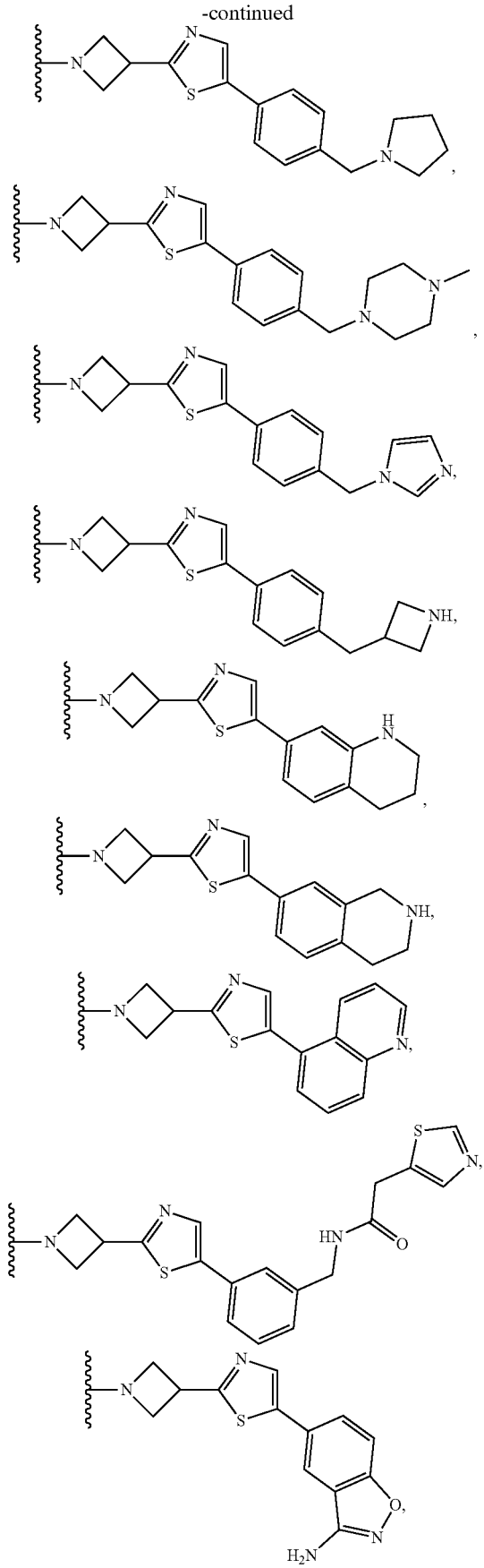
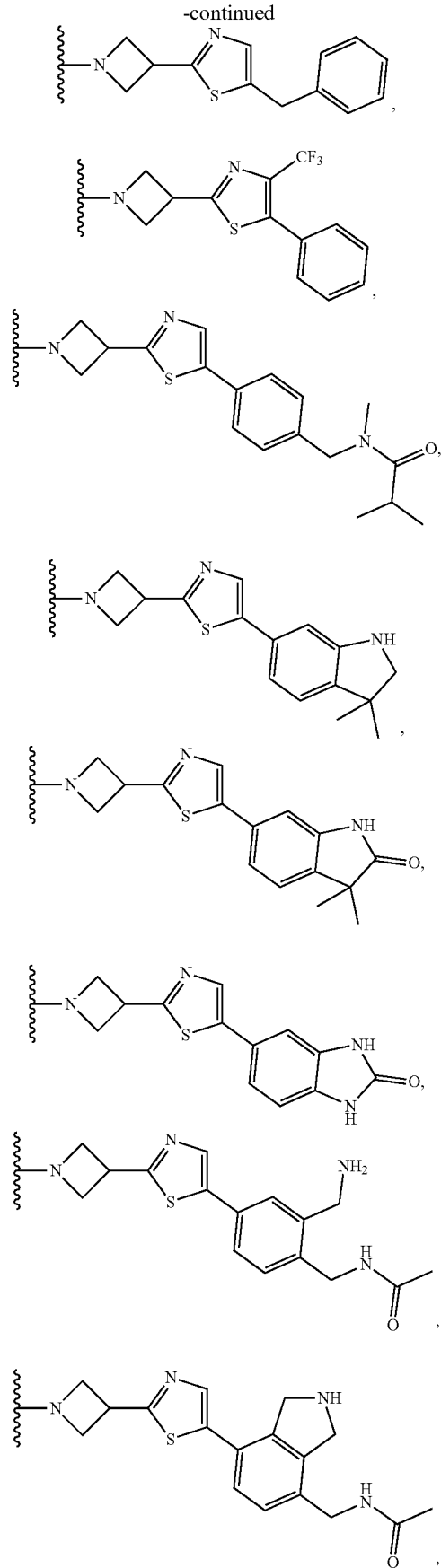

49
-continued
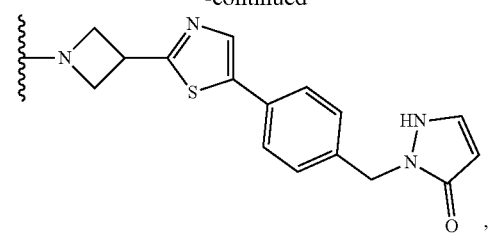
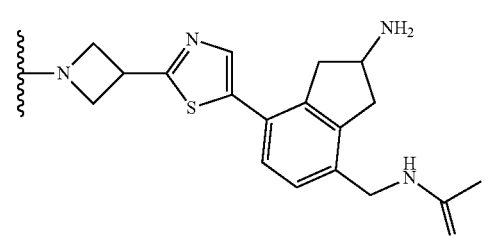
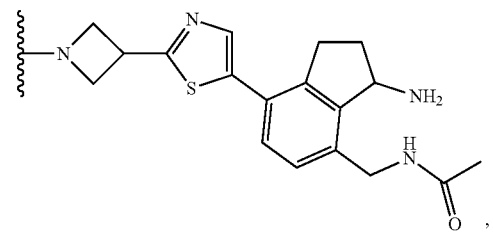
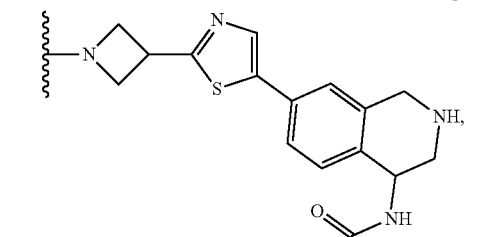
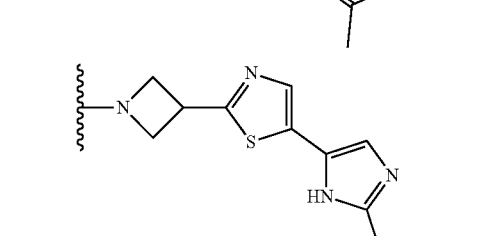
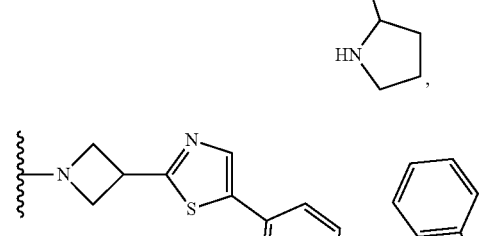
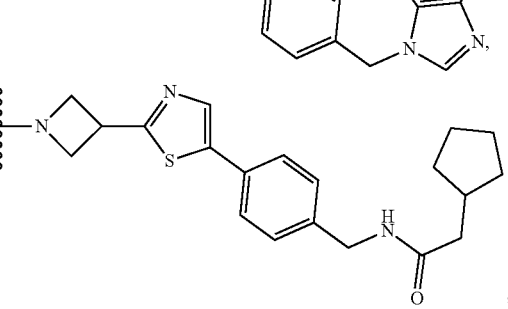
50
-continued
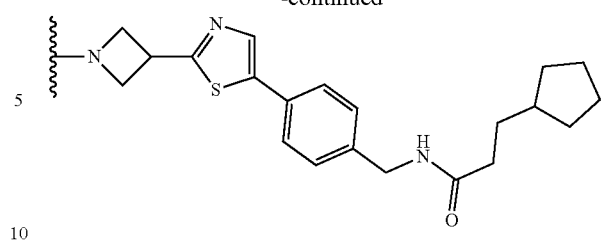
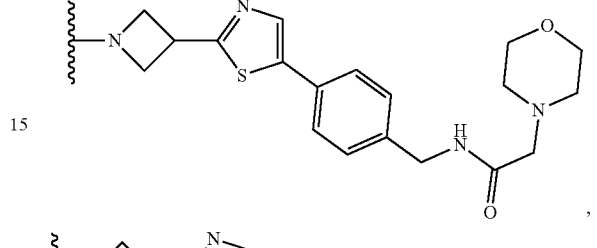
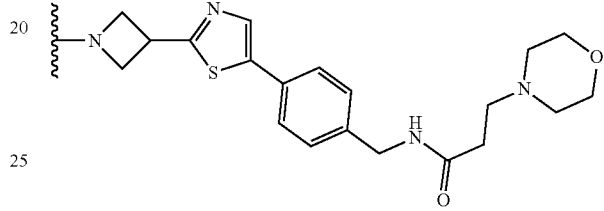
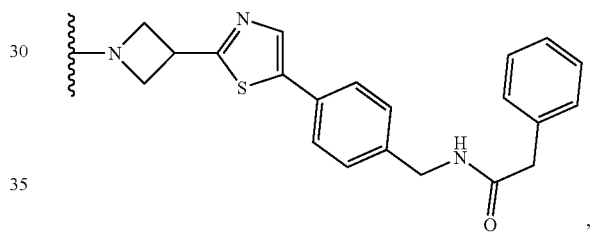
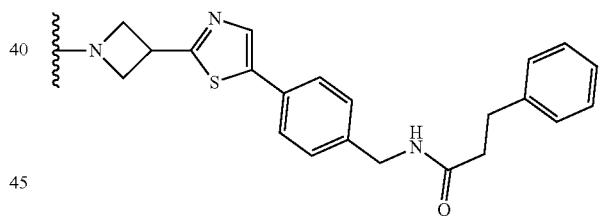
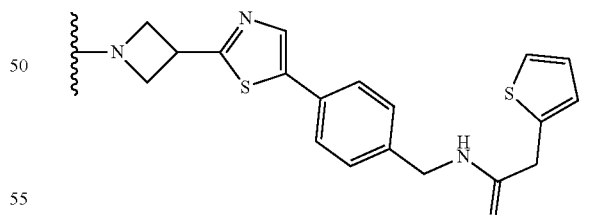
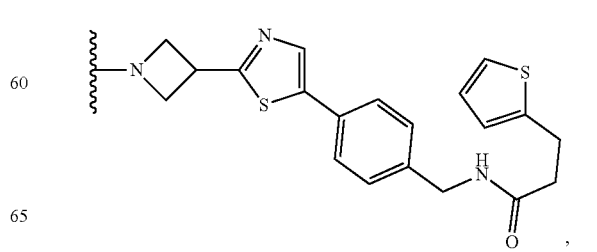

51
-continued
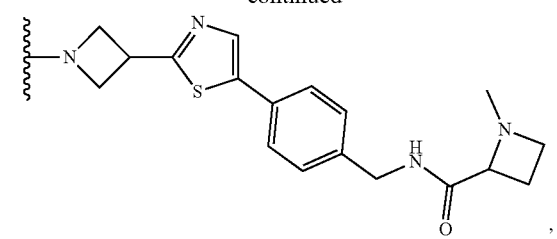
,
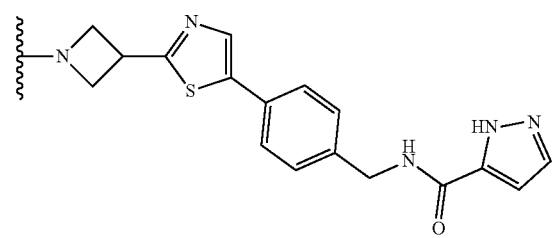
,
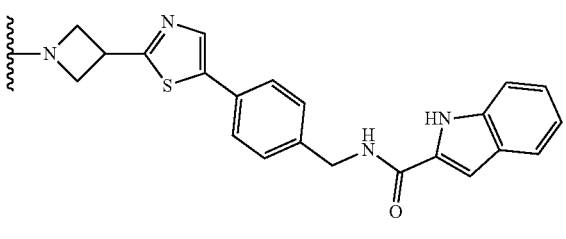
,
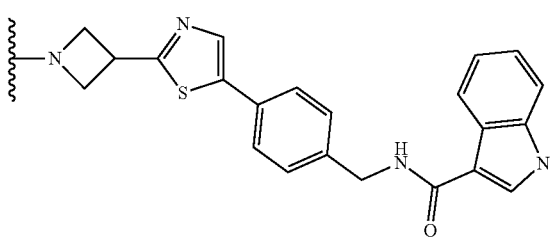
,
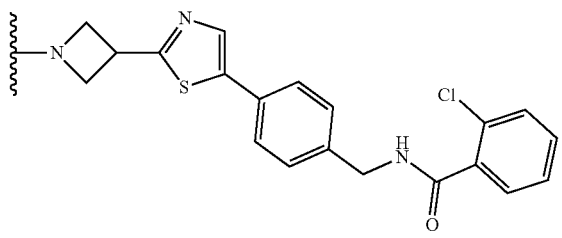
,
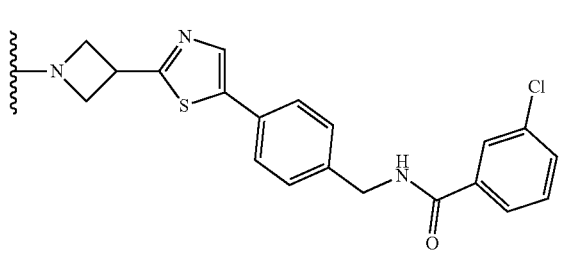
,
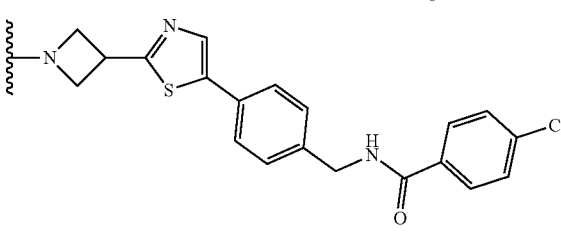
,
52
-continued
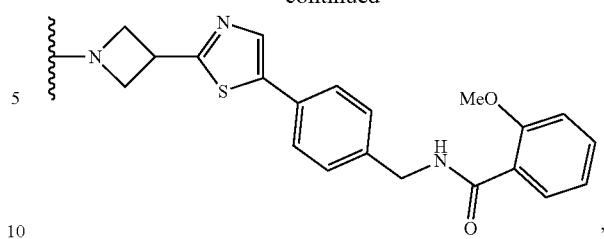
,
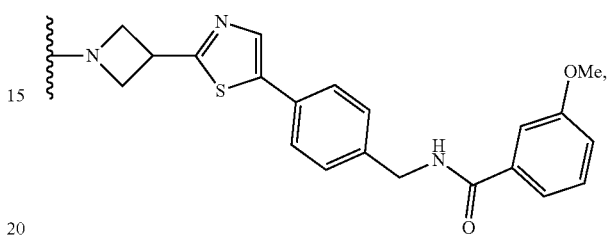
,
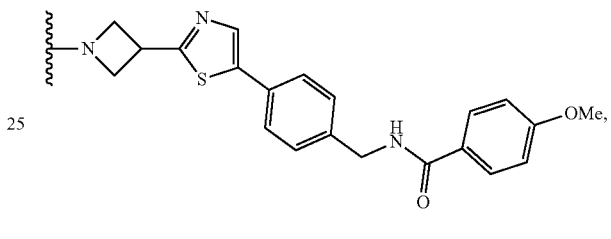
,
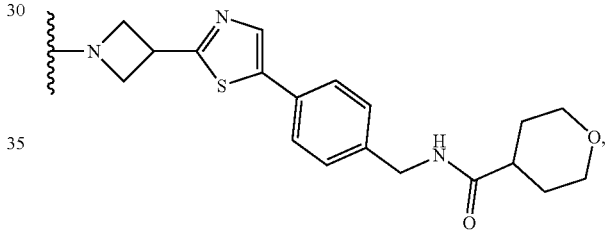
,
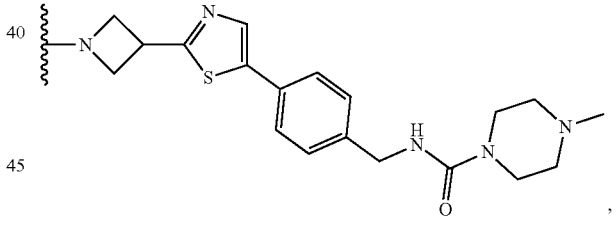
,
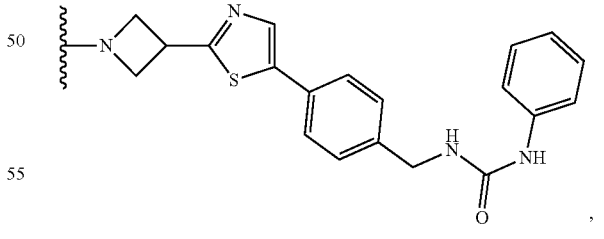
,
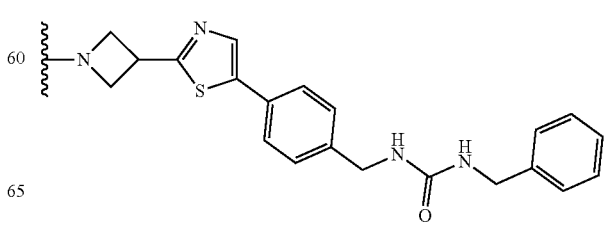
,

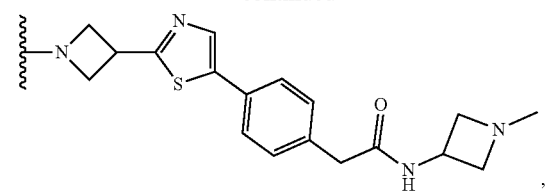,
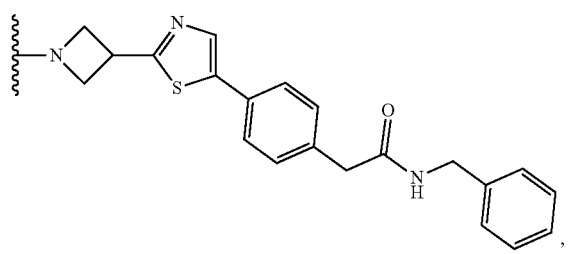,
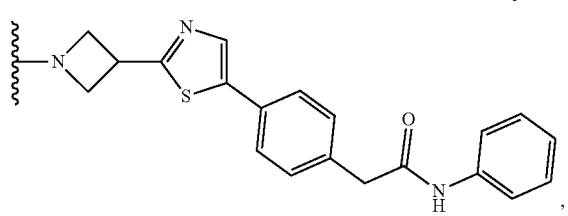,
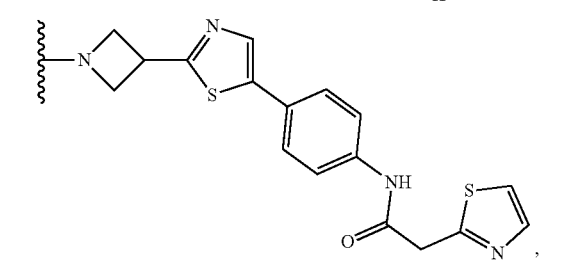,
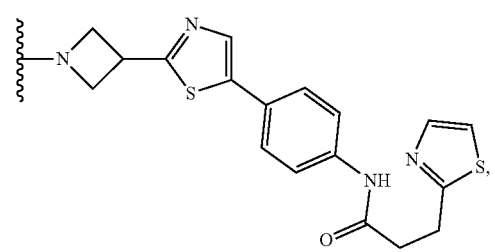,
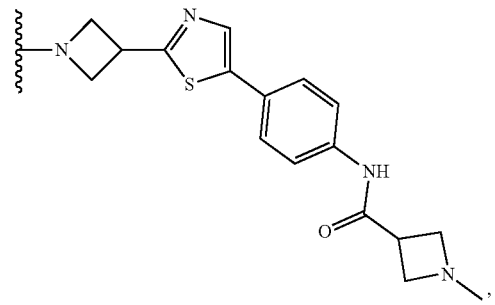,
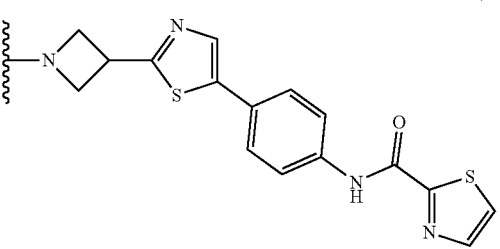,
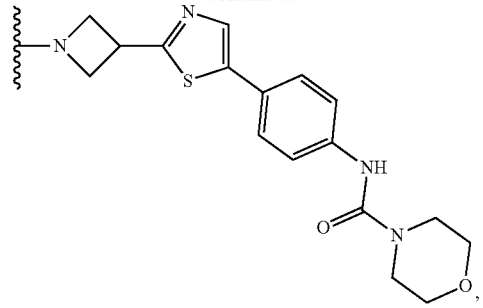,
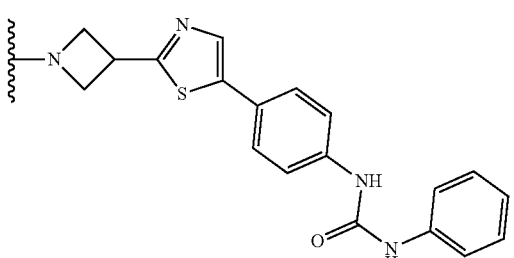,
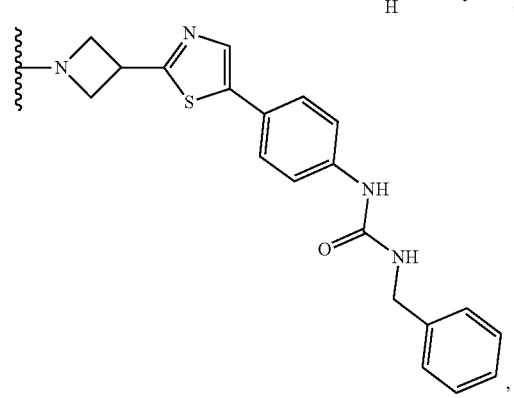,
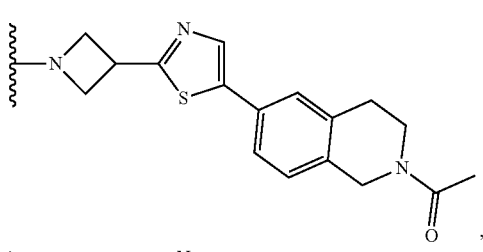,
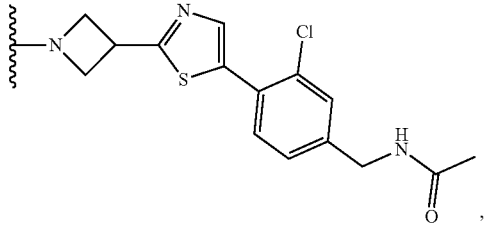,
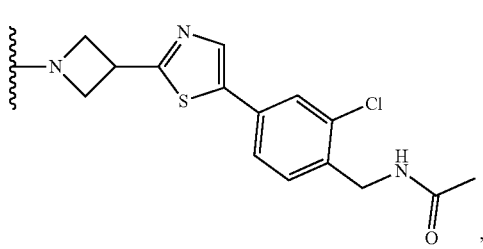, -continued
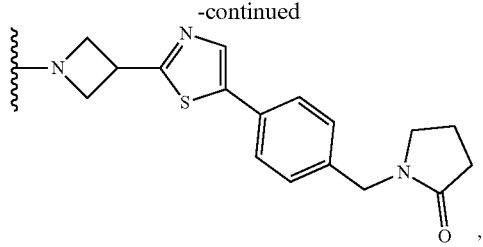
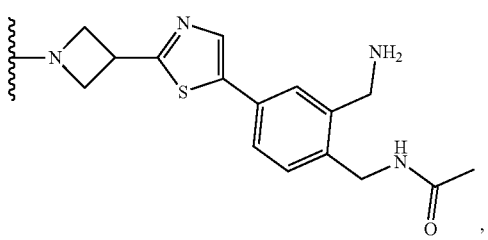
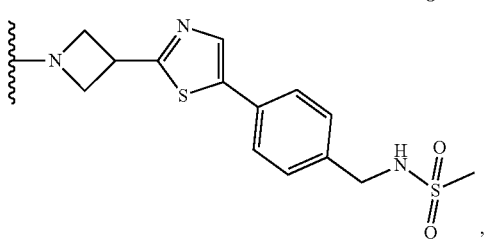
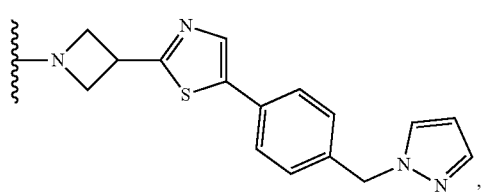
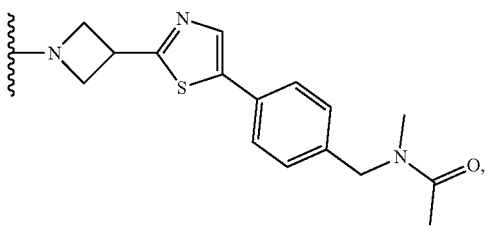
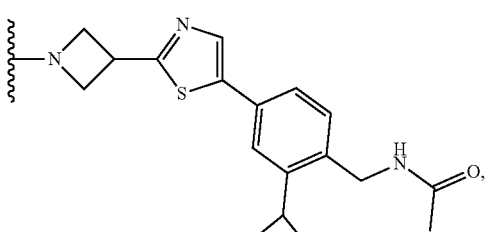
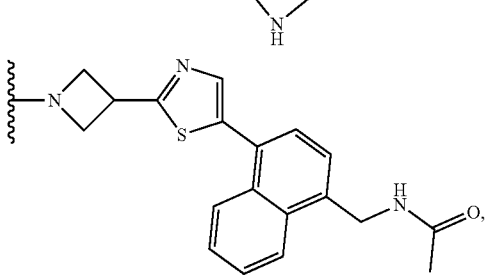
-continued
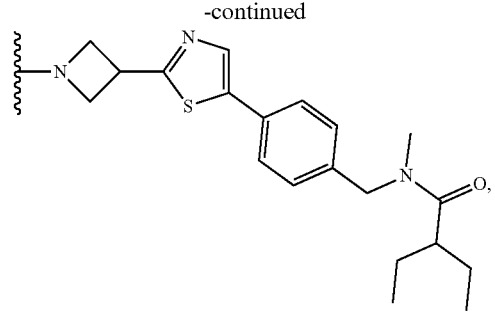
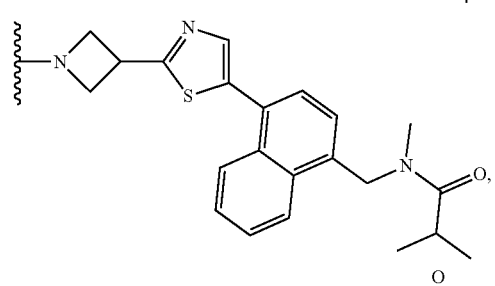
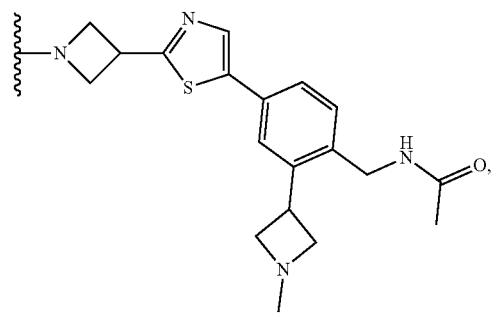
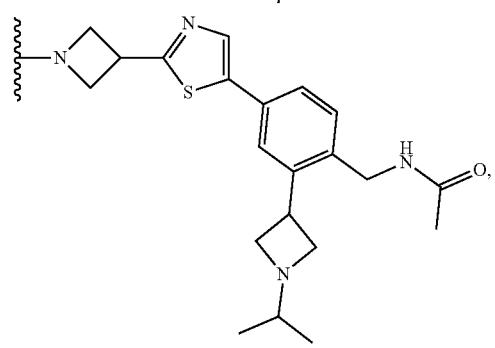
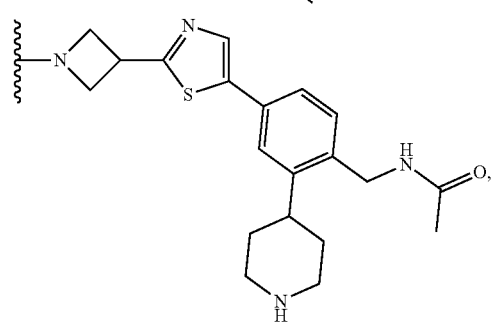

-continued

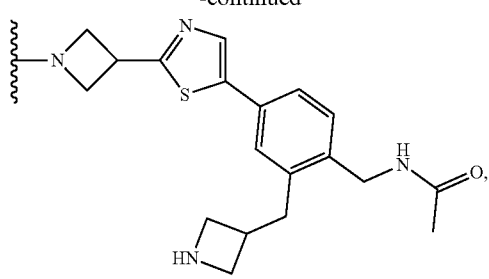

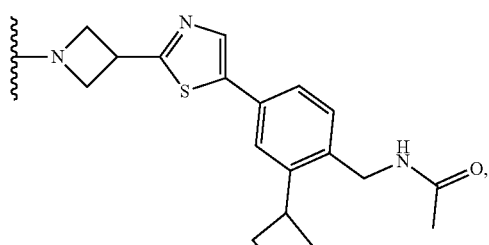

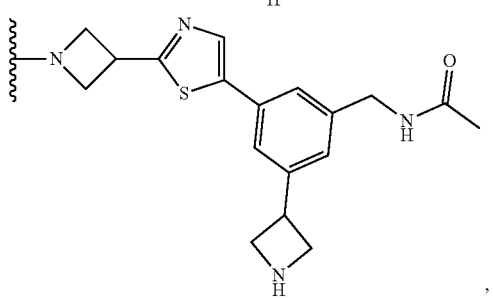

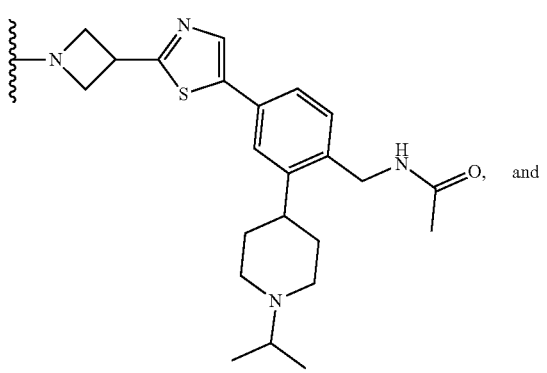

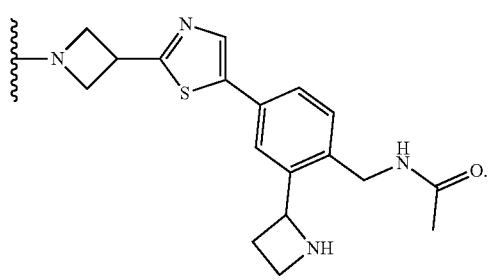

In some embodiments, the compound of formula (I) is a compound of formula (Ia):

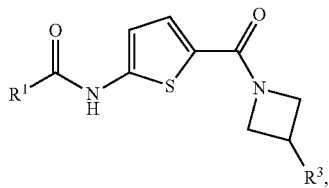

or a pharmaceutically acceptable salt thereof, wherein $R^1$ and $R^3$ have any of the meanings disclosed herein.

In some embodiments, the compound of formula (I) is a compound of formula (Ib):

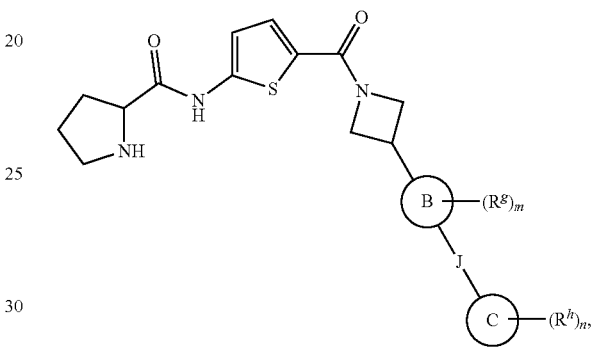

or a pharmaceutically acceptable salt thereof, wherein B, J, C, $R^g$, $R^h$, m, and n have any of the meanings disclosed herein.

In some embodiments, the compound of formula (I) is a compound of formula (Ic):

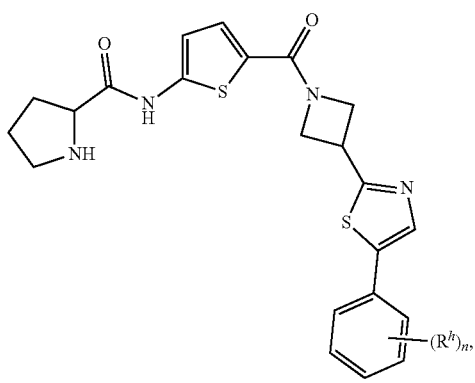

or a pharmaceutically acceptable salt thereof, wherein $R^h$ and c have any of the meanings disclosed herein.

Herein, when reference is made to a compound of formula (I) (e.g., to a pharmaceutical composition comprising a compound of formula (I) or a method of treatment using a compound of formula (I)), such reference also includes compounds of formula (Ia), (Ib), and (Ic).

In some embodiments, the compound is selected from the compounds shown in Table 1 herein, or a pharmaceutically acceptable salt thereof.

Also disclosed herein is a compound of formula (IIa):

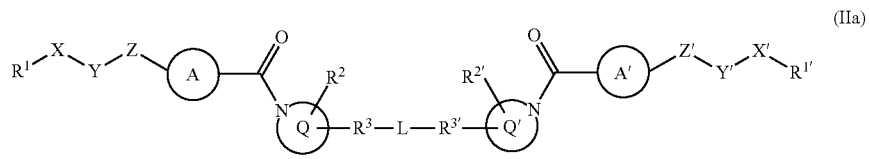

(IIa)

or a pharmaceutically acceptable salt thereof, wherein:
$R^1$ and $R^{1'}$ are each independently selected from heterocyclyl, heterocyclylalkyl, heteroaryl, heteroarylalkyl, aryl, arylalkyl, cycloalkyl, cycloalkylalkyl, alkyl, alkenyl, alkynyl, hydroxy, alkoxy, thioalkyl, halogen, haloalkyl, carboxy, acyl, amido, cyano, sulfonyl, and hydrogen;
X and X' are each independently absent or selected from —C(O)—, —C(S)—, —CH$_2$—, and —SO$_2$—;
Y and Y' are each independently —NR$^a$— or —O—;
$R^a$ is selected from hydrogen, alkyl, haloalkyl, heteroalkyl, cycloalkyl, hydroxyalkyl, and aminoalkyl, or $R^a$ is taken together with the nitrogen atom to which it is attached to form a fused ring with A, or $R^a$ and $R^1$ together with the atoms to which they are attached together form an optionally substituted heterocyclic ring;
Z and Z' are each independently absent or —CR$^b$R$^c$—;
$R^b$ and $R^c$ are each independently selected from hydrogen and alkyl;
A and A' are each independently a five-membered heteroaryl ring;
Q and Q' are each independently a four-, five-, or six-membered heterocycle;
$R^2$ and $R^{2'}$ are each independently selected from hydrogen, halo, alkyl, amino, and hydroxy;
$R^3$ and $R^{3'}$ are each independently selected from aryl, heteroaryl, cycloalkyl, heterocyclyl, and a group of formula:

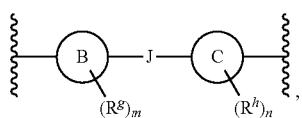

wherein B is aryl or heteroaryl; J is absent or is —CH$_2$—, —O—, —S—, or —NH—; C is selected from aryl, heteroaryl, and heterocyclyl; m is 0, 1, 2, 3, or 4; n is 0, 1, 2, 3, or 4; and $R^g$ and $R^h$ are each independently selected from alkyl, alkenyl, alkynyl, halo, haloalkyl, amino, alkylamino, dialkylamino, aminoalkyl, alkylaminoalkyl, dialkylaminoalkyl, amido, amidoalkyl, sulfonamido, sulfonamidoalkyl, urea, ureaalkyl, thiourea, thioureaalkyl, hydroxy, hydroxyalkyl, alkoxy, alkoxyalkyl, haloalkoxy, thioalkyl, acyl, carboxy, nitro, oxo, aryl, arylalkyl, heteroaryl, heteroarylalkyl, heterocyclyl, heterocyclylalkyl, cycloalkyl, and cycloalkylalkyl;
$R^d$, $R^e$, and $R^f$ are each independently selected from hydrogen, alkyl, haloalkyl, hydroxyalkyl, aminoalkyl, carboxyalkyl, heteroalkyl, aryl, arylalkyl, and heteroaryl; and
L is a linker;
wherein each alkyl, alkenyl, alkynyl, aryl, arylalkyl, heteroalkyl, heteroaryl, heteroarylalkyl, cycloalkyl, heterocyclyl, and heterocyclylalkyl is independently optionally substituted with 1, 2, 3, 4, or 5 substituents.

In some embodiments, disclosed herein is a compound of formula (IIa):

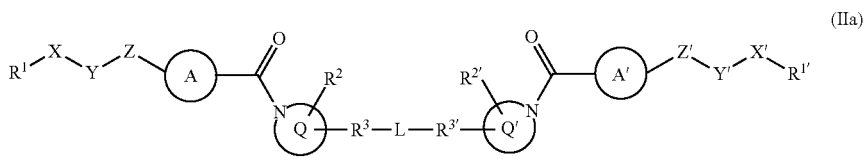

(IIa)

or a pharmaceutically acceptable salt thereof, wherein:
$R^1$ and $R^{1'}$ are each independently selected from heterocyclyl, heterocyclylalkyl, heteroaryl, heteroarylalkyl, aryl, arylalkyl, cycloalkyl, cycloalkylalkyl, alkyl, alkenyl, alkynyl, hydroxy, alkoxy, thioalkyl, halogen, haloalkyl, carboxy, acyl, amido, cyano, sulfonyl, and hydrogen;
X and X' are each independently absent or selected from —C(O)—, —C(S)—, —CH$_2$—, and —SO$_2$—;
Y and Y' are each independently —NR$^a$— or —O—;
$R^a$ is selected from hydrogen, alkyl, haloalkyl, heteroalkyl, cycloalkyl, hydroxyalkyl, and aminoalkyl, or $R^a$ is taken together with the nitrogen atom to which it is attached to form a fused ring with A
Z and Z' are each independently absent or —CR$^b$R$^c$—;
$R^b$ and $R^c$ are each independently selected from hydrogen and alkyl;
A and A' are each independently a five-membered heteroaryl ring;
Q and Q' are each independently a four-, five-, or six-membered heterocycle;
$R^2$ and $R^{2'}$ are each independently selected from hydrogen, halo, alkyl, amino, and hydroxy;
$R^3$ and $R^{3'}$ are each independently selected from aryl, heteroaryl, cycloalkyl, heterocyclyl, and a group of formula:

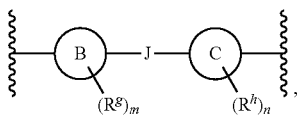

wherein B is aryl or heteroaryl; J is absent or is —CH$_2$—, —O—, —S—, or —NH—; C is selected from aryl, heteroaryl, and heterocyclyl; m is 0, 1, 2, 3, or 4; n is 0, 1, 2, 3, or 4; and R$^g$ and R$^h$ are each independently selected from alkyl, alkenyl, alkynyl, halo, haloalkyl, amino, alkylamino, dialkylamino, aminoalkyl, alkylaminoalkyl, dialkylaminoalkyl, amido, amidoalkyl, sulfonamido, sulfonamidoalkyl, urea, ureaalkyl, thiourea, thioureaalkyl, hydroxy, hydroxyalkyl, alkoxy, alkoxyalkyl, haloalkoxy, thioalkyl, acyl, carboxy, nitro, oxo, aryl, arylalkyl, heteroaryl, heteroarylalkyl, heterocyclyl, heterocyclylalkyl, cycloalkyl, and cycloalkylalkyl;

R$^d$, R$^e$, and R$^f$ are each independently selected from hydrogen, alkyl, haloalkyl, hydroxyalkyl, aminoalkyl, carboxyalkyl, heteroalkyl, aryl, arylalkyl, and heteroaryl; and L is a linker;

wherein each alkyl, alkenyl, alkynyl, aryl, arylalkyl, heteroalkyl, heteroaryl, heteroarylalkyl, cycloalkyl, heterocyclyl, and heterocyclylalkyl is independently optionally substituted with 1, 2, 3, 4, or 5 substituents.

In some embodiments, R$^1$ and R$^{1'}$ are the same, R$^2$ and R$^{2'}$ are the same, R$^3$ and R$^{3'}$ are the same, X and X' are the same, Y and Y' are the same, Z and Z' are the same, A and A' are the same, and Q and Q' are the same.

In some embodiments, R$^1$ and R$^{1'}$ are heterocyclyl, which is optionally substituted. In some embodiments, R$^1$ and R$^{1'}$ are monocyclic 4- to 6-membered heterocyclyl having 1 or 2 nitrogen atoms, which is optionally substituted. In some embodiments, R$^1$ and R$^{1'}$ are each a 4- or 5-membered monocyclic heterocyclyl, such as a 4- or 5-membered heterocyclyl having 1 nitrogen atom, which is optionally substituted. In some embodiments, R$^1$ and R$^{1'}$ are pyrrolidine, which is optionally substituted. In some embodiments, R$^1$ and R$^{1'}$ are unsubstituted pyrrolidine.

In some embodiments, X and X' are —C(O)—.

In some embodiments, Y and Y' are —NR$^a$—, and R$^a$ is selected from hydrogen and C$_1$-C$_6$ alkyl. In some embodiments, Y and Y' are —NR$^a$—, and R$^a$ is selected from hydrogen and methyl. In some embodiments, Y and Y' are —NR$^a$—, and R$^a$ is hydrogen.

In some embodiments, Z and Z' are each absent.

In some embodiments, A and A' are each a five-membered monocyclic heteroaryl having 1 or 2 heteroatoms independently selected from S and N. In some embodiments, A and A' are selected from thiophene and thiazole. In some embodiments, A and A' are thiophene.

In some embodiments, Q and Q' are each a four-, five-, or six-membered heterocyclyl having one nitrogen atom (i.e. the nitrogen atom indicated in formula (IIa)). In other words, in some embodiments, Q and Q' are selected from azetidine, pyrrolidine, and piperidine. In some embodiments, Q and Q' are selected from azetidine and pyrrolidine. In some embodiments, Q and Q' are azetidine. In some embodiments, Q and Q' are pyrrolidine.

In some embodiments, R$^2$ and R$^{2'}$ are hydrogen.

In some embodiments, R$^3$ and R$^{3'}$ are selected from aryl, heteroaryl, and a group of formula:

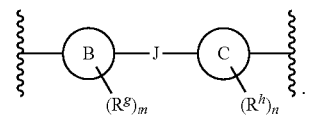

In some embodiments, R$^3$ and R$^{3'}$ are each a group of formula:

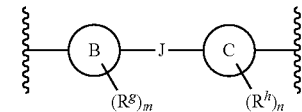

wherein B is a 5-membered monocyclic heteroaryl having 1 or 2 heteroatoms independently selected from N, S or O; J is absent; C is selected from aryl, heteroaryl, and heterocyclyl; m is 0 or 1; R$^g$ is C$_1$-C$_6$ alkyl; n is 0, 1, or 2; and each R$^h$ is independently selected from C$_1$-C$_6$ alkyl, halo, C$_1$-C$_6$ haloalkyl, amino, amino-C$_1$-C$_6$-alkyl, amido-C$_1$-C$_6$-alkyl, and heterocyclyl. In some embodiments, B is selected from thiazole and thiophene. In some embodiments, B is thiazole. In some embodiments, C is selected from aryl and monocyclic heteroaryl. In some embodiments, C is selected from phenyl and pyridyl. In some embodiments, at least one R$^h$ has formula —(CH$_2$)$_r$C(O)NR$^i$R$^j$ or —(CH$_2$)$_s$NR$^k$C(O)R$^m$, wherein:

r and s are each independently selected from 0, 1, and 2;
R$^i$ and R$^k$ are each independently selected from hydrogen and C$_1$-C$_6$ alkyl;
R$^j$ is selected from C$_1$-C$_6$-alkyl, aryl, aryl-C$_1$-C$_6$-alkyl, heteroaryl, heteroaryl-C$_1$-C$_6$-alkyl, heterocyclyl, heterocyclyl-C$_1$-C$_6$-alkyl, cycloalkyl, and cycloalkyl-C$_1$-C$_6$-alkyl;
R$^m$ is selected from C$_1$-C$_6$-alkyl, aryl, aryl-C$_1$-C$_6$-alkyl, heteroaryl, heteroaryl-C$_1$-C$_6$-alkyl, heterocyclyl, heterocyclyl-C$_1$-C$_6$-alkyl, cycloalkyl, and cycloalkyl-C$_1$-C$_6$-alkyl, amino, C$_1$-C$_6$-alkylamino, arylamino, aryl-C$_1$-C$_6$-alkylamino;
wherein each alkyl, aryl, heteroaryl, heterocyclyl, and cycloalkyl is independently unsubstituted or substituted with 1 or 2 substituents independently selected from halo, C$_1$-C$_6$-alkyl, C$_1$-C$_6$-alkoxy, hydroxy, amino and oxo.

In some embodiments, L is a linker comprising one or more groups independently selected from methylene (—CH$_2$—), vinylene (—CH=CH—), acetylene (—C≡C—), ether (—O—), amine (—NH—), alkylamine (—NR—, wherein R is an optionally substituted C$_1$-C$_6$ alkyl group), amide (—C(O)NH—), ester (—C(O)O—), carbamate (—OC(O)NH—), sulfonamide (—S(O)$_2$NH—), phenylene (—C$_6$H$_4$—), heteroarylene, heterocyclylene, and any combination thereof.

In some embodiments, L is selected from:

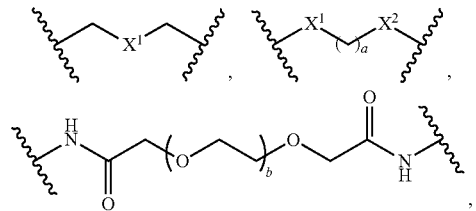

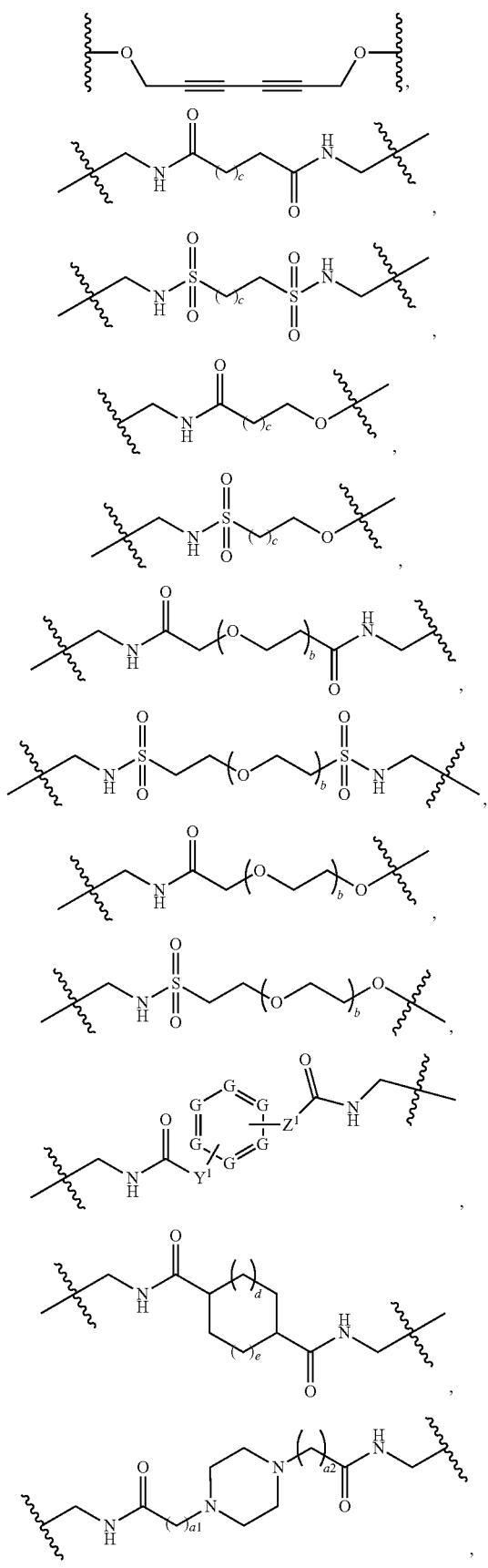

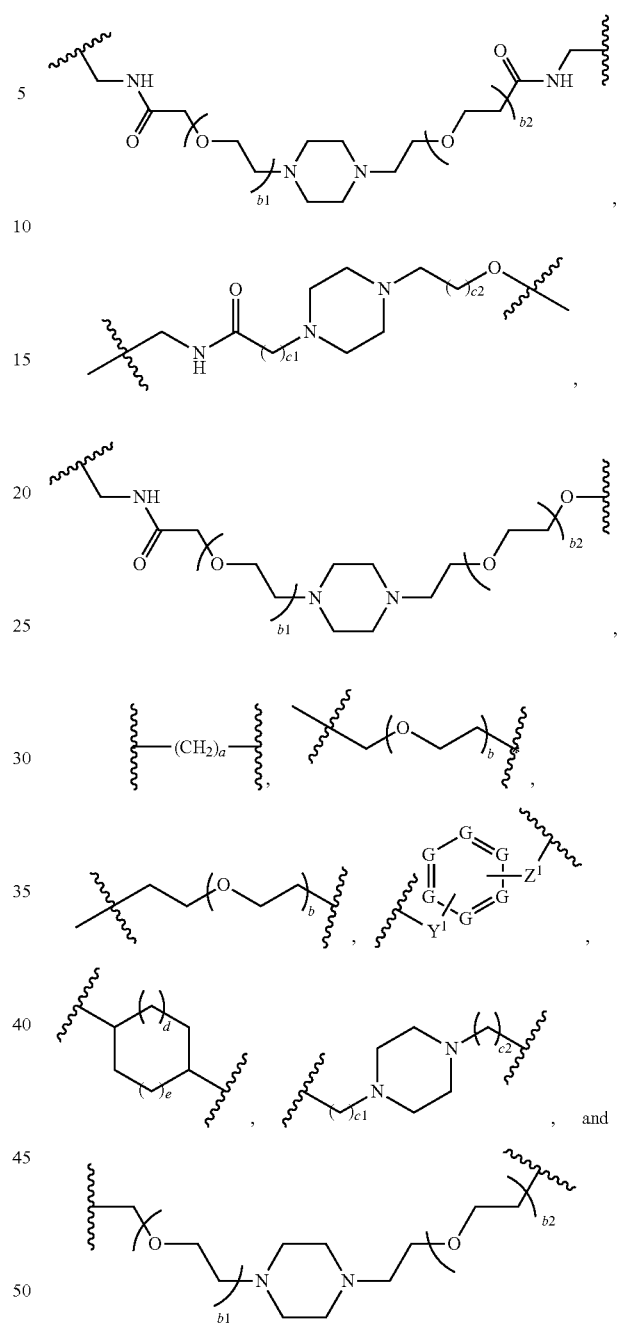

wherein a, a1, and a2 are each independently selected from 1, 2, 3, 4, 5, 6, 7, 8, 9, 10, 11, and 12; b, b1, and b2 are each independently selected from 0, 1, 2, 3, 4, 5, and 6; c, c1, and c2 are each independently selected from 0, 1, 2, 3, 4, 5, 6, 7, 8, 9, 10, 11, and 12; d and e are each independently selected form 0, 1, and 2; each G is independently selected from CH and N; $X^1$ and $X^2$ are each independently O or —$NR^x$, wherein $R^x$ is hydrogen or optionally substituted alkyl; and $Y^1$ and $Z^1$ are each independently selected from —$CH_2$—, —NH—, and —O—.

In some embodiments, the compound is selected from the compounds shown in Table 2 herein, or a pharmaceutically acceptable salt thereof.

Also disclosed herein is a compound of formula (IIb)

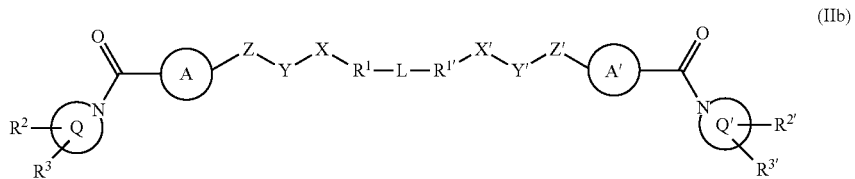

(IIb)

or a pharmaceutically acceptable salt thereof, wherein:
$R^1$ and $R^{1'}$ are each independently selected from heterocyclyl, heterocyclylalkyl, heteroaryl, heteroarylalkyl, aryl, arylalkyl, cycloalkyl, cycloalkylalkyl, alkyl, alkenyl, and alkynyl;
X and X' are each independently absent or selected from —C(O)—, —C(S)—, —CH$_2$—, and —SO$_2$—;
Y and Y' are each independently selected from —NR$^a$— or —O—;
$R^a$ is selected from hydrogen, alkyl, haloalkyl, heteroalkyl, cycloalkyl, hydroxyalkyl, and aminoalkyl, or $R^a$ is taken together with the nitrogen atom to which it is attached to form a fused ring with A;
Z and Z' are each independently absent or —CR$^b$R$^c$—;
$R^b$ and $R^c$ are each independently selected from hydrogen and alkyl;
A and A' are each independently a five-membered heteroaryl ring;
Q and Q' are each independently a four-, five-, or six-membered heterocyclyl;
$R^2$ and $R^{2'}$ are each independently selected from hydrogen, halo, alkyl, amino, and hydroxy;
$R^3$ and $R^{3'}$ are each independently selected from hydrogen, halo, —OR$^d$, —NR$^e$R$^f$, aryl, arylalkyl, heteroaryl, heteroarylalkyl, heterocyclyl, and heterocyclylalkyl, and a group of formula:

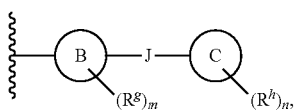

wherein B is aryl or heteroaryl; J is absent or is —CH$_2$—, —O—, —S—, or —NH—; C is selected from aryl, heteroaryl, and heterocyclyl; m is 0, 1, 2, 3, or 4; n is 0, 1, 2, 3, or 4; and $R^g$ and $R^h$ are each independently selected from alkyl, alkenyl, alkynyl, halo, haloalkyl, amino, alkylamino, dialkylamino, aminoalkyl, alkylaminoalkyl, dialkylaminoalkyl, amido, amidoalkyl, sulfonamido, sulfonamidoalkyl, urea, ureaalkyl, thiourea, thioureaalkyl, hydroxy, hydroxyalkyl, alkoxy, alkoxyalkyl, haloalkoxy, thioalkyl, acyl, carboxy, nitro, oxo, aryl, arylalkyl, heteroaryl, heteroarylalkyl, heterocyclyl, heterocyclylalkyl, cycloalkyl, and cycloalkylalkyl;
or $R^2$ and $R^3$ are taken together with the carbon atom(s) to which they are attached to form a ring selected from aryl, heteroaryl, cycloalkyl, and heterocycle; or $R^2$ and $R^3$ are taken together with the carbon atom to which they are attached to form an alkenyl group;
$R^d$, $R^e$, and $R^f$ are each independently selected from hydrogen, alkyl, haloalkyl, hydroxyalkyl, aminoalkyl, carboxyalkyl, heteroalkyl, aryl, arylalkyl, and heteroaryl; and L is a linker;
wherein each alkyl, alkenyl, alkynyl, aryl, arylalkyl, heteroalkyl, heteroaryl, heteroarylalkyl, cycloalkyl, heterocyclyl, and heterocyclylalkyl is independently optionally substituted with 1, 2, 3, 4, or 5 substituents.
In some embodiments, $R^1$ and $R^{1'}$ are the same, $R^2$ and $R^{2'}$ are the same, $R^3$ and $R^{3'}$ are the same, X and X' are the same, Y and Y' are the same, Z and Z' are the same, A and A' are the same, and Q and Q' are the same.
In some embodiments, $R^1$ and $R^{1'}$ are heterocyclyl, which is optionally substituted. In some embodiments, $R^1$ and $R^{1'}$ are monocyclic 4- to 6-membered heterocyclyl having 1 or 2 nitrogen atoms, which is optionally substituted. In some embodiments, $R^1$ and $R^{1'}$ are each a 4- or 5-membered monocyclic heterocyclyl, such as a 4- or 5-membered heterocyclyl having 1 nitrogen atom, which is optionally substituted. In some embodiments, $R^1$ and $R^{1'}$ are pyrrolidine, which is optionally substituted. In some embodiments, $R^1$ and $R^{1'}$ are unsubstituted pyrrolidine.
In some embodiments, X and X' are —C(O)—.
In some embodiments, Y and Y' are —NR$^a$—, and $R^a$ is selected from hydrogen and $C_1$-$C_6$ alkyl. In some embodiments, Y and Y' are —NR$^a$—, and $R^a$ is selected from hydrogen and methyl. In some embodiments, Y and Y' are —NR$^a$—, and $R^a$ is hydrogen.
In some embodiments, Z and Z' are each absent.
In some embodiments, A and A' are each a five-membered monocyclic heteroaryl having 1 or 2 heteroatoms independently selected from S and N. In some embodiments, A and A' are selected from thiophene and thiazole. In some embodiments, A and A' are thiophene.
In some embodiments, Q and Q' are each a four-, five-, or six-membered heterocyclyl having one nitrogen atom (i.e. the nitrogen atom indicated in formula (IIa)). In other words, in some embodiments, Q and Q' are selected from azetidine, pyrrolidine, and piperidine. In some embodiments, Q and Q' are selected from azetidine and pyrrolidine. In some embodiments, Q and Q' are azetidine. In some embodiments, Q and Q' are pyrrolidine.
In some embodiments, $R^2$ and $R^{2'}$ are hydrogen.
In some embodiments, $R^3$ and $R^{3'}$ are selected from aryl, heteroaryl, and a group of formula:

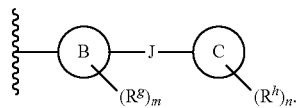

In some embodiments, $R^{3'}$ and $R^3$ are selected from monocyclic and bicyclic heteroaryl having 1, 2, or 3 heteroatoms independently selected from N and S.
In some embodiments, $R^3$ and $R^{3'}$ are each a group of formula:

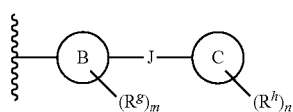

wherein B is a 5-membered monocyclic heteroaryl having 1 or 2 heteroatoms independently selected from N, S or O; J is absent; C is selected from aryl, heteroaryl, and heterocyclyl; m is 0 or 1; $R^g$ is $C_1$-$C_6$ alkyl; n is 0, 1, or 2; and each $R^h$ is independently selected from $C_1$-$C_6$ alkyl, halo, $C_1$-$C_6$ haloalkyl, amino, amino-$C_1$-$C_6$-alkyl, amido-$C_1$-$C_6$-alkyl, and heterocyclyl. In some embodiments, B is selected from thiazole and thiophene. In some embodiments, B is thiazole. In some embodiments, C is selected from aryl and monocyclic heteroaryl. In some embodiments, C is selected from phenyl and pyridyl. In some embodiments, at least one $R^h$ has formula —$(CH_2)_rC(O)NR^iR^j$ or —$(CH_2)_sNR^kC(O)R^m$, wherein:

r and s are each independently selected from 0, 1, and 2;
$R^i$ and $R^k$ are each independently selected from hydrogen and $C_1$-$C_6$ alkyl;
$R^j$ is selected from $C_1$-$C_6$-alkyl, aryl, aryl-$C_1$-$C_6$-alkyl, heteroaryl, heteroaryl-$C_1$-$C_6$-alkyl, heterocyclyl, heterocyclyl-$C_1$-$C_6$-alkyl, cycloalkyl, and cycloalkyl-$C_1$-$C_6$-alkyl;
$R^m$ is selected from $C_1$-$C_6$-alkyl, aryl, aryl-$C_1$-$C_6$-alkyl, heteroaryl, heteroaryl-$C_1$-$C_6$-alkyl, heterocyclyl, heterocyclyl-$C_1$-$C_6$-alkyl, cycloalkyl, and cycloalkyl-$C_1$-$C_6$-alkyl, amino, $C_1$-$C_6$-alkylamino, arylamino, aryl-$C_1$-$C_6$-alkylamino;
wherein each alkyl, aryl, heteroaryl, heterocyclyl, and cycloalkyl is independently unsubstituted or substituted with 1 or 2 substituents independently selected from halo, $C_1$-$C_6$-alkyl, $C_1$-$C_6$-alkoxy, hydroxy, amino and oxo.

In some embodiments, L is a linker comprising one or more groups independently selected from methylene (—$CH_2$—), vinylene (—CH=CH—), acetylene (—C≡C—), ether (—O—), amine (—NH—), alkylamine (—NR—, wherein R is an optionally substituted $C_1$-$C_6$ alkyl group), amide (—C(O)NH—), ester (—C(O)O—), carbamate (—OC(O)NH—), sulfonamide (—S(O)$_2$NH—), phenylene (—$C_6H_4$—), heteroarylene, heterocyclylene, and any combination thereof.

In some embodiments, L is selected from:

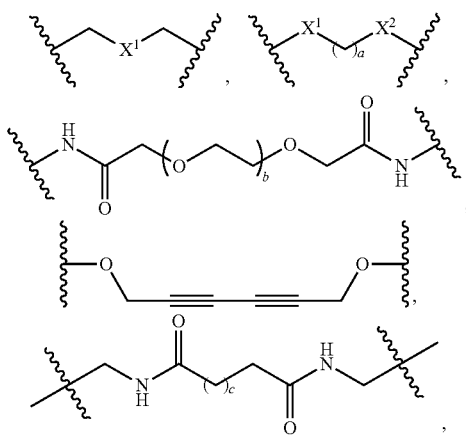

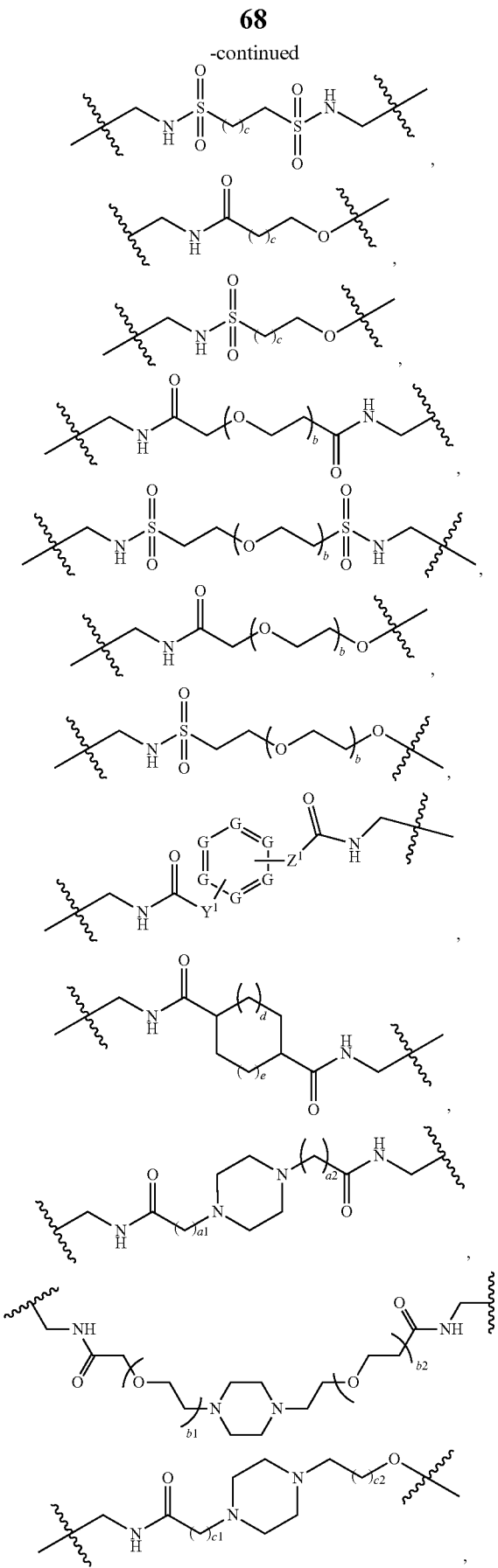

-continued

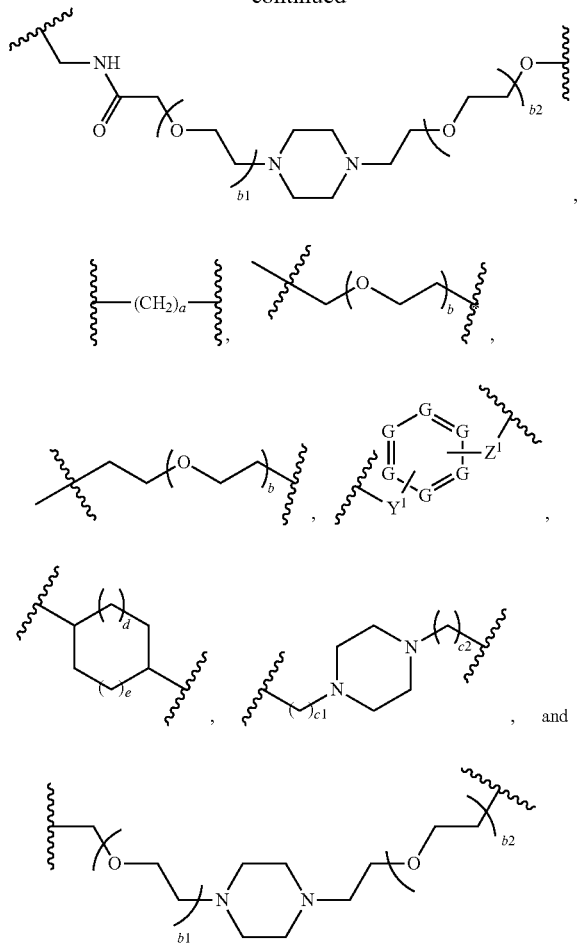

wherein a, a1, and a2 are each independently selected from 1, 2, 3, 4, 5, 6, 7, 8, 9, 10, 11, and 12; b, b1, and b2 are each independently selected from 0, 1, 2, 3, 4, 5, and 6; e, c1, and c2 are each independently selected from 0, 1, 2, 3, 4, 5, 6, 7, 8, 9, 10, 11, and 12; d and e are each independently selected form 0, 1, and 2; each G is independently selected from CH and N; $X^1$ and $X^2$ are each independently O or —$NR^x$, wherein $R^x$ is hydrogen or optionally substituted alkyl; and $Y^1$ and $Z^1$ are each independently selected from —$CH_2$—, —NH—, and —O—.

In some embodiments, the compound is selected from the compounds shown in Table 2 herein, or a pharmaceutically acceptable salt thereof.

Also disclosed herein is a compound of formula (IIc)

or a pharmaceutically acceptable salt thereof, wherein:

$R^1$ is selected from heterocyclyl, heterocyclylalkyl, heteroaryl, heteroarylalkyl, aryl, arylalkyl, cycloalkyl, cycloalkylalkyl, alkyl, alkenyl, alkynyl, hydroxy, alkoxy, thioalkyl, halogen, haloalkyl, carboxy, acyl, amido, cyano, sulfonyl, and hydrogen;

$R^{1'}$ is selected from heterocyclyl, heterocyclylalkyl, heteroaryl, heteroarylalkyl, aryl, arylalkyl, cycloalkyl, cycloalkylalkyl, alkyl, alkenyl, and alkynyl;

X and X' are each independently absent or selected from —C(O)—, —C(S)—, —$CH_2$—, and —$SO_2$—;

Y and Y' are each independently selected from —$NR^a$— or —O—;

$R^a$ is selected from hydrogen, alkyl, haloalkyl, heteroalkyl, cycloalkyl, hydroxyalkyl, and aminoalkyl, or $R^a$ is taken together with the nitrogen atom to which it is attached to form a fused ring with A, or $R^a$ and $R^1$ together with the atoms to which they are attached together form an optionally substituted heterocyclic ring;

Z and Z' are each independently absent or —$CR^bR^c$—;

$R^b$ and $R^c$ are each independently selected from hydrogen and alkyl;

A and A' are each independently a five-membered heteroaryl ring;

Q and Q' are each independently a four-, five-, or six-membered heterocycle;

$R^2$ and $R^{2'}$ are each independently selected from hydrogen, halo, alkyl, amino, and hydroxy;

$R^3$ is selected from aryl, heteroaryl, heterocyclyl, and a group of formula:

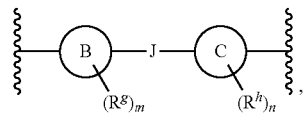

wherein B is aryl or heteroaryl; J is absent or is —$CH_2$—, —O—, —S—, or —NH—; C is selected from aryl, heteroaryl, and heterocyclyl; m is 0, 1, 2, 3, or 4; n is 0, 1, 2, 3, or 4; and $R^g$ and $R^h$ are each independently selected from alkyl, alkenyl, alkynyl, halo, haloalkyl, amino, alkylamino, dialkylamino, aminoalkyl, alkylaminoalkyl, dialkylaminoalkyl, amido, amidoalkyl, sulfonamido, sulfonamidoalkyl, urea, ureaalkyl, thiourea, thioureaalkyl, hydroxy, hydroxyalkyl, alkoxy, alkoxyalkyl, haloalkoxy, thioalkyl, acyl, carboxy, nitro, oxo, aryl, arylalkyl, heteroaryl, heteroarylalkyl, heterocyclyl, heterocyclylalkyl, cycloalkyl, and cycloalkylalkyl;

$R^{3'}$ is selected from hydrogen, halo, —$OR^{d'}$, —$NR^{e'}R^{f'}$, aryl, arylalkyl, heteroaryl, heteroarylalkyl, heterocyclyl, and heterocyclylalkyl, and a group of formula:

(IIc)

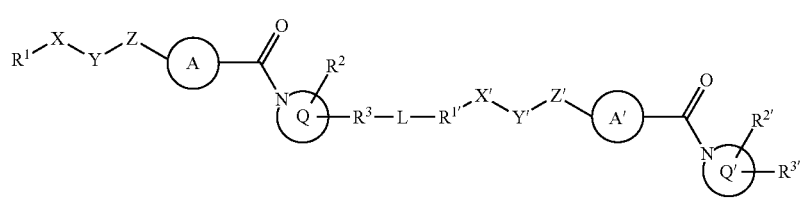

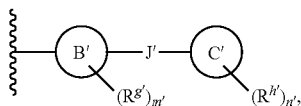

wherein B' is aryl or heteroaryl; J' is absent or is —CH$_2$—, —O—, —S—, or —NH—; C' is selected from aryl, heteroaryl, and heterocyclyl; m' is 0, 1, 2, 3, or 4; n' is 0, 1, 2, 3, or 4; and R$^{g'}$ and R$^{h'}$ are each independently selected from alkyl, alkenyl, alkynyl, halo, haloalkyl, amino, alkylamino, dialkylamino, aminoalkyl, alkylaminoalkyl, dialkylaminoalkyl, amido, amidoalkyl, sulfonamido, sulfonamidoalkyl, urea, ureaalkyl, thiourea, thioureaalkyl, hydroxy, hydroxyalkyl, alkoxy, alkoxyalkyl, haloalkoxy, thioalkyl, acyl, carboxy, nitro, oxo, aryl, arylalkyl, heteroaryl, heteroarylalkyl, heterocyclyl, heterocyclylalkyl, cycloalkyl, and cycloalkylalkyl;

R$^{d'}$, R$^{e'}$, and R$^{f'}$ are each independently selected from hydrogen, alkyl, haloalkyl, hydroxyalkyl, aminoalkyl, carboxyalkyl, heteroalkyl, aryl, arylalkyl, and heteroaryl; and L is a linker;

wherein each alkyl, alkenyl, alkynyl, aryl, arylalkyl, heteroalkyl, heteroaryl, heteroarylalkyl, cycloalkyl, heterocyclyl, and heterocyclylalkyl is independently optionally substituted with 1, 2, 3, 4, or 5 substituents.

Also disclosed herein is a compound of formula (IIc)

R$^2$ and R$^{2'}$ are each independently selected from hydrogen, halo, alkyl, amino, and hydroxy;

R$^3$ is selected from aryl, heteroaryl, heterocyclyl, and a group of formula:

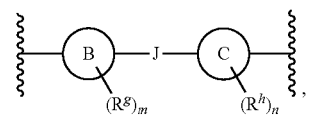

wherein B is aryl or heteroaryl; J is absent or is —CH$_2$—, —O—, —S—, or —NH—; C is selected from aryl, heteroaryl, and heterocyclyl; m is 0, 1, 2, 3, or 4; n is 0, 1, 2, 3, or 4; and R$^g$ and R$^h$ are each independently selected from alkyl, alkenyl, alkynyl, halo, haloalkyl, amino, alkylamino, dialkylamino, aminoalkyl, alkylaminoalkyl, dialkylaminoalkyl, amido, amidoalkyl, sulfonamido, sulfonamidoalkyl, urea, ureaalkyl, thiourea, thioureaalkyl, hydroxy, hydroxyalkyl, alkoxy, alkoxyalkyl, haloalkoxy, thioalkyl, acyl, carboxy, nitro, oxo, aryl, arylalkyl, heteroaryl, heteroarylalkyl, heterocyclyl, heterocyclylalkyl, cycloalkyl, and cycloalkylalkyl;

R$^{3'}$ is selected from hydrogen, halo, —OR$^{d'}$, —NR$^{e'}$R$^{f'}$, aryl, arylalkyl, heteroaryl, heteroarylalkyl, heterocyclyl, and heterocyclylalkyl, and a group of formula:

(IIc)

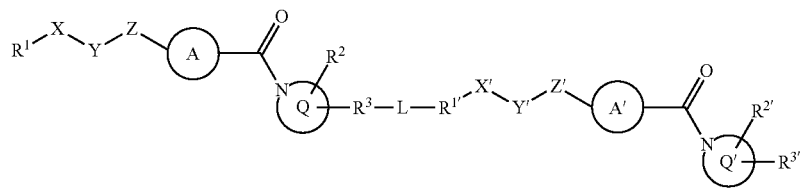

or a pharmaceutically acceptable salt thereof, wherein:

R$^1$ is selected from heterocyclyl, heterocyclylalkyl, heteroaryl, heteroarylalkyl, aryl, arylalkyl, cycloalkyl, cycloalkylalkyl, alkyl, alkenyl, alkynyl, hydroxy, alkoxy, thioalkyl, halogen, haloalkyl, carboxy, acyl, amido, cyano, sulfonyl, and hydrogen;

R$^{1'}$ is selected from heterocyclyl, heterocyclylalkyl, heteroaryl, heteroarylalkyl, aryl, arylalkyl, cycloalkyl, cycloalkylalkyl, alkyl, alkenyl, and alkynyl;

X and X' are each independently absent or selected from —C(O)—, —C(S)—, —CH$_2$—, and —SO$_2$—;

Y and Y' are each independently selected from —NR$^a$— or —O—;

R$^a$ is selected from hydrogen, alkyl, haloalkyl, heteroalkyl, cycloalkyl, hydroxyalkyl, and aminoalkyl, or R$^a$ is taken together with the nitrogen atom to which it is attached to form a fused ring with A;

Z and Z' are each independently absent or —CR$^b$R$^c$—;

R$^b$ and R$^c$ are each independently selected from hydrogen and alkyl;

A and A' are each independently a five-membered heteroaryl ring;

Q and Q' are each independently a four-, five-, or six-membered heterocycle;

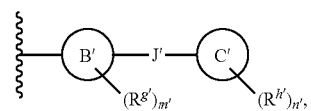

wherein B' is aryl or heteroaryl; J' is absent or is —CH$_2$—, —O—, —S—, or —NH—; C' is selected from aryl, heteroaryl, and heterocyclyl; m' is 0, 1, 2, 3, or 4; n' is 0, 1, 2, 3, or 4; and R$^{g'}$ and R$^{h'}$ are each independently selected from alkyl, alkenyl, alkynyl, halo, haloalkyl, amino, alkylamino, dialkylamino, aminoalkyl, alkylaminoalkyl, dialkylaminoalkyl, amido, amidoalkyl, sulfonamido, sulfonamidoalkyl, urea, ureaalkyl, thiourea, thioureaalkyl, hydroxy, hydroxyalkyl, alkoxy, alkoxyalkyl, haloalkoxy, thioalkyl, acyl, carboxy, nitro, oxo, aryl, arylalkyl, heteroaryl, heteroarylalkyl, heterocyclyl, heterocyclylalkyl, cycloalkyl, and cycloalkylalkyl;

R$^{d'}$, R$^{e'}$, and R$^{f'}$ are each independently selected from hydrogen, alkyl, haloalkyl, hydroxyalkyl, aminoalkyl, carboxyalkyl, heteroalkyl, aryl, arylalkyl, and heteroaryl; and L is a linker;

wherein each alkyl, alkenyl, alkynyl, aryl, arylalkyl, heteroalkyl, heteroaryl, heteroarylalkyl, cycloalkyl, heterocyclyl, and heterocyclylalkyl is independently optionally substituted with 1, 2, 3, 4, or 5 substituents.

In some embodiments, $R^1$ and $R^{1\prime}$ are the same, $R^2$ and $R^{2\prime}$ are the same, $R^3$ and $R^{3\prime}$ are the same, X and X' are the same, Y and Y' are the same, Z and Z' are the same, A and A' are the same, and Q and Q' are the same.

In some embodiments, $R^1$ and $R^{1\prime}$ are heterocyclyl, which is optionally substituted. In some embodiments, $R^1$ and $R^{1\prime}$ are monocyclic 4- to 6-membered heterocyclyl having 1 or 2 nitrogen atoms, which is optionally substituted. In some embodiments, $R^1$ and $R^{1\prime}$ are each a 4- or 5-membered monocyclic heterocyclyl, such as a 4- or 5-membered heterocyclyl having 1 nitrogen atom, which is optionally substituted. In some embodiments, $R^1$ and $R^{1\prime}$ are pyrrolidine, which is optionally substituted. In some embodiments, $R^1$ and $R^{1\prime}$ are unsubstituted pyrrolidine.

In some embodiments, X and X' are —C(O)—.

In some embodiments, Y and Y' are —$NR^a$—, and $R^a$ is selected from hydrogen and $C_1$-$C_6$ alkyl. In some embodiments, Y and Y' are —$NR^a$—, and $R^a$ is selected from hydrogen and methyl. In some embodiments, Y and Y' are —$NR^a$—, and $R^a$ is hydrogen.

In some embodiments, Z and Z' are each absent.

In some embodiments, A and A' are each a five-membered monocyclic heteroaryl having 1 or 2 heteroatoms independently selected from S and N. In some embodiments, A and A' are selected from thiophene and thiazole. In some embodiments, A and A' are thiophene.

In some embodiments, Q and Q' are each a four-, five-, or six-membered heterocyclyl having one nitrogen atom (i.e. the nitrogen atom indicated in formula (IIa)). In other words, in some embodiments, Q and Q' are selected from azetidine, pyrrolidine, and piperidine. In some embodiments, Q and Q' are selected from azetidine and pyrrolidine. In some embodiments, Q and Q' are azetidine. In some embodiments, Q and Q' are pyrrolidine.

In some embodiments, $R^2$ and $R^{2\prime}$ are hydrogen.

In some embodiments, $R^3$ is selected from aryl, heteroaryl, and a group of formula:

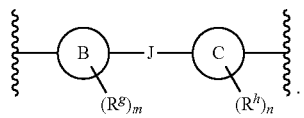

In some embodiments, $R^3$ is a group of formula:

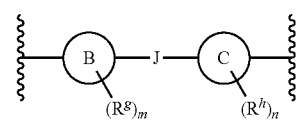

wherein B is a 5-membered monocyclic heteroaryl having 1 or 2 heteroatoms independently selected from N and S; J is absent; C is selected from aryl, heteroaryl, and heterocyclyl; m is 0 or 1; $R^g$ is $C_1$-$C_6$ alkyl; n is 0, 1, or 2; and each $R^h$ is independently selected from $C_1$-$C_6$ alkyl, halo, $C_1$-$C_6$ haloalkyl, amino, amino-$C_1$-$C_6$-alkyl, amido-$C_1$-$C_6$-alkyl, and heterocyclyl. In some embodiments, B is selected from thiazole and thiophene. In some embodiments, B is thiazole.

In some embodiments, C is selected from aryl and monocyclic heteroaryl. In some embodiments, C is selected from phenyl and pyridyl. In some embodiments, C is phenyl.

In some embodiments, $R^{3\prime}$ is selected from hydrogen, aryl, heteroaryl, and a group of formula:

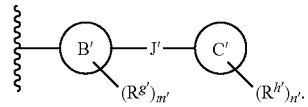

In some embodiments, $R^{3\prime}$ is selected from a monocyclic and bicyclic heteroaryl having 1, 2, or 3 heteroatoms independently selected from N and S.

In some embodiments, $R^{3\prime}$ is a group of formula:

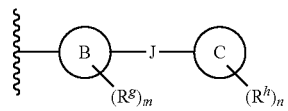

wherein B' is a 5-membered monocyclic heteroaryl having 1 or 2 heteroatoms independently selected from N and S; J' is absent; C' is selected from aryl, heteroaryl, and heterocyclyl; m' is 0 or 1; $R^{g\prime}$ is $C_1$-$C_6$ alkyl; n' is 0, 1, or 2; and each $R^{h\prime}$ is independently selected from $C_1$-$C_6$ alkyl, halo, $C_1$-$C_6$ haloalkyl, amino, amino-$C_1$-$C_6$-alkyl, amido-$C_1$-$C_6$-alkyl, and heterocyclyl. In some embodiments, B is selected from thiazole and thiophene. In some embodiments, B is thiazole. In some embodiments, C is selected from aryl and monocyclic heteroaryl. In some embodiments, C is selected from phenyl and pyridyl. In some embodiments, C is phenyl. In some embodiments, at least one $R^h$ has formula —$(CH_2)_rC(O)NR^iR^j$ or —$(CH_2)_sNR^kC(O)R^m$, wherein:

r and s are each independently selected from 0, 1, and 2;

$R^i$ and $R^k$ are each independently selected from hydrogen and $C_1$-$C_6$ alkyl;

$R^j$ is selected from $C_1$-$C_6$-alkyl, aryl, aryl-$C_1$-$C_6$-alkyl, heteroaryl, heteroaryl-$C_1$-$C_6$-alkyl, heterocyclyl, heterocyclyl-$C_1$-$C_6$-alkyl, cycloalkyl, and cycloalkyl-$C_1$-$C_6$-alkyl;

$R^m$ is selected from $C_1$-$C_6$-alkyl, aryl, aryl-$C_1$-$C_6$-alkyl, heteroaryl, heteroaryl-$C_1$-$C_6$-alkyl, heterocyclyl, heterocyclyl-$C_1$-$C_6$-alkyl, cycloalkyl, and cycloalkyl-$C_1$-$C_6$-alkyl, amino, $C_1$-$C_6$-alkylamino, arylamino, aryl-$C_1$-$C_6$-alkylamino;

wherein each alkyl, aryl, heteroaryl, heterocyclyl, and cycloalkyl is independently unsubstituted or substituted with 1 or 2 substituents independently selected from halo, $C_1$-$C_6$-alkyl, $C_1$-$C_6$-alkoxy, hydroxy, amino and oxo.

In some embodiments, L is a linker comprising one or more groups independently selected from methylene (—$CH_2$—), vinylene (—CH=CH—), acetylene (—C≡C—), ether (—O—), amine (—NH—), alkylamine (—NR—, wherein R is an optionally substituted $C_1$-$C_6$ alkyl group), amide (—C(O)NH—), ester (—C(O)O—), carbamate (—OC(O)NH—), sulfonamide (—S(O)$_2$NH—), phenylene (—$C_6H_4$—), heteroarylene, heterocyclylene, and any combination thereof.

In some embodiments, L is selected from:

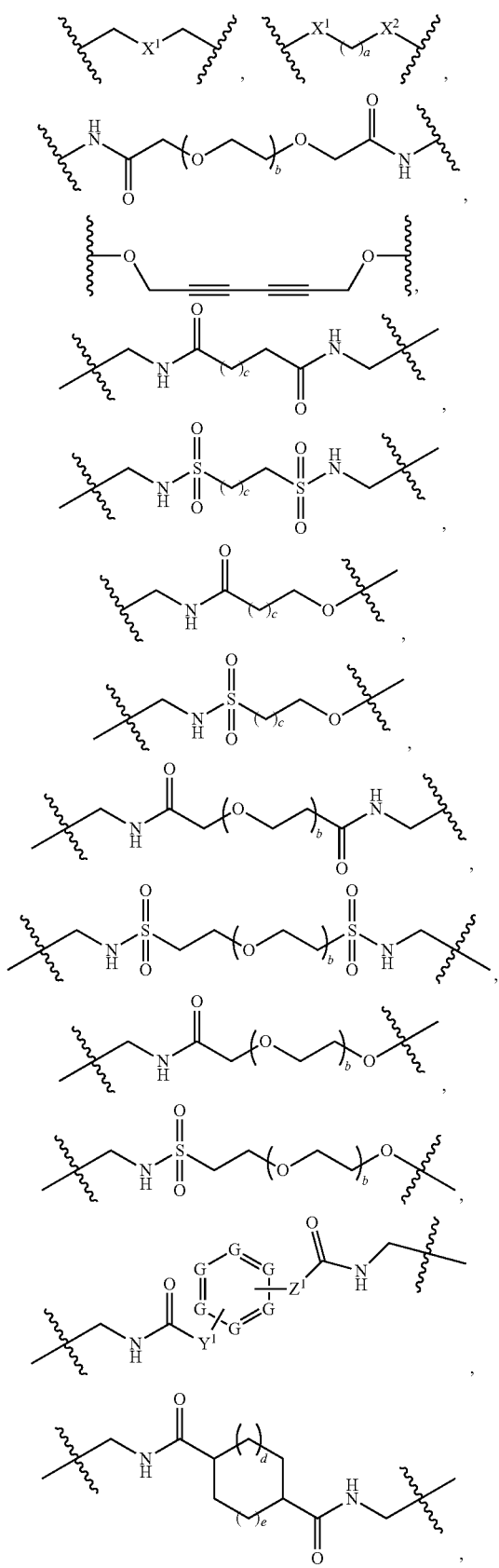
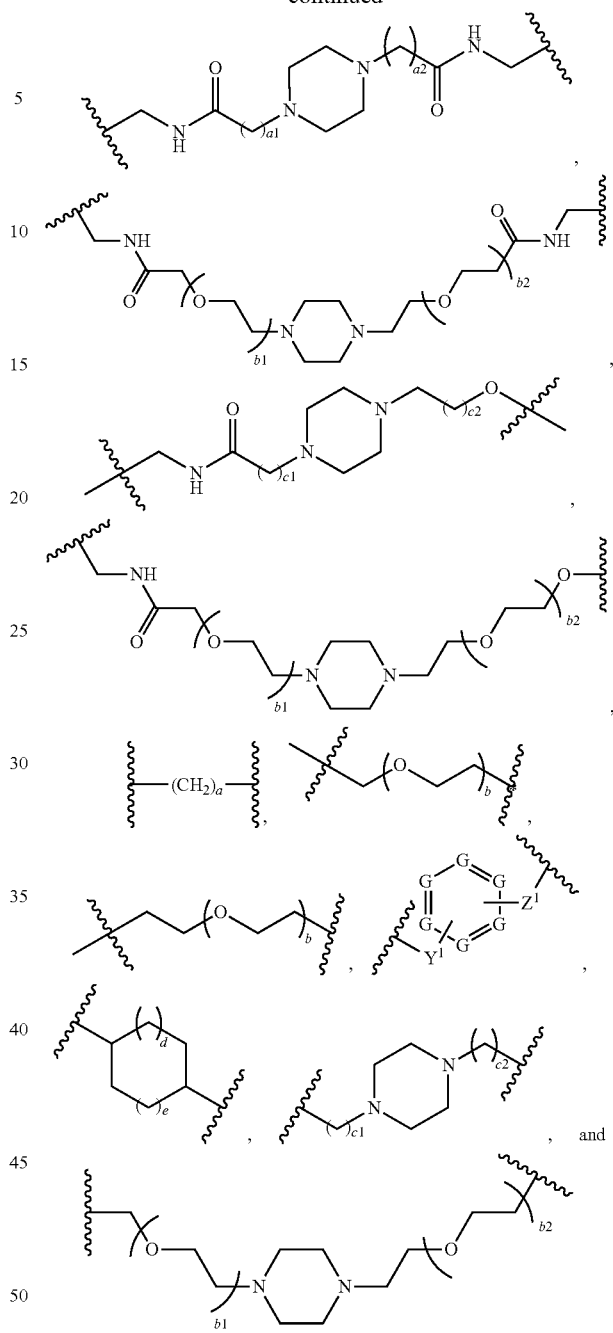

wherein a, a1, and a2 are each independently selected from 1, 2, 3, 4, 5, 6, 7, 8, 9, 10, 11, and 12; b, b1, and b2 are each independently selected from 0, 1, 2, 3, 4, 5, and 6; c, c1, and c2 are each independently selected from 0, 1, 2, 3, 4, 5, 6, 7, 8, 9, 10, 11, and 12; d and e are each independently selected form 0, 1, and 2; each G is independently selected from CH and N; $X^1$ and $X^2$ are each independently O or —$NR^x$—, wherein $R^x$ is hydrogen or optionally substituted alkyl; and $Y^1$ and $Z^1$ are each independently selected from —$CH_2$—, —NH—, and —O—.

The compounds can be synthesized in a variety of ways. For example, compounds of Formula (I) can be synthesized as shown in Schemes 1 and 2. Generally, the compounds can be synthesized by coupling appropriate amines with acids using suitable coupling agents, such as HATU. (In Schemes 1 and 2, HATU refers to (1-[bis(dimethylamino)methylene]-1H-1,2,3-triazolo[4,5-b]pyridinium 3-oxide hexafluorophosphate, DIPEA is N,N-diisopropylethylamine, DCM is dichloromethane, and Mt is a metal selected from Li, Na, K, or the like.)

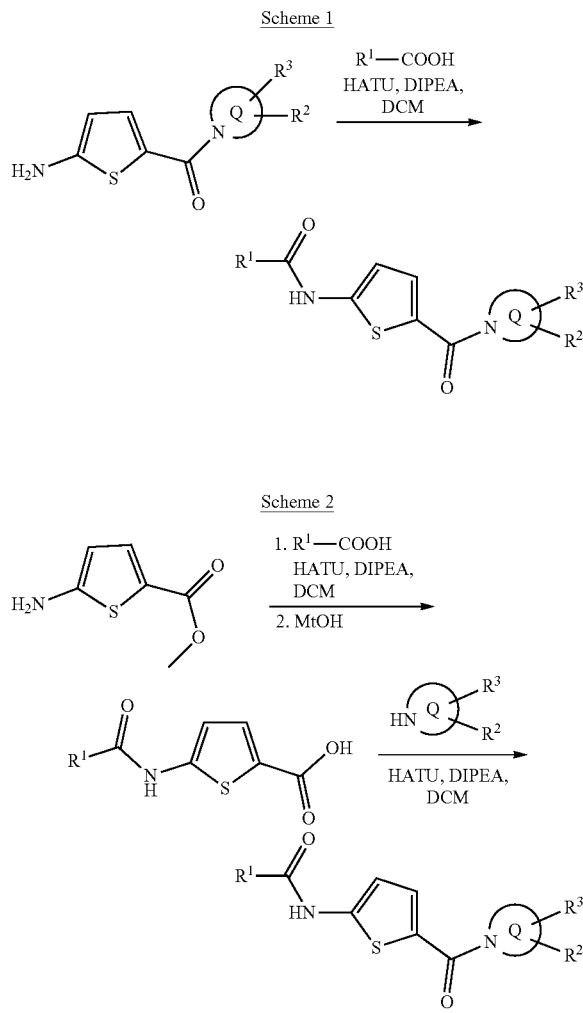

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry" 5th edition (1989), by Furniss, Hannaford, Smith, and Tatchell, pub. Longman Scientific & Technical, Essex CM20 2JE, England.

Reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the disclosure. Suitable protecting groups and the methods for protecting and deprotecting different substituents using such suitable protecting groups are well known to those skilled in the art; examples of which can be found in P G M Wuts and T W Greene, in Greene's book titled Protective Groups in Organic Synthesis (4$^{th}$ ed.), John Wiley & Sons, NY (2006), which is incorporated herein by reference in its entirety. Synthesis of the compounds of the disclosure can be accomplished by methods analogous to those described in the synthetic schemes described above and in specific examples described below.

The compounds described herein may in some cases exist as diastereomers, enantiomers, or other stereoisomeric forms. The compounds presented herein include all diastereomeric, enantiomeric, and stereoisomeric forms as well as the appropriate mixtures thereof. Separation of stereoisomers may be performed by chromatography or by the forming diastereomeric and separation by recrystallization, or chromatography, or any combination thereof. (Jean Jacques, Andre Collet, Samuel H. Wilen, "Enantiomers, Racemates and Resolutions", John Wiley And Sons, Inc., 1981, herein incorporated by reference for this disclosure). Stereoisomers may also be obtained by stereoselective synthesis.

In some embodiments, compounds may exist as tautomers. All tautomers are included within the formulas described herein.

Unless specified otherwise, divalent variables or groups described herein may be attached in the orientation in which they are depicted or they may be attached in the reverse orientation.

The methods and compositions described herein include the use of amorphous forms as well as crystalline forms (also known as polymorphs). The compounds described herein may be in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, etc. The solvated forms of the compounds presented herein are also considered to be disclosed herein.

In some embodiments, compounds or salts described herein may be prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

To produce a prodrug, a pharmaceutically active compound is modified such that the active compound will be regenerated upon in vivo administration. The prodrug can be designed to alter the metabolic stability or the transport characteristics of a drug, to mask side effects or toxicity, to improve the flavor of a drug or to alter other characteristics or properties of a drug. In some embodiments, by virtue of knowledge of pharmacodynamic processes and drug metabolism in vivo, once a pharmaceutically active compound is determined, prodrugs of the compound are designed. (see, for example, Nogrady (1985) *Medicinal Chemistry A Biochemical Approach*, Oxford University Press, New York, pages 388-392; Silverman (1992), The Organic Chemistry of Drug Design and Drug Action, Academic Press, Inc., San Diego, pages 352-401, Saulnier et al., (1994), *Bioorganic and Medicinal Chemistry Letters*, Vol. 4, p. 1985; Rooseboom et al., *Pharmacological Reviews*, 56:53-102, 2004; Miller et al., *J. Med. Chem.* Vol. 46, no. 24, 5097-5116, 2003; Aesop Cho, "Recent Advances in Oral Prodrug Discovery", *Annual Reports in Medicinal Chemistry*, Vol. 41, 395-407, 2006).

The compounds described herein may be labeled isotopically (e.g. with a radioisotope) or by other means, including, but not limited to, the use of chromophores or fluorescent moieties, bioluminescent labels, photoactivatable or chemiluminescent labels, affinity labels (e.g. biotin), etc.

Compounds and salts described herein include isotopically-labeled compounds. In general, isotopically-labeled compounds are identical to those recited in the various formulae and structures presented herein, but for the fact that one or more atoms are replaced by an atom having an atomic mass or mass number different from the atomic mass or mass number most common in nature. Examples of isotopes that can be incorporated into the present compounds include isotopes of hydrogen, carbon, nitrogen, oxygen, fluorine and chlorine, for example, $^{2}H$, $^{3}H$, $^{13}C$, $^{14}C$, $^{15}N$, $^{18}O$, $^{17}O$, $^{35}S$, $^{18}F$, or $^{36}Cl$. Certain isotopically-labeled compounds described herein, for example those into which radioactive isotopes such as $^{3}H$ and $^{14}C$ are incorporated, are useful in drug and/or substrate tissue distribution assays. Further, substitution with isotopes such as deuterium, i.e., $^{2}H$, can afford certain therapeutic advantages resulting from greater metabolic stability, such as, for example, increased in vivo half-life or reduced dosage requirements.

In additional or further embodiments, the compounds described herein are metabolized upon administration to an organism in need to produce a metabolite that is then used to produce a desired effect, including a desired therapeutic effect.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

In some embodiments, compounds described herein are in various forms, including but not limited to, amorphous forms, milled forms and nano-particulate forms. In addition, compounds described herein include crystalline forms, also known as polymorphs. Polymorphs include the different crystal packing arrangements of the same elemental composition of a compound. Polymorphs usually have different X-ray diffraction patterns, melting points, density, hardness, crystal shape, optical properties, stability, and solubility.

Various factors such as the recrystallization solvent, rate of crystallization, and storage temperature may cause a single crystal form to dominate.

The screening and characterization of the pharmaceutically acceptable salts, polymorphs and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning Calorimetry (MDCS), Thermogravimetric analysis (TGA), and Thermogravi-metric and Infrared analysis (TG/IR). X-ray diffraction methods include, but are not limited to, single crystal and powder diffractometers and synchrotron sources. The various spectroscopic techniques used include, but are not limited to, Raman, FTIR, UV-VIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

Pharmaceutical Compositions

In certain embodiments, a compound disclosed herein (e.g., a compound of formula (I), (IIa), (IIb), or (IIc)), or a pharmaceutically acceptable salt thereof, is combined with one or more additional agents to form a pharmaceutical composition. Pharmaceutical compositions may be formulated in a conventional manner using one or more physiologically acceptable carriers including excipients and auxiliaries that facilitate processing of the active compound into a preparation, which can be used pharmaceutically. Proper formulation is dependent upon the route of administration chosen. Additional details about suitable excipients for pharmaceutical compositions described herein may be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition, as used herein, refers to a mixture of a compound disclosed herein (e.g., a compound of formula (I), (IIa), (IIb), or (IIc)), or a pharmaceutically acceptable salt thereof, with other chemical components, such as carriers, stabilizers, diluents, dispersing agents, suspending agents, thickening agents, and/or excipients. The pharmaceutical composition facilitates administration of the compound to a subject. In practicing the methods of treatment or use provided herein, therapeutically effective amounts of compounds described herein are administered in a pharmaceutical composition to a subject having a disease, disorder, or condition to be treated (e.g., cancer). In some embodiments, the subject is a human. A therapeutically effective amount can vary widely depending on the severity of the disease, the age and relative health of the subject, the potency of the compound used and other factors. The compound or pharmaceutically acceptable salt thereof, can be used singly or in combination with one or more therapeutic agents as components of mixtures (as in combination therapy).

The pharmaceutical formulations described herein can be administered to a subject by multiple administration routes, including but not limited to, oral, parenteral (e.g., intravenous, subcutaneous, intramuscular), intranasal, buccal, topical, rectal, or transdermal administration routes. Moreover, the pharmaceutical compositions described herein, which include a compound disclosed herein (e.g., a compound of formula (Ia), (IIa), (IIb), or (IIc)), or a pharmaceutically acceptable salt thereof, can be formulated into any suitable dosage form, including but not limited to, aqueous oral dispersions, liquids, gels, syrups, elixirs, slurries, suspensions, aerosols, fast melt formulations, effervescent formulations, lyophilized formulations, tablets, powders, pills, dragees, and capsules.

One may administer the compounds and/or compositions in a local rather than systemic manner, for example, via injection of the compound directly into an organ or tissue, often in a depot preparation or sustained release formulation. Such long acting formulations may be administered by implantation (for example subcutaneously or intramuscularly) or by intramuscular injection. Furthermore, one may administer the drug in a targeted drug delivery system, for example, in a liposome coated with organ-specific antibody. The liposomes will be targeted to and taken up selectively by the organ. In addition, the drug may be provided in the form of a rapid release formulation, in the form of an extended release formulation, or in the form of an intermediate release formulation.

Pharmaceutical compositions including a compound described herein may be manufactured in a conventional manner, such as, by way of example only, by means of conventional mixing, dissolving, granulating, dragee-making, levigating, emulsifying, encapsulating, entrapping or compression processes.

In certain embodiments, compositions provided herein may also include one or more preservatives to inhibit microbial activity. Suitable preservatives include quaternary ammonium compounds such as benzalkonium chloride, cetyltrimethylammonium bromide and cetylpyridinium chloride.

Pharmaceutical preparations for oral use can be obtained by mixing one or more solid excipients with one or more of the compounds disclosed herein (e.g., a compound of formula (I), (IIa), (IIb), or (IIc)), or a pharmaceutically acceptable salt thereof, optionally grinding the resulting mixture, and processing the mixture of granules, after adding suitable auxiliaries, if desired, to obtain tablets, pills, or capsules. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents may be added, such as the cross-linked croscarmellose sodium, polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

In some embodiments, the solid dosage forms disclosed herein may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, solid solution, bio-erodible dosage form, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations of the compounds described herein may be administered as a single capsule or in multiple capsule dosage form. In some embodiments, the pharmaceutical formulation is administered in two, or three, or four, capsules or tablets.

In some embodiments, solid dosage forms, e.g., tablets, effervescent tablets, and capsules, are prepared by mixing particles of a compound disclosed herein (e.g., a compound of formula (I), (IIa), (IIb), or (IIc)), or a pharmaceutically acceptable salt thereof, with one or more pharmaceutical excipients to form a bulk blend composition. When referring to these bulk blend compositions as homogeneous, it is meant that the particles of the compound are dispersed evenly throughout the composition so that the composition may be subdivided into equally effective unit dosage forms, such as tablets, pills, and capsules. The individual unit dosages may also include film coatings, which disintegrate upon oral ingestion or upon contact with diluent. These formulations can be manufactured by conventional pharmacological techniques.

The pharmaceutical solid dosage forms described herein can include a compound disclosed herein (e.g., a compound of formula (I), (IIa), (IIb), or (IIc)), or a pharmaceutically acceptable salt thereof, and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in Remington's Pharmaceutical Sciences, 20th Edition (2000), a film coating is provided around the formulation of the compound described herein. In one embodiment, some or all of the particles of the compound described herein are coated. In another embodiment, some or all of the particles of the compound described herein are microencapsulated. In still another embodiment, the particles of the compound described herein are not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethycellulose phthalate, hydroxypropylmethylcellulose acetate stearate (HPMCAS), sucrose, xylitol, lactitol, mannitol, sorbitol, sodium chloride, polyethylene glycol, and the like.

In order to release the compound from a solid dosage form matrix as efficiently as possible, disintegrants are often used in the formulation, especially when the dosage forms are compressed with binder. Disintegrants help rupturing the dosage form matrix by swelling or capillary action when moisture is absorbed into the dosage form. Suitable disintegrants for use in the solid dosage forms described herein include, but are not limited to, natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Veegum®, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. In some embodiments, formulators determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumarate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 5400 to about 7000, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

There is considerable overlap between additives used in the solid dosage forms described herein. Thus, the above-listed additives should be taken as merely exemplary, and not limiting, of the types of additives that can be included in solid dosage forms of the pharmaceutical compositions described herein.

In other embodiments, one or more layers of the pharmaceutical formulation are plasticized. Illustratively, a plasticizer is generally a high boiling point solid or liquid. Suitable plasticizers can be added from about 0.01% to about 50% by weight (w/w) of the coating composition. Plasticizers include, but are not limited to, diethyl phthalate, citrate esters, polyethylene glycol, glycerol, acetylated glycerides, triacetin, polypropylene glycol, polyethylene glycol, triethyl citrate, dibutyl sebacate, stearic acid, stearol, stearate, and castor oil.

Compressed tablets are solid dosage forms prepared by compacting the bulk blend of the formulations described above. In various embodiments, compressed tablets which are designed to dissolve in the mouth will include one or more flavoring agents. In other embodiments, the compressed tablets will include a film surrounding the final compressed tablet. In some embodiments, the film coating aids in patient compliance (e.g., Opadry® coatings or sugar coating). Film coatings including Opadry® typically range from about 1% to about 3% of the tablet weight. In other embodiments, the compressed tablets include one or more excipients.

A capsule may be prepared, for example, by placing the bulk blend of the formulation of the compound described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule may be swallowed whole or the capsule may be opened and the contents sprinkled on food prior to eating. In some embodiments, the therapeutic dose is split into multiple (e.g., two, three, or four) capsules. In some embodiments, the entire dose of the formulation is delivered in a capsule form.

In various embodiments, the particles of the compound disclosed herein (e.g., a compound of formula (I), (IIa), (IIb), or (IIc), or a pharmaceutically acceptable salt thereof), and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In another aspect, dosage forms may include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Materials useful for the microencapsulation described herein include materials compatible with compounds described herein, which sufficiently isolate the compound from other non-compatible excipients.

In still other embodiments, effervescent powders are also prepared in accordance with the present disclosure. Effervescent salts have been used to disperse medicines in water for oral administration. Effervescent salts are granules or coarse powders containing a medicinal agent in a dry mixture, usually composed of sodium bicarbonate, citric acid and/or tartaric acid. When such salts are added to water, the acids and the base react to liberate carbon dioxide gas, thereby causing "effervescence." Examples of effervescent salts include, e.g., the following ingredients: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In other embodiments, the formulations described herein are solid dispersions. Methods of producing such solid dispersions include, but are not limited to, for example, U.S. Pat. Nos. 4,343,789, 5,340,591, 5,456,923, 5,700,485, 5,723,269, and U.S. patent publication no. 2004/0013734. In still other embodiments, the formulations described herein are solid solutions. Solid solutions incorporate a substance together with the active agent and other excipients such that heating the mixture results in dissolution of the drug and the resulting composition is then cooled to provide a solid blend which can be further formulated or directly added to a capsule or compressed into a tablet. Methods of producing such solid solutions include, but are not limited to, for example, U.S. Pat. Nos. 4,151,273, 5,281,420, and 6,083,518.

In some embodiments, pharmaceutical formulations are provided that include particles of the compound disclosed herein (e.g., a compound of formula (I), (IIa), (IIb), or (IIc)), or a pharmaceutically acceptable salt thereof, and at least one dispersing agent or suspending agent for oral administration to a subject. The formulations may be a powder and/or granules for suspension, and upon admixture with water, a substantially uniform suspension is obtained.

Liquid formulation dosage forms for oral administration can be aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002).

The aqueous suspensions and dispersions described herein can remain in a homogenous state, as defined in The USP Pharmacists' Pharmacopeia (2005 edition, chapter 905), for at least 4 hours. The homogeneity should be determined by a sampling method consistent with regard to determining homogeneity of the entire composition. In one embodiment, an aqueous suspension can be re-suspended into a homogenous suspension by physical agitation lasting less than 1 minute. In another embodiment, an aqueous suspension can be re-suspended into a homogenous suspension by physical agitation lasting less than 45 seconds. In yet another embodiment, an aqueous suspension can be re-suspended into a homogenous suspension by physical agitation lasting less than 30 seconds. In still another embodiment, no agitation is necessary to maintain a homogeneous aqueous dispersion.

The pharmaceutical compositions described herein may include sweetening agents such as, but not limited to, acacia syrup, acesulfame K, alitame, anise, apple, aspartame, banana, Bavarian cream, berry, black currant, butterscotch, calcium citrate, camphor, caramel, cherry, cherry cream, chocolate, cinnamon, bubble gum, citrus, citrus punch, citrus cream, cotton candy, cocoa, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, monoammonium glyrrhizinate (MagnaSweet®), maltol, mannitol, maple, marshmallow, menthol, mint cream, mixed berry, neohesperidine DC, neotame, orange, pear, peach, peppermint, peppermint cream, Prosweet® Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, sucralose, sorbitol, swiss cream, tagatose, tangerine, thaumatin, tutti fruitti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

In some embodiments, the pharmaceutical formulations described herein can be self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase can be added just prior to administration, which ensures stability of an unstable or hydrophobic active ingredient. Thus, the SEDDS provides an effective delivery system for oral and parenteral delivery of hydrophobic active ingredients. SEDDS may provide improvements in the bioavailability of hydrophobic active ingredients. Methods of producing self-emulsifying dosage forms include, but are not limited to, for example, U.S. Pat. Nos. 5,858,401, 6,667,048, and 6,960,563.

There is overlap between the above-listed additives used in the aqueous dispersions or suspensions described herein, since a given additive is often classified differently by different practitioners in the field, or is commonly used for any of several different functions. Thus, the above-listed additives should be taken as merely exemplary, and not limiting, of the types of additives that can be included in formulations described herein.

Potential excipients for intranasal formulations include, for example, U.S. Pat. Nos. 4,476,116, 5,116,817 and 6,391,452. Formulations solutions in saline, employing benzyl alcohol or other suitable preservatives, fluorocarbons, and/or other solubilizing or dispersing agents. See, for example, Ansel, H. C. et al., Pharmaceutical Dosage Forms and Drug Delivery Systems, Sixth Ed. (1995). Preferably these compositions and formulations are prepared with suitable non-toxic pharmaceutically acceptable ingredients. The choice of suitable carriers is highly dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents may also be present. Preferably, the nasal dosage form should be isotonic with nasal secretions.

For administration by inhalation, the compounds described herein may be in a form as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

Buccal formulations that include compounds described herein may be administered using a variety of formulations which include, but are not limited to, U.S. Pat. Nos. 4,229, 447, 4,596,795, 4,755,386, and 5,739,136. In addition, the buccal dosage forms described herein can further include a bioerodible (hydrolysable) polymeric carrier that also serves to adhere the dosage form to the buccal mucosa. The buccal dosage form is fabricated so as to erode gradually over a predetermined time period, wherein the delivery of the compound is provided essentially throughout. Buccal drug delivery avoids the disadvantages encountered with oral drug administration, e.g., slow absorption, degradation of the active agent by fluids present in the gastrointestinal tract and/or first-pass inactivation in the liver. With regard to the bioerodible (hydrolysable) polymeric carrier, virtually any such carrier can be used, so long as the desired drug release profile is not compromised, and the carrier is compatible with the compounds described herein, and any other components that may be present in the buccal dosage unit. Generally, the polymeric carrier comprises hydrophilic (water-soluble and water-swellable) polymers that adhere to the wet surface of the buccal mucosa. Examples of polymeric carriers useful herein include acrylic acid polymers and co, e.g., those known as "carbomers" (Carbopol®, which may be obtained from B.F. Goodrich, is one such polymer). Other components may also be incorporated into the buccal dosage forms described herein include, but are not limited to, disintegrants, diluents, binders, lubricants, flavoring, colorants, preservatives, and the like. For buccal or sublingual administration, the compositions may take the form of tablets, lozenges, or gels formulated in a conventional manner.

Transdermal formulations described herein may be administered using a variety of devices including but not limited to, U.S. Pat. Nos. 3,598,122, 3,598,123, 3,710,795, 3,731,683, 3,742,951, 3,814,097, 3,921,636, 3,972,995, 3,993,072, 3,993,073, 3,996,934, 4,031,894, 4,060,084, 4,069,307, 4,077,407, 4,201,211, 4,230,105, 4,292,299, 4,292,303, 5,336,168, 5,665,378, 5,837,280, 5,869,090, 6,923,983, 6,929,801 and 6,946,144.

The transdermal dosage forms described herein may incorporate certain pharmaceutically acceptable excipients which are conventional in the art. In one embodiment, the transdermal formulations described herein include at least three components: (1) a formulation of a compound disclosed herein (e.g., a compound of formula (I), (IIa), (IIb), or (IIc)), or a pharmaceutically acceptable salt thereof; (2) a penetration enhancer; and (3) an aqueous adjuvant. In addition, transdermal formulations can include additional components such as, but not limited to, gelling agents, creams and ointment bases, and the like. In some embodiments, the transdermal formulation can further include a woven or non-woven backing material to enhance absorption and prevent the removal of the transdermal formulation from the skin. In other embodiments, the transdermal formulations described herein can maintain a saturated or supersaturated state to promote diffusion into the skin.

Formulations suitable for transdermal administration of compounds described herein may employ transdermal delivery devices and transdermal delivery patches and can be lipophilic emulsions or buffered, aqueous solutions, dissolved and/or dispersed in a polymer or an adhesive. Such patches may be constructed for continuous, pulsatile, or on demand delivery of pharmaceutical agents. Still further, transdermal delivery of the compounds described herein can be accomplished by means of iontophoretic patches and the like. Additionally, transdermal patches can provide controlled delivery of the compounds described herein. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Formulations suitable for intramuscular, subcutaneous, or intravenous injection may include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Formulations suitable for subcutaneous injection may also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. It may also be desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections, compounds described herein may be formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally recognized in the field. For other parenteral injections, appropriate formulations may include aqueous or nonaqueous solutions, preferably with physiologically compatible buffers or excipients. Such excipients are generally recognized in the field.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active ingredient may be in powder form for constitution with a suitable vehicle, e.g., sterile pyrogen-free water, before use.

In certain embodiments, delivery systems for pharmaceutical compounds may be employed, such as, for example, liposomes and emulsions. In certain embodiments, compositions provided herein also include an mucoadhesive polymer, selected from among, for example, carboxymethylcellulose, carbomer (acrylic acid polymer), poly (methylmethacrylate), polyacrylamide, polycarbophil, acrylic acid/butyl acrylate copolymer, sodium alginate and dextran.

In some embodiments, the compounds described herein may be administered topically and are formulated into a variety of topically administrable compositions, such as solutions, suspensions, lotions, gels, pastes, medicated sticks, balms, creams or ointments. Such pharmaceutical compounds can contain solubilizers, stabilizers, tonicity enhancing agents, buffers and preservatives.

The compounds described herein may also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG, and the like. In suppository forms of the compositions, a low-melting wax such as, but not limited to, a mixture of fatty acid glycerides, optionally in combination with cocoa butter is first melted.

Generally, an agent, such as a compound disclosed herein (e.g., a compound of formula (I), (IIa), (IIb), or (IIc) or a pharmaceutically acceptable salt thereof), is administered in an amount effective for amelioration of, or prevention of the development of symptoms of, the disease or disorder (i.e., a therapeutically effective amount). Thus, a therapeutically effective amount can be an amount that is capable of at least partially preventing or reversing a disease or disorder. The dose required to obtain an effective amount may vary depending on the agent, formulation, disease or disorder, and individual to whom the agent is administered.

Determination of effective amounts may also involve in vitro assays in which varying doses of agent are administered to cells in culture and the concentration of agent effective for ameliorating some or all symptoms is determined in order to calculate the concentration required in vivo. Effective amounts may also be based in in vivo animal studies.

An agent can be administered prior to, concurrently with and subsequent to the appearance of symptoms of a disease or disorder. In some embodiments, an agent is administered to a subject with a family history of the disease or disorder, or who has a phenotype that may indicate a predisposition to a disease or disorder, or who has a genotype which predisposes the subject to the disease or disorder.

In some embodiments, the compositions described herein are provided as pharmaceutical and/or therapeutic compositions. The pharmaceutical and/or therapeutic compositions of the present invention can be administered in a number of ways depending upon whether local or systemic treatment is desired and upon the area to be treated. Administration can be topical (including ophthalmic and to mucous membranes including vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Compositions and formulations for topical administration can include transdermal patches, ointments, lotions, creams, gels, drops, suppositories, sprays, liquids and powders. Conventional carriers; aqueous, powder, or oily bases; thickeners; and the like can be necessary or desirable. Compositions and formulations for oral administration include powders or granules, suspensions or solutions in water or non-aqueous media, capsules, sachets or tablets. Thickeners, flavoring agents, diluents, emulsifiers, dispersing aids or binders can be desirable. Compositions and formulations for parenteral, intrathecal or intraventricular administration can include sterile aqueous solutions that can also contain buffers, diluents and other suitable additives such as, but not limited to, penetration enhancers, carrier compounds and other pharmaceutically acceptable carriers or excipients. Pharmaceutical and/or therapeutic compositions of the present invention include, but are not limited to, solutions, emulsions, and liposome containing formulations. These compositions can be generated from a variety of components that include, but are not limited to, preformed liquids, self-emulsifying solids and self-emulsifying semisolids.

The pharmaceutical and/or therapeutic formulations, which can conveniently be presented in unit dosage form, can be prepared according to conventional techniques well known in the pharmaceutical/nutriceutical industries. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product. The compositions of the present invention can be formulated into any of many possible dosage forms such as, but not limited to, tablets, capsules, liquid syrups, soft gels, suppositories, and enemas. The compositions of the present invention can also be formulated as suspensions in aqueous, non-aqueous, oil-based, or mixed media. Suspensions can further contain substances that increase the viscosity of the suspension including, for example, sodium carboxymethylcellulose, sorbitol and/or dextran. The suspension can also contain stabilizers. In one embodiment of the present invention the pharmaceutical compositions can be formulated and used as foams. Pharmaceutical foams include formulations such as, but not limited to, emulsions, microemulsions, creams, jellies and liposomes. While basically similar in nature these formulations vary in the components and the consistency of the final product.

The pharmaceutical composition described herein may be in unit dosage forms suitable for single administration of precise dosages. In unit dosage form, the formulation is divided into unit doses containing appropriate quantities of one or more compound. The unit dosage may be in the form of a package containing discrete quantities of the formulation. Non-limiting examples are packaged tablets or capsules, and powders in vials or ampoules. Aqueous suspension compositions can be packaged in single-dose non-reclosable containers. Alternatively, multiple-dose reclosable containers can be used, in which case it is typical to include a preservative in the composition. By way of example only, formulations for parenteral injection may be presented in unit dosage form, which include, but are not limited to ampoules, or in multi-dose containers, with an added preservative.

Dosing and administration regimes are tailored by the clinician, or others skilled in the pharmacological arts, based upon well-known pharmacological and therapeutic considerations including, but not limited to, the desired level of therapeutic effect, and the practical level of therapeutic effect obtainable. Generally, it is advisable to follow well-known pharmacological principles for administrating chemotherapeutic agents (e.g., it is generally advisable to not change dosages by more than 50% at time and no more than every 3-4 agent half-lives). For compositions that have relatively little or no dose-related toxicity considerations, and where maximum efficacy is desired, doses in excess of the average required dose are not uncommon. This approach to dosing is commonly referred to as the "maximal dose" strategy. In certain embodiments, the compounds are administered to a subject at a dose of about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone. Dosing may be once per day or multiple times per day for one or more consecutive days.

Methods of Use/Treatment

The present disclosure provides methods of using the compounds and compositions described herein (e.g., compounds of formula (I), (IIa), (IIb), and (IIc), or pharmaceutically acceptable salts thereof). The methods include methods of inhibiting GAS41 and methods of treating diseases such as cancer.

In certain embodiments, the disclosure provides a method of inhibiting GAS41 activity in a sample, comprising contacting the sample with an effective amount a compound described herein or a pharmaceutically acceptable salt thereof (e.g., a compound of formula (I), (IIa), (IIb), or (IIc), or a pharmaceutically acceptable salt thereof). The sample may be an in vitro or ex vivo sample (e.g., a sample comprising cells, tissue, or an organ).

In some embodiments, the disclosure provides a method of inhibiting GAS41 activity by contacting the GAS41 with an effective amount of a compound described herein or a pharmaceutically acceptable salt thereof (e.g., a compound of formula (I), (IIa), (IIb), or (IIc), or a pharmaceutically acceptable salt thereof), e.g., by contacting a cell, tissue, or organ that expresses GAS41 with the compound or the salt thereof. In some embodiments, the disclosure provides a method of inhibiting GAS41 activity in subject (including but not limited to rodents and mammals, e.g., humans), by administering into the subject an effective amount of a compound described herein or a pharmaceutically acceptable salt thereof (e.g., a compound of formula (I), (IIa), (IIb), or (IIc), or a pharmaceutically acceptable thereof). In some embodiments, the percentage inhibition exceeds 25%, 30%, 40%, 50%, 60%, 70%, 80%, or 90%.

In some embodiments, the disclosure provides methods of inhibiting GAS41 activity in a cell, comprising contacting the cell with an amount of a compound described herein (e.g., a compound of formula (I), (IIa), (IIb), or (IIc), or a pharmaceutically acceptable salt thereof) sufficient to inhibit the activity. In some embodiments, the disclosure provides methods of inhibiting GAS41 activity in a tissue by contacting the tissue with an amount of a compound described herein or a pharmaceutically acceptable salt thereof (e.g., a compound of formula (I), (IIa), (IIb), or (IIc), or a pharmaceutically acceptable salt thereof), sufficient to inhibit the GAS41 activity in the tissue. In some embodiments, the disclosure provides methods of inhibiting GAS41 activity in an organism (e.g., mammal, human, etc.) by contacting the organism with an amount of a compound described herein or a pharmaceutically acceptable salt thereof (e.g., a compound of formula (I), (IIa), (IIb), or (IIc), or a pharmaceutically acceptable salt thereof), sufficient to inhibit GAS41 activity in the organism.

Inhibition of GAS41 activity may be assessed and demonstrated by a wide variety of ways known in the art. Non-limiting examples include measure (a) a direct decrease in GAS41 activity; (b) a decrease in cell proliferation and/or cell viability; (c) an increase in cell differentiation; (d) a decrease in the levels of downstream targets of GAS41 activity; and (e) decrease in tumor volume and/or tumor volume growth rate. Kits and commercially available assays can be utilized for determining one or more of the above.

The disclosure also provides methods for treating cancer in a subject in need thereof (e.g., a subject suffering from cancer), comprising administering a compound or pharmaceutical composition described herein (e.g., a compound of formula (I), (IIa) or (IIb) or a pharmaceutically acceptable salt thereof, or a pharmaceutical composition comprising a compound of formula (I), (IIa) or (IIb) or a pharmaceutically acceptable salt thereof) to the subject. In certain embodiments, the cancer is associated with GAS41 expression (e.g., aberrant expression, overexpression, etc.) and/or activity. In certain embodiments, the cancer is brain cancer (e.g., an astrocytoma or glioblastoma), a sarcoma, colorectal cancer, lung cancer (e.g., non-small cell lung cancer), or gastric cancer.

In certain embodiments, the disclosure provides a method of treating cancer in a subject, wherein the method comprises determining if the subject has a GAS41-mediated cancer, and administering to the subject a therapeutically effective amount of a compound described herein or a pharmaceutically acceptable salt thereof (e.g., a compound of formula (I), (IIa), (IIb), or (IIc), or a pharmaceutically acceptable salt thereof).

Determining whether a tumor or cancer expresses (e.g., overexpresses, aberrantly expresses, etc.) GAS41 can be undertaken by assessing the nucleotide sequence encoding GAS41 or by assessing the amino acid sequence of GAS41. Methods for detecting a GAS41 nucleotide sequence are known by those of skill in the art. These methods include, but are not limited to, polymerase chain reaction-restriction fragment length polymorphism (PCR-RFLP) assays, polymerase chain reaction-single strand conformation polymorphism (PCR-SSCP) assays, real-time PCR assays, PCR sequencing, mutant allele-specific PCR amplification (MASA) assays, direct sequencing, primer extension reactions, electrophoresis, oligonucleotide ligation assays, hybridization assays, TaqMan assays, SNP genotyping assays, high resolution melting assays, and microarray analyses. Methods for detecting a GAS41 protein are known by those of skill in the art. These methods include, but are not limited to, detection using a binding agent, e.g., an antibody specific for GAS41, protein electrophoresis and Western blotting, and direct peptide sequencing.

Methods for determining whether a tumor or cancer expresses (e.g., overexpresses, aberrantly expresses, etc.) GAS41 or is mediated by GAS41 activity can use a variety of samples. In some embodiments, the sample is taken from a subject having a cancer or tumor. In some embodiments, the sample is a fresh tumor/cancer sample. In some embodiments, the sample is a frozen tumor/cancer sample. In some embodiments, the sample is a formalin-fixed paraffin-embedded sample. In some embodiments, the sample is processed to a cell lysate. In some embodiments, the sample is processed to DNA or RNA.

The disclosure also relates to a method of treating a hyperproliferative disorder in a mammal that comprises administering to the mammal a therapeutically effective amount of a compound described herein or a pharmaceutically acceptable salt thereof (e.g., a compound of formula (I), (IIa), (IIb), or (IIc), or a pharmaceutically acceptable salt thereof). In some embodiments, the method relates to the treatment of cancer such as acute myeloid leukemia, cancer in adolescents, adrenocortical carcinoma childhood, AIDS-related cancers, e.g., Lymphoma and Kaposi's Sarcoma, anal cancer, angiosarcoma, appendix cancer, astrocytomas, atypical teratoid rhabdoid tumor, basal cell carcinoma, bile duct cancer, bladder cancer, bone cancer, brain stem glioma, brain tumor, breast cancer, bronchial tumors, Burkitt lymphoma, carcinoid tumor, chondrosarcoma, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myeloproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, epithelioid sarcoma, esophageal cancer, esthesioneuroblastoma, Ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, glioblastoma, hairy cell leukemia, head and neck cancer, heart cancer, liver cancer, Hodgkin lymphoma, hypopharyngeal cancer, intraocular melanoma, islet cell tumors, pancreatic neuroendocrine tumors, kidney cancer, laryngeal cancer, leiomyosarcoma, lip and oral cavity cancer, liposarcoma, liver cancer, lobular carcinoma in situ (LCIS), lung cancer, lymphoma, metastatic squamous neck cancer with occult primary, midline tract carcinoma, mouth cancer, multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, myxofibrosarcoma, nasal cavity and paranasal sinus cancer, nasopharyngeal cancer, neuroblastoma, non-Hodgkin lymphoma, non-small cell lung cancer (NSCLC), oral cancer, lip and oral cavity cancer, oropharyngeal cancer, osteosarcoma, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, synovial sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some embodiments, the method relates to the treatment of a non-cancerous hyperproliferative disorder such as benign hyperplasia of the skin, e.g., psoriasis, restenosis, or prostate, e.g., benign prostatic hypertrophy (BPH). In some embodiments, the method relates to the treatment of brain cancer (e.g., astrocytoma or glioblastoma), a sarcoma, colorectal cancer, lung cancer (e.g., non-small cell lung cancer), or gastric cancer.

Subjects that can be treated with compounds of the disclosure according to the methods of this disclosure include, for example, subjects that have been diagnosed as having acute myeloid leukemia, cancer in adolescents, adrenocortical carcinoma childhood, AIDS-related cancers, e.g., Lymphoma and Kaposi's Sarcoma, anal cancer, angiosarcoma, appendix cancer, astrocytomas, atypical teratoid rhabdoid tumor, basal cell carcinoma, bile duct cancer, bladder cancer, bone cancer, brain stem glioma, brain tumor, breast cancer, bronchial tumors, Burkitt lymphoma, carcinoid tumor, chondrosarcoma, embryonal tumors, germ cell tumor, primary lymphoma, cervical cancer, childhood cancers, chordoma, cardiac tumors, chronic lymphocytic leukemia (CLL), chronic myelogenous leukemia (CML), chronic myleoproliferative disorders, colon cancer, colorectal cancer, craniopharyngioma, cutaneous T-cell lymphoma, extrahepatic ductal carcinoma in situ (DCIS), embryonal tumors, CNS cancer, endometrial cancer, ependymoma, epithelioid sarcoma, esophageal cancer, esthesioneuroblastoma, Ewing sarcoma, extracranial germ cell tumor, extragonadal germ cell tumor, eye cancer, fibrous histiocytoma of bone, gall bladder cancer, gastric cancer, gastrointestinal carcinoid tumor, gastrointestinal stromal tumors (GIST), germ cell tumor, gestational trophoblastic tumor, glioblastoma, hairy cell leukemia, head and neck cancer, heart cancer, liver cancer, Hodgkin lymphoma, hypopharyngeal cancer, intraocular melanoma, islet cell tumors, pancreatic neuroendocrine tumors, kidney cancer, laryngeal cancer, leiomyosarcoma, lip and oral cavity cancer, liposarcoma, liver cancer, lobular carcinoma in situ (LCIS), lung cancer, lymphoma, metastatic squamous neck cancer with occult primary, midline tract carcinoma, mouth cancer, multiple endocrine neoplasia syndromes, multiple myeloma/plasma cell neoplasm, mycosis fungoides, myelodysplastic syndromes, myelodysplastic/myeloproliferative neoplasms, multiple myeloma, merkel cell carcinoma, malignant mesothelioma, malignant fibrous histiocytoma of bone and osteosarcoma, myxofibrosarcoma, nasal cavity and paranasal sinus cancer, nasopharyngeal cancer, neuroblastoma, non-Hodgkin lymphoma, non-small cell lung cancer (NSCLC), oral cancer, lip and oral cavity cancer, oropharyngeal cancer, osteosarcoma, ovarian cancer, pancreatic cancer, papillomatosis, paraganglioma, paranasal sinus and nasal cavity cancer, parathyroid cancer, penile cancer, pharyngeal cancer, pleuropulmonary blastoma, primary central nervous system (CNS) lymphoma, prostate cancer, rectal cancer, transitional cell cancer, retinoblastoma, rhabdomyosarcoma, salivary gland cancer, skin cancer, stomach (gastric) cancer, small cell lung cancer, small intestine cancer, soft tissue sarcoma, synovial sarcoma, T-Cell lymphoma, testicular cancer, throat cancer, thymoma and thymic carcinoma, thyroid cancer, transitional cell cancer of the renal pelvis and ureter, trophoblastic tumor, unusual cancers of childhood, urethral cancer, uterine sarcoma, vaginal cancer, vulvar cancer, or Viral-Induced cancer. In some embodiments, the method relates to the treatment of a non-cancerous hyperproliferative disorder such as benign hyperplasia of the skin, e.g., psoriasis, restenosis, or prostate, e.g., benign prostatic hypertrophy (BPH). In some embodiments, the subject has been diagnosed with brain cancer (e.g., astrocytoma or glioblastoma), a sarcoma, colorectal cancer, lung cancer (e.g., non-small cell lung cancer), or gastric cancer The compositions containing the compounds or salts thereof described herein can be administered for prophylactic and/or therapeutic treatments. In therapeutic applications, the compounds or compositions are administered to a patient already suffering from a disease, in an amount sufficient to cure or at least partially arrest the symptoms of the disease. Amounts effective for this use will depend on the severity and course of the disease, previous therapy, the patient's health status, weight, and response to the drugs, and the judgment of the treating clinician.

In prophylactic applications, compositions containing the compounds or salts thereof described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating clinician.

In the case wherein the patient's condition does not improve, upon the clinician's discretion the administration of the compounds may be administered chronically, that is, for an extended period of time, including throughout the duration of the patient's life in order to ameliorate or otherwise control or limit the symptoms of the patient's disease.

In the case wherein the patient's status does improve, upon the clinician's discretion the administration of the compounds may be given continuously; alternatively, the dose of drug being administered may be temporarily reduced or temporarily suspended for a certain length of time (i.e., a "drug holiday"). The length of the drug holiday can vary between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday may be from about 10% to about 100%, including, by way of example only, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

The amount of a given agent that will correspond to such an amount will vary depending upon factors such as the particular compound, disease and its severity, the identity (e.g., weight) of the subject or host in need of treatment, but can nevertheless be determined in a manner recognized in the field according to the particular circumstances surrounding the case, including, e.g., the specific agent being administered, the route of administration, the condition being treated, and the subject or host being treated. In general, however, doses employed for adult human treatment will typically be in the range of about 0.02-about 5000 mg per day, in some embodiments, about 1-about 1500 mg per day. The desired dose may conveniently be presented in a single dose or as divided doses administered simultaneously (or over a short period of time) or at appropriate intervals, for example as two, three, four or more sub-doses per day.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Combination Therapies

Provided herein are methods for combination therapies in which an agent known to modulate other pathways, or other components of the same pathway, or even overlapping sets of target enzymes are used in combination with a compound described herein or a pharmaceutically acceptable salt thereof (e.g., a compound of formula (I), (IIa), (IIb), or (IIc), or a pharmaceutically acceptable salt thereof). In one aspect, such therapy includes but is not limited to the combination of one or more compounds of the disclosure with chemotherapeutic agents, targeted agents, therapeutic antibodies, and/or radiation treatment, to provide a synergistic or additive therapeutic effect.

In general, the compounds and compositions described herein and, in embodiments where combinational therapy is employed, other agents do not have to be administered in the same pharmaceutical composition, and may, because of different physical and chemical characteristics, have to be administered by different routes. The determination of the mode of administration and the advisability of administration, where possible, in the same pharmaceutical composition, is well within the knowledge of the clinician. The initial administration can be made according to established protocols recognized in the field, and then, based upon the observed effects, the dosage, modes of administration and times of administration can be modified by the clinician.

In certain instances, it may be appropriate to administer at least one compound described herein in combination with another therapeutic agent. By way of example only, if one of the side effects experienced by a patient upon receiving a compound described herein (e.g., a compound of formula (I), (IIa), (IIb), or (IIc), or a pharmaceutically acceptable salt thereof), is nausea, then it may be appropriate to administer an anti-nausea agent in combination with the initial therapeutic agent. Or, by way of example only, the therapeutic effectiveness of one of the compounds described herein may be enhanced by administration of an adjuvant (i.e., by itself the adjuvant may have minimal therapeutic benefit, but in combination with another therapeutic agent, the overall therapeutic benefit to the patient is enhanced). Or, by way of example only, the benefit experienced by a patient may be increased by administering one of the compounds described herein with another therapeutic agent (which also includes a therapeutic regimen) that also has therapeutic benefit. In any case, regardless of the disease, disorder or condition being treated, the overall benefit experienced by the patient may simply be additive of the two therapeutic agents or the patient may experience a synergistic benefit.

The particular choice of compounds used will depend upon the diagnosis and judgment of the condition of the patient and the appropriate treatment protocol. The compounds may be administered concurrently (e.g., simultaneously, essentially simultaneously or within the same treatment protocol) or sequentially, depending upon the nature of the disease, disorder, or condition, the condition of the patient, and the actual choice of compounds used. The determination of the order of administration, and the number of repetitions of administration of each therapeutic agent during a treatment protocol, is well within the knowledge of the clinician after evaluation of the disease being treated and the condition of the patient.

Therapeutically-effective dosages can vary when the drugs are used in treatment combinations. Methods for experimentally determining therapeutically-effective dosages of drugs and other agents for use in combination treatment regimens are described in the literature. For example, the use of metronomic dosing, i.e., providing more frequent, lower doses in order to minimize toxic side effects, has been described extensively in the literature. Combination treatment further includes periodic treatments that start and stop at various times to assist with the clinical management of the patient.

For combination therapies described herein, dosages of the co-administered compounds will of course vary depending on the type of co-drug employed, on the specific drug employed, on the disease being treated and so forth. In addition, when co-administered with one or more biologically active agents, the compound provided herein may be administered either simultaneously with the biologically active agent(s), or sequentially. If administered sequentially, the attending physician will decide on the appropriate sequence of administering protein in combination with the biologically active agent(s).

In any case, the multiple therapeutic agents (one of which is a compound described herein or a pharmaceutically acceptable salt thereof (e.g., a compound of formula (I), (IIa), (IIb), or (IIc), or a pharmaceutically acceptable salt thereof)), may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may vary from more than zero weeks to less than four weeks. In addition, the combination methods, compositions and formulations are not to be limited to the use of only two agents; the use of multiple therapeutic combinations are also envisioned.

It is understood that the dosage regimen to treat, prevent, or ameliorate the condition(s) for which relief is sought, can be modified in accordance with a variety of factors. These factors include the disorder or condition from which the subject suffers, as well as the age, weight, sex, diet, and medical condition of the subject. Thus, the dosage regimen actually employed can vary widely and therefore can deviate from the dosage regimens set forth herein.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration. The two-step administration regimen may call for sequential administration of the active agents or spaced-apart administration of the separate active agents. The time period between the multiple administration steps may range from, a few minutes to several hours, depending upon the properties of each pharmaceutical agent, such as potency, solubility, bioavailability, plasma half-life and kinetic profile of the pharmaceutical agent. Circadian variation of the target molecule concentration may also determine the optimal dose interval.

In addition, the compounds described herein also may be used in combination with procedures that may provide additional or synergistic benefit to the patient. By way of example only, patients are expected to find therapeutic and/or prophylactic benefit in the methods described herein, wherein pharmaceutical composition of a compound disclosed herein and/or combinations with other therapeutics are combined with genetic testing to determine whether that individual is a carrier of a mutant gene that is known to be correlated with certain diseases or conditions.

The compounds described herein and combination therapies can be administered before, during or after the occurrence of a disease, and the timing of administering the composition containing a compound can vary. Thus, for example, the compounds can be used as a prophylactic and can be administered continuously to subjects with a propensity to develop conditions or diseases in order to prevent the occurrence of the disease. The compounds and compositions can be administered to a subject during or as soon as possible after the onset of the symptoms. The administration of the compounds can be initiated within the first 48 hours of the onset of the symptoms, preferably within the first 48 hours of the onset of the symptoms, more preferably within the first 6 hours of the onset of the symptoms, and most preferably within 3 hours of the onset of the symptoms. The initial administration can be via any route practical, such as, for example, an intravenous injection, a bolus injection, infusion over about 5 minutes to about 5 hours, a pill, a capsule, transdermal patch, buccal delivery, and the like, or combination thereof. A compound is preferably administered as soon as is practicable after the onset of a disease is detected or suspected, and for a length of time necessary for the treatment of the disease, such as, for example, from 1 day to about 3 months. The length of treatment can vary for each subject, and the length can be determined using the known criteria. For example, the compound or a formulation containing the compound can be administered for at least 2 weeks, preferably about 1 month to about 5 years.

Compounds and pharmaceutical compositions disclosed herein may be co-administered with one or more chemotherapeutics. Many chemotherapeutics are presently known in the art and can be used in combination with the compounds herein. In some embodiments, the chemotherapeutic is selected from the group consisting of mitotic inhibitors, alkylating agents, anti-metabolites, intercalating antibiotics, growth factor inhibitors, cell cycle inhibitors, enzyme inhibitors, topoisomerase inhibitors, protein-protein interaction inhibitors, biological response modifiers, anti-hormones, angiogenesis inhibitors, and anti-androgens.

Non-limiting examples are chemotherapeutic agents, cytotoxic agents, and non-peptide small molecules such as Gleevec® (Imatinib Mesylate), Velcade® (bortezomib), Casodex (bicalutamide), Iressa® (gefitinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen, (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO). Where desired, the compounds or pharmaceutical composition of the present invention can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris(2-chloroethyl)amine, Troxacitabine, Uramustine, Vadimezan, Vinflunine, ZD6126 or Zosuquidar.

Embodiments herein further relate to methods for using a compound disclosed herein (e.g., a compound of formula (I), (IIa), (IIb), or (IIc), or a pharmaceutically acceptable salt thereof), or a pharmaceutical composition provided herein, in combination with radiation therapy for inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

The compounds or pharmaceutical compositions herein are also used in combination with an amount of one or more substances selected from anti-angiogenesis agents, signal transduction inhibitors, antiproliferative agents, glycolysis inhibitors, or autophagy inhibitors.

Anti-angiogenesis agents, such as MMP-2 (matrix-metalloproteinase 2) inhibitors, MMP-9 (matrix-metalloproteinase 9) inhibitors, and COX-11 (cyclooxygenase 11) inhibitors, can be used in conjunction with a compound of the disclosure and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or AMP-9 relative to the other matrix-metalloproteinases (e.g., MAP-1, MMP-3, MMP-4, MMP-5, MMP-6, MMP-7, MMP-8, MMP-10, MMP-ll, MMP-12, and MMP-13). Some specific examples of MMP inhibitors useful in the invention are AG-3340, RO 32-3555, and RS 13-0830.

Autophagy inhibitors include, but are not limited to chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, N6-mercaptopurine riboside, and vinblastine. In addition, antisense or siRNA that inhibits expression of proteins including but not limited to ATG5 (which are implicated in autophagy), may also be used.

In some embodiments, the compounds described herein are formulated or administered in conjunction with liquid or solid tissue barriers also known as lubricants. Examples of tissue barriers include, but are not limited to, polysaccharides, polyglycans, seprafilm, interceed and hyaluronic acid.

In some embodiments, medicaments which are administered in conjunction with the compounds described herein include any suitable drugs usefully delivered by inhalation for example, analgesics, e.g., codeine, dihydromorphine, ergotamine, fentanyl or morphine; anginal preparations, e.g., diltiazem; antiallergics, e.g., cromoglycate, ketotifen or nedocromil; anti-infectives, e.g., cephalosporins, penicillins, streptomycin, sulphonamides, tetracyclines or pentamidine; antihistamines, e.g., methapyrilene; anti-inflammatories, e.g., beclomethasone, flunisolide, budesonide, tipredane, triamcinolone acetonide or fluticasone; antitussives, e.g., noscapine; bronchodilators, e.g., ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g., amiloride; anticholinergics e.g., ipratropium, atropine or oxitropium; hormones, e.g., cortisone, hydrocortisone or prednisolone; xanthines e.g., aminophylline, choline theophyllinate, lysine theophyllinate or theophylline; and therapeutic proteins and peptides, e.g., insulin or glucagon. It will be clear to a person skilled in the art that, where appropriate, the medicaments are used in the form of salts (e.g., as alkali metal or amine salts or as acid addition salts) or as esters (e.g., lower alkyl esters) or as solvates (e.g., hydrates) to optimize the activity and/or stability of the medicament.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Other suitable therapeutic agents for coadministration with compounds herein also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated for co-administration with compounds and compositions herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated for co-administration with compounds and compositions herein include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, β-lactam antibiotics, an agent comprising an aminoglycoside, protein synthesis inhibitors, drugs used in the chemotherapy of tuberculosis, *Mycobacterium avium* complex disease, and leprosy, antifungal agents, antiviral agents including nonretroviral agents and antiretroviral agents.

Examples of therapeutic antibodies that can be combined with a compound herein include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

Further therapeutic agents that can be combined with a compound herein are found in Goodman and Gilman's "The Pharmacological Basis of Therapeutics" Tenth Edition edited by Hardman, Limbird and Gilman or the Physician's Desk Reference, both of which are incorporated herein by reference in their entirety.

In some embodiments, a compound described herein is co-administered with another therapeutic agent effective in treating brain cancer, such as glioblastoma or astrocytoma. In some embodiments, the other therapeutic agent may be bevacizumab, carmustine (e.g., carmustine wafer), cisplatin, everolimus, lomustine, procarbazine, temozolomide, vincristine, or any combination thereof (e.g., a combination of procarbazine hydrochloride, lomustine, and vincristine sulfate).

In some embodiments, a compound described herein is co-administered with one or more therapeutic agents approved for the treatment of a sarcoma, such as adriamycin, bevacizumab, carboplatin, cisplatin, cyclophosphamide, dacarbazine, dactinomycin, docetaxel, doxorubicin (e.g., doxorubicin hydrochloride liposome), epirubicin, eribulin, etoposide, gemcitabine, ifosfamide, imatinib, ixabepilone, methotrexate, paclitaxel, pazopanib, pomalidomide, recombinant interferon alfa-2b, tazemetostat, temozolomide, topotecan, trabectedin, vinblastine, vincristine, vinorelbine, or any combination thereof.

In some embodiments, a compound described herein is co-administered with one or more therapeutic agents approved for the treatment of colorectal cancer, such as 5-fluorouracil, bevacizumab, capecitabine, cetuximab, ipilmumab, irinotecan, leucovorin, nivolumab, oxaliplatin, panitumumab, pembrolizumab, ramucirumab, regorafenib, tipiracil, trifluridine, ziv-afibercept, or any combination thereof.

In some embodiments, a compound described herein is co-administered with one or more therapeutic agents approved for the treatment of lung cancer, such as non-small cell lung cancer. In such embodiments, the other therapeutic agent may be afatinib, alectinib, atezolizumab, bevacizumab, brigatinib, capmatinib, carboplatin, ceritinib, cisplatin, crizotinib, dabrafenib, dacomitinib, docetaxel, doxorubicin, durvalumab, entrectinib, erlotinib, everolimus, gefitinib, gemcitabine, ipilimumab, lorlatinib, mechlorethamine, methotrexate, necitumumab, nivolumab, osimertinib, paclitaxel, pembrolizumab, pemetrexed, ramucirumab, selpercatinib, trametinib, vinorelbine, or any combination thereof.

In some embodiments, a compound described herein is co-administered with one or more therapeutic agents approved for the treatment of gastric cancer, such as 5-fluorouracil, capecitabine, carboplatin, cisplatin, docetaxel, epirubicin, irinotecan, oxaliplatin, paclitaxel, trifluridine, tipiracil, trastuzumab, or any combination thereof.

In some embodiments, a compound described herein is co-administered with one or more alkylating agents (e.g., for the treatment of cancer) selected from, for example, nitrogen mustard N-oxide, cyclophosphamide, ifosfamide, thiotepa, ranimustine, nimustine, temozolomide, altretamine, apaziquone, brostallicin, bendamustine, carmustine, estramustine, fotemustine, glufosfamide, mafosfamide, bendamustin, mitolactol, cisplatin, carboplatin, eptaplatin, lobaplatin, nedaplatin, oxaliplatin, and satraplatin.

In some embodiments, a compound described herein is co-administered with one or more anti-metabolites (e.g., for the treatment of cancer) selected from, for example, methotrexate, 6-mercaptopurineriboside, mercaptopurine, 5-fluorouracil, tegafur, doxifluridine, carmofur, cytarabine, cytarabine ocfosfate, enocitabine, gemcitabine, fludarabin, 5-azacitidine, capecitabine, cladribine, clofarabine, decitabine, eflornithine, ethynylcytidine, cytosine arabinoside, hydroxyurea, melphalan, nelarabine, nolatrexed, ocfosf [iota]te, disodium premetrexed, pentostatin, pelitrexol, raltitrexed, triapine, trimetrexate, vidarabine, vincristine, and vinorelbine;

In some embodiments, a compound described herein is co-administered with one or more hormonal therapy agents (e.g., for the treatment of cancer) selected from, for example, exemestane, Lupron, anastrozole, doxercalciferol, fadrozole, formestane, abiraterone acetate, finasteride, epristeride, tamoxifen citrate, fulvestrant, Trelstar, toremifene, raloxifene, lasofoxifene, letrozole, sagopilone, ixabepilone, epothilone B, vinblastine, vinflunine, docetaxel, and paclitaxel;

In some embodiments, a compound described herein is co-administered with one or more cytotoxic topoisomerase inhibiting agents (e.g., for the treatment of cancer) selected from, for example, aclarubicin, doxorubicin, amonafide, belotecan, camptothecin, 10-hydroxycamptothecin, 9-aminocamptothecin, diflomotecan, irinotecan, topotecan, edotecarin, epimbicin, etoposide, exatecan, gimatecan, lurtotecan, mitoxantrone, pirambicin, pixantrone, rubitecan, sobuzoxane, tafluposide, etc.

In some embodiments, a compound described herein is co-administered with one or more anti-angiogenic compounds (e.g., for the treatment of cancer) selected from, for example, acitretin, aflibercept, angiostatin, aplidine, asentar, axitinib, recentin, bevacizumab, brivanib alaninat, cilengtide, combretastatin, DAST, endostatin, fenretinide, halofuginone, pazopanib, ranibizumab, rebimastat, removab, revlimid, sorafenib, vatalanib, squalamine, sunitinib, telatinib, thalidomide, ukrain, and vitaxin.

In some embodiments, a compound described herein is co-administered with one or more antibodies (e.g., for the treatment of cancer) selected from, for example, trastuzumab, cetuximab, bevacizumab, rituximab, ticilimumab, ipilimumab, lumiliximab, catumaxomab, atacicept, oregovomab, and alemtuzumab.

In some embodiments, a compound described herein is co-administered with one or more VEGF inhibitors (e.g., for the treatment of cancer) selected from, for example, sorafenib, DAST, bevacizumab, sunitinib, recentin, axitinib, aflibercept, telatinib, brivanib alaninate, vatalanib, pazopanib, and ranibizumab.

In some embodiments, a compound described herein is co-administered with one or more EGFR inhibitors (e.g., for the treatment of cancer) selected from, for example, cetuximab, panitumumab, vectibix, gefitinib, erlotinib, and Zactima.

In some embodiments, a compound described herein is co-administered with one or more HER2 inhibitors (e.g., for the treatment of cancer) selected from, for example, lapatinib, tratuzumab, and pertuzumab; CDK inhibitor is selected from roscovitine and flavopiridol;

In some embodiments, a compound described herein is co-administered with one or more proteasome inhibitors (e.g., for the treatment of cancer) selected from, for example, bortezomib and carfilzomib.

In some embodiments, a compound described herein is co-administered with one or more serine/threonine kinase inhibitors (e.g., for the treatment of cancer), for example, MEK inhibitors and Raf inhibitors such as sorafenib.

In some embodiments, a compound described herein is co-administered with one or more tyrosine kinase inhibitors (e.g., for the treatment of cancer) selected from, for example, dasatinib, nilotibib, DAST, bosutinib, sorafenib, bevacizumab, sunitinib, AZD2171, axitinib, aflibercept, telatinib, imatinib mesylate, brivanib alaninate, pazopanib, ranibizumab, vatalanib, cetuximab, panitumumab, vectibix, gefitinib, erlotinib, lapatinib, tratuzumab and pertuzumab.

In some embodiments, a compound described herein is co-administered with one or more androgen receptor antagonists (e.g., for the treatment of cancer) selected from, for example, nandrolone decanoate, fluoxymesterone, Android, Prostaid, andromustine, bicalutamide, flutamide, apocyproterone, apoflutamide, chlormadinone acetate, Androcur, Tabi, cyproterone acetate, and nilutamide.

In some embodiments, a compound described herein is co-administered with one or more aromatase inhibitors (e.g., for the treatment of cancer) selected from, for example, anastrozole, letrozole, testolactone, exemestane, aminoglutethimide, and formestane.

In some embodiments, a compound described herein is co-administered with one or more other anti-cancer agents including, e.g., alitretinoin, ampligen, atrasentan bexarotene, borte-zomib, bosentan, calcitriol, exisulind, fotemustine, ibandronic acid, miltefosine, mitoxantrone, 1-asparaginase, procarbazine, dacarbazine, hydroxycarbamide, pegaspargase, pentostatin, tazaroten, velcade, gallium nitrate, canfosfamide, darinaparsin, and tretinoin. In a preferred embodiment, the compounds of the present disclosure may be used in combination with chemotherapy (e.g., cytotoxic agents), anti-hormones and/or targeted therapies such as other kinase inhibitors, mTOR inhibitors and angiogenesis inhibitors.

In embodiments in which the compounds and pharmaceutical compositions herein are used for the treatment or prevention of non-cancer diseases and/or conditions, the compounds and pharmaceutical compositions herein may be co-administered with therapeutics and/or therapies known in the field to be appropriate for the treatment of such diseases and/or conditions.

Kits

For use in the therapeutic applications described herein, kits and articles of manufacture are also provided, which include a compound or pharmaceutical composition described herein (e.g., a compound of formula (I), (IIa), (IIb), or (IIc), or a pharmaceutically acceptable salt thereof, or a pharmaceutical composition comprising a compound of formula (I), (IIa), (IIb), or (IIc), or a pharmaceutically acceptable salt thereof). In some embodiments, such kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from a variety of materials such as glass or plastic.

The articles of manufacture provided herein contain packaging materials. Packaging materials for use in packaging pharmaceutical products include those found in, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. For example, in some embodiments the container(s) includes a compound of formula (I), (IIa), (IIb), or (IIc), or a pharmaceutically acceptable salt thereof, optionally in a composition or in combination with another agent as disclosed herein. The container(s) optionally have a sterile access port (for example the container is an intravenous solution bag or a vial having a stopper pierceable by a hypodermic injection needle). Such kits optionally comprising a compound with an identifying description or label or instructions relating to its use in the methods described herein.

For example, a kit typically includes one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included. A label is optionally on or associated with the container. For example, a label is on a container when letters, numbers or other characters forming the label are attached, molded or etched into the container itself, a label is associated with a container when it is present within a receptacle or carrier that also holds the container, e.g., as a package insert. In addition, a label is used to indicate that the contents are to be used for a specific therapeutic application. In addition, the label indicates directions for use of the contents, such as in the methods described herein. In certain embodiments, the pharmaceutical composition is presented in a pack or dispenser device which contains one or more unit dosage forms containing a compound provided herein. The pack, for example, contains metal or plastic foil, such as a blister pack. Or, the pack or dispenser device is accompanied by instructions for administration. Or, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, is the labeling approved by the U.S. Food and Drug Administration for prescription drugs, or the approved product insert. In some embodiments, compositions containing a compound provided herein formulated in a compatible pharmaceutical carrier are prepared, placed in an appropriate container, and labeled for treatment of an indicated condition.

EXAMPLES

Abbreviations used in the following examples include the following: ACN is acetonitrile; Boc is tert-butyloxycarbonyl; DCM is dichloromethane; DIPEA is N,N-diisopropylethylamine; DMA is dimethylacetamide; dppf is 1,1'-bis(diphenylphosphino)ferrocene; EtOAc is ethyl acetate; HATU is (1-[bis(dimethylamino)methylene]-1H-1,2,3-triazolo[4,5-b]pyridinium 3-oxide hexafluorophosphate; MeOH is methanol; RPH refers to reversed phase chromatography; RT is room temperature; and TFA is trifluoroacetic acid.

General Synthesis Methods

General Procedure A:

To a screw cap 10 dr vial were added carboxylic acid (1.1 eq.), DIPEA (2 eq., in case of amine hydrochloride 3 eq.), HATU (1.2 eq) and anhydrous DCM (5 ml). The mixture was stirred for 15 min at RT, then corresponding amine or its hydrochloride (1.2 eq) was added, the vial was sealed and the reaction mixture was heated at 45° C. overnight. After cooling to the RT mixture was diluted with DCM (20 mL), and sequentially washed with water, sat. aqueous NaHCO$_3$, and brine. Organic phase was dried over Na$_2$SO$_4$, concentrated in vacuo and purified by silica gel column chromatography (DCM: EtOAc or DCM: MeOH) and then (if needed) by RPH chromatography (10-100% gradient of MeOH in water) providing a titled compound.

General Procedure B:

To a solution of corresponding methyl ester (1 mmol, 1 eq.) in MeOH (2 mL/mmol) was added 1M LiOH solution (2 eq.) and the mixture was stirred at RT for 4 h (for proline esters) or overnight (for aromatic esters). The mixture was concentrated in vacuo and the crude was diluted with water (5 mL) and acidified to pH 4 with 1M HCl. Obtained mixture was extracted with EtOAc (3*10 mL), and combined organics were washed with brine (3*10 mL), dried over Na$_2$SO$_4$ and concentrated providing the product that either was used directly in the next step without further purification or was purified by silica gel column chromatography.

General Procedure C:

To a de-gassed suspension of zinc powder (217 mg, 3.338 mmol, 1.8 eq.) in DMA (2 mL) in the screw cap vial was added drop-wise a mixture of chlorotrimethylsilane (67.3 µL, 57.6 mg, 0.53 mmol, 0.3 eq.) and 1,2-dibromoethane (45.9 µL, 99.6 mg, 0.53 mmol, 0.3 eq.) and the resultant mixture was stirred at room temperature under Ar for 15 minutes. To this mixture was then added dropwise neat 3-iodoazetidine-1-carboxylic acid tert-butyl ester (753 mg, 2.661 mmol, 1.4 eq.) and the resultant mixture was stirred at room temperature for 15 minutes. In a separate vial, PdCl$_2$(dppf)*DCM (65.2 mg, 0.08 mmol, 0.04 eq.), and copper iodide (30 mg, 0.157 mmol, 0.08 mmol) were added to a degassed solution of corresponding het(aryl)bromide (1.862 mmol, 1 eq.) in DMA (1 mL). After stirring for 30 minutes, the zinc suspension above was added to the solution suspension of het(aryl)bromide, PdCl$_2$(dppf)*DCM and copper iodide and the reaction mixture was allowed to stir at 80° C. for 2 hours under argon. The resultant mixture was cooled to RT diluted with EtOAc and filtered through the pad with Celite, the pad was washed with EtOAc, and collected organics were washed with mixture of saturated ammonium chloride solution and ammonium hydroxide (15:1). The organic phase was dried over anhydrous sodium sulfate, filtered and concentrated under reduced pressure. The residue was purified by silica gel flash chromatography (0-100% ethyl acetate in hexanes), fractions with the corresponding pick in the LC-MS were combined, concentrated and used in the next step without further purification.

General Procedure D:

To a solution of Boc-protected substituted azetidine (1 mmol) in the 3 mL of 1,4-dioxane 4M HCl in 1,4-dioxane (3 mL) was added dropwise, and the mixture was stirred overnight at RT. After this all volatiles were removed under reduced pressure, the residue was triturated with dry ACN, and ACN was decanted, remained solid was dried in vacuo providing the corresponding dihydrochloride as a white solid with quantitative yield.

General Procedure E:

To a degassed suspension of boronic acid or boronic acid pinacol ester (1.3 eq., 0.65 mmol), bromide (1 eq., 0.5 mmol), NaHCO$_3$ (3 eq., 1.5 mmol) in mixture 1,4-dioxane:water=10:1 PdCl$_2$(dppf)*DCM (0.025 mmol) was added in one portion. Obtained suspension was degassed one time more, refilled with Ar and allowed to stir at 80° C. overnight under argon. The resultant mixture was cooled to RT diluted with EtOAc and filtered through the pad with Celite, the pad was washed with EtOAc, and collected organics were washed with brine, dried over anhydrous sodium sulfate, filtered and concentrated under reduced pressure. The residue was purified by silica gel flash chromatography (0-100% ethyl acetate in hexanes then 0-20% methanol in dichloromethane), fractions with the corresponding pick in the LC-MS were combined, concentrated and the residue was re-dissolved in the DCM (5 mL). To this mixture TFA (30 eq.) was added dropwise at 0° C., and the mixture was stirred at 0° C. for 60 min. The mixture was concentrated in vacuo and the crude was triturated with 7N ammonia in methanol and concentrated again. Obtained residue was purified by silica gel column chromatography (0-100% Hexane/EtOAc to DCM/MeOH) then RPH (0-100% MeOH/Water) to afford the titled compound as an off white solid.

General Procedure F:

To a screw cap 10 dr vial were added amine (1 eq.), DIPEA (2 eq.) and anhydrous DCM (5 ml). The mixture was stirred for 15 min at 0° C., then corresponding acylchloride was added, the vial was sealed and the reaction mixture was stirred at RT overnight. After cooling to the RT mixture was diluted with DCM (20 mL), and sequentially washed with water, sat. aqueous NaHCO$_3$, and brine. Organic phase was dried over sodium sulfate, concentrated in vacuo and the residue was re-dissolved in the DCM (2 mL) at 0° C. and TFA (30 eq.) was added dropwise, and the mixture was stirred at 0° C. for 60 min. The mixture was concentrated in vacuo and the crude was triturated with 7N ammonia in methanol and concentrated again. Obtained residue was purified by silica gel column chromatography (0-100% Hexane/EtOAc to DCM/MeOH) then RPH (0-100% MeOH/Water) to afford the titled compound as an off white solid.

General Procedure G:

The Boc-protected compound was dissolved in the DCM (2 mL) at 0° C. and TFA (30 eq.) was added dropwise. The mixture was stirred at 0° C. for 60 min. and then was concentrated in vacuo and the crude was triturated with 7N ammonia in methanol and concentrated again. Obtained residue was purified by silica gel column chromatography (0-100% Hexane/EtOAc to DCM/MeOH) then RPH (0-100% MeOH/Water) to afford the titled compound as an off white solid.

Example 1

Compound Syntheses—Monomers

Compound 14: N-((5-(pyrrolidine-1-carbonyl)thiophen-2-yl)methyl)azetidine-3-carboxamide

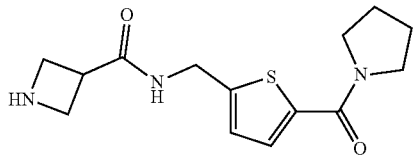 [SMILES: O=C(NCc1ccc(C(=O)N2CCCC2)s1)C1CNC1]

Synthesized according to general procedure A with using (5-aminothiophen-2-yl)(pyrrolidin-1-yl)methanone and 1-Boc-azetidine-3-carboxylic acid, and general procedure G to afford Compound 14 (10 mg, 72%) as an off white solid. $^1$H NMR (600 MHz, CD$_3$OD): δ 7.46 (d, J=3.8 Hz, 1H), 7.00 (d, J=3.8 Hz, 1H), 4.56 (s, 2H), 3.96 (br.s, 2H), 3.78 (br.s, 4H), 3.59 (br.s, 3H), 2.02 (br.s, 2H), 1.95 (br.s, 2H). $^{13}$C NMR (125 MHz, CD$_3$OD): δ 174.9, 163.6, 148.3, 139.1, 131.4, 127.1, 118.1, 68.1, 50.3, 49.6, 39.0, 27.6, 24.9. HR-MS (ESI): [M+H$^+$] calculated 294.1271, found 294.1270.

Compound 37: N-(5-(pyrrolidine-1-carbonyl)thiophen-2-yl)azetidine-2-carboxamide

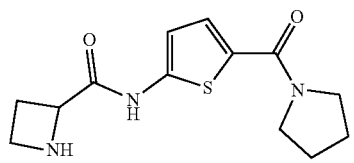 [SMILES: O=C(Nc1ccc(C(=O)N2CCCC2)s1)C1CCN1]

Synthesized according to general procedure A with using (5-aminothiophen-2-yl)(pyrrolidin-1-yl)methanone and (rac)-1-Boc-azetidine-2-carboxylic acid, and general procedure G to afford Compound 20 (13 mg, 79%) as an off white solid. $^1$H NMR (600 MHz, CD$_3$OD): δ 7.44 (d, J=4.2 Hz, 1H), 6.79 (d, J=4.2 Hz, 1H), 4.46 (dd, J=9.1, 7.1 Hz, 1H), 3.82 (s, 2H), 3.69 (q, J=7.9 Hz, 1H), 3.61 (s, 2H), 3.49 (td, J=8.5, 5.1 Hz, 1H), 2.70 (ddt, J=8.9, 6.2, 4.4 Hz, 1H), 2.48-2.36 (m, 1H), 2.04 (s, 2H), 1.96 (s, 2H). $^{13}$C NMR (125 MHz, CD$_3$OD): δ 173.0, 164.3, 145.5, 130.6, 129.9, 113.4, 60.0, 50.2, 47.5 (from HSQC) 44.6, 27.6, 26.8, 24.9. HR-MS (ESI) [M+H$^+$] calculated 280.1114, found 280.1117.

Compound 44: (S)—N-(5-(pyrrolidine-1-carbonyl)thiophen-2-yl)pyrrolidine-2-carboxamide

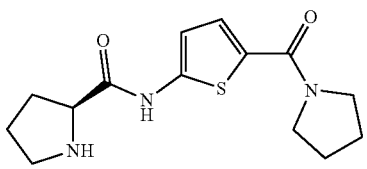 [SMILES: O=C(Nc1ccc(C(=O)N2CCCC2)s1)[C@@H]1CCCN1]

Synthesized according to general procedure A, from corresponding amine and N-Boc-L-proline, and general procedure G to afford the titled compound as an off white solid (18 mg, 83%). $^1$H NMR MeOD (600 MHz): δ 7.44 (d, J=4.2 Hz, 1H), 6.78 (d, J=4.2 Hz, 1H), 3.89-3.77 (m, 3H), 3.60 (s, 2H), 3.06 (dt, J=10.5, 6.5 Hz, 1H), 2.97 (dt, J=10.5, 6.5 Hz, 1H), 2.19 (dt, J=12.7, 6.8 Hz, 1H), 2.04 (s, 2H), 1.95 (s, 2H), 1.91-1.85 (m, 1H), 1.82-1.75 (m, 2H); $^{13}$C NMR MeOD (150 MHz), mixture of rotamers (1:1): δ 174.1, 164.4, 145.5, 130.5, 129.9, 113.3, 61.6, 49.8, 48.1, 32.0, 27.6, 27.0, 24.9; HR-ESI-MS: C$_{14}$H$_{20}$N$_3$O$_2$S [M+H]$^+$ m/z calculated 294.1271, found 294.1275.

Compound 85. (S)—N-(5-(3-(thiazol-2-yl)azetidine-1-carbonyl)thiophen-2-yl)pyrrolidine-2-carboxamide

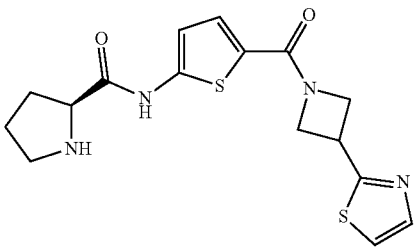 [SMILES: O=C(Nc1ccc(C(=O)N2CC(c3nccs3)C2)s1)[C@@H]1CCCN1]

Step 1. tert-butyl (S)-2-((5-(methoxycarbonyl)thiophen-2-yl)carbamoyl)pyrrolidine-1-carboxylate Synthesized according to general procedure A, from methyl 5-amino-2-thiophenecarboxylate and N-Boc-L-proline. Obtained residue was purified by silica gel column chromatography (0-100% DCM/EtOAc) to afford the titled compound as a semi-solid (182 mg, 73%). $^1$H NMR DMSO-$d_6$ (600 MHz) (mixture of rotamers 2:1): δ 11.66 (s, 1H), 7.60 (d, J=4.1 Hz, 1H), 6.75 (d, J=4.1 Hz, 1H), 4.34-4.18 (m, 1H), 3.77 (s, 3H), 3.50-3.40 (m, 1H), 3.40-3.32 (m, 1H), 2.30-2.13 (m, 1H), 1.95-1.76 (m, 3H), 1.40 (s, 3H), 1.23 (s, 6H); $^{13}$C NMR DMSO-$d_6$ (150 MHz) (mixture of rotamers 2:1): δ 170.7, 170.2, 162.5, 153.6, 152.9, 146.3, 146.2, 132.0, 131.9, 121.9, 121.8, 112.0, 111.9, 78.9, 78.7, 59.8, 59.4, 51.7, 46.7, 46.8, 30.8, 30.6, 30.0, 28.1, 27.9, 27.8, 24.0, 23.4; HR-ESI-MS: C$_{16}$H$_{23}$N$_2$O$_5$S [M+H]$^+$ m/z calculated 355.1322, found 355.1336.

Step 2. (S)-5-(1-(tert-butoxycarbonyl)pyrrolidine-2-carboxamido)thiophene-2-carboxylic Acid Synthesized according to general procedure B, from tert-butyl (S)-2-((5-(methoxycarbonyl)thiophen-2-yl)carbamoyl)pyrrolidine-1-carboxylate. Obtained residue was purified by silica gel column chromatography (0-100% DCM/EtOAc) to afford the titled compound as a semi-solid (120 mg, 93%). $^1$H NMR DMSO-$_{d6}$ (600 MHz) (mixture of rotamers 2:1): δ 12.54 (s, 1H), 11.56 (s, 1H), 7.51 (d, J=4.1 Hz, 1H), 6.72 (d, J=4.1 Hz, 1H), 4.28 (dd, J=8.2, 4.8 Hz, 0.3H), 4.21 (dd, J=8.2, 4.8 Hz, 0.7H), 3.51-3.40 (m, 1H), 3.40-3.31 (m, 1H, overlapped with HDO pick), 2.29-2.14 (m, 1H), 1.96-1.79 (m, 3H), 1.40 (s, 3H), 1.24 (s, 6H); $^{13}$C NMR DMSO-$_{d6}$ (150 MHz) (mixture of rotamers 2:1 based on $^1$H NMR): δ 170.5, 170.1, 163.6, 153.6, 152.9, 145.8, 145.7, 131.4, 131.4, 123.8, 123.7, 111.8, 111.8, 78.9, 78.7, 59.8, 59.4, 46.7, 46.5, 30.9, 30.1, 28.1, 27.8, 24.0, 23.4; HR-ESI-MS: $C_{15}H_{21}N_2O_5S$ [M+H]$^+$ m/z calculated 341.1166, found 341.1179.

Step 3. (S)—N-(5-(3-(thiazol-2-yl)azetidine-1-carbonyl)thiophen-2-yl)pyrrolidine-2-carboxamide (Compound 85)

Synthesized according to general procedure A, from (S)-5-(1-(tert-butoxycarbonyl)pyrrolidine-2-carboxamido)thiophene-2-carboxylic acid and 2-(azetidin-3-yl)thiazole dihydrochloride. Obtained residue was used in the next step without further purification. To a solution of the residue from the previous step in the DCM (2 mL) at 0° C. TFA (0.5 mL) was added dropwise, and the mixture was stirred at 0° C. for 30 min. After this all volatiles were removed under reduced pressure, the residue was triturated with 7N ammonia solution in methanol, re-concentrated and purified by silica gel column chromatography (0-100% DCM/MeOH+0.5% ammonia (v/v)) to afford the titled compound as an off-white solid (9 mg, 75%). $^1$H NMR MeOD (600 MHz) δ: 7.80 (d, J=3.3 Hz, 1H), 7.56 (d, J=3.3 Hz, 1H), 7.40 (d, J=4.2 Hz, 1H), 6.80 (d, J=4.2 Hz, 1H), 4.96 (s, 1H), 4.67 (s, 2H), 4.41 (m, 2H), 3.83 (dd, J=8.7, 5.9 Hz, 1H), 3.05 (dt, J=10.5, 6.5 Hz, 1H), 2.97 (dt, J=10.5, 6.5 Hz, 1H), 2.20 (td, J=15.6, 12.7, 7.3 Hz, 1H), 1.88 (td, J=15.6, 12.7, 7.3 Hz, 1H), 1.80 (p, J=6.9 Hz, 2H); $^{13}$C NMR MeOD (150 MHz) δ: 174.3, 172.1, 165.7, 146.3, 143.8, 130.4, 127.5, 120.9, 113.6, 61.6, 60.3 (azetidine CH2, identified from HSQC spectrum), 56.8 (azetidine CH2, identified from HSQC spectrum), 48.1, 33.3, 32.0, 27.0. HR-ESI-MS: $C_{16}H_{19}N_4O_2S_2$ [M+H]$^+$ m/z calculated 363.0944, found 363.0952.

Compound 90. ((S)—N-(5-(3-(5-phenylthiazol-2-yl)azetidine-1-carbonyl)thiophen-2-yl)pyrrolidine-2-carboxamide

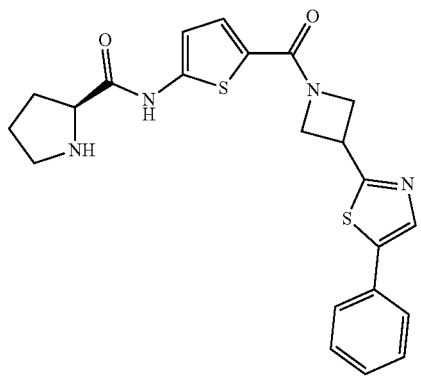 [SMILES: O=C(Nc1ccc(C(=O)N2CC(c3ncc(-c4ccccc4)s3)C2)s1)[C@@H]1CCCN1]

Step 1. 2-(azetidin-3-yl)-5-phenylthiazole Hydrochloride

Synthesized according to general procedures C and D to afford 2-(azetidin-3-yl)-5-phenylthiazole hydrochloride (70 mg, 15%) as an off white solid. $^1$H NMR (600 MHz, DMSO-d6) δ 9.51 (s, 1H), 9.22 (s, 1H), 8.24 (s, 1H), 7.70-7.63 (m, 2H), 7.46 (t, J=7.7 Hz, 2H), 7.41-7.34 (m, 1H), 4.50 (p, J=8.3 Hz, 1H), 4.38-4.28 (m, 2H), 4.26-4.18 (m, 2H). $^{13}$C NMR (150 MHz, DMSO-d6): δ 166.6, 139.4, 138.5, 130.6, 129.3, 128.5, 126.4, 50.6, 33.5. MS (m/z) [M+H$^+$]: calculated 217, found 217.

(S)—N-(5-(3-(5-phenylthiazol-2-yl)azetidine-1-carbonyl)thiophen-2-yl)pyrrolidine-2-carboxamide (Compound 91)

Synthesized according to general procedure A with using (S)-5-(1-(tert-butoxycarbonyl)pyrrolidine-2-carboxamido)thiophene-2-carboxylic acid and 2-(azetidin-3-yl)-5-phenylthiazole hydrochloride, and general procedure G to afford Compound 90 (8 mg, 79%) as an off white solid. $^1$H NMR (600 MHz, CD$_3$OD) δ 7.91 (s, 1H), 7.55 (d, J=9.6 Hz, 1H), 7.41-7.37 (m, 3H), 7.33 (t, J=7.4 Hz, 1H), 6.75 (d, J=4.2 Hz, 1H), 4.94 (s, 1H), 4.81 (s, 2H), 4.48 (s, 2H), 4.33 (tt, J=8.8, 5.8 Hz, 1H), 3.86-3.80 (m, 1H), 3.07 (dt, J=11.1, 6.5 Hz, 1H), 3.04-2.96 (m, 1H), 2.28-2.16 (m, 1H), 1.92 (dq, J=12.9, 6.6 Hz, 1H), 1.81 (p, J=6.9 Hz, 2H). HR-MS (ESI): [M+H$^+$] calculated 439.1257, found 439.1259.

Compound 123. (S)—N-(5-(3-(5-(4-(acetamidomethyl)phenyl)thiazol-2-yl)azetidine-1-carbonyl)thiophen-2-yl)pyrrolidine-2-carboxamide

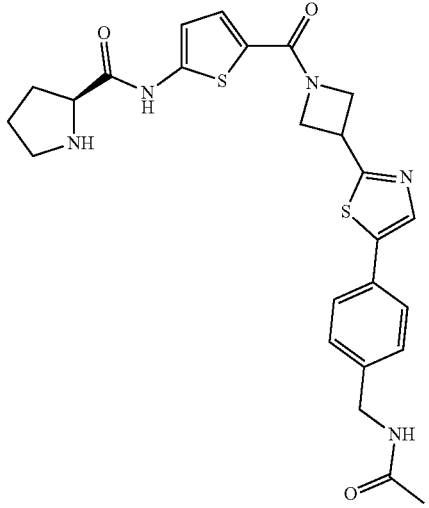 [SMILES: CC(=O)NCc1ccc(-c2cnc(C3CN(C(=O)c4ccc(NC(=O)[C@@H]5CCCN5)s4)C3)s2)cc1]

Synthesized according to general procedure F with using (S)—N-(5-(3-(5-(4-(aminomethyl)phenyl)thiazol-2-yl)azetidine-1-carbonyl)thiophen-2-yl)pyrrolidine-2-carboxamide (obtained by general procedure E Boc-intermediate was used directly) and acetylchloride to afford Compound 123 (8 mg, 86%) as an off white solid. $^1$H NMR (600 MHz, CD$_3$OD+30% DMSO-d6) δ 8.07 (s, 1H), 7.64-7.58 (m, 2H), 7.39-7.33 (m, 3H), 6.84 (d, J=4.2 Hz, 1H), 4.90 (br.s, 1H), 4.65 (br.s, 2H), 4.40-4.36 (m, 1H), 4.34 (s, 3H), 3.90 (dd, J=8.8, 5.9 Hz, 1H), 3.02 (dtd, J=17.1, 10.5, 6.7 Hz, 2H), 2.19 (dq, J=12.6, 7.5 Hz, 1H), 1.96 (s, 3H), 1.93-1.84 (m, 1H), 1.78 (p, J=7.0 Hz, 2H). $^{13}$C NMR (150 MHz, CD$_3$OD+30% DMSO-d6): δ 173.2, 172.2, 170.7, 165.0, 146.0, 141.1, 140.6, 139.5, 131.1, 130.0, 129.5, 128.0, 127.8, 113.8, 61.5, 60.0, 56.3, 48.0, 43.5, 33.6, 31.7, 26.8, 23.1. HR-MS (ESI): [M+H⁺] calculated 510.1628, found 510.1628.

Compound 125. (S)—N-(5-(3-(5-(4-(aminomethyl)phenyl)thiazol-2-yl)azetidine-1-carbonyl)thiophen-2-yl)pyrrolidine-2-carboxamide

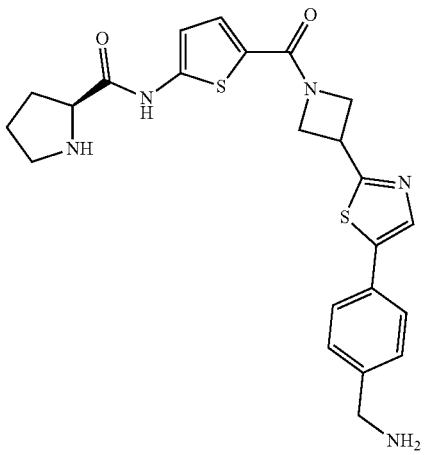 [SMILES: NCc1ccc(-c2cnc(C3CN(C(=O)c4ccc(NC(=O)[C@@H]5CCCN5)s4)C3)s2)cc1]

Step 1. tert-Butyl 3-(5-bromothiazol-2-yl)azetidine-1-carboxylate

Corresponding Boc-intermediate was synthesized according to general procedure C and was used in the next step without further purification. To a solution of tert-butyl 3-(thiazol-2-yl)azetidine-1-carboxylate (1 g, 4.17 mmol, 1 eq.) in 20 mL of anhydrous DMF NBS (890 mg, 5 mmol, 1.2 eq.) was added portion wise at RT. The mixture was stirred 12 h at RT, poured on ice and extracted with EtOAc (3*50 mL). Collected organics were washed with brine, dried over anhydrous sodium sulfate, filtered and concentrated under reduced pressure. The residue was purified by silica gel flash chromatography (0-60% ethyl acetate in hexanes) to afford tert-butyl 3-(5-bromothiazol-2-yl)azetidine-1-carboxylate (665 mg, 50%) as a clear oil. ¹H NMR (600 MHz, CDCl₃) δ 7.62 (s, 1H), 4.33 (t, J=8.6 Hz, 2H), 4.14 (dd, J=8.6, 5.9 Hz, 2H), 4.02 (tt, J=8.7, 5.9 Hz, 1H), 1.45 (s, 9H). ¹³C NMR (150 MHz, CDCl₃): δ 172.3, 156.3, 144.1, 108.6, 80.1, 55.5, 32.4, 28.5. MS (m/z) [M+H⁺]: calculated 262, 264, found 262, 264.

Step 2. tert-butyl (S)-2-((5-(3-(5-bromothiazol-2-yl)azetidine-1-carbonyl)thiophen-2-yl)carbamoyl)pyrrolidine-1-carboxylate Synthesized according to general procedure A with using (S)-5-(1-(tert-butoxycarbonyl)pyrrolidine-2-carboxamido)thiophene-2-carboxylic acid and 3-(5-bromothiazol-2-yl)azetidin-1-ium trifluoroacetate (obtained by treating of tert-butyl 3-(5-bromothiazol-2-yl)azetidine-1-carboxylate solution in DCM with TFA (30 eq.) at 0° C., stirring at 0° C. for 60 min and removing of all volatiles in vacuo. Obtained residue was used in the HATU-assisted coupling reaction without further purification) to afford tert-butyl (S)-2-((5-(3-(5-bromothiazol-2-yl)azetidine-1-carbonyl)thiophen-2-yl)carbamoyl)pyrrolidine-1-carboxylate (58 mg, 57%) as an off white solid. ¹H NMR (600 MHz, CDCl₃, mixture of rotamers) δ 10.72 (s, 1H), 7.61 (s, 1H), 7.31 (br.s, 1H), 6.54 (br.s, 0.5H), 6.45 (br.s, 0.5H), 4.71 (br.s, 2H), 4.49 (br.s, 2H), 4.20 (tt, J=8.8, 5.9 Hz, 1H), 3.78-3.68 (m, 1H), 3.46 (s, 1H), 3.36 (s, 1H), 3.24-3.14 (m, 1H), 1.98 (s, 1H), 1.91 (s, 2H), 1.48 (s, 9H). MS (m/z) [M+H⁺]: calculated 541 and 543, found 541 and 543.

Step 3. (S)—N-(5-(3-(5-(4-(aminomethyl)phenyl)thiazol-2-yl)azetidine-1-carbonyl)thiophen-2-yl)pyrrolidine-2-carboxamide (Compound 125)

Synthesized according to general procedure E with using tert-butyl (S)-2-((5-(3-(5-bromothiazol-2-yl)azetidine-1-carbonyl)thiophen-2-yl)carbamoyl)pyrrolidine-1-carboxylate and (4-aminomethylphenyl)boronic acid hydrochloride, obtained Boc-analog was further re-dissolved in DCM (2 mL) at 0° C. and treated with TFA (0.5 mL) the mixture was stirred at 0° C. for 30 min. After this, all volatiles were removed under reduced pressure, the residue was triturated with 7N ammonia solution in methanol, re-concentrated and purified by silica gel column chromatography (0-100% DCM/MeOH+0.5% ammonia (v/v)) to afford the titled compound as an off-white solid (8 mg, 53%). ¹H NMR (600 MHz, CD₃OD) δ 8.09 (s, 1H), 7.71 (d, J=7.8 Hz, 2H), 7.55 (d, J=7.9 Hz, 2H), 7.41 (d, J=4.1 Hz, 1H), 6.86 (d, J=4.0 Hz, 1H), 4.99 (s, 1H), 2H are in the pick of water, present in HSQC at 59.8, 4.65 (s, 1H), 4.57-4.49 (m, 1H), 4.49-4.25 (m, 1H), 4.16 (s, 2H), 3.48 (q, J=6.5, 5.9 Hz, 1H), 3.44 (q, J=5.6, 5.0 Hz, 1H), 2.65-2.48 (m, 1H), 2.20-2.08 (m, 3H). ¹³C NMR (150 MHz, CD₃OD): δ 171.5, 166.7, 165.3, 145.4, 140.3, 139.9, 134.7, 133.1, 131.0, 130.4, 128.6, 128.3, 114.6, 61.3, 60.2, 56.5, 47.5, 43.9, 33.6, 30.8, 25.0. HR-MS (ESI): [M+H⁺] calculated 468.1522, found 468.1499.

Other Compounds

Additional compounds were synthesized according to similar procedures using appropriate starting materials. Compound structures and HR-MS data are shown in Table 1.

TABLE 1

Exemplary Compounds

| Number | Structure | HRMS (M − H+), calculated | HRMS (M − H+), found |
|---|---|---|---|
| 1 | 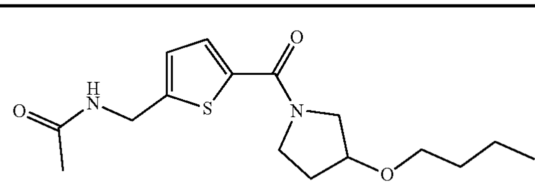 | 325.1580 | 325.1590 |

TABLE 1-continued

Exemplary Compounds

| Number | Structure | HRMS (M − H+), calculated | HRMS (M − H+), found |
| --- | --- | --- | --- |
| 2 | 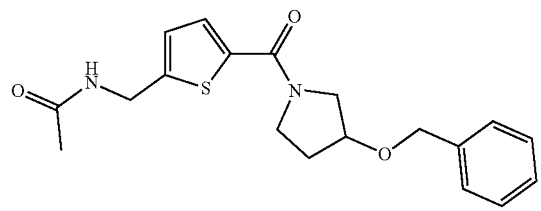 [SMILES: CC(=O)NCc1ccc(C(=O)N2CCC(OCc3ccccc3)C2)s1] | 359.1424 | 359.1455 |
| 3 | 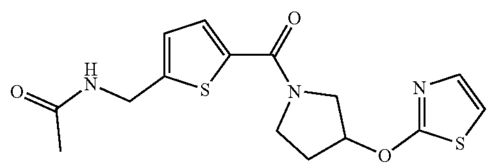 [SMILES: CC(=O)NCc1ccc(C(=O)N2CCC(Oc3nccs3)C2)s1] | 352.0784 | 352.0795 |
| 4 | 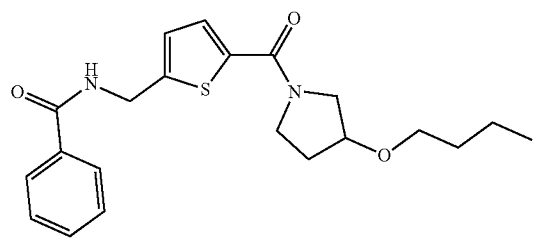 [SMILES: CCCCOC1CCN(C(=O)c2ccc(CNC(=O)c3ccccc3)s2)C1] | 387.1737 | 387.1748 |
| 5 | 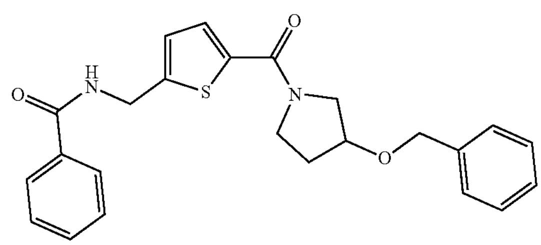 [SMILES: O=C(NCc1ccc(C(=O)N2CCC(OCc3ccccc3)C2)s1)c1ccccc1] | 421.1580 | 421.1590 |
| 6 | 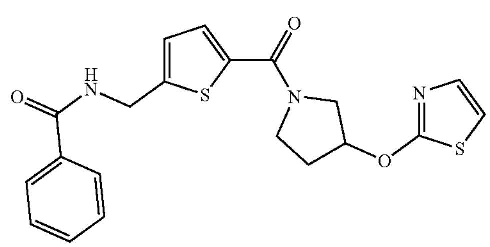 [SMILES: O=C(NCc1ccc(C(=O)N2CCC(Oc3nccs3)C2)s1)c1ccccc1] | 414.0941 | 414.0948 |
| 7 | 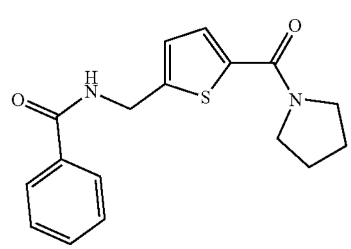 [SMILES: O=C(NCc1ccc(C(=O)N2CCCC2)s1)c1ccccc1] | 315.1162 | 315.1164 |

TABLE 1-continued

Exemplary Compounds

| Number | Structure | HRMS (M − H+), calculated | HRMS (M − H+), found |
|---|---|---|---|
| 8 | 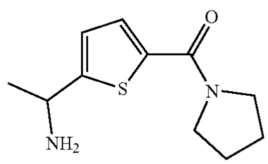 | 225.1056 | 226.1044 |
| 9 | 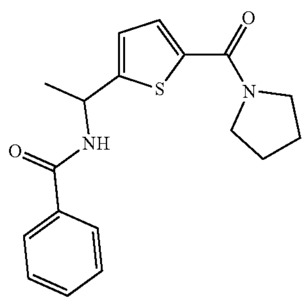 [SMILES: CC(NC(=O)c1ccccc1)c1ccc(C(=O)N2CCCC2)s1] | 329.1318 | 329.1317 |
| 10 | 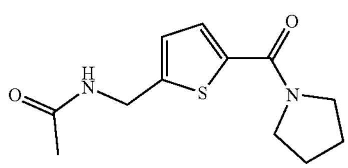 [SMILES: CC(=O)NCc1ccc(C(=O)N2CCCC2)s1] | 253.1005 | 253.1006 |
| 11 | 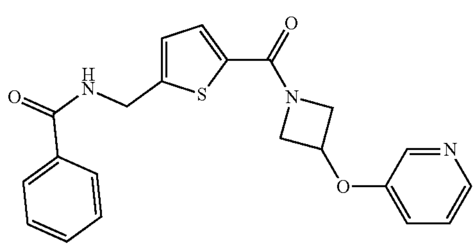 [SMILES: O=C(NCc1ccc(C(=O)N2CC(Oc3cccnc3)C2)s1)c1ccccc1] | 394.1220 | 394.1219 |
| 12 | 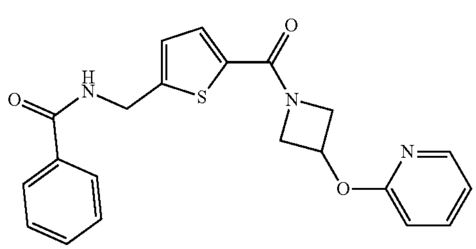 [SMILES: O=C(NCc1ccc(C(=O)N2CC(Oc3ccccn3)C2)s1)c1ccccc1] | 394.1220 | 394.1227 |
| 13 | 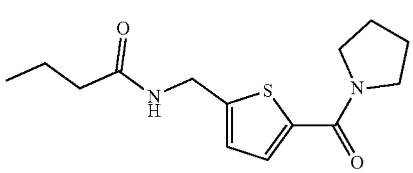 [SMILES: CCCC(=O)NCc1ccc(C(=O)N2CCCC2)s1] | 281.1318 | 281.1317 |
| 14 | 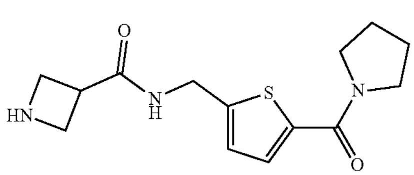 [SMILES: O=C(NCc1ccc(C(=O)N2CCCC2)s1)C1CNC1] | 294.1271 | 294.1270 |

TABLE 1-continued

Exemplary Compounds

| Number | Structure | HRMS (M − H+), calculated | HRMS (M − H+), found |
|---|---|---|---|
| 15 | 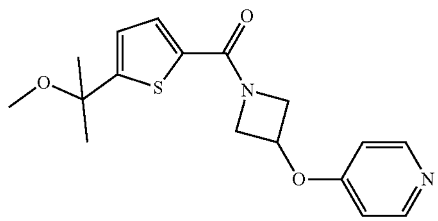 [SMILES: COC(C)(C)c1ccc(C(=O)N2CC(Oc3ccncc3)C2)s1] | 333.1267 | 333.1267 |
| 16 | 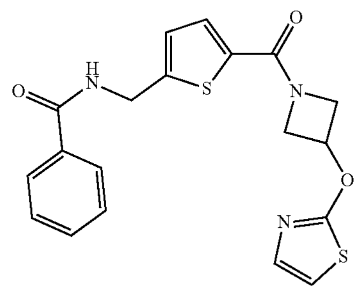 [SMILES: O=C(NCc1ccc(C(=O)N2CC(Oc3nccs3)C2)s1)c1ccccc1] | 400.0784 | 400.0785 |
| 17 | 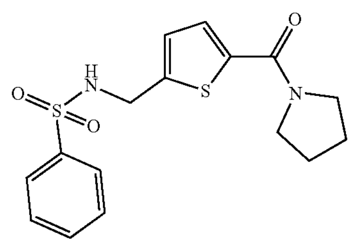 [SMILES: O=C(c1ccc(CNS(=O)(=O)c2ccccc2)s1)N1CCCC1] | 351.0832 | 351.0836 |
| 18 | 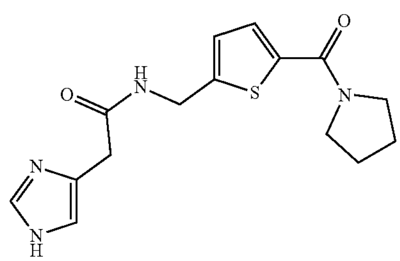 [SMILES: O=C(Cc1c[nH]cn1)NCc1ccc(C(=O)N2CCCC2)s1] | 319.1223 | 319.1224 |
| 19 | 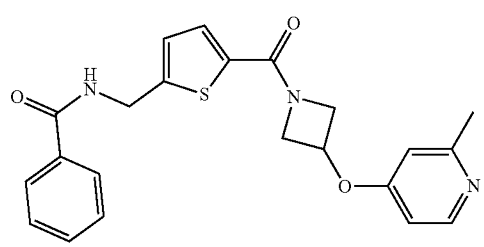 [SMILES: Cc1cc(OC2CN(C(=O)c3ccc(CNC(=O)c4ccccc4)s3)C2)ccn1] | 408.1376 | 408.1378 |
| 20 | 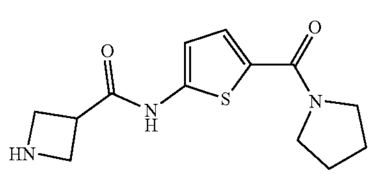 [SMILES: O=C(Nc1ccc(C(=O)N2CCCC2)s1)C1CNC1] | 280.1114 | 280.1114 |

TABLE 1-continued

Exemplary Compounds

| Number | Structure | HRMS (M − H+), calculated | HRMS (M − H+), found |
|---|---|---|---|
| 21 | 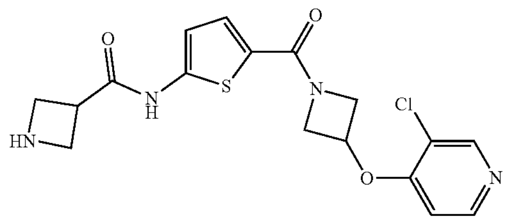 [SMILES: O=C(Nc1ccc(C(=O)N2CC(Oc3ccncc3Cl)C2)s1)C1CNC1] | 393.0783 | 393.0785 |
| 22 | 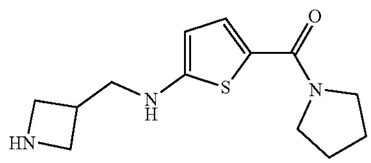 [SMILES: O=C(c1ccc(NCC2CNC2)s1)N1CCCC1] | 266.1322 | 266.1323 |
| 23 | 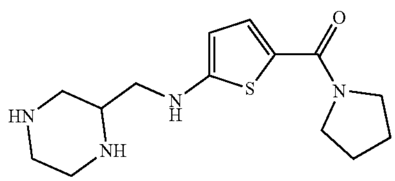 [SMILES: O=C(c1ccc(NCC2CNCCN2)s1)N1CCCC1] | 309.1380 | 309.1383 |
| 24 | 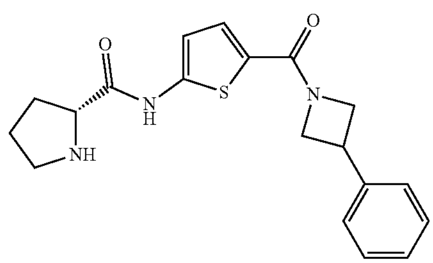 [SMILES: O=C(Nc1ccc(C(=O)N2CC(c3ccccc3)C2)s1)[C@H]1CCCN1] | 356.1427 | 356.1439 |
| 25 | 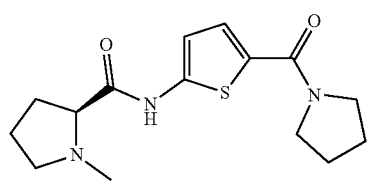 [SMILES: CN1CCC[C@H]1C(=O)Nc1ccc(C(=O)N2CCCC2)s1] | 308.1427 | 308.1439 |
| 26 | 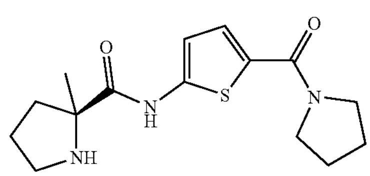 [SMILES: C[C@@]1(C(=O)Nc2ccc(C(=O)N3CCCC3)s2)CCCN1] | 308.1427 | 308.1437 |
| 27 | 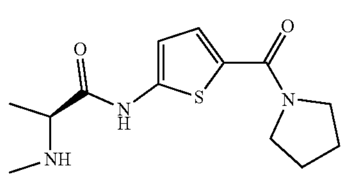 [SMILES: CN[C@@H](C)C(=O)Nc1ccc(C(=O)N2CCCC2)s1] | 282.1271 | 282.1278 |

TABLE 1-continued

Exemplary Compounds

| Number | Structure | HRMS (M − H+), calculated | HRMS (M − H+), found |
| --- | --- | --- | --- |
| 28 | 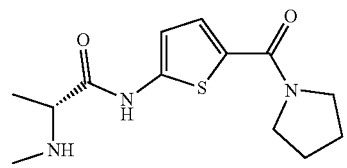 [SMILES: CN[C@H](C)C(=O)Nc1ccc(C(=O)N2CCCC2)s1] | 282.1271 | 282.1278 |
| 29 | 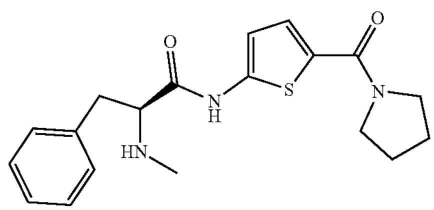 [SMILES: CN[C@@H](Cc1ccccc1)C(=O)Nc1ccc(C(=O)N2CCCC2)s1] | 358.1584 | 358.1588 |
| 30 | 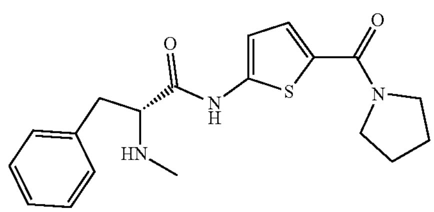 [SMILES: CN[C@H](Cc1ccccc1)C(=O)Nc1ccc(C(=O)N2CCCC2)s1] | 358.1584 | 358.1588 |
| 31 | 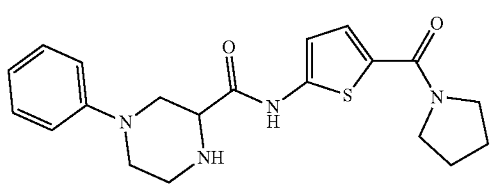 [SMILES: O=C(Nc1ccc(C(=O)N2CCCC2)s1)C1CN(c2ccccc2)CCN1] | 385.1693 | 385.1700 |
| 32 | 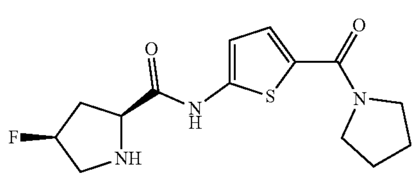 [SMILES: O=C(Nc1ccc(C(=O)N2CCCC2)s1)[C@@H]1C[C@H](F)CN1] | 312.1177 | 312.1183 |
| 33 | 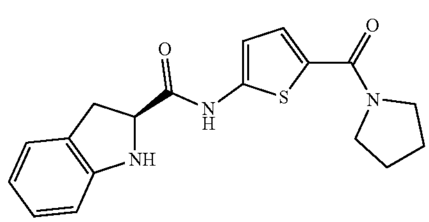 [SMILES: O=C(Nc1ccc(C(=O)N2CCCC2)s1)[C@@H]1Cc2ccccc2N1] | 342.1271 | 342.1280 |
| 34 | 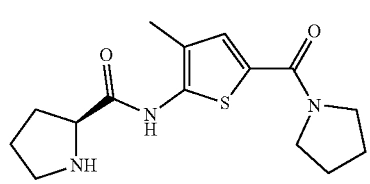 [SMILES: Cc1cc(C(=O)N2CCCC2)sc1NC(=O)[C@@H]1CCCN1] | 308.1427 | 308.1433 |

TABLE 1-continued
Exemplary Compounds
| Number | Structure | HRMS (M − H+), calculated | HRMS (M − H+), found |
| --- | --- | --- | --- |
| 35 | 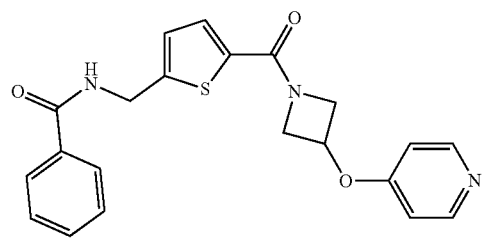 [SMILES: O=C(NCc1ccc(C(=O)N2CC(Oc3ccncc3)C2)s1)c1ccccc1] | 394.1220 | 394.1228 |
| 36 | 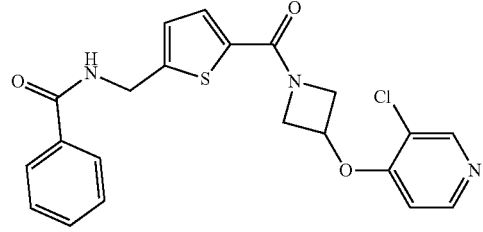 [SMILES: O=C(NCc1ccc(C(=O)N2CC(Oc3ccncc3Cl)C2)s1)c1ccccc1] | 428.0830 | 428.0831 |
| 37 | 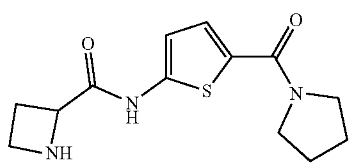 [SMILES: O=C(Nc1ccc(C(=O)N2CCCC2)s1)C1CCN1] | 280.1114 | 280.1117 |
| 38 | 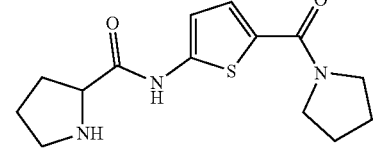 | 294.1271 | 294.1275 |
| 39 | 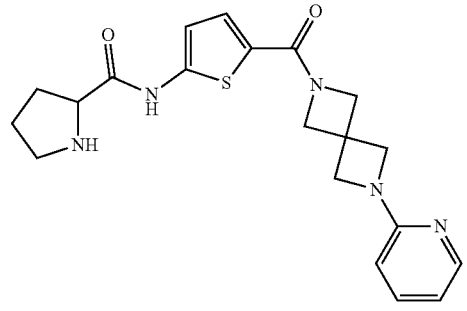 [SMILES: O=C(Nc1ccc(C(=O)N2CC3(C2)CN(c2ccccn2)C3)s1)C1CCCN1] | 398.1645 | 398.1653 |
| 40 | 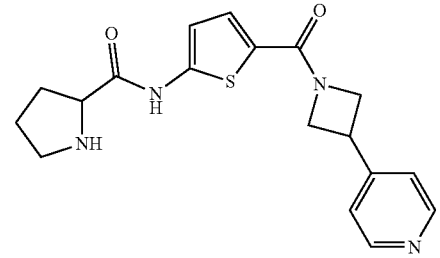 [SMILES: O=C(Nc1ccc(C(=O)N2CC(c3ccncc3)C2)s1)C1CCCN1] | 357.1380 | 357.1389 |

TABLE 1-continued
Exemplary Compounds
| Number | Structure | HRMS (M − H+), calculated | HRMS (M − H+), found |
|---|---|---|---|
| 41 | 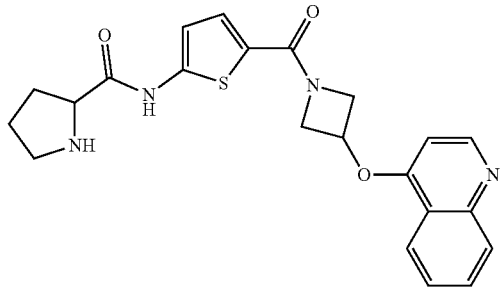 [SMILES: O=C(Nc1ccc(C(=O)N2CC(Oc3ccnc4ccccc34)C2)s1)C1CCCN1] | 423.1485 | 423.1491 |
| 42 | 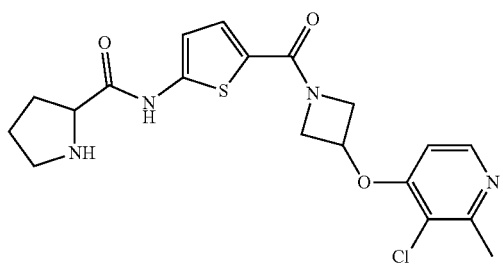 [SMILES: Cc1nccc(OC2CN(C(=O)c3ccc(NC(=O)C4CCCN4)s3)C2)c1Cl] | 421.1096 | 421.1098 |
| 43 | 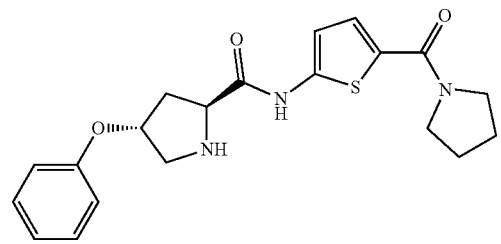 [SMILES: O=C(Nc1ccc(C(=O)N2CCCC2)s1)[C@@H]1C[C@@H](Oc2ccccc2)CN1] | 386.1533 | 386.1543 |
| 44 | 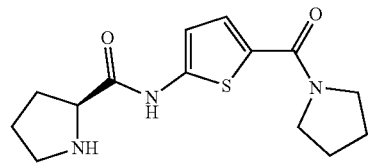 [SMILES: O=C(Nc1ccc(C(=O)N2CCCC2)s1)[C@@H]1CCCN1] | 294.1271 | 294.1275 |
| 45 | 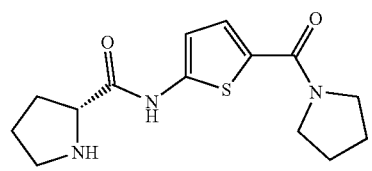 | 294.1271 | 294.1275 |
| 46 | 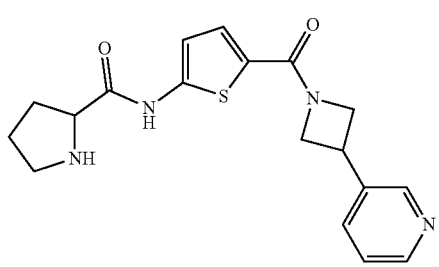 [SMILES: O=C(Nc1ccc(C(=O)N2CC(c3cccnc3)C2)s1)C1CCCN1] | 357.1380 | 357.1389 |

TABLE 1-continued

Exemplary Compounds

| Number | Structure | HRMS (M − H+), calculated | HRMS (M − H+), found |
|---|---|---|---|
| 47 | 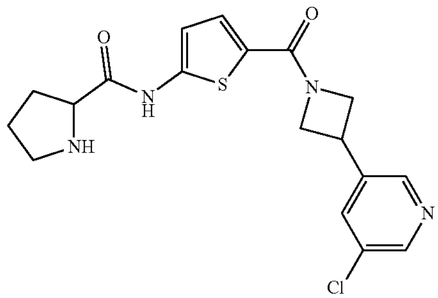 [SMILES: O=C(Nc1ccc(C(=O)N2CC(c3cncc(Cl)c3)C2)s1)C1CCCN1] | 391.0990 | 391.1000 |
| 48 | 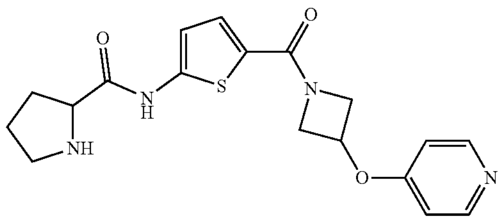 [SMILES: O=C(Nc1ccc(C(=O)N2CC(Oc3ccncc3)C2)s1)C1CCCN1] | 373.1329 | 373.1334 |
| 49 | 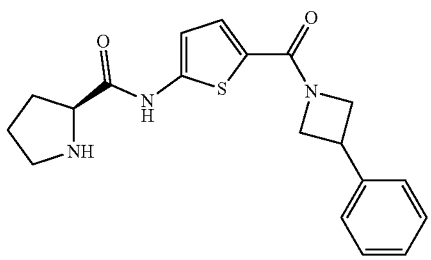 [SMILES: O=C(Nc1ccc(C(=O)N2CC(c3ccccc3)C2)s1)[C@@H]1CCCN1] | 356.1427 | 356.1439 |
| 50 | 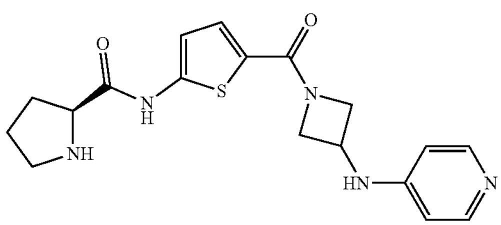 [SMILES: O=C(Nc1ccc(C(=O)N2CC(Nc3ccncc3)C2)s1)[C@@H]1CCCN1] | 372.1489 | 372.1498 |
| 51 | 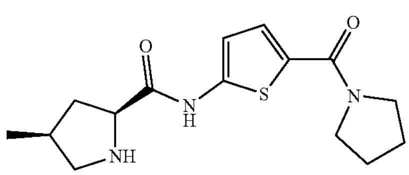 [SMILES: C[C@@H]1CN[C@H](C(=O)Nc2ccc(C(=O)N3CCCC3)s2)C1] | 308.1427 | 308.1434 |
| 52 | 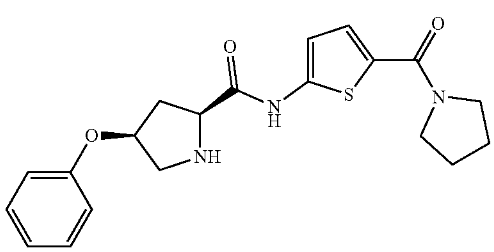 [SMILES: O=C(Nc1ccc(C(=O)N2CCCC2)s1)[C@@H]1C[C@H](Oc2ccccc2)CN1] | 386.1533 | 386.1540 |

TABLE 1-continued
Exemplary Compounds
| Number | Structure | HRMS (M − H+), calculated | HRMS (M − H+), found |
|---|---|---|---|
| 53 | 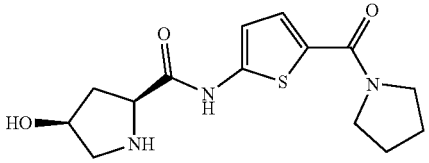 [SMILES: O=C(Nc1ccc(C(=O)N2CCCC2)s1)[C@@H]1C[C@H](O)CN1] | 310.1220 | 310.1226 |
| 54 | 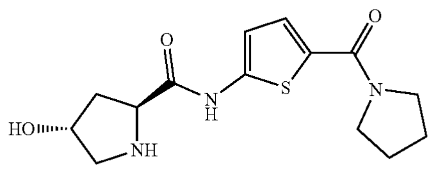 [SMILES: O=C(Nc1ccc(C(=O)N2CCCC2)s1)[C@@H]1C[C@@H](O)CN1] | 310.1220 | 310.1220 |
| 55 | 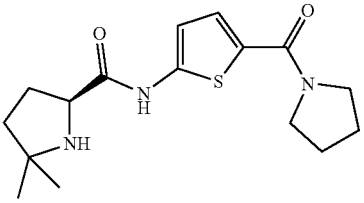 [SMILES: CC1(C)CC[C@@H](C(=O)Nc2ccc(C(=O)N3CCCC3)s2)N1] | 322.1584 | 322.1592 |
| 56 | 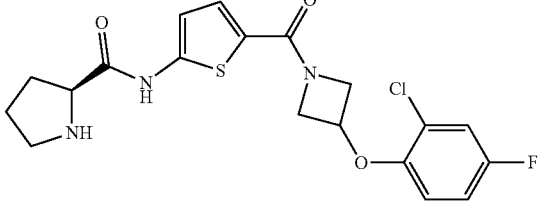 | 424.0892 | 424.0898 |
| 57 | 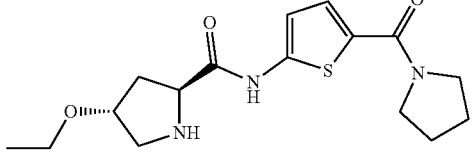 | 338.1533 | 338.1539 |
| 58 | 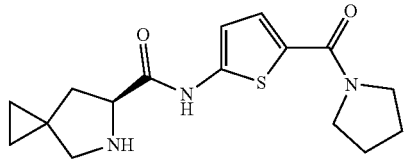 [SMILES: O=C(Nc1ccc(C(=O)N2CCCC2)s1)[C@@H]1CC2(CC2)CN1] | 320.1427 | 320.1432 |
| 59 | 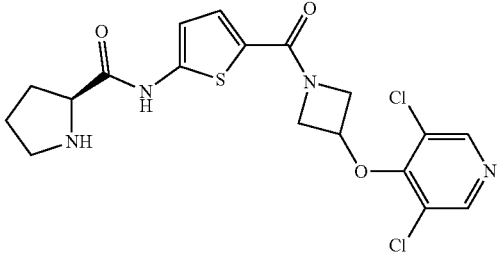 [SMILES: O=C(Nc1ccc(C(=O)N2CC(Oc3c(Cl)cncc3Cl)C2)s1)[C@@H]1CCCN1] | 441.0549 | 441.0553 |

TABLE 1-continued
Exemplary Compounds
| Number | Structure | HRMS (M − H+), calculated | HRMS (M − H+), found |
|---|---|---|---|
| 60 | 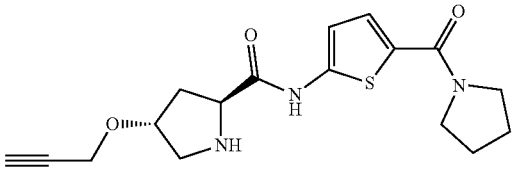 [SMILES: C#CCO[C@H]1CN[C@H](C(=O)Nc2ccc(C(=O)N3CCCC3)s2)C1] | 348.1376 | 348.1385 |
| 61 | 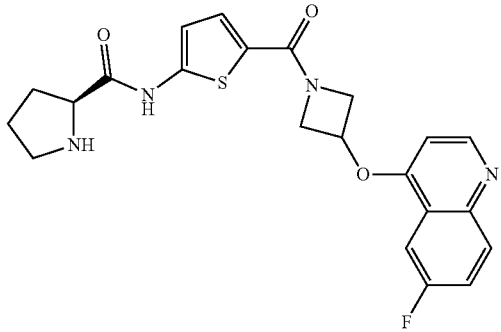 [SMILES: O=C(Nc1ccc(C(=O)N2CC(Oc3ccnc4ccc(F)cc34)C2)s1)[C@@H]1CCCN1] | 441.1391 | 441.1399 |
| 62 | 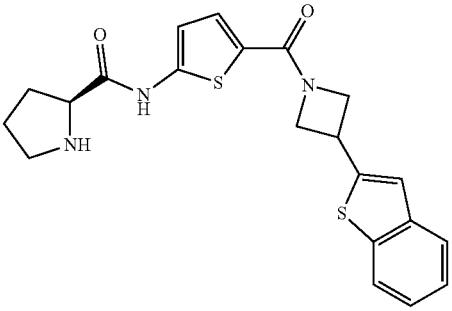 [SMILES: O=C(Nc1ccc(C(=O)N2CC(c3cc4ccccc4s3)C2)s1)[C@@H]1CCCN1] | 412.1148 | 412.1156 |
| 63 | 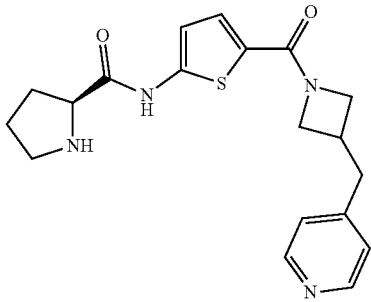 [SMILES: O=C(Nc1ccc(C(=O)N2CC(Cc3ccncc3)C2)s1)[C@@H]1CCCN1] | 371.1536 | 371.1543 |
| 64 | 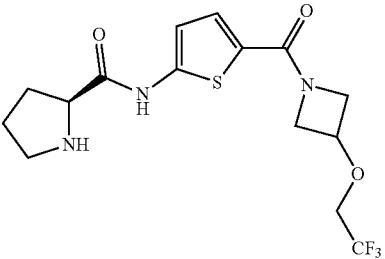 [SMILES: O=C(Nc1ccc(C(=O)N2CC(OCC(F)(F)F)C2)s1)[C@@H]1CCCN1] | 378.1094 | 378.1107 |

TABLE 1-continued
Exemplary Compounds
| Number | Structure | HRMS (M − H+), calculated | HRMS (M − H+), found |
|---|---|---|---|
| 65 | 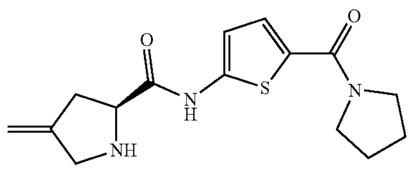 [SMILES: C=C1CN[C@H](C(=O)Nc2ccc(C(=O)N3CCCC3)s2)C1] | 306.1271 | 306.1279 |
| 66 | 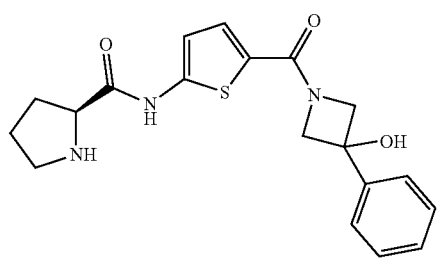 [SMILES: O=C(Nc1ccc(C(=O)N2CC(O)(c3ccccc3)C2)s1)[C@@H]1CCCN1] | 372.1376 | 372.1383 |
| 67 | 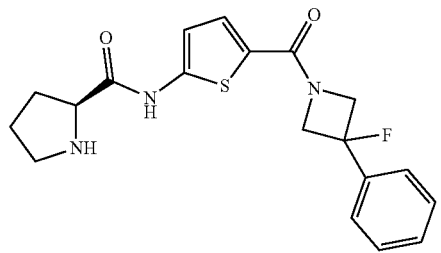 [SMILES: O=C(Nc1ccc(C(=O)N2CC(F)(c3ccccc3)C2)s1)[C@@H]1CCCN1] | 374.1333 | 374.1339 |
| 68 | 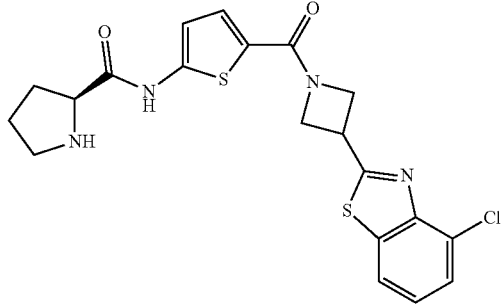 [SMILES: O=C(Nc1ccc(C(=O)N2CC(c3nc4c(Cl)cccc4s3)C2)s1)[C@@H]1CCCN1] | 447.0711 | 447.0714 |
| 69 | 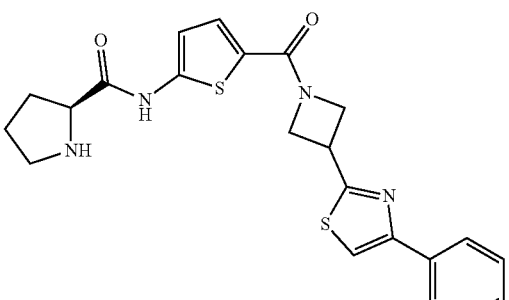 | 439.1257 | 439.1260 |

TABLE 1-continued

Exemplary Compounds

| Number | Structure | HRMS (M − H+), calculated | HRMS (M − H+), found |
| --- | --- | --- | --- |
| 70 | 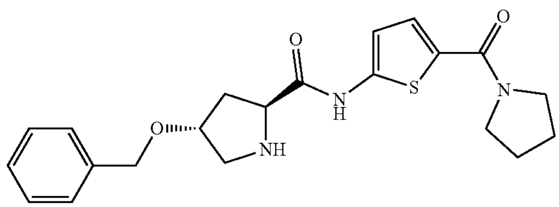 [SMILES: O=C(Nc1ccc(C(=O)N2CCCC2)s1)[C@@H]1C[C@@H](OCc2ccccc2)CN1] | 400.1689 | 400.1695 |
| 71 | 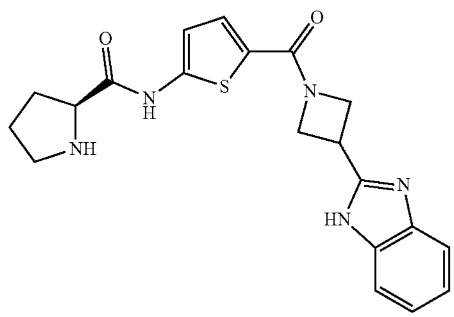 [SMILES: O=C(Nc1ccc(C(=O)N2CC(c3nc4ccccc4[nH]3)C2)s1)[C@@H]1CCCN1] | 396.1489 | 396.1493 |
| 72 | 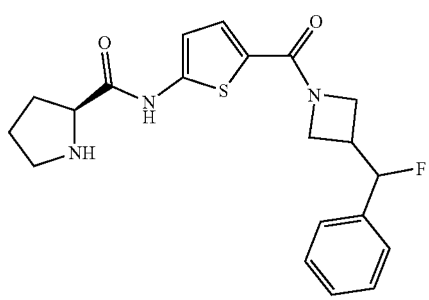 [SMILES: O=C(Nc1ccc(C(=O)N2CC(C(F)c3ccccc3)C2)s1)[C@@H]1CCCN1] | 388.1490 | 388.1498 |
| 73 | 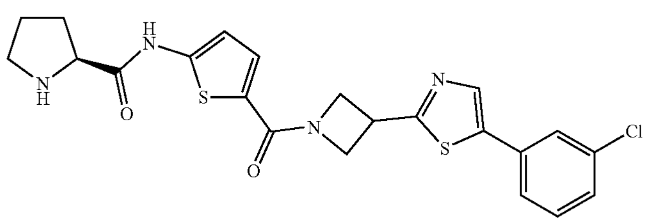 [SMILES: O=C(Nc1ccc(C(=O)N2CC(c3ncc(-c4cccc(Cl)c4)s3)C2)s1)[C@@H]1CCCN1] | 473.0867 | 473.0871 |
| 74 | 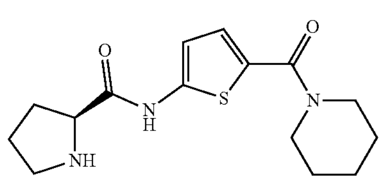 [SMILES: O=C(Nc1ccc(C(=O)N2CCCCC2)s1)[C@@H]1CCCN1] | 308.1427 | 308.1434 |

TABLE 1-continued

Exemplary Compounds

| Number | Structure | HRMS (M − H+), calculated | HRMS (M − H+), found |
| --- | --- | --- | --- |
| 75 | 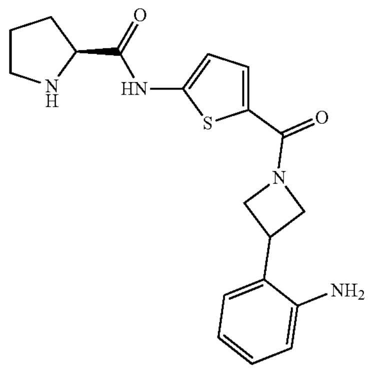 [SMILES: Nc1ccccc1C1CN(C(=O)c2ccc(NC(=O)[C@@H]3CCCN3)s2)C1] | 308.1427 | 308.1437 |
| 76 | 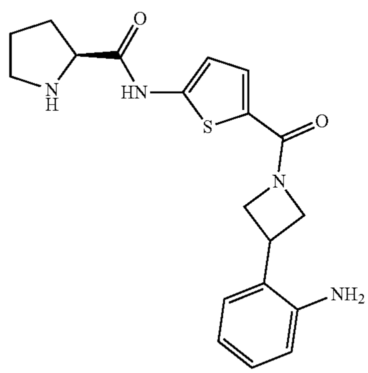 [SMILES: Nc1ccccc1C1CN(C(=O)c2ccc(NC(=O)[C@@H]3CCCN3)s2)C1] | 371.1536 | 371.1543 |
| 77 | 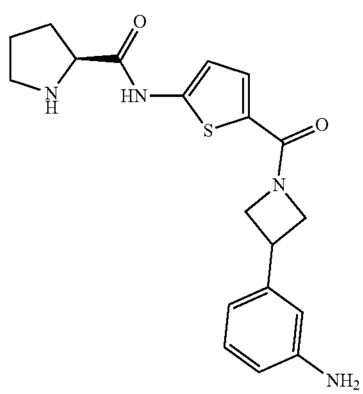 [SMILES: Nc1cccc(C2CN(C(=O)c3ccc(NC(=O)[C@@H]4CCCN4)s3)C2)c1] | 371.1536 | 371.1545 |
| 78 | 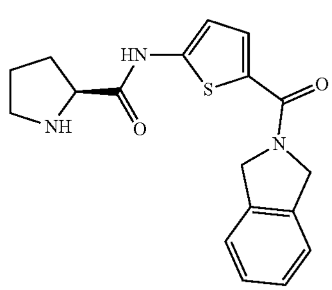 [SMILES: O=C(Nc1ccc(C(=O)N2Cc3ccccc3C2)s1)[C@@H]1CCCN1] | 342.1271 | 342.1275 |

TABLE 1-continued

Exemplary Compounds

| Number | Structure | HRMS (M − H+), calculated | HRMS (M − H+), found |
|---|---|---|---|
| 79 | 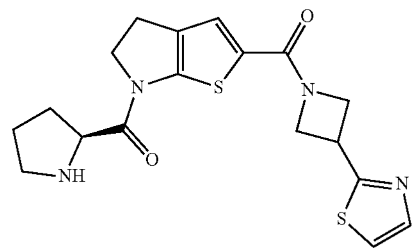 [SMILES: O=C(c1cc2c(s1)N(C(=O)[C@@H]1CCCN1)CC2)N1CC(c2nccs2)C1] | 389.1100 | 389.1109 |
| 80 | 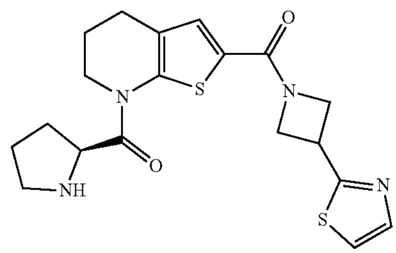 [SMILES: O=C(c1cc2c(s1)N(C(=O)[C@@H]1CCCN1)CCC2)N1CC(c2nccs2)C1] | 403.1257 | 403.1264 |
| 81 | 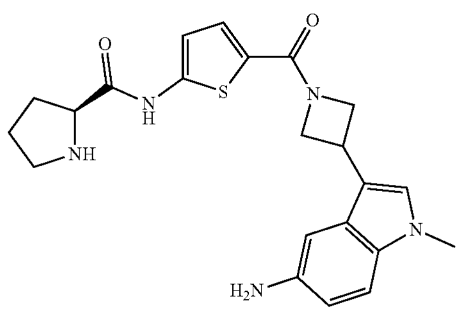 [SMILES: Cn1cc(C2CN(C(=O)c3ccc(NC(=O)[C@@H]4CCCN4)s3)C2)c2cc(N)ccc21] | 424.1802 | 424.1811 |
| 82 | 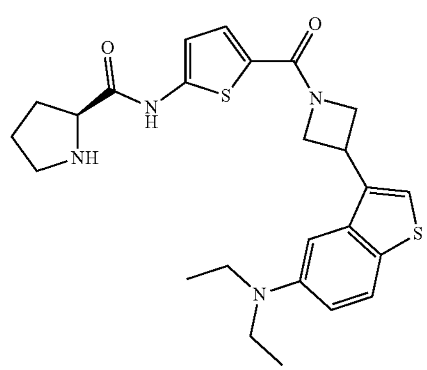 [SMILES: CCN(CC)c1ccc2scc(C3CN(C(=O)c4ccc(NC(=O)[C@@H]5CCCN5)s4)C3)c2c1] | 483.1883 | 483.1892 |
| 83 | 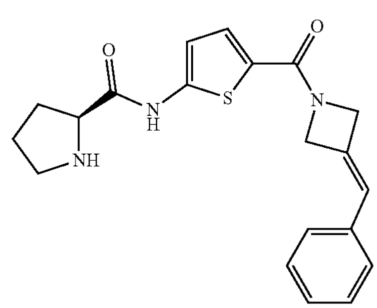 [SMILES: O=C(Nc1ccc(C(=O)N2CC(=Cc3ccccc3)C2)s1)[C@@H]1CCCN1] | 368.1427 | 368.1428 |

TABLE 1-continued

Exemplary Compounds

| Number | Structure | HRMS (M − H+), calculated | HRMS (M − H+), found |
|---|---|---|---|
| 84 | | 364.0896 | 364.0903 |
| 85 | | 363.0944 | 363.0952 |
| 86 | | 357.1380 | 357.1389 |
| 87 | | 457.1096 | 457.1100 |
| 88 | | 413.1100 | 413.1106 |

TABLE 1-continued

Exemplary Compounds

| Number | Structure | HRMS (M − H+), calculated | HRMS (M − H+), found |
|---|---|---|---|
| 89 | 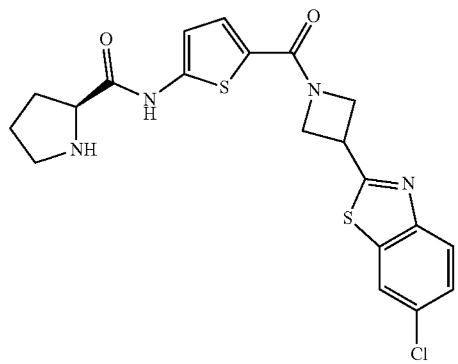 [SMILES: O=C(Nc1ccc(C(=O)N2CC(c3nc4ccc(Cl)cc4s3)C2)s1)[C@@H]1CCCN1] | 447.0711 | 447.0715 |
| 90 | 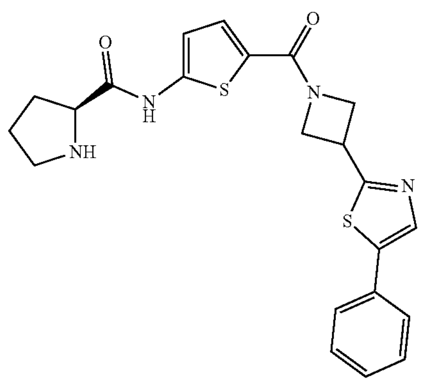 [SMILES: O=C(Nc1ccc(C(=O)N2CC(c3ncc(-c4ccccc4)s3)C2)s1)[C@@H]1CCCN1] | 439.1257 | 439.1259 |
| 91 | 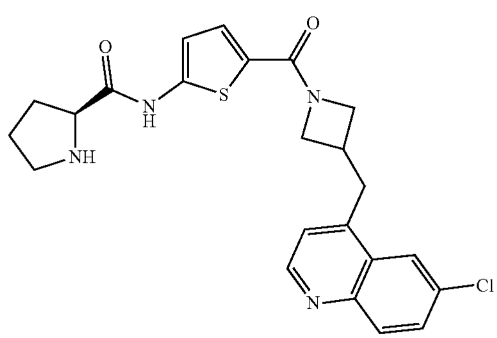 [SMILES: O=C(Nc1ccc(C(=O)N2CC(Cc3ccnc4ccc(Cl)cc34)C2)s1)[C@@H]1CCCN1] | 455.1303 | 455.1305 |
| 92 | 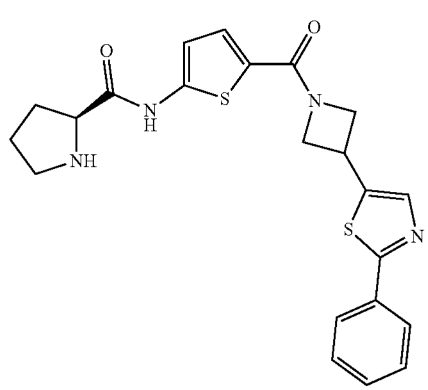 [SMILES: O=C(Nc1ccc(C(=O)N2CC(c3cnc(-c4ccccc4)s3)C2)s1)[C@@H]1CCCN1] | 439.1257 | 439.1259 |

TABLE 1-continued
Exemplary Compounds
| Number | Structure | HRMS (M − H+), calculated | HRMS (M − H+), found |
|---|---|---|---|
| 93 | 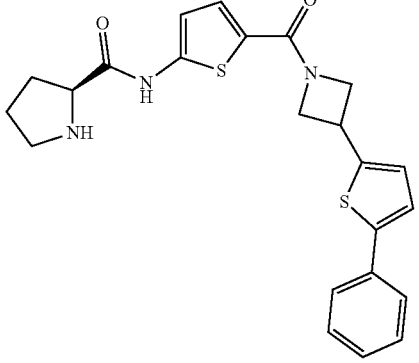 | 438.1304 | 438.1311 |
| 94 | 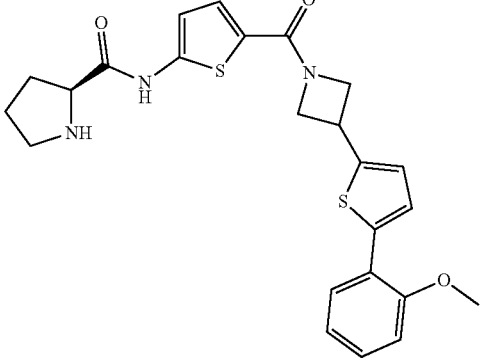 | 469.1363 | 469.1370 |
| 95 | 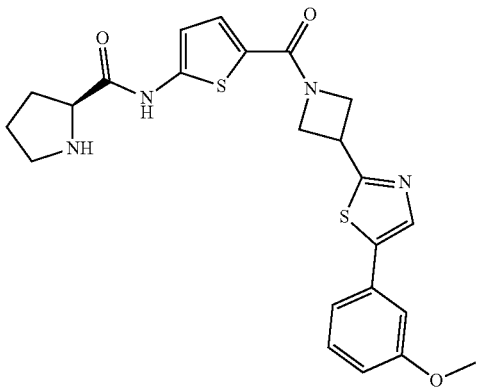 [SMILES: COc1cccc(-c2cnc(C3CN(C(=O)c4ccc(NC(=O)[C@@H]5CCCN5)s4)C3)s2)c1] | 469.1363 | 469.1372 |
| 96 | 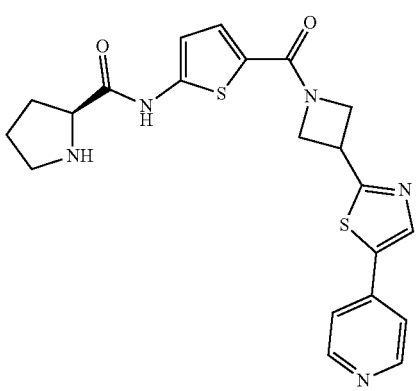 [SMILES: O=C(Nc1ccc(C(=O)N2CC(c3ncc(-c4ccncc4)s3)C2)s1)[C@@H]1CCCN1] | 440.1209 | 440.1214 |

TABLE 1-continued

Exemplary Compounds

| Number | Structure | HRMS (M − H+), calculated | HRMS (M − H+), found |
| --- | --- | --- | --- |
| 97 | 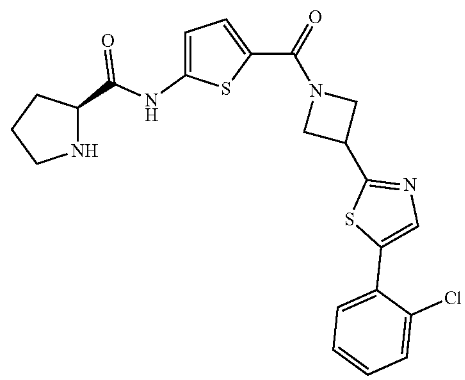 [SMILES: O=C(Nc1ccc(C(=O)N2CC(c3ncc(-c4ccccc4Cl)s3)C2)s1)[C@@H]1CCCN1] | 473.0867 | 473.0871 |
| 98 | 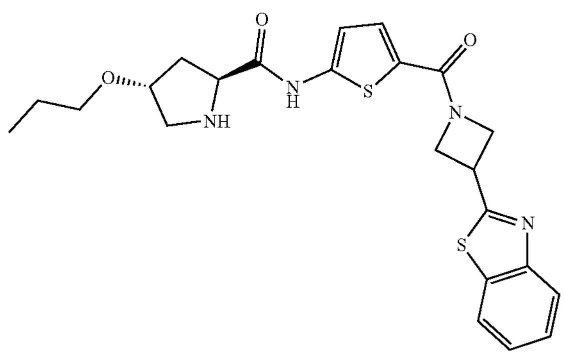 [SMILES: CCCO[C@H]1CN[C@H](C(=O)Nc2ccc(C(=O)N3CC(c4nc5ccccc5s4)C3)s2)C1] | 471.1519 | 471.1520 |
| 99 | 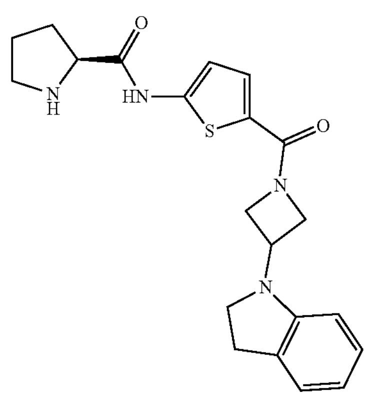 [SMILES: O=C(Nc1ccc(C(=O)N2CC(N3CCc4ccccc43)C2)s1)[C@@H]1CCCN1] | 397.1693 | 397.1700 |
| 100 | 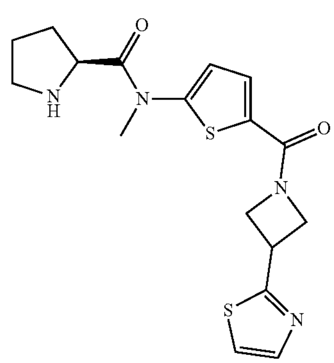 [SMILES: CN(C(=O)[C@@H]1CCCN1)c1ccc(C(=O)N2CC(c3nccs3)C2)s1] | 377.1100 | 377.1090 |

TABLE 1-continued

Exemplary Compounds

| Number | Structure | HRMS (M − H+), calculated | HRMS (M − H+), found |
|---|---|---|---|
| 101 | 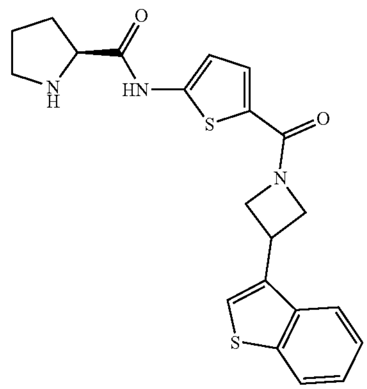 [SMILES: O=C(Nc1ccc(C(=O)N2CC(c3csc4ccccc34)C2)s1)[C@@H]1CCCN1] | 412.1148 | 412.1154 |
| 102 | 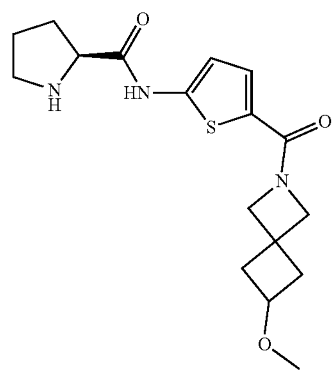 [SMILES: COC1CC2(C1)CN(C(=O)c1ccc(NC(=O)[C@@H]3CCCN3)s1)C2] | 350.1533 | 350.1538 |
| 103 | 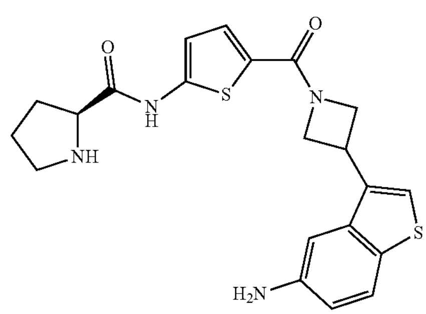 [SMILES: Nc1ccc2scc(C3CN(C(=O)c4ccc(NC(=O)[C@@H]5CCCN5)s4)C3)c2c1] | 427.1257 | 427.1269 |
| 104 | 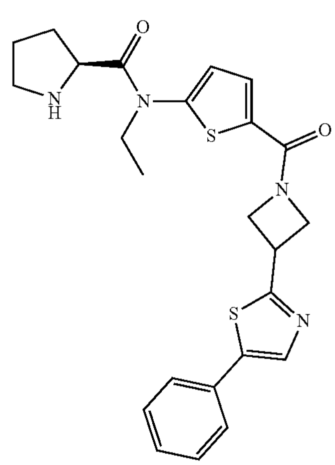 [SMILES: CCN(C(=O)[C@@H]1CCCN1)c1ccc(C(=O)N2CC(c3ncc(-c4ccccc4)s3)C2)s1] | 467.157 | 467.158 |

TABLE 1-continued
Exemplary Compounds
| Number | Structure | HRMS (M − H+), calculated | HRMS (M − H+), found |
|---|---|---|---|
| 105 | 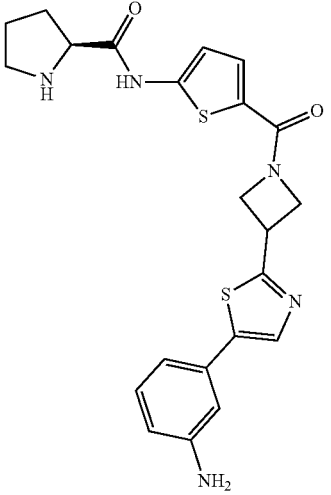 [SMILES: Nc1cccc(-c2cnc(C3CN(C(=O)c4ccc(NC(=O)[C@@H]5CCCN5)s4)C3)s2)c1] | 454.1366 | 454.137 |
| 106 | 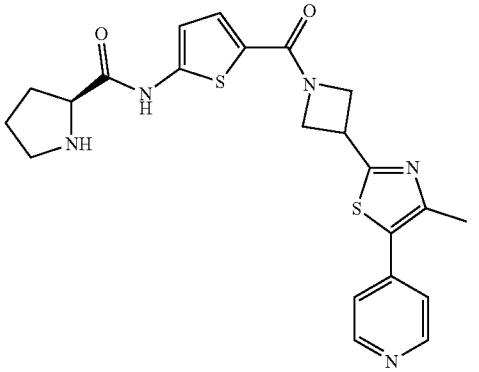 [SMILES: Cc1nc(C2CN(C(=O)c3ccc(NC(=O)[C@@H]4CCCN4)s3)C2)sc1-c1ccncc1] | 454.1366 | 454.1374 |
| 107 | 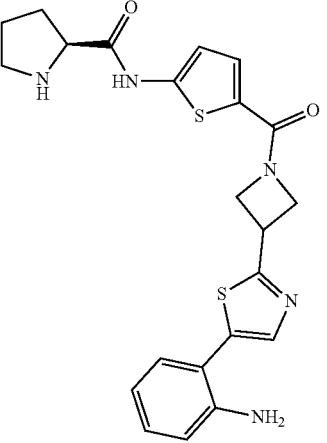 [SMILES: Nc1ccccc1-c1cnc(C2CN(C(=O)c3ccc(NC(=O)[C@@H]4CCCN4)s3)C2)s1] | 454.1366 | 454.1369 |

TABLE 1-continued

Exemplary Compounds

| Number | Structure | HRMS (M − H+), calculated | HRMS (M − H+), found |
|---|---|---|---|
| 108 | 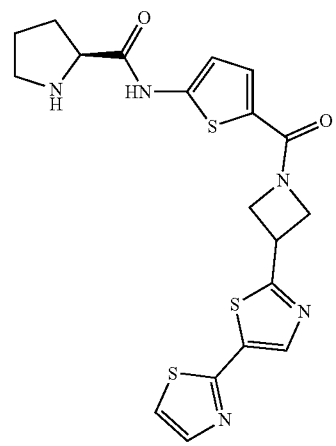 [SMILES: O=C(Nc1ccc(C(=O)N2CC(c3ncc(-c4nccs4)s3)C2)s1)[C@@H]1CCCN1] | 446.0774 | 446.0780 |
| 109 | 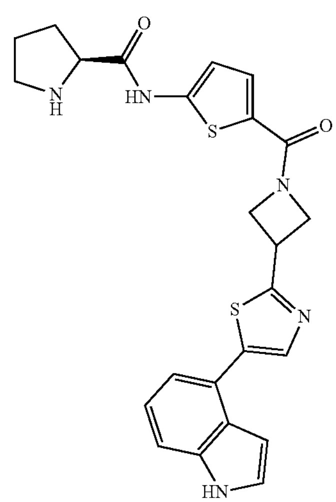 [SMILES: O=C(Nc1ccc(C(=O)N2CC(c3ncc(-c4cccc5[nH]ccc45)s3)C2)s1)[C@@H]1CCCN1] | 478.1366 | 478.1376 |
| 110 | 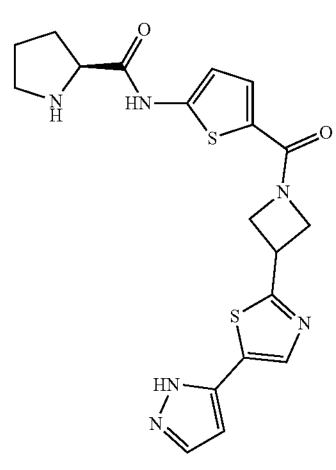 [SMILES: O=C(Nc1ccc(C(=O)N2CC(c3ncc(-c4ccn[nH]4)s3)C2)s1)[C@@H]1CCCN1] | 429.1162 | 429.1176 |

TABLE 1-continued

Exemplary Compounds

| Number | Structure | HRMS (M − H+), calculated | HRMS (M − H+), found |
|---|---|---|---|
| 111 | 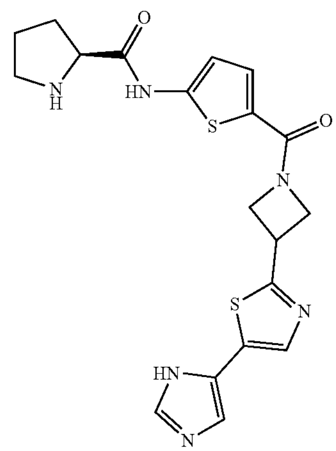 [SMILES: O=C(Nc1ccc(C(=O)N2CC(c3ncc(-c4cnc[nH]4)s3)C2)s1)[C@@H]1CCCN1] | 429.1162 | 429.1173 |
| 112 | 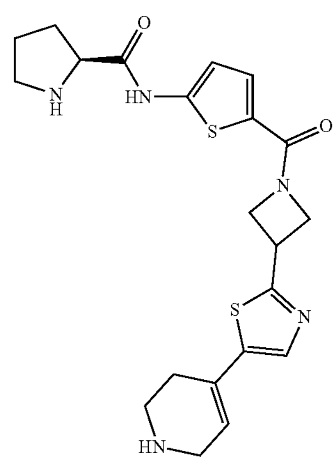 [SMILES: O=C(Nc1ccc(C(=O)N2CC(c3ncc(C4=CCNCC4)s3)C2)s1)[C@@H]1CCCN1] | 444.1522 | 444.1523 |
| 113 | 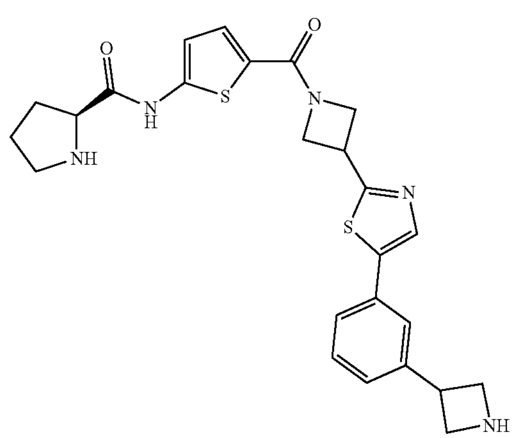 [SMILES: O=C(Nc1ccc(C(=O)N2CC(c3ncc(-c4cccc(C5CNC5)c4)s3)C2)s1)[C@@H]1CCCN1] | 494.1679 | 494.1698 |

TABLE 1-continued
Exemplary Compounds
| Number | Structure | HRMS (M − H+), calculated | HRMS (M − H+), found |
|---|---|---|---|
| 114 | 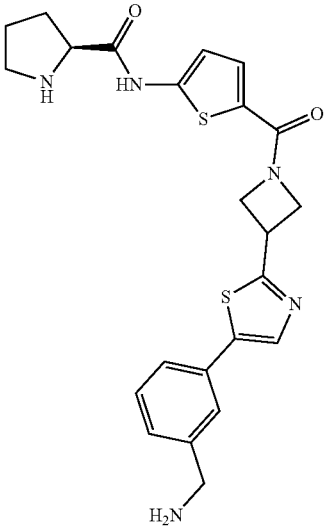 [SMILES: NCc1cccc(-c2cnc(C3CN(C(=O)c4ccc(NC(=O)[C@@H]5CCCN5)s4)C3)s2)c1] | 468.1522 | 468.1532 |
| 115 | 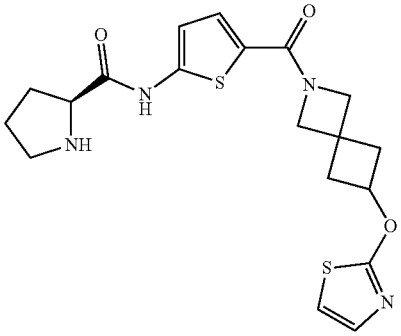 [SMILES: O=C(Nc1ccc(C(=O)N2CC3(CC(Oc4nccs4)C3)C2)s1)[C@@H]1CCCN1] | 419.1206 | 419.1219 |
| 116 | 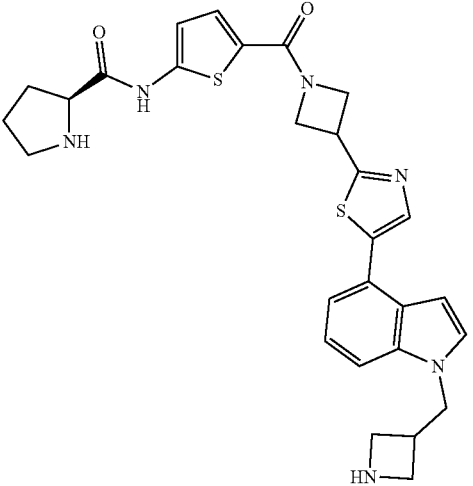 [SMILES: O=C(Nc1ccc(C(=O)N2CC(c3ncc(-c4cccc5c4ccn5CC4CNC4)s3)C2)s1)[C@@H]1CCCN1] | 547.1944 | 547.1956 |

TABLE 1-continued
Exemplary Compounds
| Number | Structure | HRMS (M − H+), calculated | HRMS (M − H+), found |
|---|---|---|---|
| 117 | 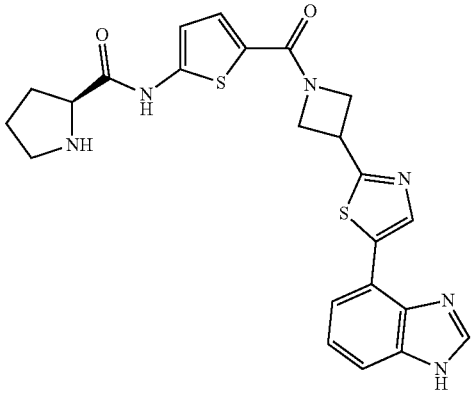 [SMILES: O=C(Nc1ccc(C(=O)N2CC(c3ncc(-c4cccc5[nH]cnc45)s3)C2)s1)[C@@H]1CCCN1] | 479.1318 | 479.1342 |
| 118 | 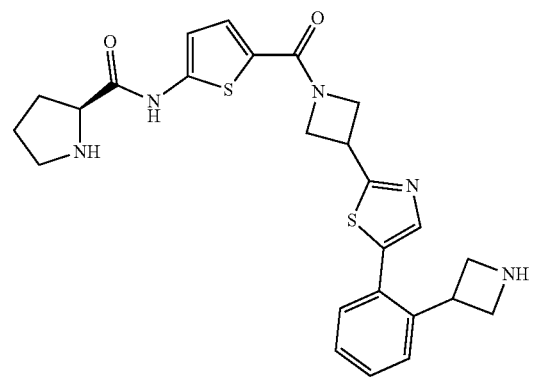 [SMILES: O=C(Nc1ccc(C(=O)N2CC(c3ncc(-c4ccccc4C4CNC4)s3)C2)s1)[C@@H]1CCCN1] | 494.1679 | 494.1681 |
| 119 | 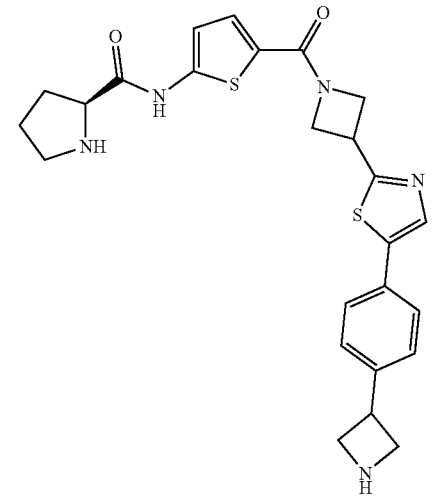 [SMILES: O=C(Nc1ccc(C(=O)N2CC(c3ncc(-c4ccc(C5CNC5)cc4)s3)C2)s1)[C@@H]1CCCN1] | 494.1679 | 494.1679 |

TABLE 1-continued

Exemplary Compounds

| Number | Structure | HRMS (M − H+), calculated | HRMS (M − H+), found |
|---|---|---|---|
| 120 | 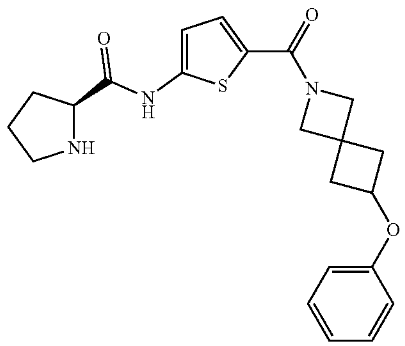 [SMILES: O=C(Nc1ccc(C(=O)N2CC3(CC(Oc4ccccc4)C3)C2)s1)[C@@H]1CCCN1] | 412.1689 | 412.1691 |
| 121 | 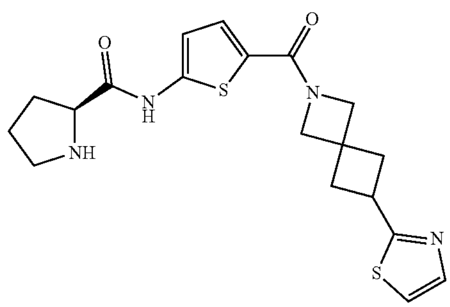 [SMILES: O=C(Nc1ccc(C(=O)N2CC3(CC(c4nccs4)C3)C2)s1)[C@@H]1CCCN1] | 403.1257 | 403.1267 |
| 122 | 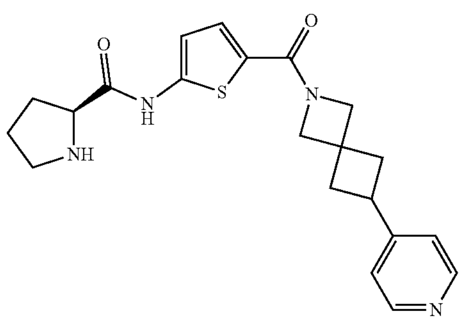 [SMILES: O=C(Nc1ccc(C(=O)N2CC3(CC(c4ccncc4)C3)C2)s1)[C@@H]1CCCN1] | 397.1693 | 397.1698 |
| 123 | 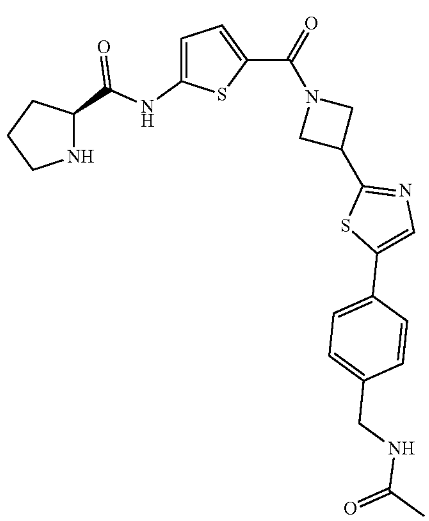 [SMILES: CC(=O)NCc1ccc(-c2cnc(C3CN(C(=O)c4ccc(NC(=O)[C@@H]5CCCN5)s4)C3)s2)cc1] | 510.1628 | 510.1628 |

TABLE 1-continued
Exemplary Compounds
| Number | Structure | HRMS (M − H+), calculated | HRMS (M − H+), found |
|---|---|---|---|
| 124 | 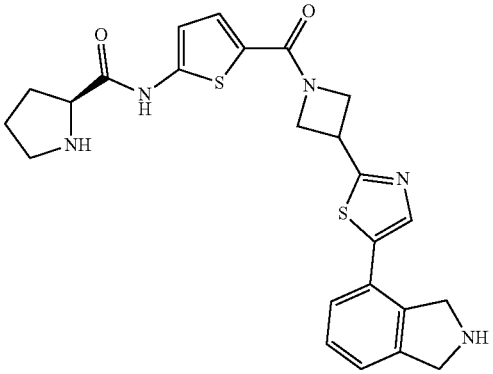 [SMILES: O=C(Nc1ccc(C(=O)N2CC(c3ncc(-c4cccc5c4CNC5)s3)C2)s1)[C@@H]1CCCN1] | 480.1522 | 480.1533 |
| 125 | 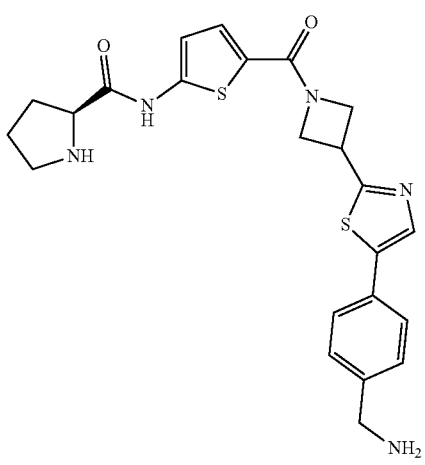 [SMILES: NCc1ccc(-c2cnc(C3CN(C(=O)c4ccc(NC(=O)[C@@H]5CCCN5)s4)C3)s2)cc1] | 468.1522 | 468.1499 |
| 126 | 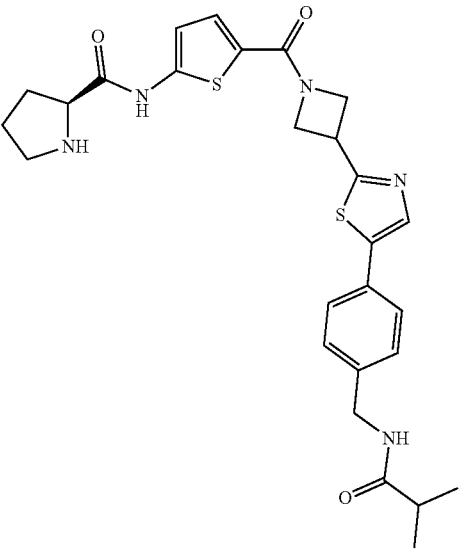 [SMILES: CC(C)C(=O)NCc1ccc(-c2cnc(C3CN(C(=O)c4ccc(NC(=O)[C@@H]5CCCN5)s4)C3)s2)cc1] | 538.1941 | 538.1950 |

TABLE 1-continued
Exemplary Compounds
| Number | Structure | HRMS (M − H+), calculated | HRMS (M − H+), found |
|---|---|---|---|
| 127 | 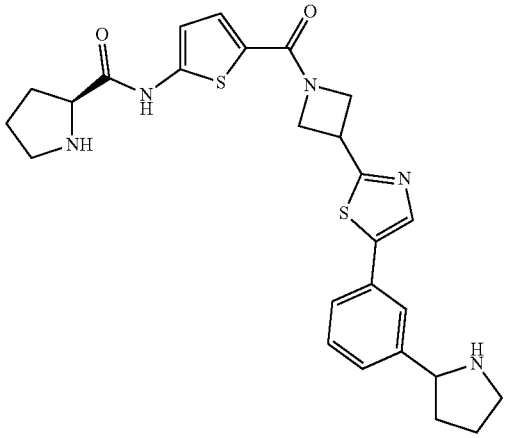 [SMILES: O=C(Nc1ccc(C(=O)N2CC(c3ncc(-c4cccc(C5CCCN5)c4)s3)C2)s1)[C@@H]1CCCN1] | 508.1835 | 508.1839 |
| 128 | 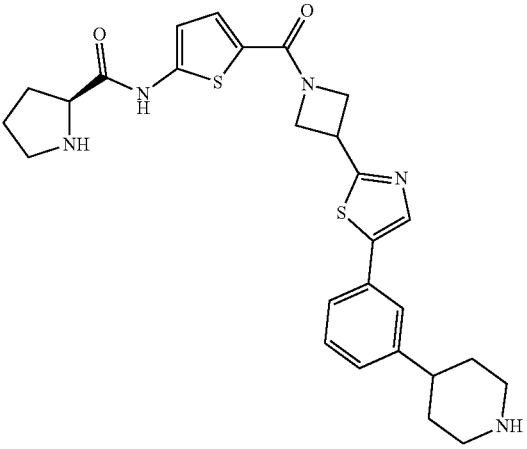 [SMILES: O=C(Nc1ccc(C(=O)N2CC(c3ncc(-c4cccc(C5CCNCC5)c4)s3)C2)s1)[C@@H]1CCCN1] | 522.1992 | 522.1993 |
| 129 | 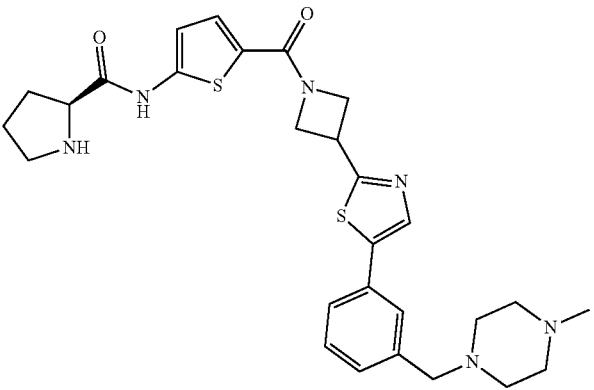 [SMILES: CN1CCN(Cc2cccc(-c3cnc(C4CN(C(=O)c5ccc(NC(=O)[C@@H]6CCCN6)s5)C4)s3)c2)CC1] | 551.2257 | 551.2265 |

TABLE 1-continued
Exemplary Compounds
| Number | Structure | HRMS (M − H+), calculated | HRMS (M − H+), found |
|---|---|---|---|
| 130 | 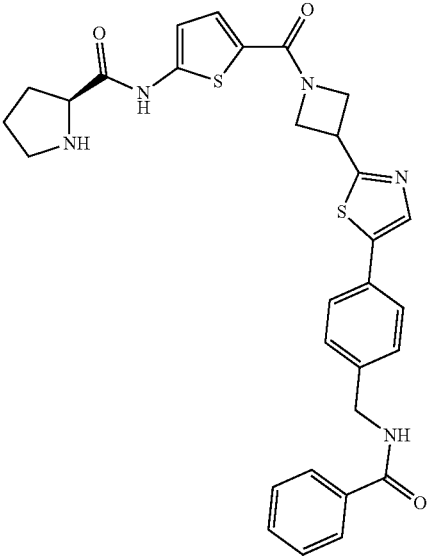 [SMILES: O=C(NCc1ccc(-c2cnc(C3CN(C(=O)c4ccc(NC(=O)[C@@H]5CCCN5)s4)C3)s2)cc1)c1ccccc1] | 572.1785 | 572.1786 |
| 131 | 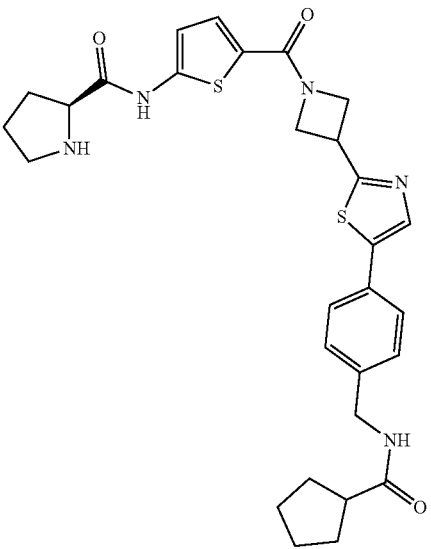 [SMILES: O=C(NCc1ccc(-c2cnc(C3CN(C(=O)c4ccc(NC(=O)[C@@H]5CCCN5)s4)C3)s2)cc1)C1CCCC1] | 564.2098 | 564.2105 |

TABLE 1-continued

Exemplary Compounds

| Number | Structure | HRMS (M − H+), calculated | HRMS (M − H+), found |
|---|---|---|---|
| 132 | 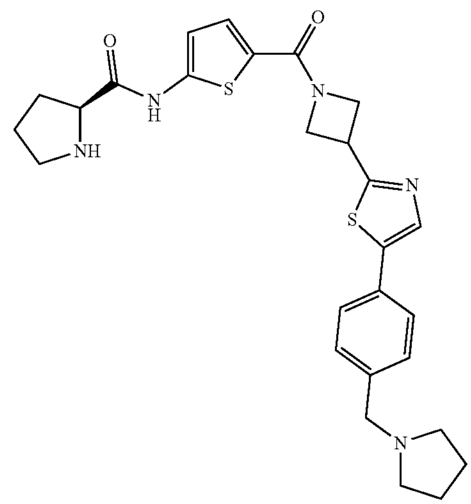 [SMILES: O=C(Nc1ccc(C(=O)N2CC(c3ncc(-c4ccc(CN5CCCC5)cc4)s3)C2)s1)[C@@H]1CCCN1] | 522.1992 | 522.1994 |
| 133 | 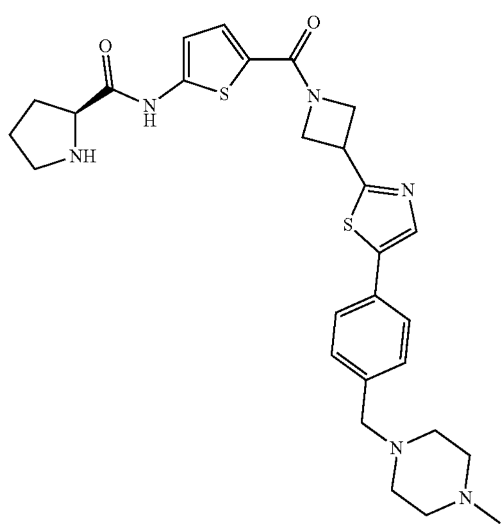 [SMILES: CN1CCN(Cc2ccc(-c3cnc(C4CN(C(=O)c5ccc(NC(=O)[C@@H]6CCCN6)s5)C4)s3)cc2)CC1] | 551.2257 | 551.2263 |
| 134 | 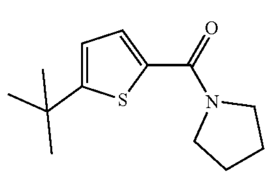 [SMILES: CC(C)(C)c1ccc(C(=O)N2CCCC2)s1] | 238.1260 | 238.1278 |

TABLE 1-continued

Exemplary Compounds

| Number | Structure | HRMS (M − H+), calculated | HRMS (M − H+), found |
| --- | --- | --- | --- |
| 135 | 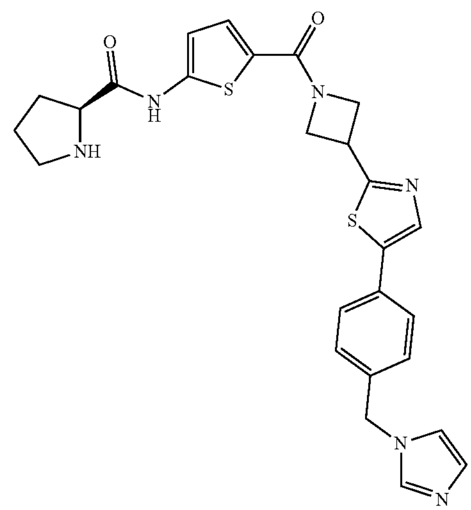 [SMILES: O=C(Nc1ccc(C(=O)N2CC(c3ncc(-c4ccc(Cn5ccnc5)cc4)s3)C2)s1)[C@@H]1CCCN1] | 519.1631 | |
| 136 | 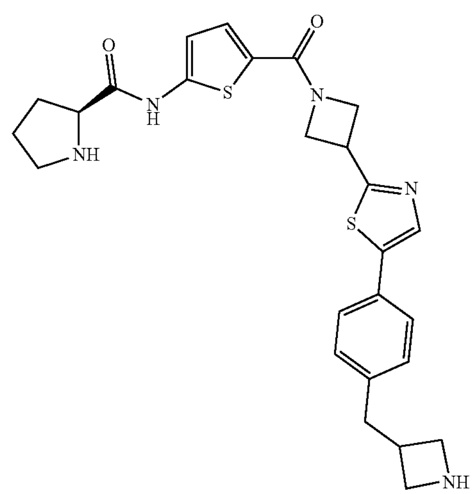 [SMILES: O=C(Nc1ccc(C(=O)N2CC(c3ncc(-c4ccc(CC5CNC5)cc4)s3)C2)s1)[C@@H]1CCCN1] | 508.1835 | |
| 137 | 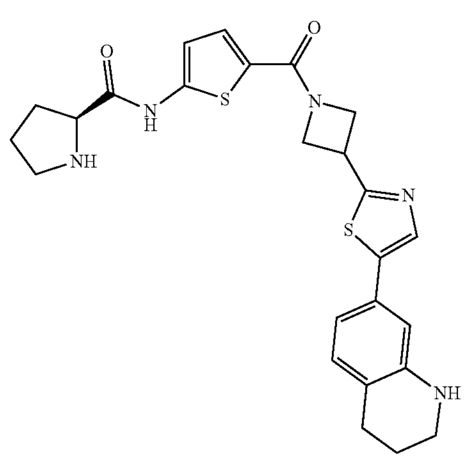 [SMILES: O=C(Nc1ccc(C(=O)N2CC(c3ncc(-c4ccc5c(c4)NCCC5)s3)C2)s1)[C@@H]1CCCN1] | 494.1679 | |

TABLE 1-continued
Exemplary Compounds
| Number | Structure | HRMS (M − H+), calculated | HRMS (M − H+), found |
|---|---|---|---|
| 138 | 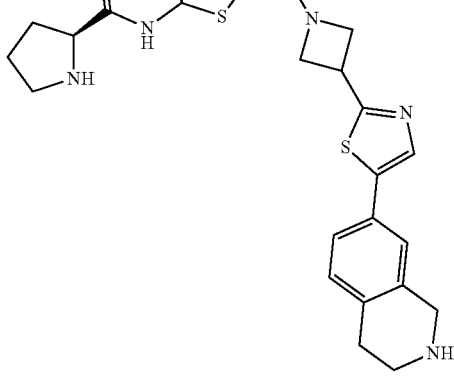 | 494.1679 | |
| 139 | 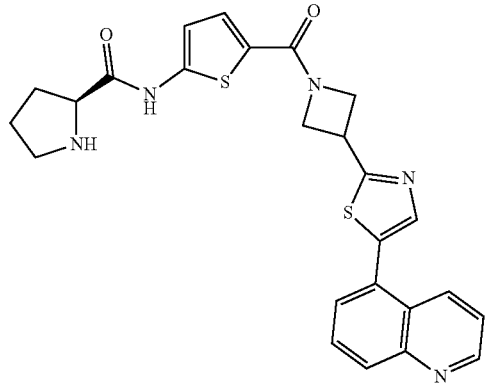 [SMILES: O=C(Nc1ccc(C(=O)N2CC(c3ncc(-c4cccc5ncccc45)s3)C2)s1)[C@@H]1CCCN1] | 490.1366 | |
| 140 | 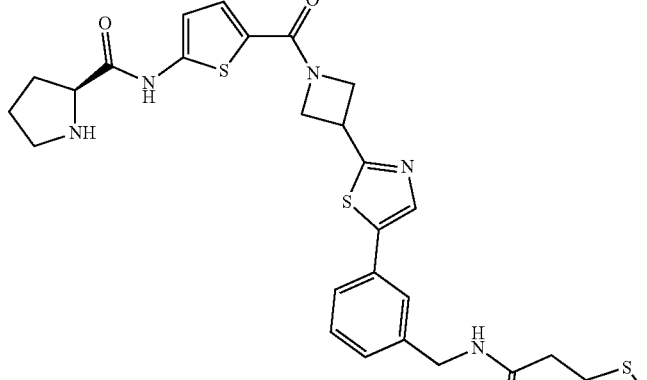 | 593.1458 | |

TABLE 1-continued
Exemplary Compounds
| Number | Structure | HRMS (M − H+), calculated | HRMS (M − H+), found |
|---|---|---|---|
| 141 | 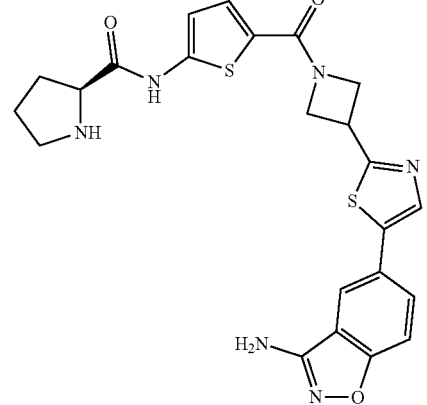 | 495.1268 | |
| 142 | 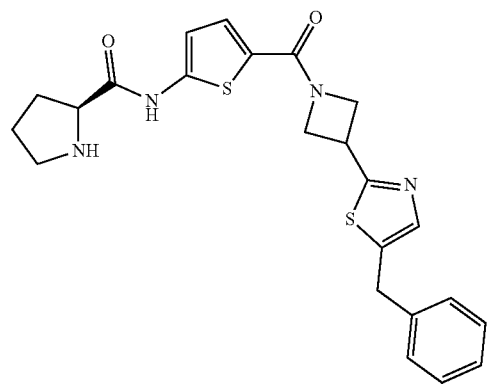 [SMILES: O=C(Nc1ccc(C(=O)N2CC(c3ncc(Cc4ccccc4)s3)C2)s1)[C@@H]1CCCN1] | 453.1413 | |
| 143 | 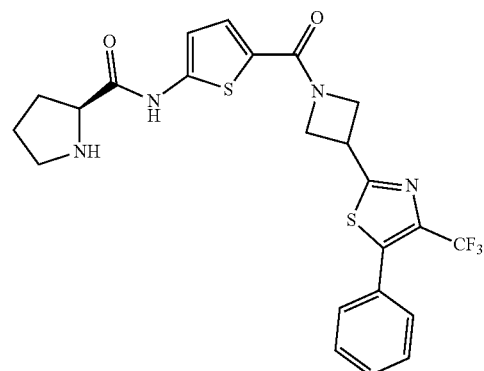 [SMILES: O=C(Nc1ccc(C(=O)N2CC(c3nc(C(F)(F)F)c(-c4ccccc4)s3)C2)s1)[C@@H]1CCCN1] | 507.1131 | |

TABLE 1-continued
Exemplary Compounds
| Number | Structure | HRMS (M − H+), calculated | HRMS (M − H+), found |
|---|---|---|---|
| 144 | 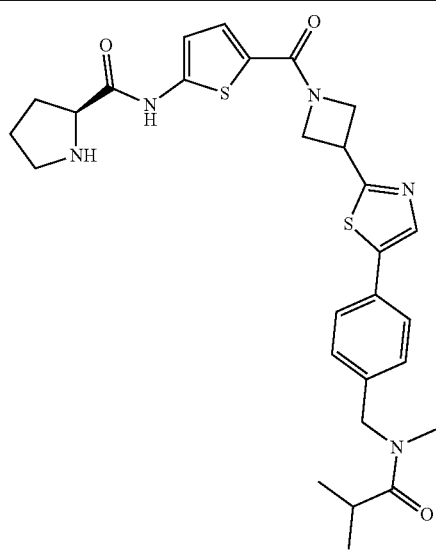 | 552.2098 | |
| 145 | 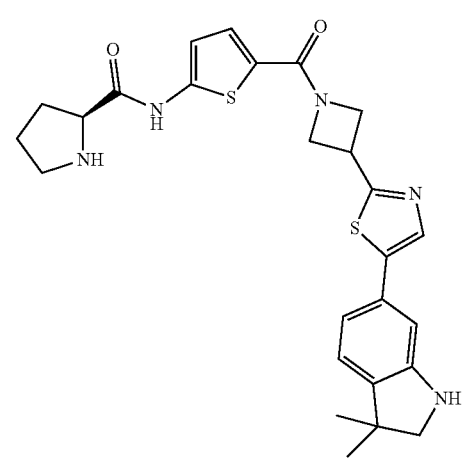 [SMILES: CC1(C)CNc2cc(-c3cnc(C4CN(C(=O)c5ccc(NC(=O)[C@@H]6CCCN6)s5)C4)s3)ccc21] | 508.1835 | |
| 146 | 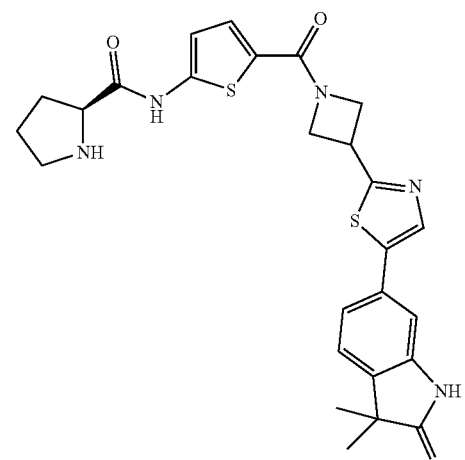 | 522.1628 | |

TABLE 1-continued

Exemplary Compounds

| Number | Structure | HRMS (M − H+), calculated | HRMS (M − H+), found |
|---|---|---|---|
| 147 | 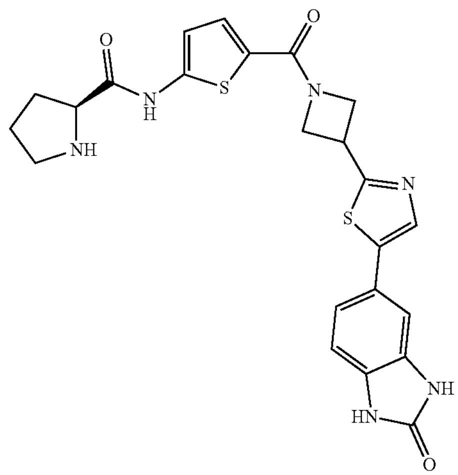 [SMILES: O=C(Nc1ccc(C(=O)N2CC(c3ncc(-c4ccc5[nH]c(=O)[nH]c5c4)s3)C2)s1)[C@@H]1CCCN1] | 495.1268 | |
| 148 | 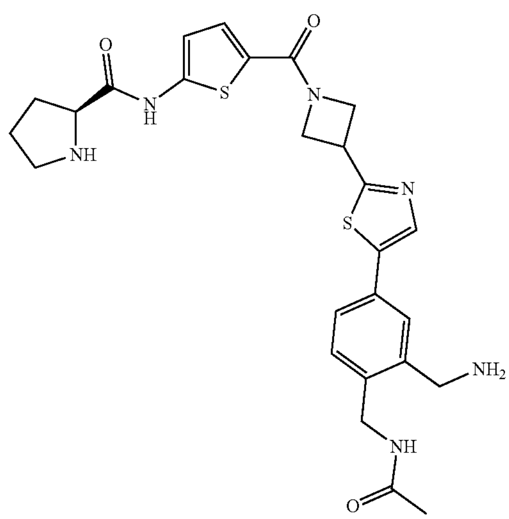 [SMILES: CC(=O)NCc1ccc(-c2cnc(C3CN(C(=O)c4ccc(NC(=O)[C@@H]5CCCN5)s4)C3)s2)cc1CN] | 539.1894 | 539.1901 |
| 149 | 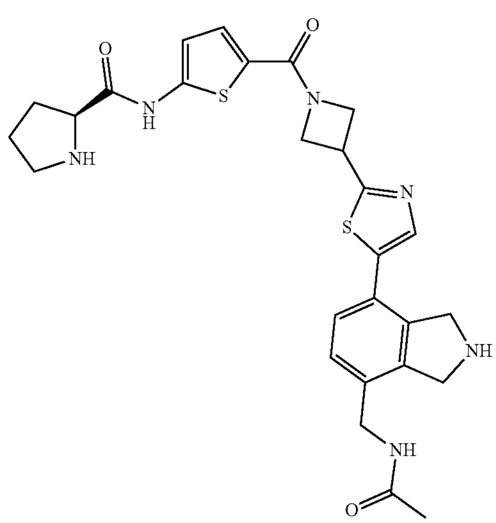 [SMILES: CC(=O)NCc1ccc(-c2cnc(C3CN(C(=O)c4ccc(NC(=O)[C@@H]5CCCN5)s4)C3)s2)c2c1CNC2] | 551.1894 | 551.1905 |

TABLE 1-continued
Exemplary Compounds
| Number | Structure | HRMS (M − H+), calculated | HRMS (M − H+), found |
|---|---|---|---|
| 150 | 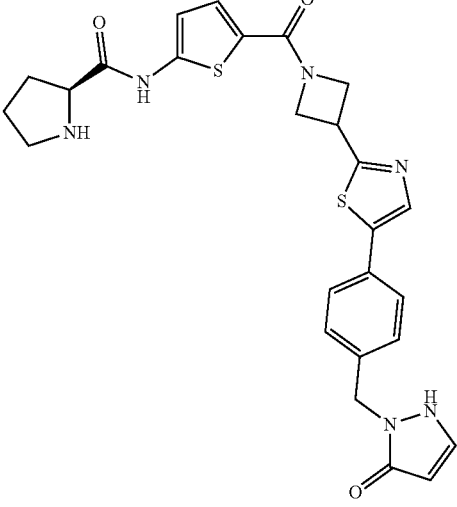 | | 535.1581 |
| 151 | 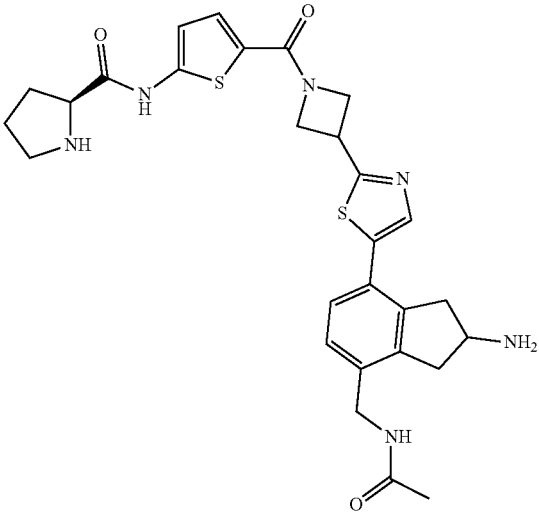 [SMILES: CC(=O)NCc1ccc(-c2cnc(C3CN(C(=O)c4ccc(NC(=O)[C@@H]5CCCN5)s4)C3)s2)c2c1CC(N)C2] | | 565.2050 |

TABLE 1-continued
Exemplary Compounds
| Number | Structure | HRMS (M − H+), calculated | HRMS (M − H+), found |
|---|---|---|---|
| 152 | 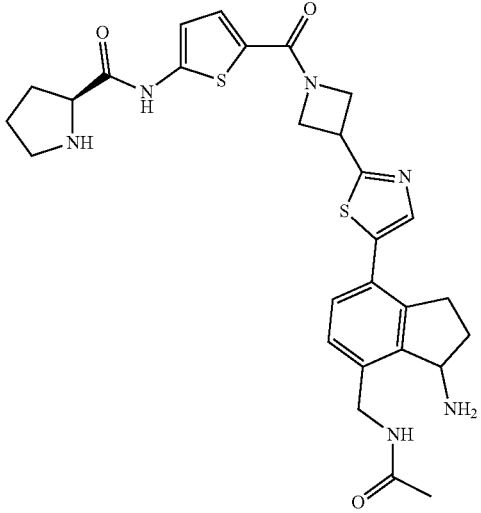 [SMILES: CC(=O)NCc1ccc(-c2cnc(C3CN(C(=O)c4ccc(NC(=O)[C@@H]5CCCN5)s4)C3)s2)c2c1C(N)CC2] | | 565.2050 |
| 153 | 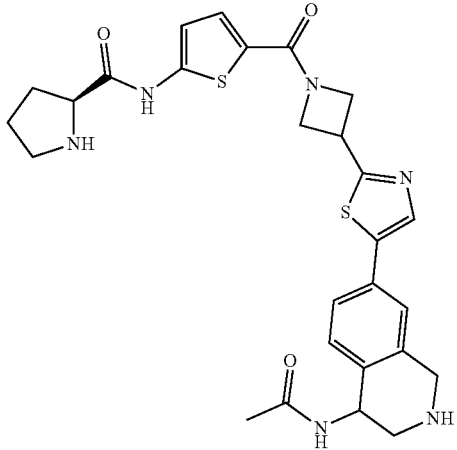 [SMILES: CC(=O)NC1CNCc2cc(-c3cnc(C4CN(C(=O)c5ccc(NC(=O)[C@@H]6CCCN6)s5)C4)s3)ccc21] | | 551.1894 |
| 154 | 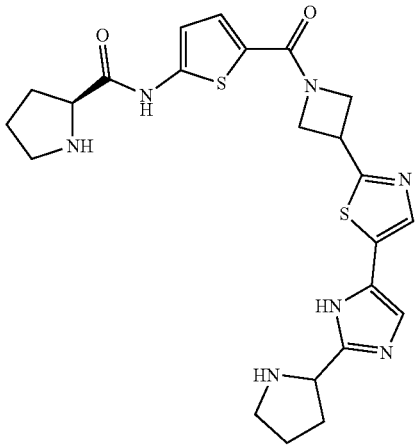 [SMILES: O=C(Nc1ccc(C(=O)N2CC(c3ncc(-c4cnc(C5CCCN5)[nH]4)s3)C2)s1)[C@@H]1CCCN1] | | 498.1740 |

TABLE 1-continued

Exemplary Compounds

| Number | Structure | HRMS (M − H+), calculated | HRMS (M − H+), found |
|---|---|---|---|
| 155 | 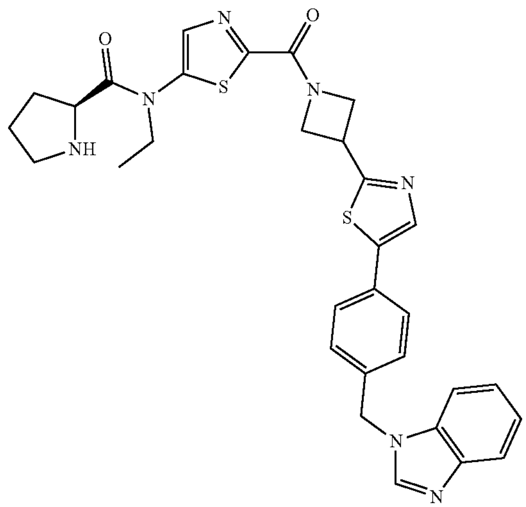 [SMILES: CCN(C(=O)[C@@H]1CCCN1)c1cnc(C(=O)N2CC(c3ncc(-c4ccc(Cn5cnc6ccccc65)cc4)s3)C2)s1] | | 598.2053 |
| 156 | 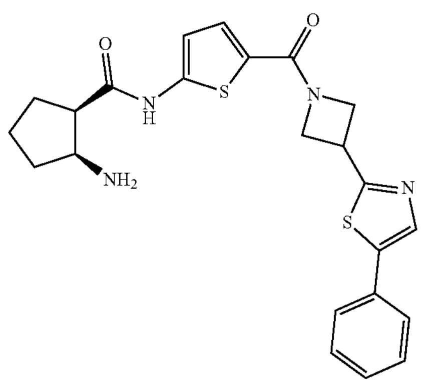 [SMILES: N[C@H]1CCC[C@H]1C(=O)Nc1ccc(C(=O)N2CC(c3ncc(-c4ccccc4)s3)C2)s1] | | 453.1413 |
| 157 | 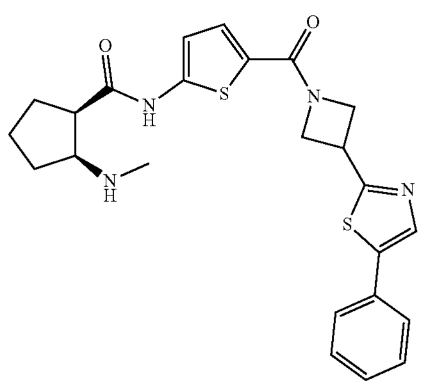 [SMILES: CN[C@H]1CCC[C@H]1C(=O)Nc1ccc(C(=O)N2CC(c3ncc(-c4ccccc4)s3)C2)s1] | | 467.1570 |

TABLE 1-continued

Exemplary Compounds

| Number | Structure | HRMS (M − H+), calculated | HRMS (M − H+), found |
|---|---|---|---|
| 158 | 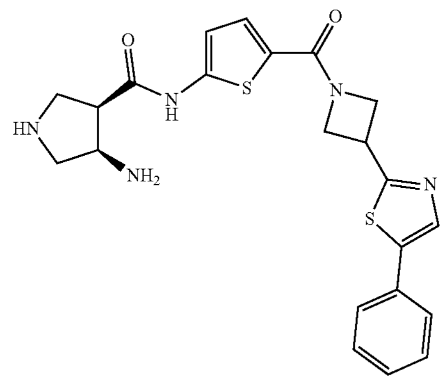 [SMILES: N[C@H]1CNC[C@H]1C(=O)Nc1ccc(C(=O)N2CC(c3ncc(-c4ccccc4)s3)C2)s1] | 454.1366 | |
| 159 | 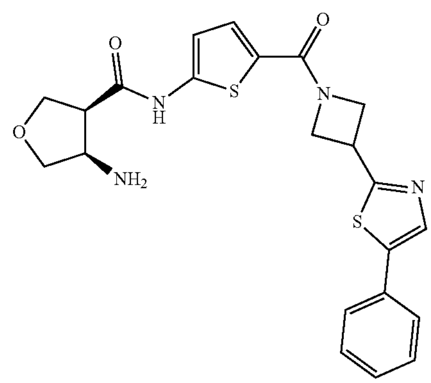 [SMILES: N[C@H]1COC[C@H]1C(=O)Nc1ccc(C(=O)N2CC(c3ncc(-c4ccccc4)s3)C2)s1] | 455.1209 | |
| 160 | 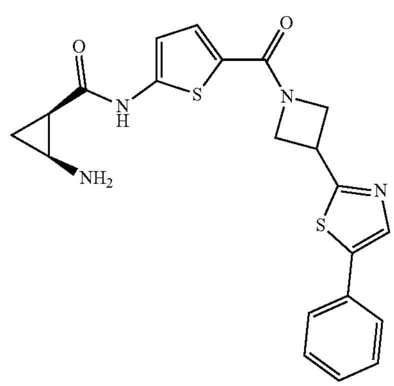 [SMILES: N[C@H]1C[C@H]1C(=O)Nc1ccc(C(=O)N2CC(c3ncc(-c4ccccc4)s3)C2)s1] | 425.1100 | |
| 161 | 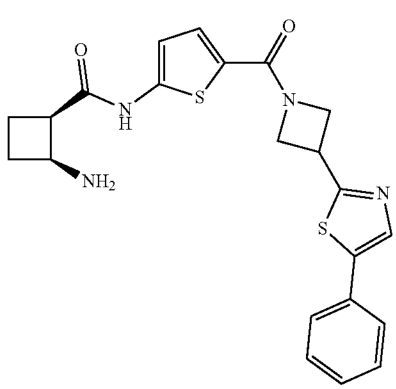 [SMILES: N[C@H]1CC[C@H]1C(=O)Nc1ccc(C(=O)N2CC(c3ncc(-c4ccccc4)s3)C2)s1] | 439.1257 | |

TABLE 1-continued
Exemplary Compounds
| Number | Structure | HRMS (M − H+), calculated | HRMS (M − H+), found |
|---|---|---|---|
| 162 | 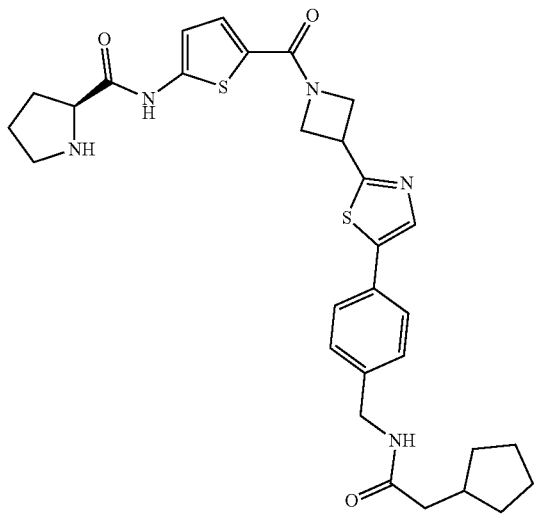 [SMILES: O=C(CC1CCCC1)NCc1ccc(-c2cnc(C3CN(C(=O)c4ccc(NC(=O)[C@@H]5CCCN5)s4)C3)s2)cc1] | 578.2254 | |
| 163 | 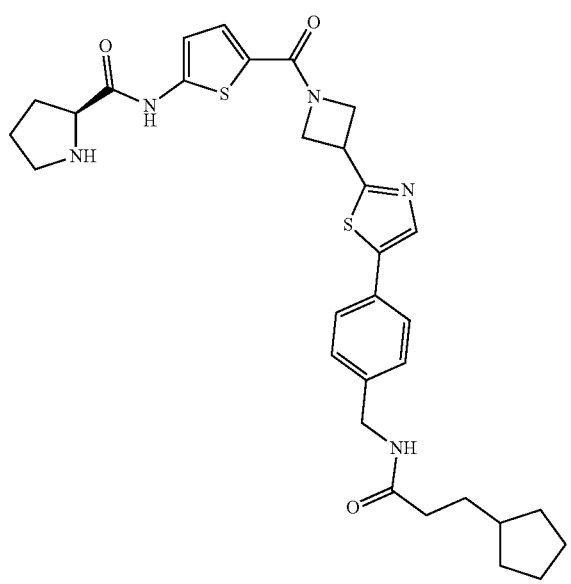 [SMILES: O=C(CCC1CCCC1)NCc1ccc(-c2cnc(C3CN(C(=O)c4ccc(NC(=O)[C@@H]5CCCN5)s4)C3)s2)cc1] | 592.2411 | |

TABLE 1-continued
Exemplary Compounds
| Number | Structure | HRMS (M − H+), calculated | HRMS (M − H+), found |
|---|---|---|---|
| 164 | 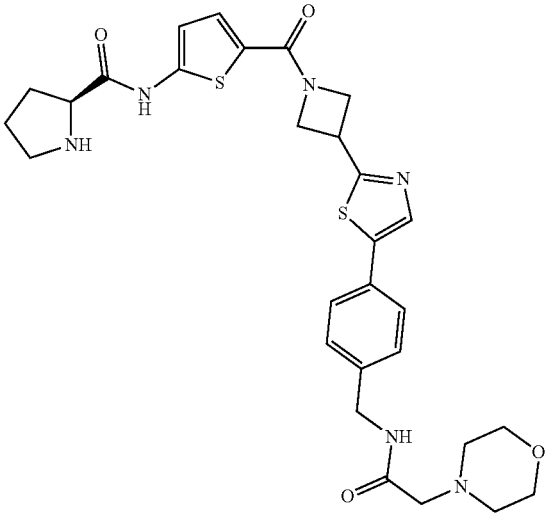 [SMILES: O=C(CN1CCOCC1)NCc1ccc(-c2cnc(C3CN(C(=O)c4ccc(NC(=O)[C@@H]5CCCN5)s4)C3)s2)cc1] | | 595.2156 |
| 165 | 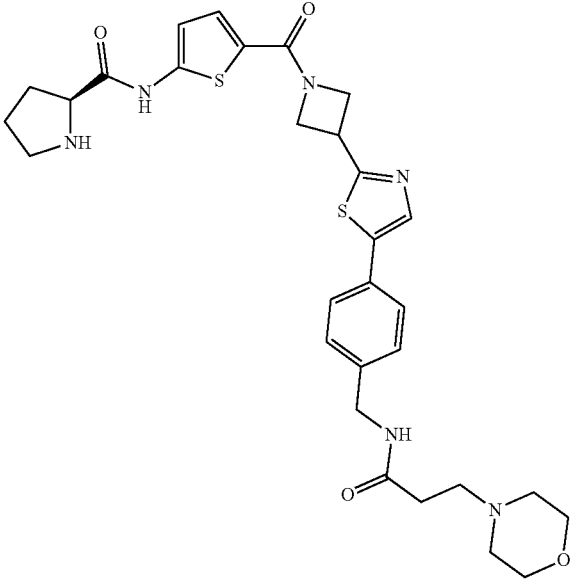 [SMILES: O=C(CCN1CCOCC1)NCc1ccc(-c2cnc(C3CN(C(=O)c4ccc(NC(=O)[C@@H]5CCCN5)s4)C3)s2)cc1] | | 609.2312 |

TABLE 1-continued
Exemplary Compounds
| Number | Structure | HRMS (M − H+), calculated | HRMS (M − H+), found |
|---|---|---|---|
| 166 | 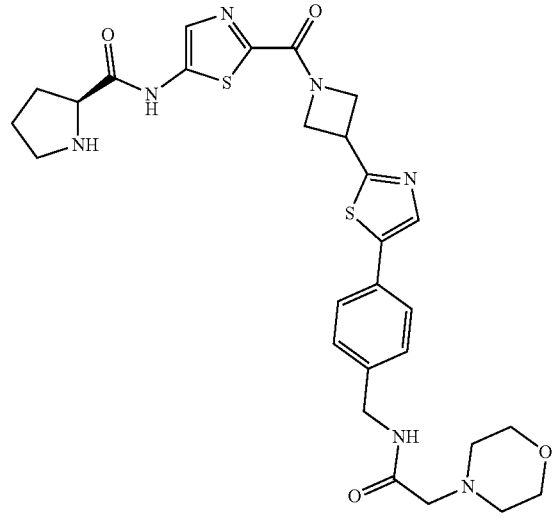 [SMILES: O=C(CN1CCOCC1)NCc1ccc(-c2cnc(C3CN(C(=O)c4ncc(NC(=O)[C@@H]5CCCN5)s4)C3)s2)cc1] | | 596.2108 |
| 167 | 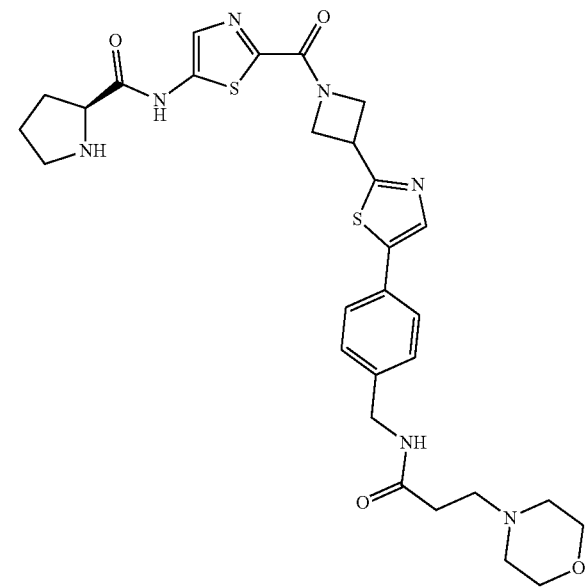 [SMILES: O=C(CCN1CCOCC1)NCc1ccc(-c2cnc(C3CN(C(=O)c4ncc(NC(=O)[C@@H]5CCCN5)s4)C3)s2)cc1] | | 610.2265 |

TABLE 1-continued
Exemplary Compounds
| Number | Structure | HRMS (M − H+), calculated | HRMS (M − H+), found |
|---|---|---|---|
| 168 | 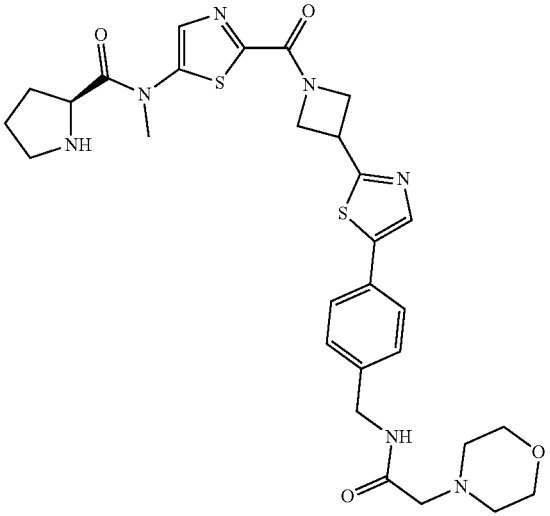 [SMILES: CN(C(=O)[C@@H]1CCCN1)c1cnc(C(=O)N2CC(c3ncc(-c4ccc(CNC(=O)CN5CCOCC5)cc4)s3)C2)s1] | 610.2265 | |
| 169 | 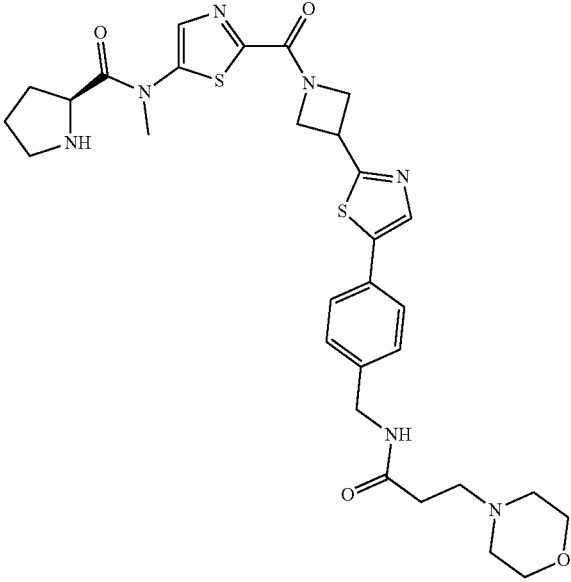 [SMILES: CN(C(=O)[C@@H]1CCCN1)c1cnc(C(=O)N2CC(c3ncc(-c4ccc(CNC(=O)CCN5CCOCC5)cc4)s3)C2)s1] | 624.2421 | |

TABLE 1-continued
Exemplary Compounds
| Number | Structure | HRMS (M − H+), calculated | HRMS (M − H+), found |
|---|---|---|---|
| 170 | 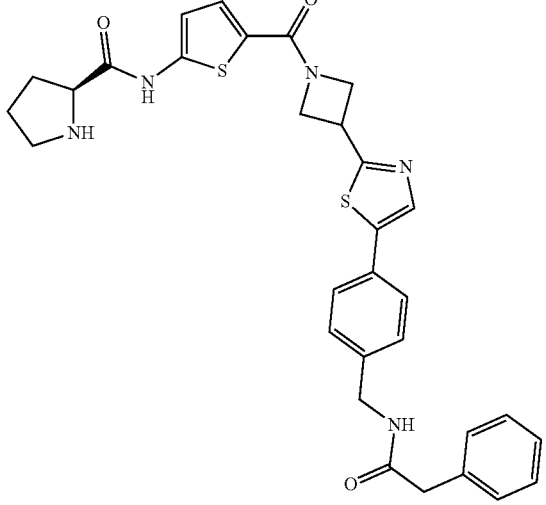 | | 586.1941 |
| 171 | 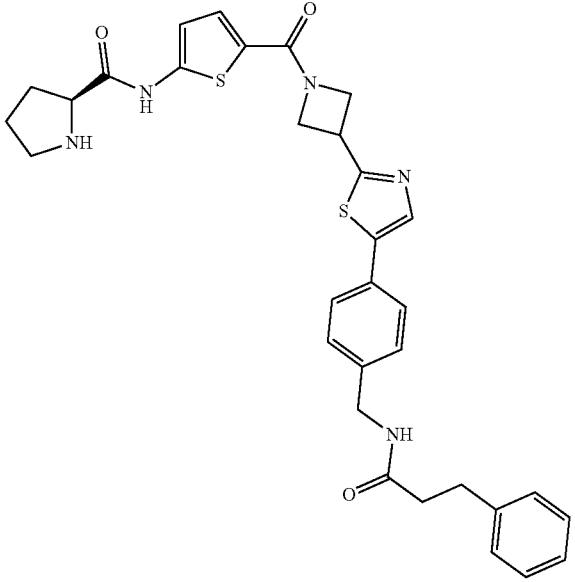 [SMILES: O=C(CCc1ccccc1)NCc1ccc(-c2cnc(C3CN(C(=O)c4ccc(NC(=O)[C@@H]5CCCN5)s4)C3)s2)cc1] | | 600.2098 |

US 11,858,925 B2
203                                                                                                         204
TABLE 1-continued
Exemplary Compounds
| Number | Structure | HRMS (M − H+), calculated | HRMS (M − H+), found |
|---|---|---|---|
| 172 | 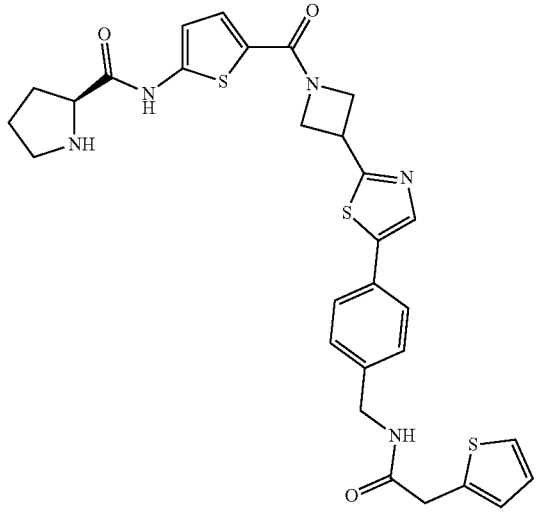 [SMILES: O=C(Cc1cccs1)NCc1ccc(-c2cnc(C3CN(C(=O)c4ccc(NC(=O)[C@@H]5CCCN5)s4)C3)s2)cc1] | | 592.1505 |
| 173 | 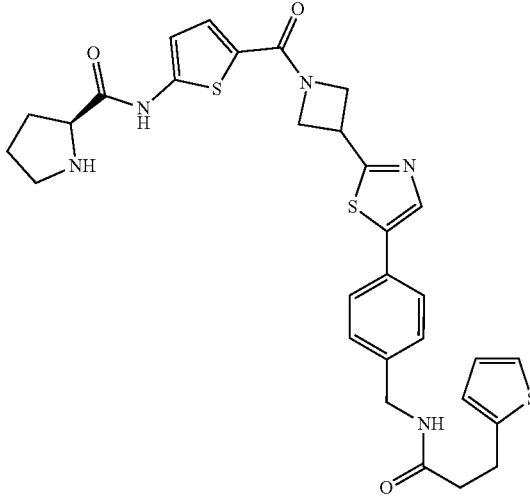 | | 606.1662 |

TABLE 1-continued
Exemplary Compounds
| Number | Structure | HRMS (M − H+), calculated | HRMS (M − H+), found |
|---|---|---|---|
| 174 | 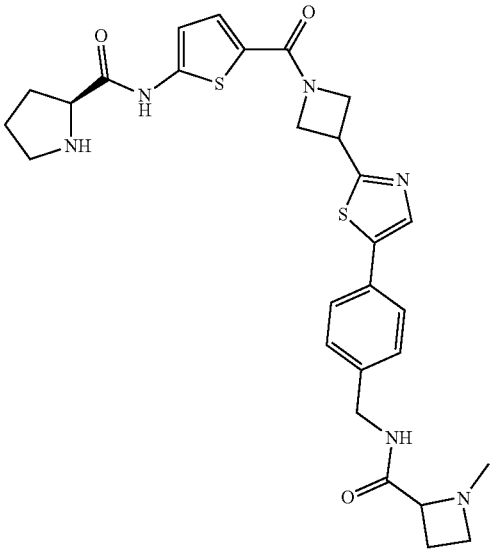 [SMILES: CN1CCC1C(=O)NCc1ccc(-c2cnc(C3CN(C(=O)c4ccc(NC(=O)[C@@H]5CCCN5)s4)C3)s2)cc1] | | 565.2050 |
| 175 | 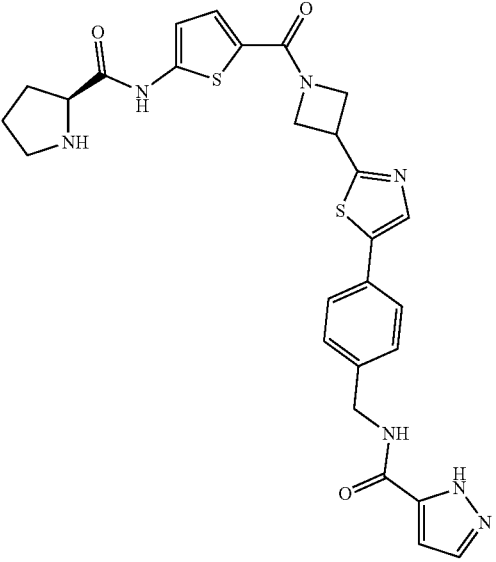 [SMILES: O=C(NCc1ccc(-c2cnc(C3CN(C(=O)c4ccc(NC(=O)[C@@H]5CCCN5)s4)C3)s2)cc1)c1ccn[nH]1] | | 562.1690 |

TABLE 1-continued
Exemplary Compounds
| Number | Structure | HRMS (M − H+), calculated | HRMS (M − H+), found |
|---|---|---|---|
| 176 | 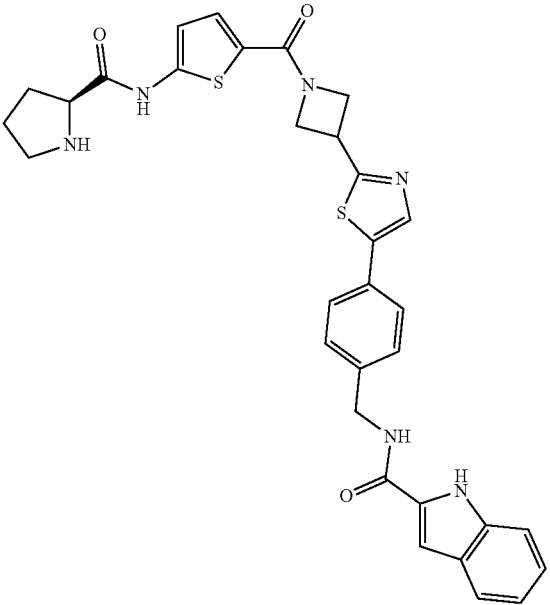 [SMILES: O=C(NCc1ccc(-c2cnc(C3CN(C(=O)c4ccc(NC(=O)[C@@H]5CCCN5)s4)C3)s2)cc1)c1cc2ccccc2[nH]1] | 611.1894 | |
| 177 | 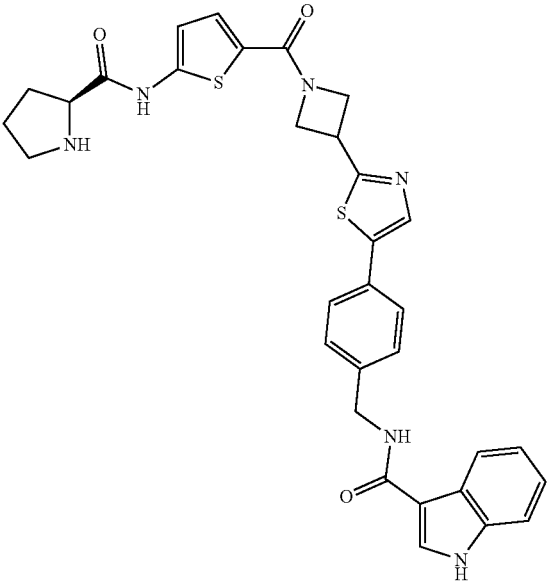 [SMILES: O=C(NCc1ccc(-c2cnc(C3CN(C(=O)c4ccc(NC(=O)[C@@H]5CCCN5)s4)C3)s2)cc1)c1c[nH]c2ccccc12] | 611.1894 | |

TABLE 1-continued
Exemplary Compounds
| Number | Structure | HRMS (M − H+), calculated | HRMS (M − H+), found |
|---|---|---|---|
| 178 | 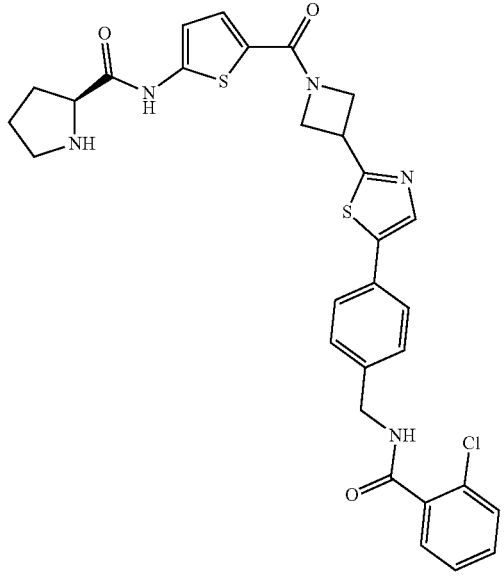 [SMILES: O=C(NCc1ccc(-c2cnc(C3CN(C(=O)c4ccc(NC(=O)[C@@H]5CCCN5)s4)C3)s2)cc1)c1ccccc1Cl] | 606.1395 | |
| 179 | 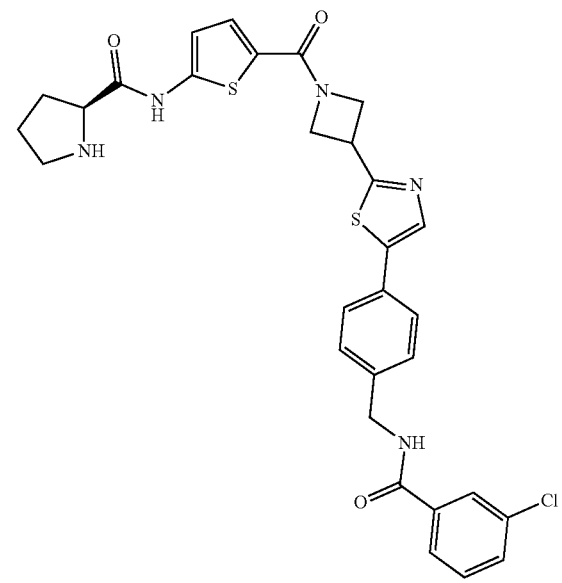 [SMILES: O=C(NCc1ccc(-c2cnc(C3CN(C(=O)c4ccc(NC(=O)[C@@H]5CCCN5)s4)C3)s2)cc1)c1cccc(Cl)c1] | 606.1395 | |

TABLE 1-continued
Exemplary Compounds
| Number | Structure | HRMS (M − H+), calculated | HRMS (M − H+), found |
|---|---|---|---|
| 180 | 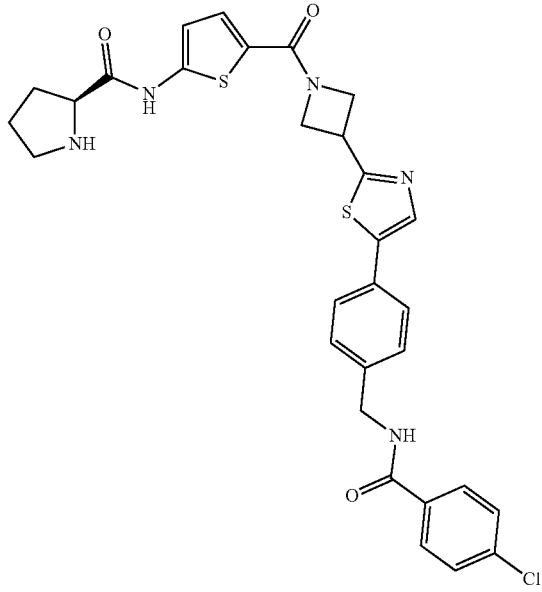 [SMILES: O=C(NCc1ccc(-c2cnc(C3CN(C(=O)c4ccc(NC(=O)[C@@H]5CCCN5)s4)C3)s2)cc1)c1ccc(Cl)cc1] | | 606.1395 |
| 181 | 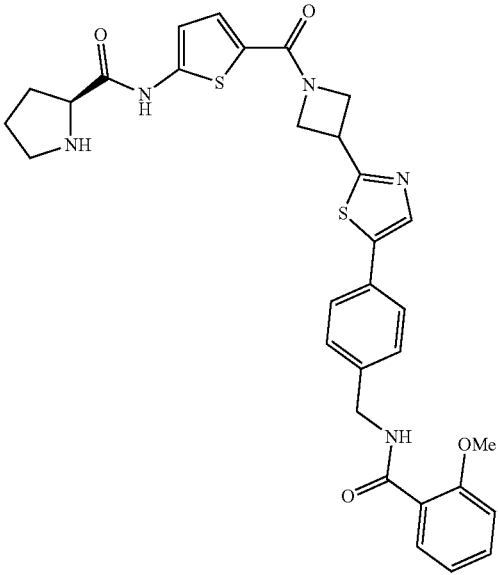 [SMILES: COc1ccccc1C(=O)NCc1ccc(-c2cnc(C3CN(C(=O)c4ccc(NC(=O)[C@@H]5CCCN5)s4)C3)s2)cc1] | | 602.1890 |

TABLE 1-continued
Exemplary Compounds
| Number | Structure | HRMS (M − H+), calculated | HRMS (M − H+), found |
|---|---|---|---|
| 182 | 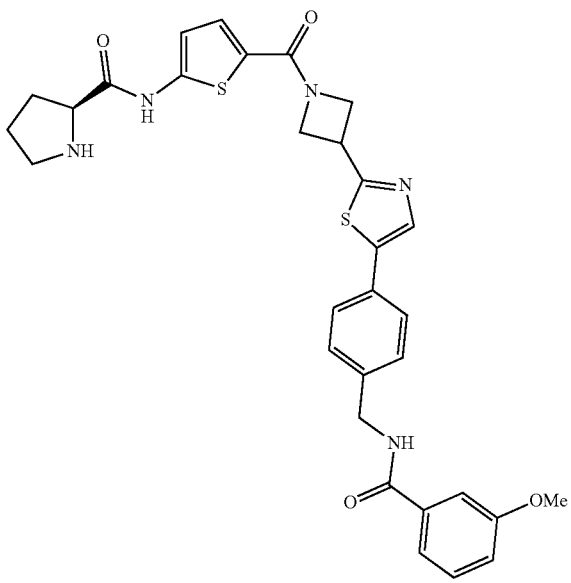 [SMILES: COc1cccc(C(=O)NCc2ccc(-c3cnc(C4CN(C(=O)c5ccc(NC(=O)[C@@H]6CCCN6)s5)C4)s3)cc2)c1] | 602.1890 | |
| 183 | 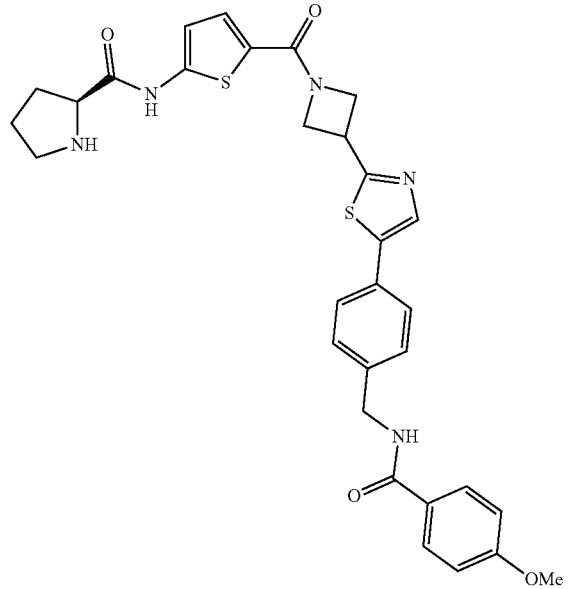 [SMILES: COc1ccc(C(=O)NCc2ccc(-c3cnc(C4CN(C(=O)c5ccc(NC(=O)[C@@H]6CCCN6)s5)C4)s3)cc2)cc1] | 602.1890 | |

TABLE 1-continued
Exemplary Compounds
| Number | Structure | HRMS (M − H+), calculated | HRMS (M − H+), found |
|---|---|---|---|
| 184 | 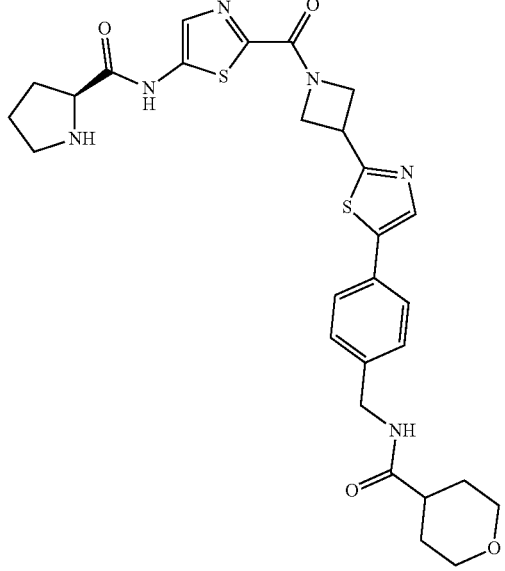 [SMILES: O=C(NCc1ccc(-c2cnc(C3CN(C(=O)c4ncc(NC(=O)[C@@H]5CCCN5)s4)C3)s2)cc1)C1CCOCC1] | 581.1999 | |
| 185 | 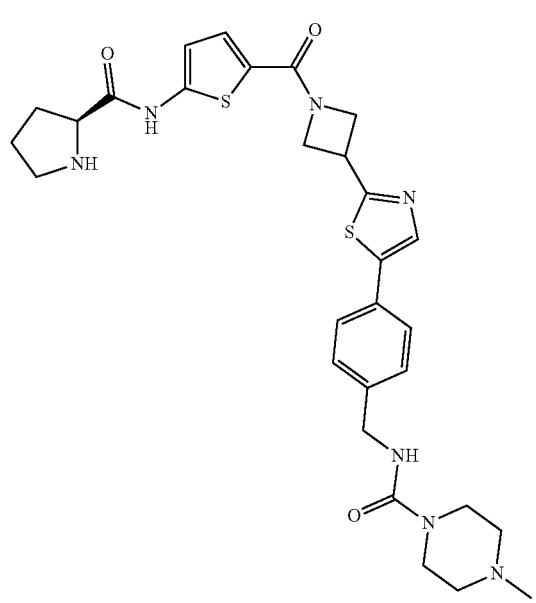 [SMILES: CN1CCN(C(=O)NCc2ccc(-c3cnc(C4CN(C(=O)c5ccc(NC(=O)[C@@H]6CCCN6)s5)C4)s3)cc2)CC1] | 594.2316 | |

TABLE 1-continued
Exemplary Compounds
| Number | Structure | HRMS (M − H+), calculated | HRMS (M − H+), found |
|---|---|---|---|
| 186 | 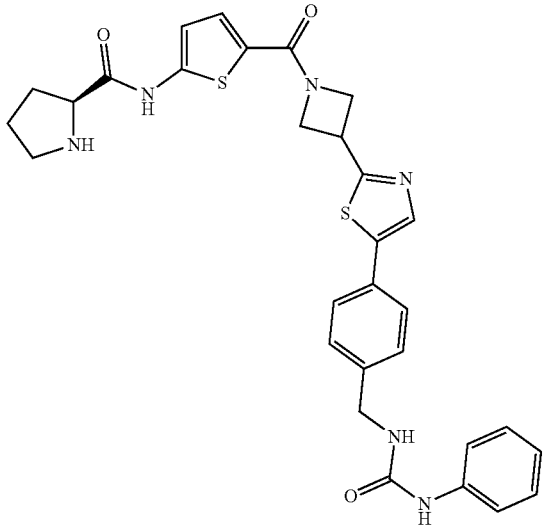 [SMILES: O=C(NCc1ccc(-c2cnc(C3CN(C(=O)c4ccc(NC(=O)[C@@H]5CCCN5)s4)C3)s2)cc1)Nc1ccccc1] | | 587.1894 |
| 187 | 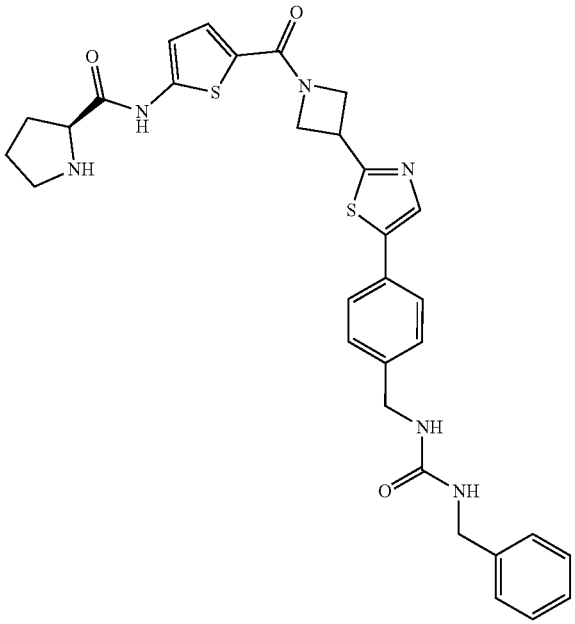 [SMILES: O=C(NCc1ccccc1)NCc1ccc(-c2cnc(C3CN(C(=O)c4ccc(NC(=O)[C@@H]5CCCN5)s4)C3)s2)cc1] | | 601.2050 |

US 11,858,925 B2
219                                                                                                220
TABLE 1-continued
Exemplary Compounds
| Number | Structure | HRMS (M − H+), calculated | HRMS (M − H+), found |
|---|---|---|---|
| 188 | 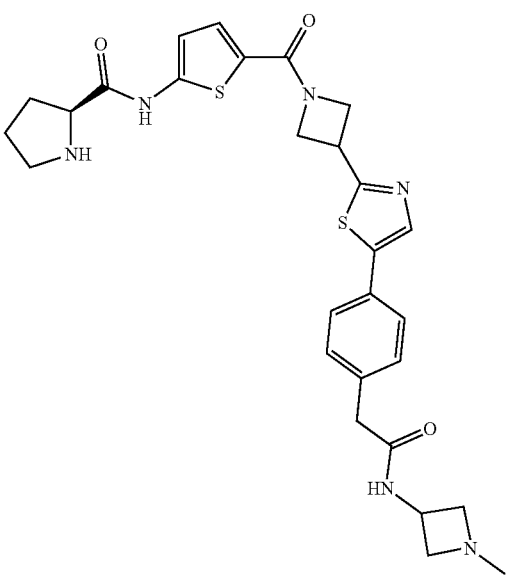 [SMILES: CN1CC(NC(=O)Cc2ccc(-c3cnc(C4CN(C(=O)c5ccc(NC(=O)[C@@H]6CCCN6)s5)C4)s3)cc2)C1] | | 565.2050 |
| 189 | 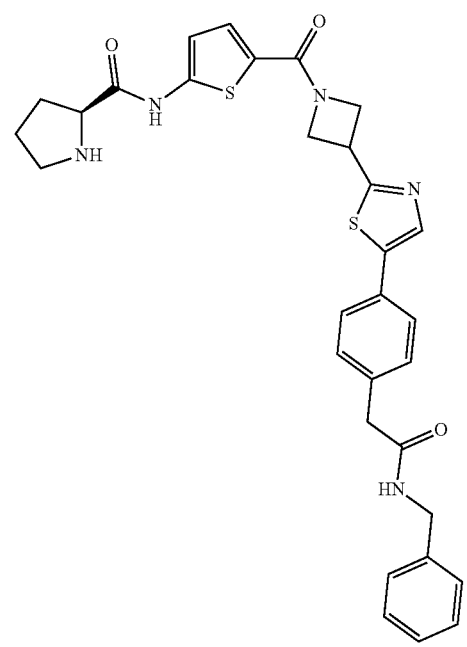 [SMILES: O=C(Cc1ccc(-c2cnc(C3CN(C(=O)c4ccc(NC(=O)[C@@H]5CCCN5)s4)C3)s2)cc1)NCc1ccccc1] | | 586.1941 |

TABLE 1-continued
Exemplary Compounds
| Number | Structure | HRMS (M − H+), calculated | HRMS (M − H+), found |
|---|---|---|---|
| 190 | 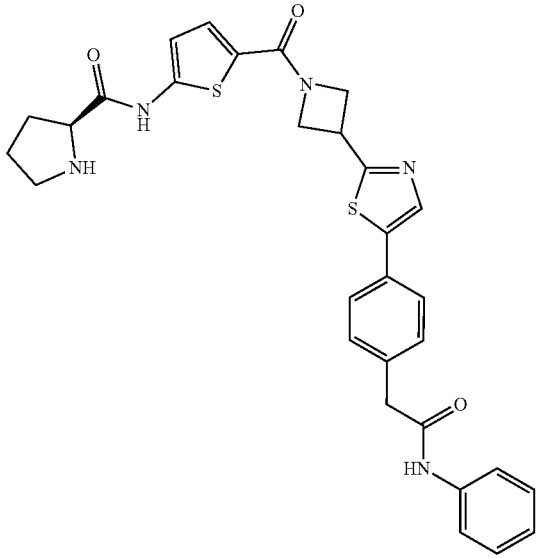 [SMILES: O=C(Cc1ccc(-c2cnc(C3CN(C(=O)c4ccc(NC(=O)[C@@H]5CCCN5)s4)C3)s2)cc1)Nc1ccccc1] | 572.1785 | |
| 191 | 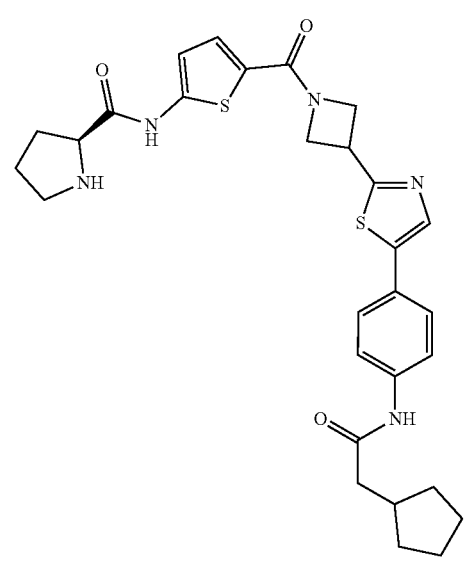 [SMILES: O=C(CC1CCCC1)Nc1ccc(-c2cnc(C3CN(C(=O)c4ccc(NC(=O)[C@@H]5CCCN5)s4)C3)s2)cc1] | 564.2098 | |

TABLE 1-continued
Exemplary Compounds
| Number | Structure | HRMS (M − H+), calculated | HRMS (M − H+), found |
|---|---|---|---|
| 192 | 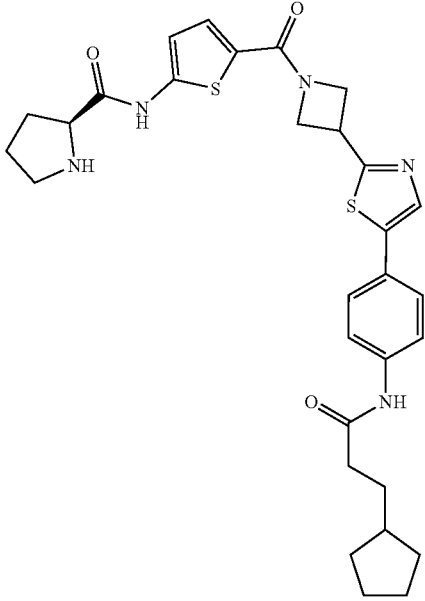 [SMILES: O=C(CCC1CCCC1)Nc1ccc(-c2cnc(C3CN(C(=O)c4ccc(NC(=O)[C@@H]5CCCN5)s4)C3)s2)cc1] | 578.2254 | |
| 193 | 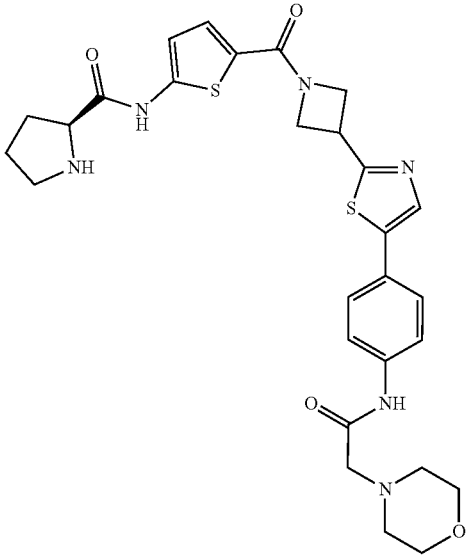 [SMILES: O=C(CN1CCOCC1)Nc1ccc(-c2cnc(C3CN(C(=O)c4ccc(NC(=O)[C@@H]5CCCN5)s4)C3)s2)cc1] | 581.1999 | |

TABLE 1-continued
Exemplary Compounds
| Number | Structure | HRMS (M − H+), calculated | HRMS (M − H+), found |
|---|---|---|---|
| 194 | 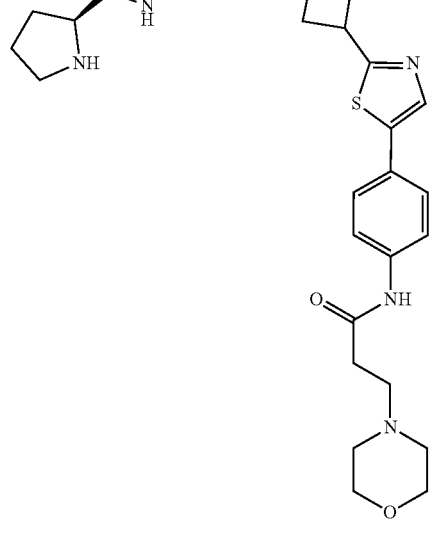 | 595.2156 | |
| 195 | 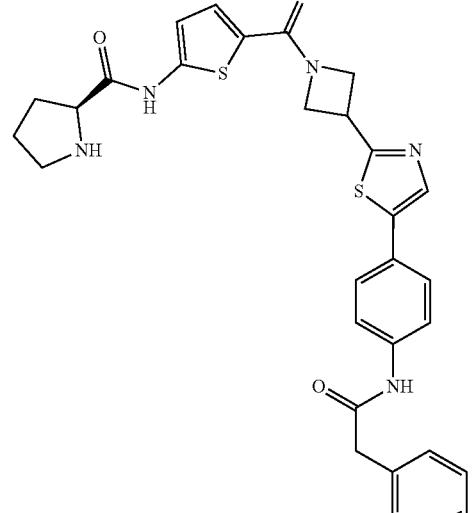 | 572.1785 | |

TABLE 1-continued
Exemplary Compounds
| Number | Structure | HRMS (M − H+), calculated | HRMS (M − H+), found |
|---|---|---|---|
| 196 | 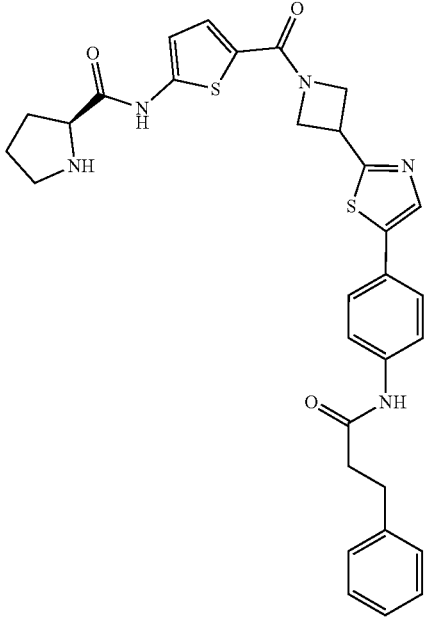 [SMILES: O=C(CCc1ccccc1)Nc1ccc(-c2cnc(C3CN(C(=O)c4ccc(NC(=O)[C@@H]5CCCN5)s4)C3)s2)cc1] | | 586.1941 |
| 197 | 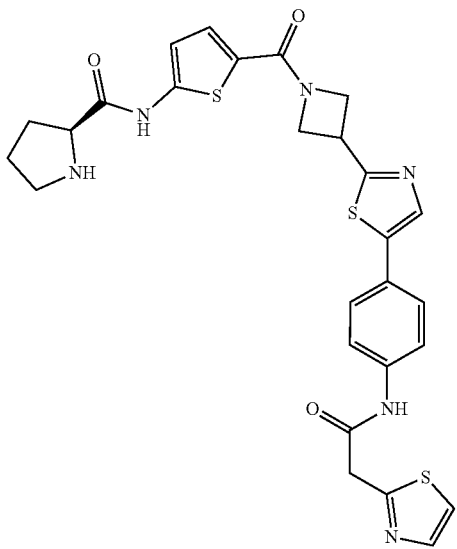 [SMILES: O=C(Cc1nccs1)Nc1ccc(-c2cnc(C3CN(C(=O)c4ccc(NC(=O)[C@@H]5CCCN5)s4)C3)s2)cc1] | | 579.1301 |

TABLE 1-continued
Exemplary Compounds
| Number | Structure | HRMS (M − H+), calculated | HRMS (M − H+), found |
| --- | --- | --- | --- |
| 198 | 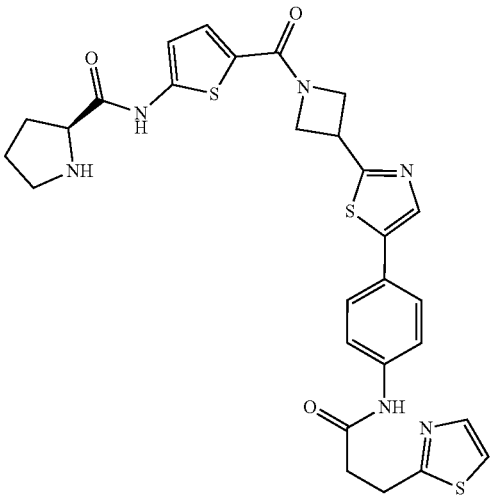 [SMILES: O=C(CCc1nccs1)Nc1ccc(-c2cnc(C3CN(C(=O)c4ccc(NC(=O)[C@@H]5CCCN5)s4)C3)s2)cc1] | | 593.1458 |
| 199 | 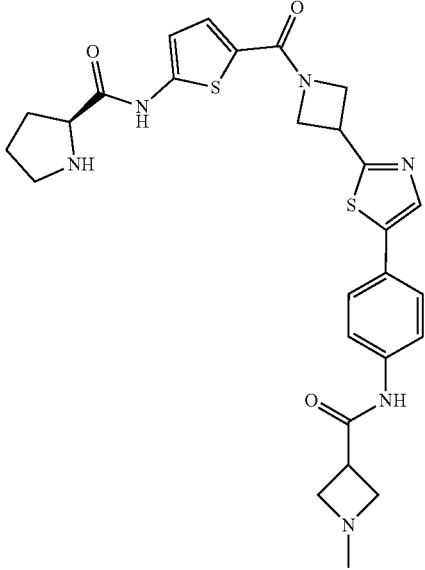 [SMILES: CN1CC(C(=O)Nc2ccc(-c3cnc(C4CN(C(=O)c5ccc(NC(=O)[C@@H]6CCCN6)s5)C4)s3)cc2)C1] | | 551.1894 |

TABLE 1-continued
Exemplary Compounds
| Number | Structure | HRMS (M − H+), calculated | HRMS (M − H+), found |
|---|---|---|---|
| 200 | 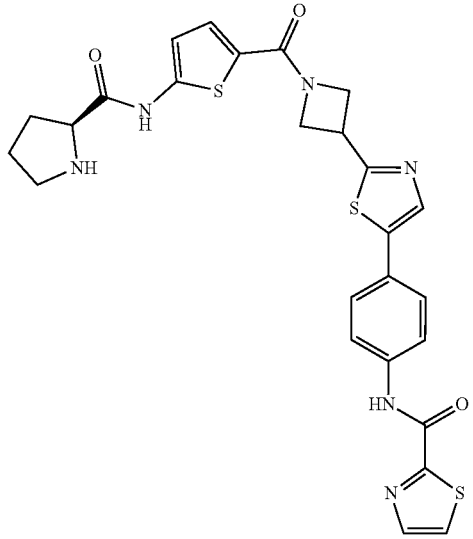 [SMILES: O=C(Nc1ccc(-c2cnc(C3CN(C(=O)c4ccc(NC(=O)[C@@H]5CCCN5)s4)C3)s2)cc1)c1nccs1] | | 565.1145 |
| 201 | 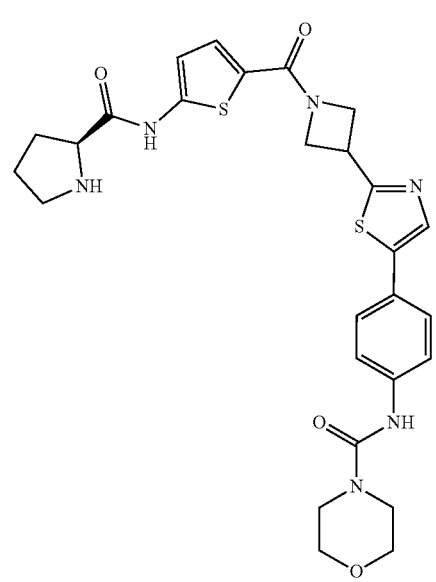 [SMILES: O=C(Nc1ccc(C(=O)N2CC(c3ncc(-c4ccc(NC(=O)N5CCOCC5)cc4)s3)C2)s1)[C@@H]1CCCN1] | | 567.1843 |

TABLE 1-continued

Exemplary Compounds

| Number | Structure | HRMS (M − H+), calculated | HRMS (M − H+), found |
|---|---|---|---|
| 202 | 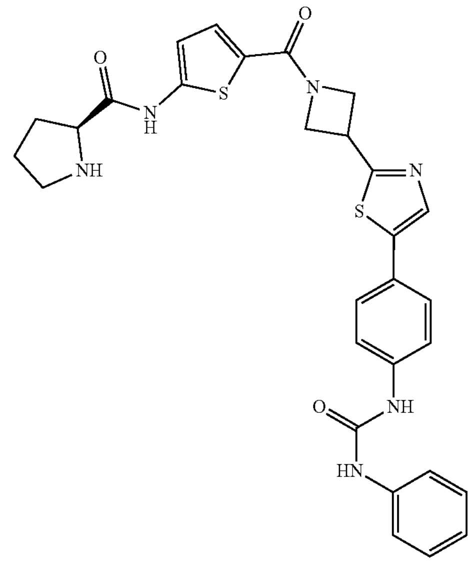 [SMILES: O=C(Nc1ccccc1)Nc1ccc(-c2cnc(C3CN(C(=O)c4ccc(NC(=O)[C@@H]5CCCN5)s4)C3)s2)cc1] | 573.1737 | |
| 203 | 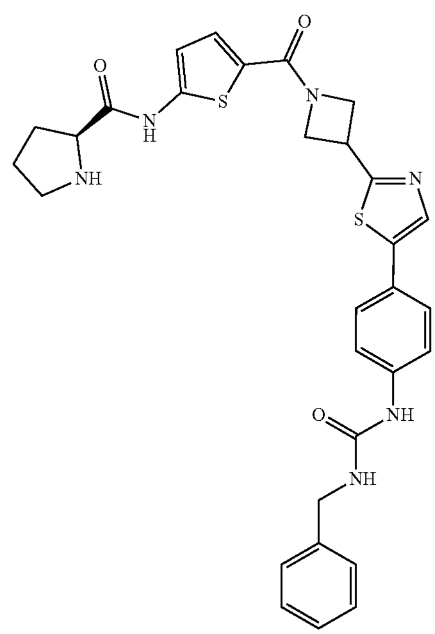 [SMILES: O=C(NCc1ccccc1)Nc1ccc(-c2cnc(C3CN(C(=O)c4ccc(NC(=O)[C@@H]5CCCN5)s4)C3)s2)cc1] | 587.1894 | |

TABLE 1-continued
Exemplary Compounds
| Number | Structure | HRMS (M − H+), calculated | HRMS (M − H+), found |
|---|---|---|---|
| 204 | 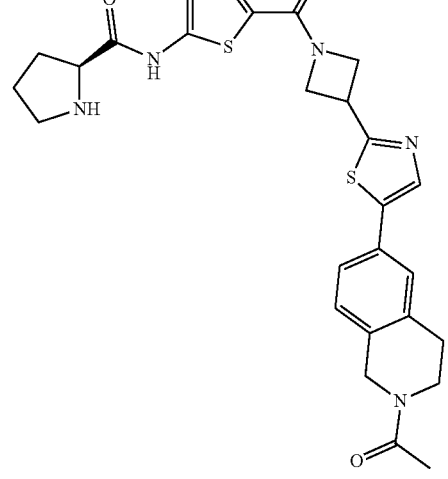 | 536.6885 | 536.1793 |
| 205 | 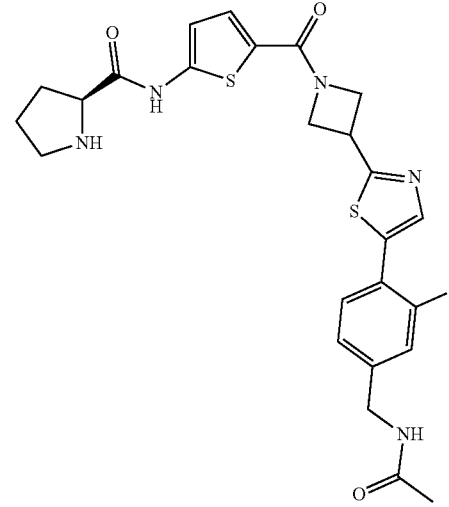 [SMILES: CC(=O)N1CCc2cc(-c3cnc(C4CN(C(=O)c5ccc(NC(=O)[C@@H]6CCCN6)s5)C4)s3)ccc2C1] | 544.1238 | 544.1243 |
| 206 | 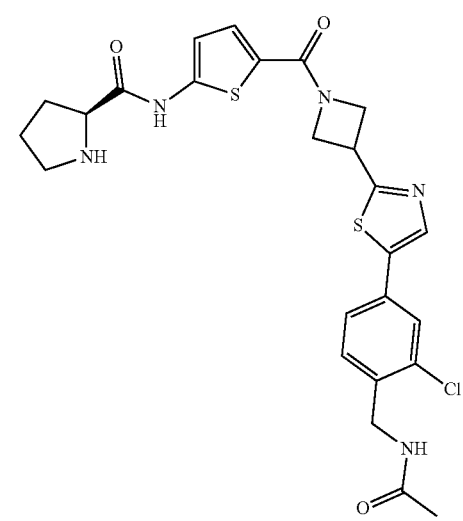 [SMILES: CC(=O)NCc1ccc(-c2cnc(C3CN(C(=O)c4ccc(NC(=O)[C@@H]5CCCN5)s4)C3)s2)cc1Cl] | 544.1238 | 544.1246 |

TABLE 1-continued

Exemplary Compounds

| Number | Structure | HRMS (M − H+), calculated | HRMS (M − H+), found |
|---|---|---|---|
| 207 | 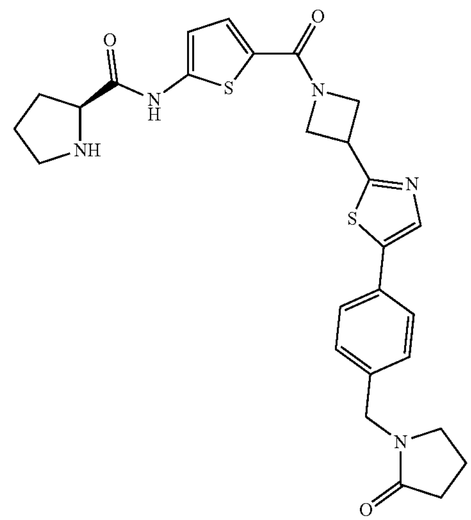 [SMILES: O=C(Nc1ccc(C(=O)N2CC(c3ncc(-c4ccc(CN5CCCC5=O)cc4)s3)C2)s1)[C@@H]1CCCN1] | 536.1785 | 536.1789 |
| 208 | 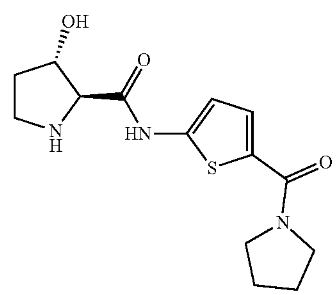 [SMILES: O=C(Nc1ccc(C(=O)N2CCCC2)s1)[C@H]1NCC[C@@H]1O] | 310.1220 | 310.1225 |
| 209 | 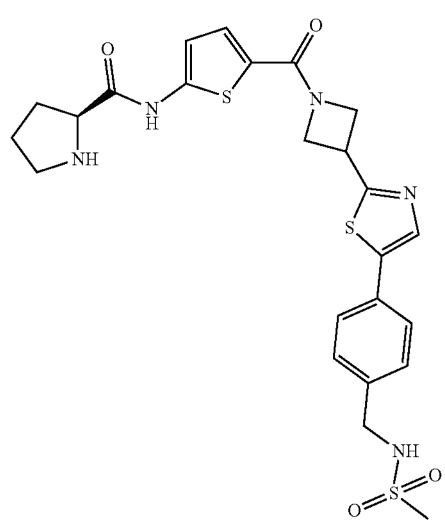 [SMILES: CS(=O)(=O)NCc1ccc(-c2cnc(C3CN(C(=O)c4ccc(NC(=O)[C@@H]5CCCN5)s4)C3)s2)cc1] | 546.1298 | |

TABLE 1-continued
Exemplary Compounds
| Number | Structure | HRMS (M − H+), calculated | HRMS (M − H+), found |
| --- | --- | --- | --- |
| 234 | 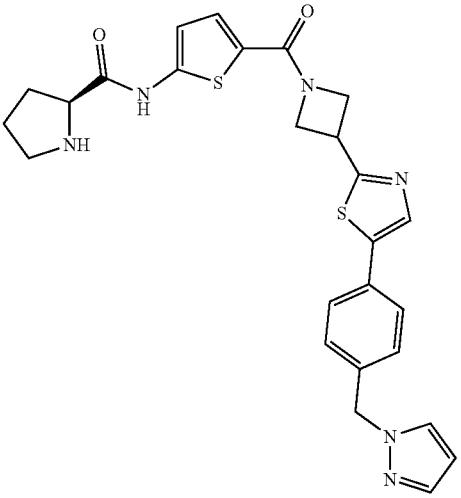 [SMILES: O=C(Nc1ccc(C(=O)N2CC(c3ncc(-c4ccc(Cn5cccn5)cc4)s3)C2)s1)[C@@H]1CCCN1] | 519.1631 | 519.1639 |
| 235 | 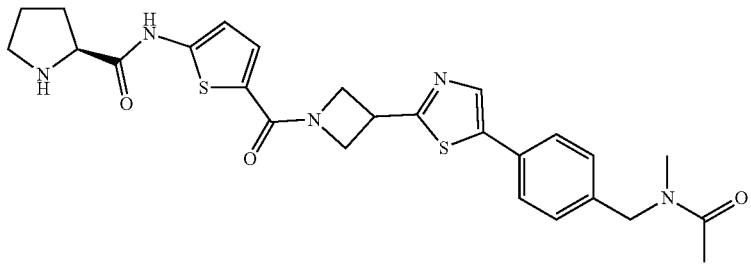 [SMILES: CC(=O)N(C)Cc1ccc(-c2cnc(C3CN(C(=O)c4ccc(NC(=O)[C@@H]5CCCN5)s4)C3)s2)cc1] | 524.1785 | 524.1794 |
| 236 | 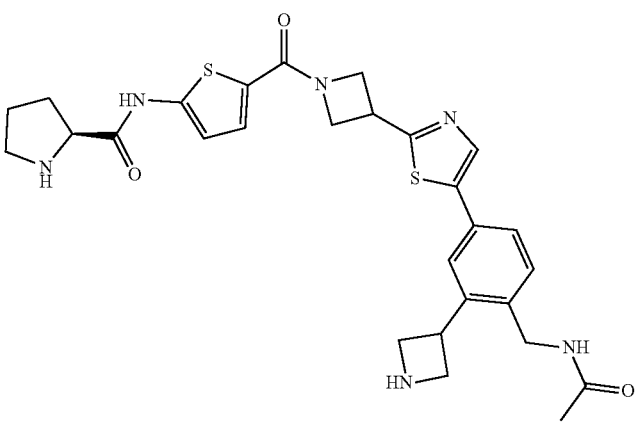 [SMILES: CC(=O)NCc1ccc(-c2cnc(C3CN(C(=O)c4ccc(NC(=O)[C@@H]5CCCN5)s4)C3)s2)cc1C1CNC1] | 565.2050 | 565.2056 |

TABLE 1-continued

Exemplary Compounds

| Number | Structure | HRMS (M − H+), calculated | HRMS (M − H+), found |
|---|---|---|---|
| 237 | 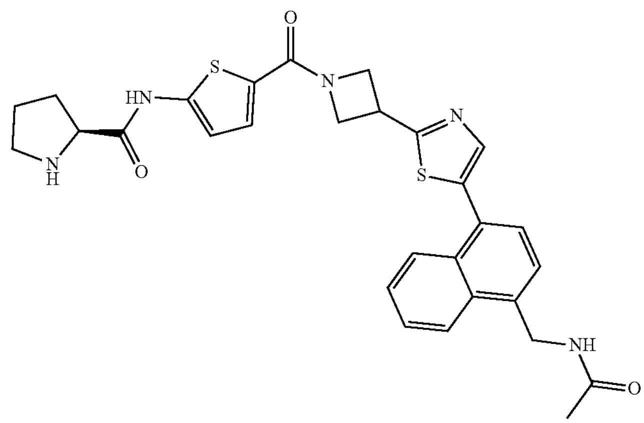 [SMILES: CC(=O)NCc1ccc(-c2cnc(C3CN(C(=O)c4ccc(NC(=O)[C@@H]5CCCN5)s4)C3)s2)c2ccccc12] | 560.1785 | 560.1788 |
| 238 | 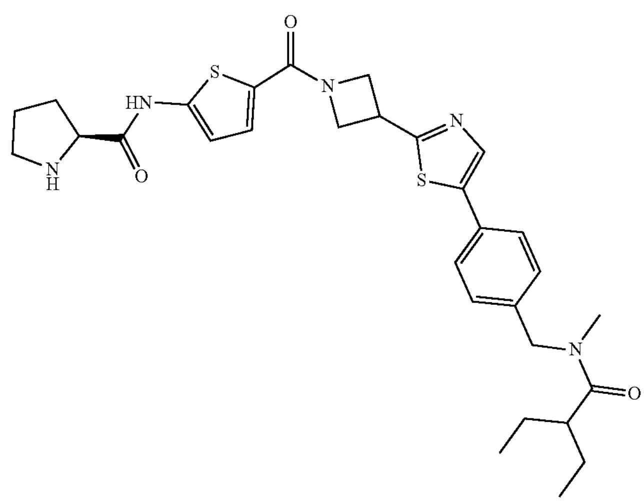 [SMILES: CCC(CC)C(=O)N(C)Cc1ccc(-c2cnc(C3CN(C(=O)c4ccc(NC(=O)[C@@H]5CCCN5)s4)C3)s2)cc1] | 580.2411 | 580.2417 |
| 239 | 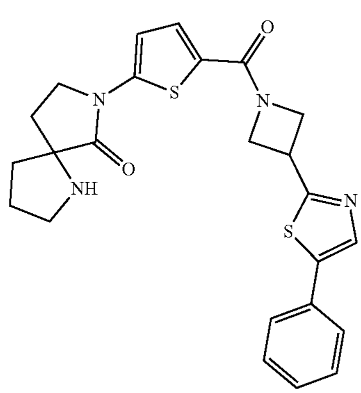 [SMILES: O=C(c1ccc(N2CCC3(CCCN3)C2=O)s1)N1CC(c2ncc(-c3ccccc3)s2)C1] | 465.1413 | 465.1416 |

TABLE 1-continued
Exemplary Compounds
| Number | Structure | HRMS (M − H+), calculated | HRMS (M − H+), found |
|---|---|---|---|
| 240 | 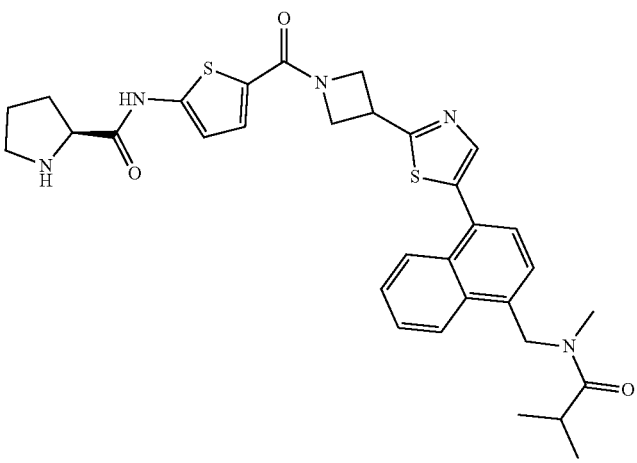 [SMILES: CC(C)C(=O)N(C)Cc1ccc(-c2cnc(C3CN(C(=O)c4ccc(NC(=O)[C@@H]5CCCN5)s4)C3)s2)c2ccccc12] | 602.2254 | 602.2258 |
| 241 | 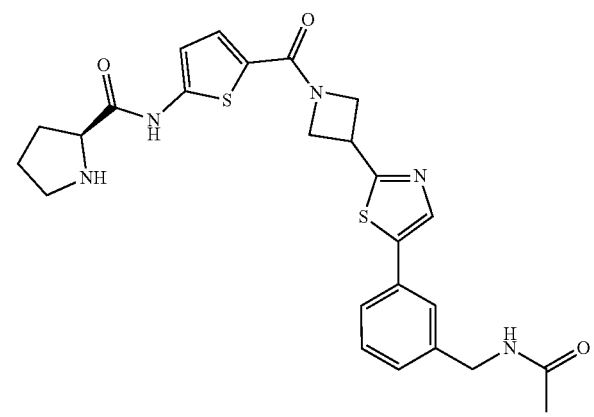 [SMILES: CC(=O)NCc1cccc(-c2cnc(C3CN(C(=O)c4ccc(NC(=O)[C@@H]5CCCN5)s4)C3)s2)c1] | 510.1628 | 510.1633 |
| 242 | 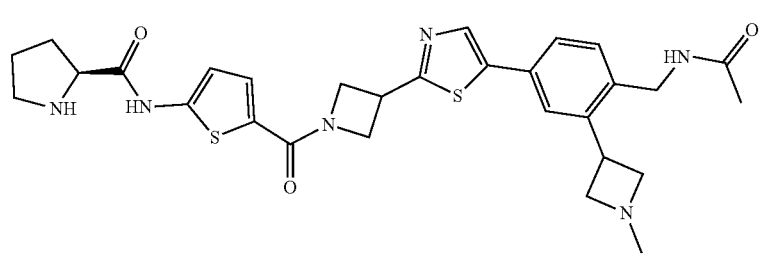 [SMILES: CC(=O)NCc1ccc(-c2cnc(C3CN(C(=O)c4ccc(NC(=O)[C@@H]5CCCN5)s4)C3)s2)cc1C1CN(C)C1] | 579.2207 | 579.2212 |
| 243 | 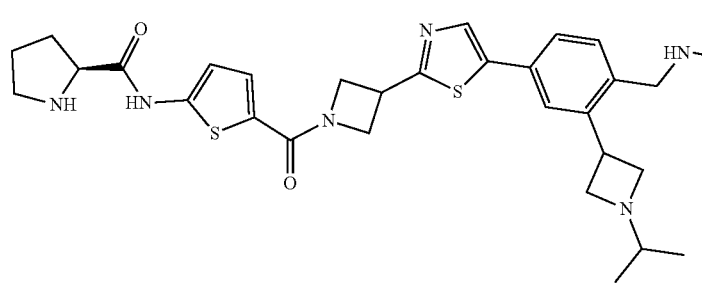 | 607.2520 | 607.2529 |

TABLE 1-continued

Exemplary Compounds

| Number | Structure | HRMS (M − H+), calculated | HRMS (M − H+), found |
|---|---|---|---|
| 244 | 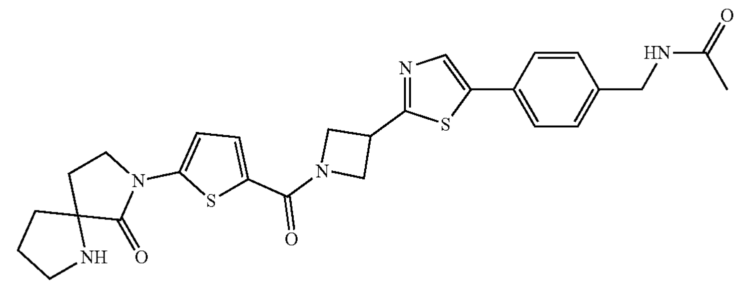 [SMILES: CC(=O)NCc1ccc(-c2cnc(C3CN(C(=O)c4ccc(N5CCC6(CCCN6)C5=O)s4)C3)s2)cc1] | 536.1785 | 536.1789 |
| 245 | 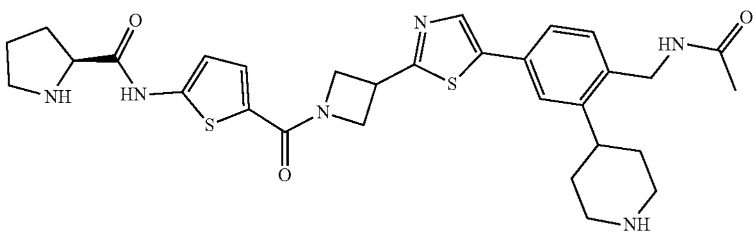 [SMILES: CC(=O)NCc1ccc(-c2cnc(C3CN(C(=O)c4ccc(NC(=O)[C@@H]5CCCN5)s4)C3)s2)cc1C1CCNCC1] | 593.2363 | 593.2370 |
| 246 | 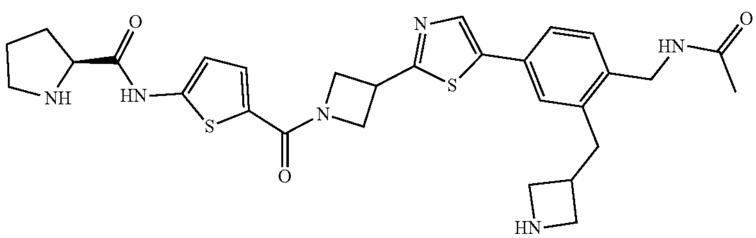 [SMILES: CC(=O)NCc1ccc(-c2cnc(C3CN(C(=O)c4ccc(NC(=O)[C@@H]5CCCN5)s4)C3)s2)cc1CC1CNC1] | 579.2207 | 579.2211 |
| 247 | 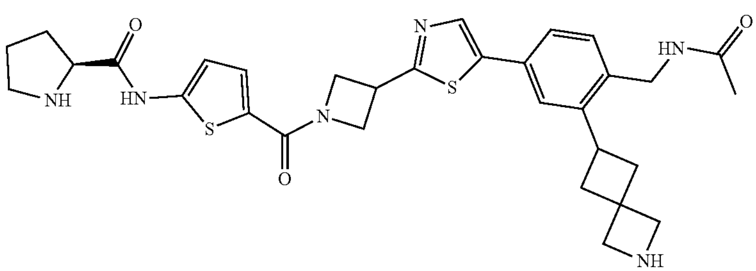 [SMILES: CC(=O)NCc1ccc(-c2cnc(C3CN(C(=O)c4ccc(NC(=O)[C@@H]5CCCN5)s4)C3)s2)cc1C1CC2(CNC2)C1] | 605.2363 | |
| 248 | 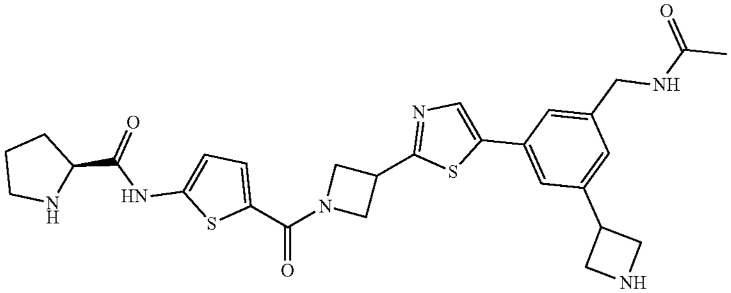 [SMILES: CC(=O)NCc1cc(-c2cnc(C3CN(C(=O)c4ccc(NC(=O)[C@@H]5CCCN5)s4)C3)s2)cc(C2CNC2)c1] | 565.2050 | |

TABLE 1-continued
Exemplary Compounds
| Number | Structure | HRMS (M − H+), calculated | HRMS (M − H+), found |
|---|---|---|---|
| 249 | 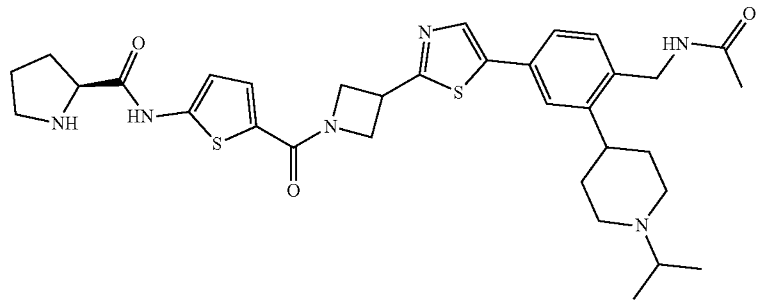 [SMILES: CC(=O)NCc1ccc(-c2cnc(C3CN(C(=O)c4ccc(NC(=O)[C@@H]5CCCN5)s4)C3)s2)cc1C1CCN(C(C)C)CC1] | | 635.2833 |
| 251 | 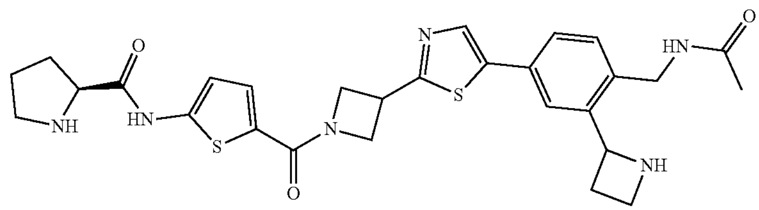 [SMILES: CC(=O)NCc1ccc(-c2cnc(C3CN(C(=O)c4ccc(NC(=O)[C@@H]5CCCN5)s4)C3)s2)cc1C1CCN1] | | 565.2050 |
Example 2
Compound Syntheses—Dimers
Compound 223. (2S,2'S,4R,4'R)-4,4'-(hexane-1,6-diylbis(oxy))bis(N-(5-(3-(thiazol-2-yl)azetidine-1-carbonyl)thiophen-2-yl)pyrrolidine-2-carboxamide)
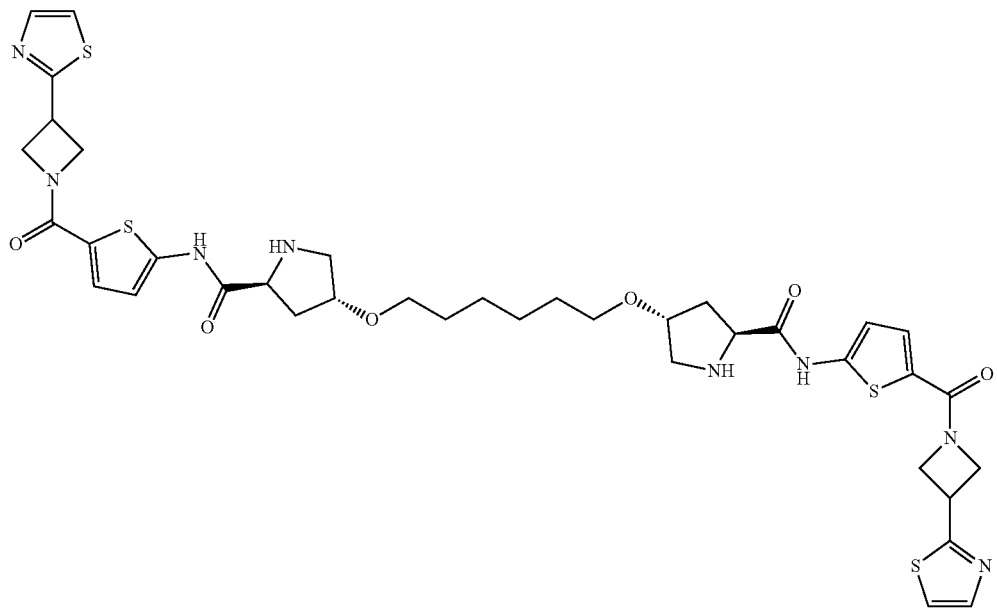 [SMILES: O=C(Nc1ccc(C(=O)N2CC(c3nccs3)C2)s1)[C@@H]1C[C@@H](OCCCCCCO[C@H]2CN[C@H](C(=O)Nc3ccc(C(=O)N4CC(c5nccs5)C4)s3)C2)CN1]

Step 1. 1-di-tert-butyl 2-dimethyl 4,4'-(hexane-1,6-diylbis(oxy))(2S,2'S,4R,4'R)-bis(pyrrolidine-1,2-dicarboxylate)

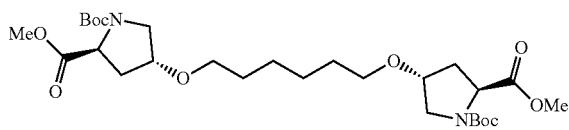 [SMILES: COC(=O)[C@@H]1C[C@@H](OCCCCCCO[C@@H]2C[C@@H](C(=O)OC)N(C(=O)OC(C)(C)C)C2)CN1C(=O)OC(C)(C)C]

To a suspension of NaH (60% dispersion in mineral oil, 400 mg, 0.01 mol) in dry DMF (10 mL) at 0° C. was added solution of 1-(tert-butyl) 2-methyl (2S,4R)-4-hydroxypyrrolidine-1,2-dicarboxylate (2.45 g, 0.01 mol) dropwise. The mixture was stirred for 30 min at 0° C. before adding 1,6-diiodohexane (1.54 g, 750 μL, 4.55 mmol). The temperature was allowed to increase slowly up to rt and the reaction mixture was stirred during 16 h before treatment with saturated aqueous NH₄Cl. The aqueous layer was extracted with ethyl acetate and the combined organic layers were washed with brine, dried over MgSO₄ and concentrated under reduced pressure. The crude mixture was purified by silica gel chromatography (gradient of EtOAc in hexanes from 10 to 100%) providing the targeted 1-di-tert-butyl 2-dimethyl 4,4'-(hexane-1,6-diylbis(oxy))(2S,2'S,4R,4'R)-bis(pyrrolidine-1,2-dicarboxylate) as a clear oil. Yield 521 mg (20%). ¹H NMR (600 MHz, Methanol-$d_4$, mixture of rotamers) δ 4.40-4.25 (m, 2H), 4.14-4.01 (m, 2H), 3.78-3.67 (m, 6H), 3.62-3.34 (m, 8H), 2.41-2.20 (m, 2H), 2.07-1.99 (m, 2H), 1.60-1.53 (m, 2H), 1.50-1.40 (m, 18H), 1.40-1.27 (m, 6H). ¹³C NMR (125 MHz, Methanol-$d_4$, mixture of rotamers) δ 175.2, 174.9, 174.3, 174.1, 172.9, 156.3, 156.2, 155.9, 155.7, 81.7, 81.6, 81.5, 78.7, 78.5, 77.9, 77.8, 70.1, 70.0, 70.0, 69.9, 69.8, 61.5, 59.5, 59.2, 59.1, 58.8, 53.4, 53.2, 52.8, 52.7, 52.7, 52.7, 52.6, 52.6, 52.6, 37.4, 37.4, 36.9, 36.6, 36.6, 36.0, 32.7, 30.9, 30.8, 30.8, 30.8, 30.7, 30.1, 28.7, 28.7, 28.6, 28.6, 27.1, 27.0, 26.9, 26.9, 23.7, 20.9, 14.5, 14.4; HR-ESI-MS: $C_{28}H_{49}N_2O_{10}$ [M+H]⁺ m/z calculated 573.3382, found 573.3356.

Step 2. (2'S,4R,4'R)-4,4'-(hexane-1,6-diylbis(oxy))bis(1-(tert-butoxycarbonyl)-L-proline)

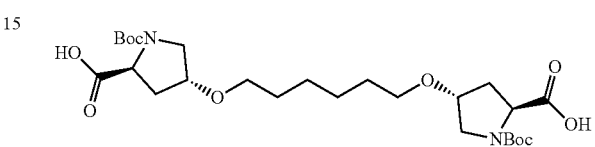

Synthesized according to general procedure B from 1-di-tert-butyl 2-dimethyl 4,4'-(hexane-1,6-diylbis(oxy))(2S,2'S,4R,4'R)-bis(pyrrolidine-1,2-dicarboxylate). Clear oil. Yield 485 mg (98%). ¹H NMR (600 MHz, Methanol-$d_4$, mixture of rotamers) δ=4.37-4.20 (m, 2H), 4.17-4.02 (m, 2H), 3.65-3.34 (m, 8H), 2.42-2.18 (m, 2H), 2.11-2.01 (m, 2H), 1.59-1.50 (m, 4H), 1.49-1.41 (m, 18H), 1.40-1.30 (m, 4H). ¹³C NMR (125 MHz, Methanol-$d_4$, mixture of rotamers) δ=176.6, 176.2, 175.7, 175.6, 175.4, 175.4, 156.4, 156.3, 156.0, 155.9, 81.8, 81.8, 81.5, 81.4, 78.7, 78.5, 77.9, 77.7, 77.7, 70.1, 70.1, 70.1, 70.0, 70.0, 70.0, 69.9, 59.5, 59.1, 58.9, 58.7, 53.5, 53.2, 53.2, 52.7, 52.7, 52.7, 37.5, 37.5, 36.8, 36.8, 36.8, 36.7, 35.9, 30.8, 30.8, 30.7, 30.7, 29.9, 28.8, 28.7, 28.6, 28.6, 27.0, 27.0, 26.9, 26.9, 24.2. HR-ESI-MS: $C_{26}H_{45}N_2O_{10}$ [M+H]⁺ m/z calculated 545.3069, found 545.3075.

Step 3. 5,5'-(((2S,2'S,4R,4'R)-4,4'-(hexane-1,6-diylbis(oxy))bis(1-(tert-butoxycarbonyl)pyrrolidine-4,2-diyl-2-carbonyl))bis(azanediyl))bis(thiophene-2-carboxylic Acid)

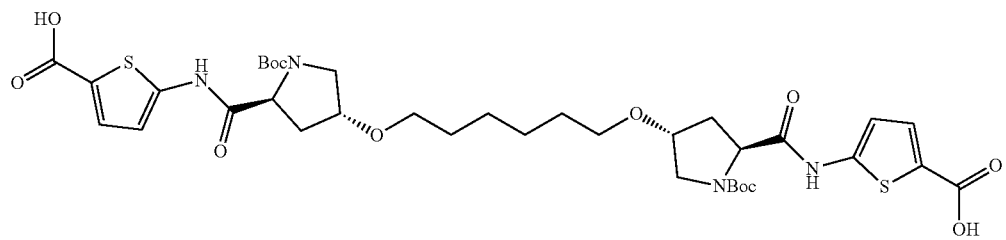 [SMILES: CC(C)(C)OC(=O)N1C[C@H](OCCCCCCO[C@@H]2C[C@@H](C(=O)Nc3ccc(C(=O)O)s3)N(C(=O)OC(C)(C)C)C2)C[C@H]1C(=O)Nc1ccc(C(=O)O)s1]

Synthesized according to general procedure A, from (2'S, 4R,4'R)-4,4'-(hexane-1,6-diylbis(oxy))bis(1-(tert-butoxycarbonyl)-L-proline) and methyl 5-amino-2-thiophenecarboxylate. Obtained crude was directly submitted to hydrolysis (general procedure B) and then purified by silica gel column chromatography (0-100% EtOAc in DCM) providing titled compound as off white solid. Yield 87 mg (61% on 2 steps). $^1$H NMR (600 MHz, Methanol-$d_4$, mixture of rotamers) δ 7.60-7.54 (m, 2H), 6.76-6.70 (m, 2H), 4.49-4.33 (m, 2H), 4.17-4.00 (m, 2H), 3.65-3.55 (m, 4H), 3.52-3.41 (m, 4H), 2.50-2.35 (m, 2H), 2.14-1.97 (m, 2H), 1.64-1.54 (m, 4H), 1.50-1.42 (m, 4H), 1.40-1.31 (m, 18H). $^{13}$C NMR (125 MHz, Methanol-$d_4$, mixture of rotamers) δ 172.4, 166.7, 155.8, 147.0, 132.6, 126.8, 113.7, 113.6, 113.5, 82.0, 82.0, 82.0, 78.7, 78.1, 78.0, 70.0, 70.0, 69.9, 60.8, 60.8, 60.3, 53.3, 53.3, 38.0, 37.9, 31.0, 30.8, 30.8, 28.7, 28.6, 28.5, 27.1, 27.1, 26.9. HR-ESI-MS: $C_{36}H_{51}N_4O_{12}S_2$ [M+H]$^+$ m/z calculated 795.2939, found 795.2948.

Step 4. (2S,2'S,4R,4'R)-4,4'-(hexane-1,6-diylbis(oxy))bis(N-(5-(3-(thiazol-2-yl)azetidine-1-carbonyl)thiophen-2-yl)pyrrolidine-2-carboxamide) (Compound 223)

Synthesized according to general procedure A, from 5,5'-(((2S,2'S,4R,4'R)-4,4'-(hexane-1,6-diylbis(oxy))bis(1-(tert-butoxycarbonyl)pyrrolidine-4,2-diyl-2-carbonyl))bis(azanediyl))bis(thiophene-2-carboxylic acid) and 2-(azetidin-3-yl)thiazole dihydrochloride. Obtained residue was used in the next step without further purification. To a solution of the residue from the previous step in the DCM (2 mL) at 0° C. TFA (0.5 mL) was added dropwise, and the mixture was stirred at 0° C. for 30 min. After this all volatiles were removed under reduced pressure, the residue was triturated with 7N ammonia solution in methanol, re-concentrated and purified by silica gel column chromatography (0-100% DCM/MeOH+0.5% ammonia (v/v)) to afford the titled compound in form of free base, which was re-dissolved in 1 mL of DCM and treated with 200 uL of TFA at 0° C. After stirring for 10 min, mixture was concentrated under reduced pressure, the residue was re-dissolved in MeOH and passed through a pad with Amberlite IRA402 Cl-form, obtained solution was re-concentrated providing the titled compound in form of dihydrochloride (23 mg, 52% in 2 steps). $^1$H NMR (600 MHz, Methanol-$d_4$) δ 7.80 (d, J=3.3 Hz, 2H), 7.56 (d, J=3.3 Hz, 2H), 7.38 (d, J=4.2 Hz, 2H), 6.84 (d, J=4.2 Hz, 2H), 4.97 (s, 2H), 4.76-4.56 (br.s., 4H), 4.53 (dd, J=10.4, 7.4 Hz, 2H), 4.46-4.37 (m, 3H), 4.36-4.28 (m, 3H), 3.59-3.48 (m, 4H), 3.46 (s, 4H), 2.70 (dd, J=13.7, 7.4 Hz, 2H), 2.11 (ddd, J=14.2, 10.4, 4.3 Hz, 2H), 1.63 (t, J=6.9 Hz, 4H), 1.51-1.40 (m, 4H). $^{13}$C NMR (151 MHz, Methanol-$d_4$) δ 171.9, 167.5, 165.3, 145.3, 143.8, 130.2, 128.8, 121.0, 114.5, 79.4, 70.2, 60.4 (2 overlapped carbons, one is azetidine CH2, identified from HSQC spectrum), 56.7 (azetidine CH2, identified from HSQC spectrum), 52.8, 49.8, 37.0, 33.3, 30.8, 27.1. HR-ESI-MS: $C_{38}H_{47}N_8O_6S_4$ [M+H]$^+$ m/z calculated 839.2496, found 839.2498.

Other Compounds

Additional dimer compounds were synthesized according to similar procedures using appropriate starting materials. Compound structures and HR-MS data are shown in Table 2.

TABLE 2

Exemplary Compounds

| Number | Structure | HRMS (M – H+), calc'd | HRMS (M – H+), found |
|---|---|---|---|
| 210 | 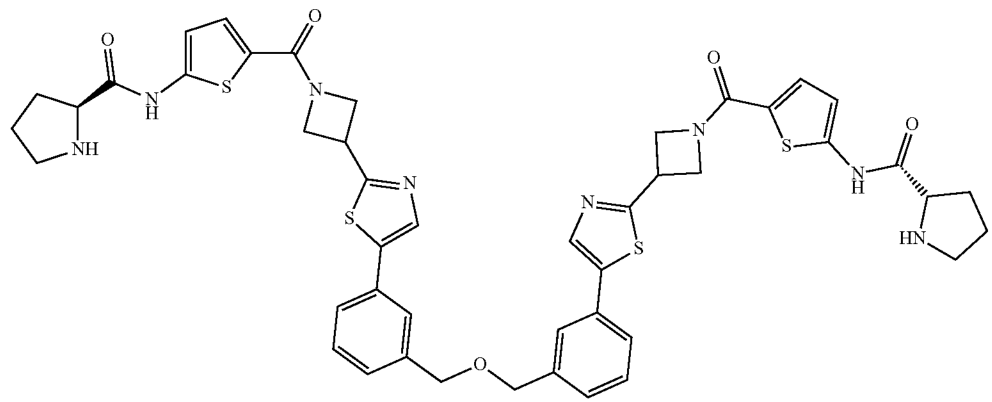 | 919.2547 | 919.2579 |
| 211 | 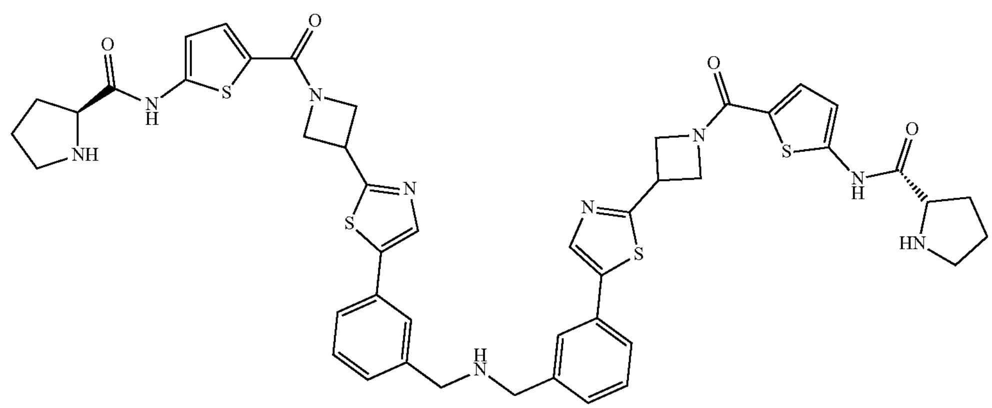 | 918.2707 | 918.2713 |

TABLE 2-continued
Exemplary Compounds
| Number | Structure | HRMS (M − H+), calc'd | HRMS (M − H+), found |
|---|---|---|---|
| 212 | 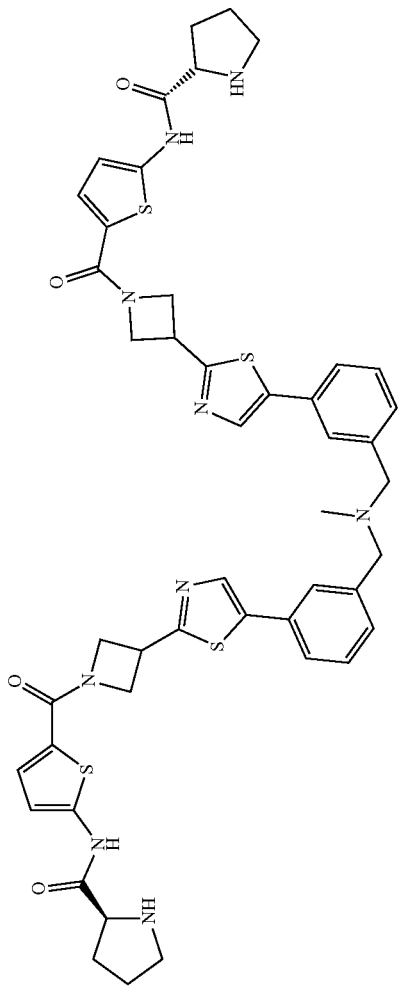 | 932.2863 | 932.2877 |

TABLE 2-continued

Exemplary Compounds

| Number | Structure | HRMS (M − H+), calc'd | HRMS (M − H+), found |
|---|---|---|---|
| 213 | 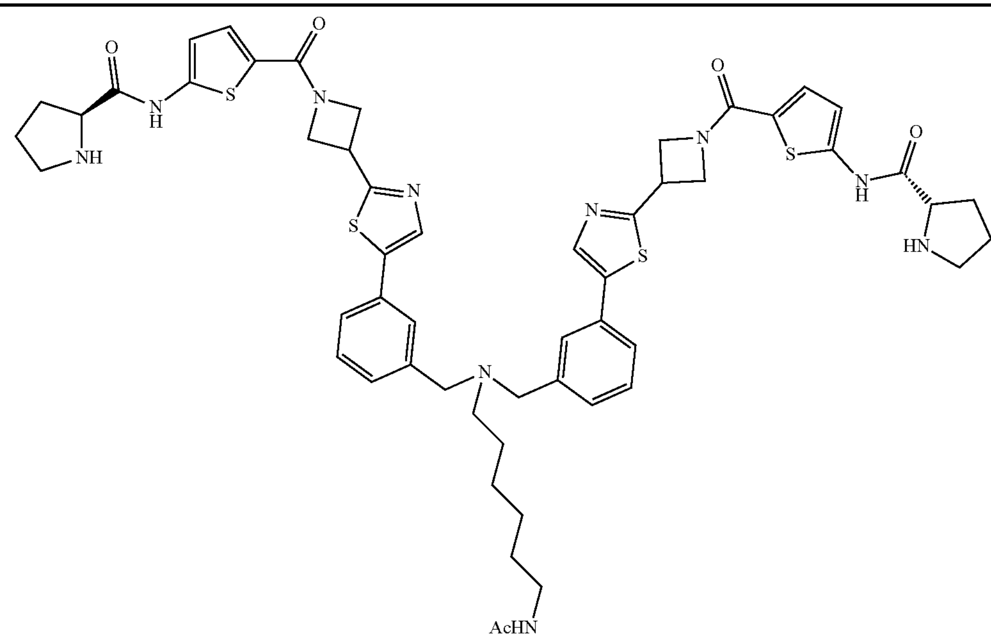 | 1059.3860 also [M − H + H]²⁺ 2530.1972 | 1059.3843 also [M − H + H]²⁺ 2530.1957 |
| 214 | 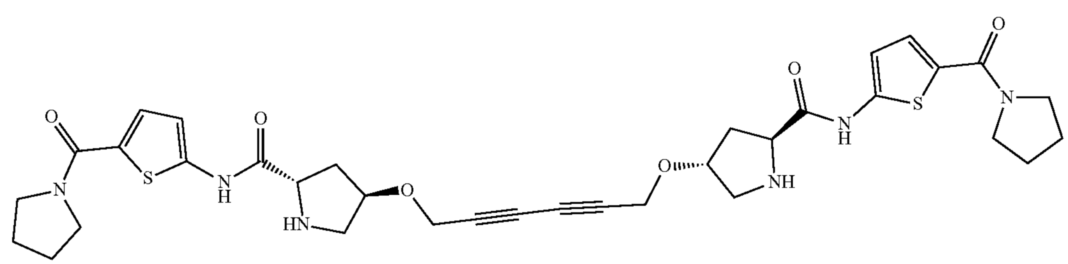 [SMILES: O=C(Nc1ccc(C(=O)N2CCCC2)s1)[C@@H]1C[C@@H](OCC#CC#CCO[C@H]2CN[C@H](C(=O)Nc3ccc(C(=O)N4CCCC4)s3)C2)CN1] | 693.2594 | 693.2528 |

TABLE 2-continued

Exemplary Compounds

| Number | Structure | HRMS (M − H+), calc'd | HRMS (M − H+), found |
|---|---|---|---|
| 215 | 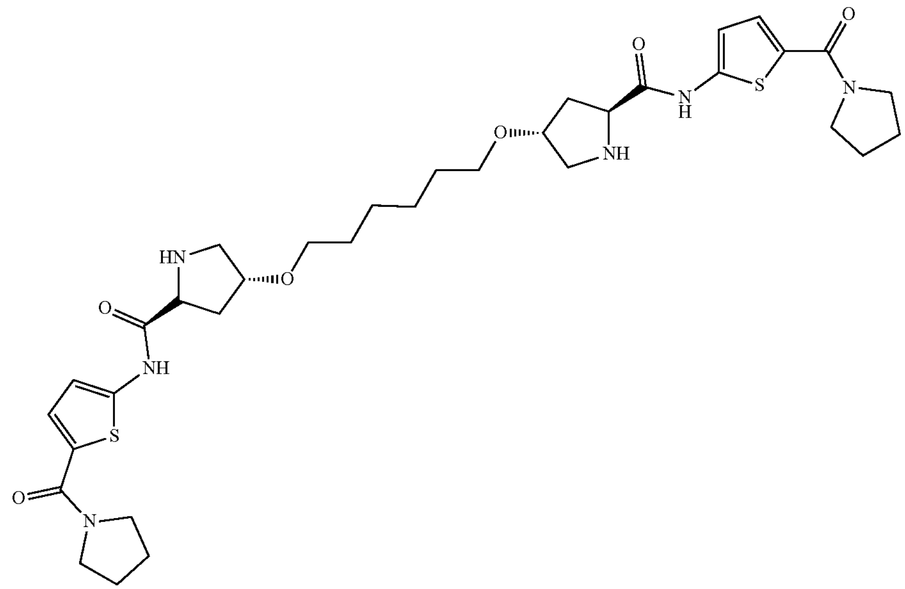 | 701.3150 | 701.3159 |
| 216 | 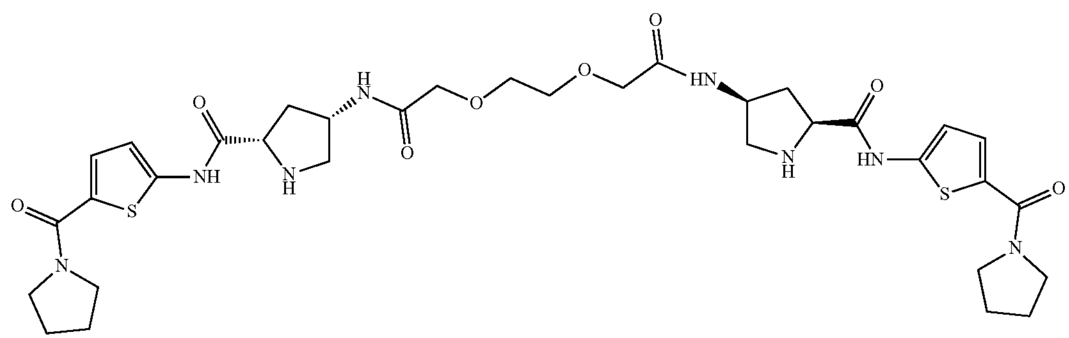 [SMILES: O=C(COCCOCC(=O)N[C@@H]1CN[C@H](C(=O)Nc2ccc(C(=O)N3CCCC3)s2)C1)N[C@@H]1CN[C@H](C(=O)Nc2ccc(C(=O)N3CCCC3)s2)C1] | 759.2953 | 759.2961 |

TABLE 2-continued

Exemplary Compounds

| Number | Structure | HRMS (M − H+), calc'd | HRMS (M − H+), found |
|---|---|---|---|
| 217 | 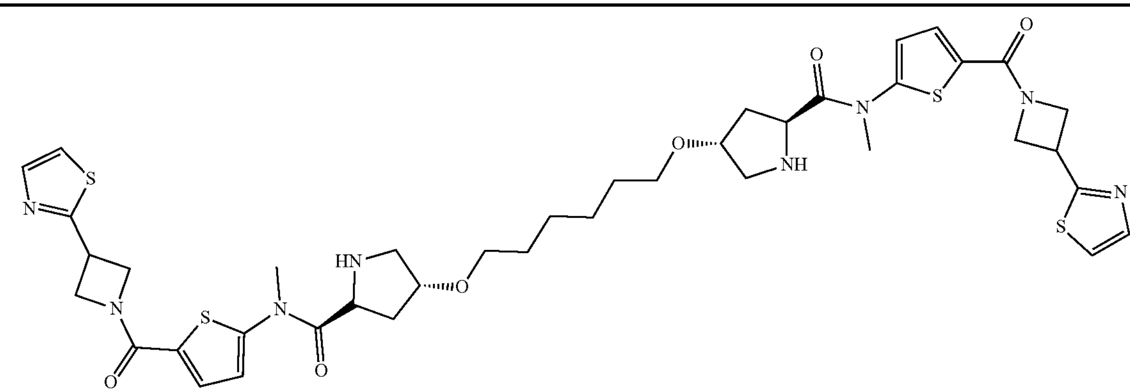 | 867.2809 | 867.2818 |
| 218 | 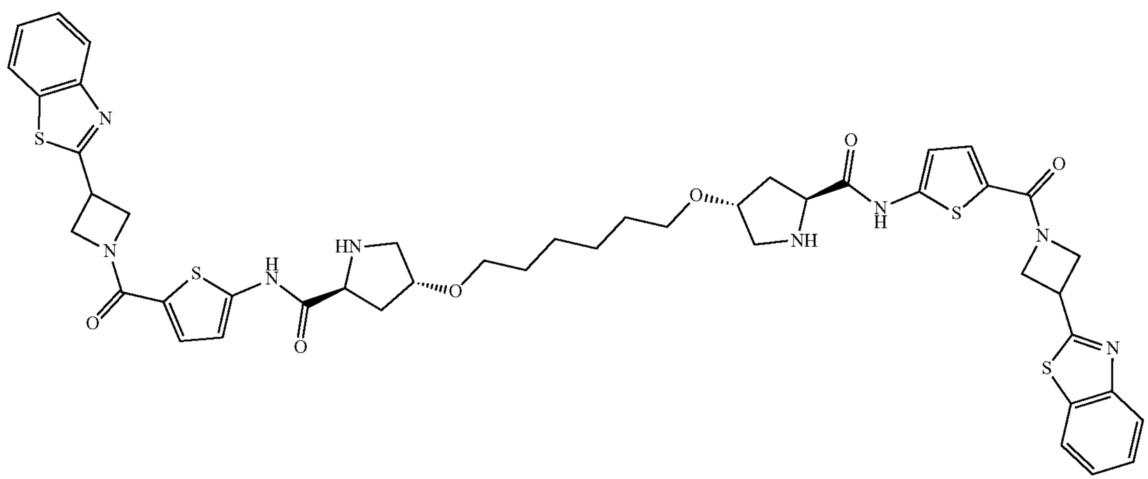 [SMILES: O=C(Nc1ccc(C(=O)N2CC(c3nc4ccccc4s3)C2)s1)[C@@H]1C[C@@H](OCCCCCCO[C@H]2CN[C@H](C(=O)Nc3ccc(C(=O)N4CC(c5nc6ccccc6s5)C4)s3)C2)CN1] | 939.2809 | 939.2818 |

TABLE 2-continued

Exemplary Compounds

| Number | Structure | HRMS (M − H+), calc'd | HRMS (M − H+), found |
|---|---|---|---|
| 219 | 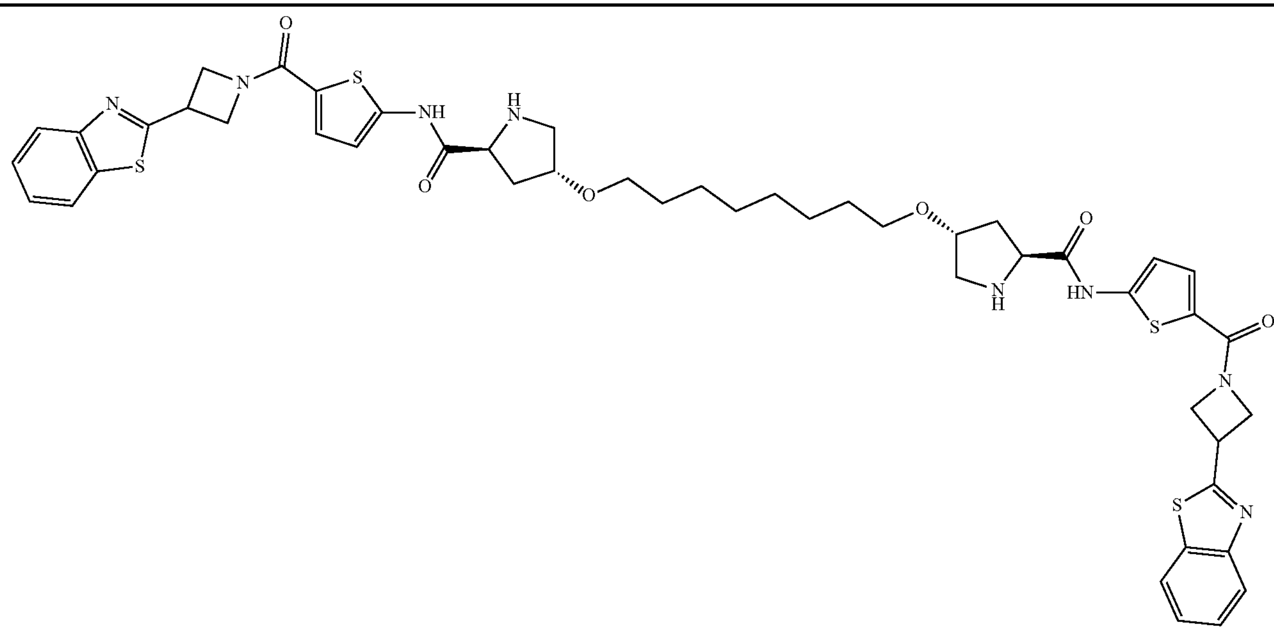 | 967.3122 | 967.3128 |

TABLE 2-continued
Exemplary Compounds
| Number | Structure | HRMS (M − H+), calc'd | HRMS (M − H+), found |
|---|---|---|---|
| 220 | 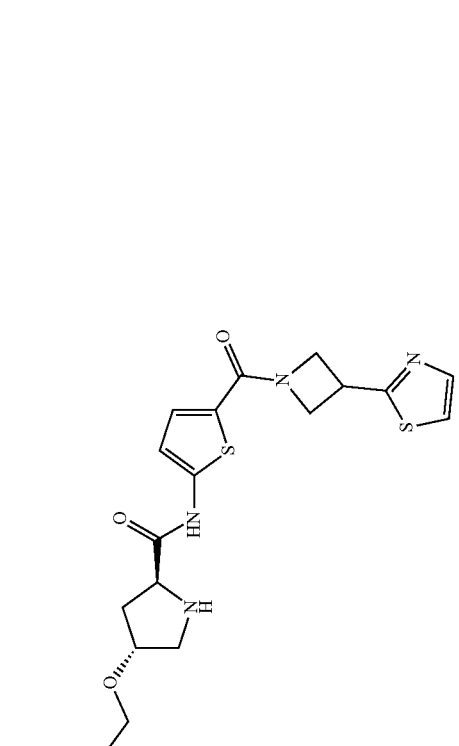 | 867.2809 | 867.2809 |

TABLE 2-continued

Exemplary Compounds

| Number | Structure | HRMS (M – H+), calc'd | HRMS (M – H+), found |
|---|---|---|---|
| 221 | 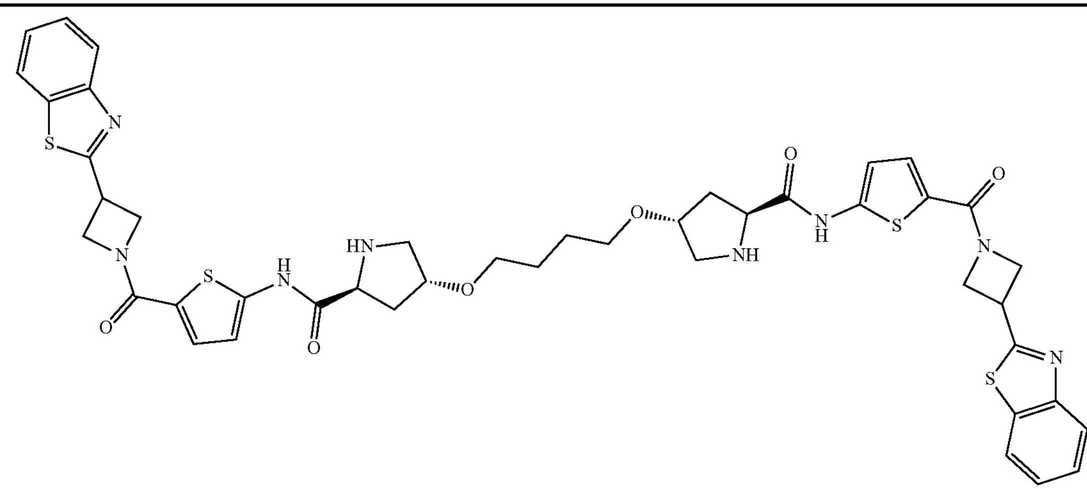 | 911.2496 | 911.2496 |

TABLE 2-continued

Exemplary Compounds

| Number | Structure | HRMS (M − H+), calc'd | HRMS (M − H+), found |
|---|---|---|---|
| 222 | 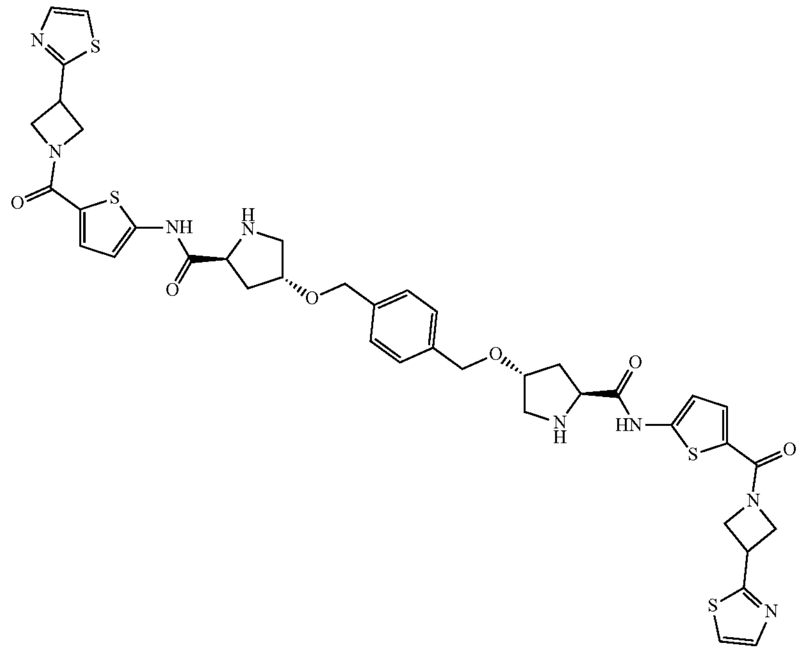 [SMILES: O=C(Nc1ccc(C(=O)N2CC(c3nccs3)C2)s1)[C@@H]1C[C@@H](OCc2ccc(CO[C@H]3CN[C@H](C(=O)Nc4ccc(C(=O)N5CC(c6nccs6)C5)s4)C3)cc2)CN1] | 859.2183 | 859.2193 |
| 223 | 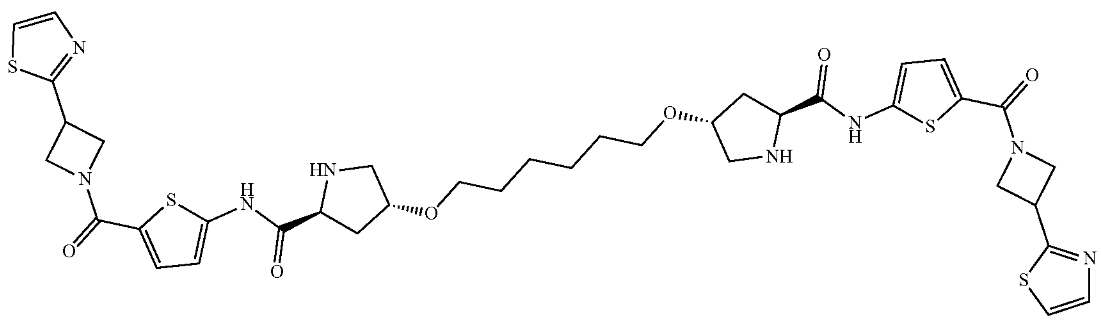 [SMILES: O=C(Nc1ccc(C(=O)N2CC(c3nccs3)C2)s1)[C@@H]1C[C@@H](OCCCCCCO[C@H]2CN[C@H](C(=O)Nc3ccc(C(=O)N4CC(c5nccs5)C4)s3)C2)CN1] | 839.2496 | 839.2498 |

TABLE 2-continued

Exemplary Compounds

| Number | Structure | HRMS (M − H+), calc'd | HRMS (M − H+), found |
|---|---|---|---|
| 224 | 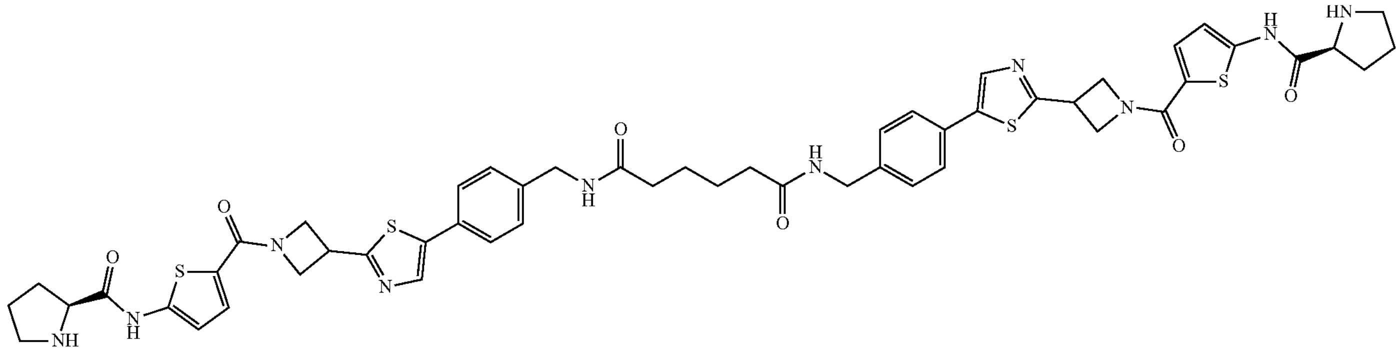 [SMILES: O=C(CCCCC(=O)NCc1ccc(-c2cnc(C3CN(C(=O)c4ccc(NC(=O)[C@@H]5CCCN5)s4)C3)s2)cc1)NCc1ccc(-c2cnc(C3CN(C(=O)c4ccc(NC(=O)[C@@H]5CCCN5)s4)C3)s2)cc1] | 1045.3340 | |
| 225 | 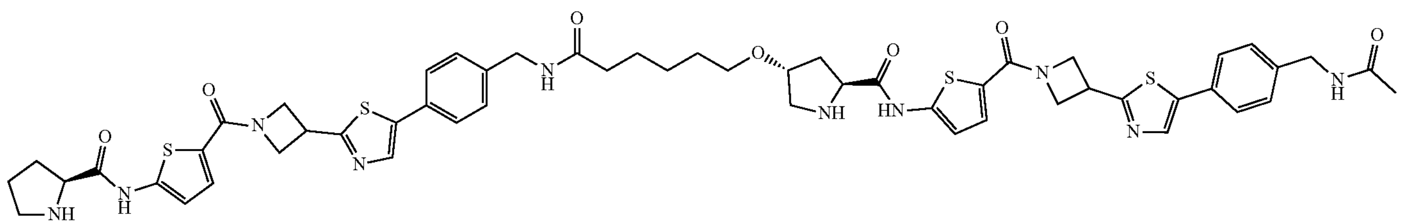 [SMILES: CC(=O)NCc1ccc(-c2cnc(C3CN(C(=O)c4ccc(NC(=O)[C@@H]5C[C@@H](OCCCCCC(=O)NCc6ccc(-c7cnc(C8CN(C(=O)c9ccc(NC(=O)[C@@H]%10CCCN%10)s9)C8)s7)cc6)CN5)s4)C3)s2)cc1] | 1089.3602 | |
| 226 | 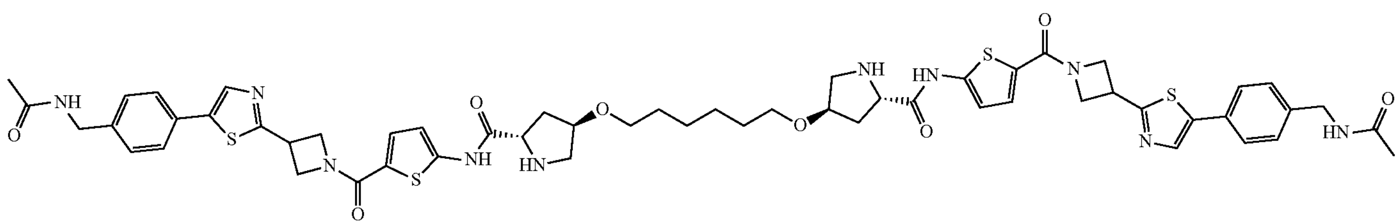 [SMILES: CC(=O)NCc1ccc(-c2cnc(C3CN(C(=O)c4ccc(NC(=O)[C@@H]5C[C@@H](OCCCCCCO[C@H]6CN[C@H](C(=O)Nc7ccc(C(=O)N8CC(c9ncc(-c%10ccc(CNC(C)=O)cc%10)s9)C8)s7)C6)CN5)s4)C3)s2)cc1] | 1133.3864 | |

TABLE 2-continued

Exemplary Compounds

| Number | Structure | HRMS (M − H+), calc'd | HRMS (M − H+), found |
|---|---|---|---|
| 227 | 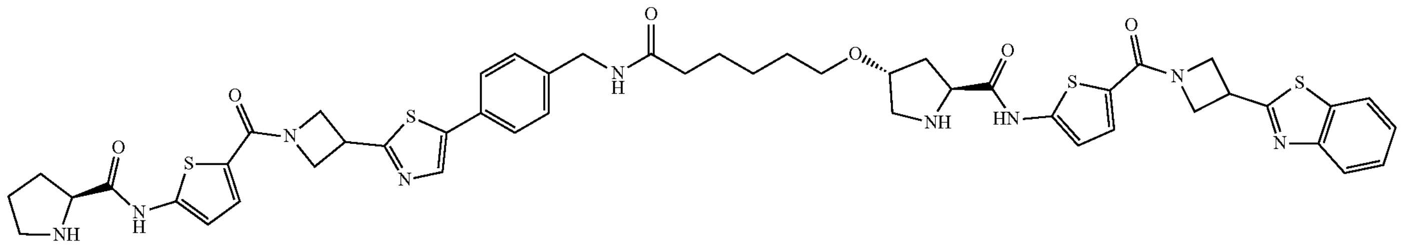 [SMILES: O=C(CCCCCO[C@H]1CN[C@H](C(=O)Nc2ccc(C(=O)N3CC(c4nc5ccccc5s4)C3)s2)C1)NCc1ccc(-c2cnc(C3CN(C(=O)c4ccc(NC(=O)[C@@H]5CCCN5)s4)C3)s2)cc1] | 992.3074 | |
| 228 | 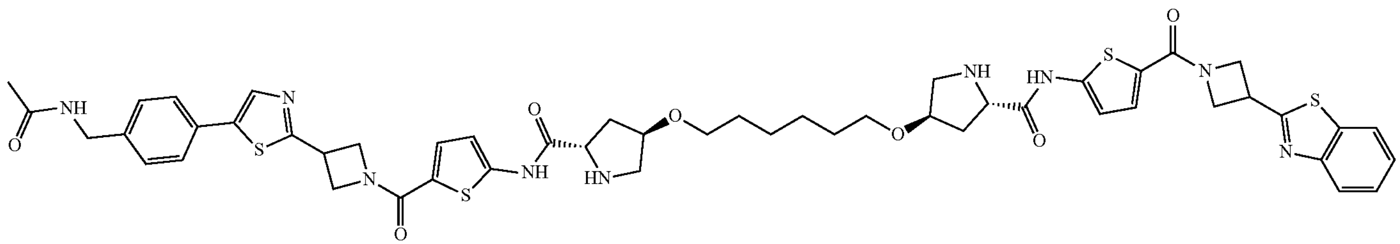 [SMILES: CC(=O)NCc1ccc(-c2cnc(C3CN(C(=O)c4ccc(NC(=O)[C@@H]5C[C@@H](OCCCCCCO[C@H]6CN[C@H](C(=O)Nc7ccc(C(=O)N8CC(c9nc%10ccccc%10s9)C8)s7)C6)CN5)s4)C3)s2)cc1] | 1036.3337 | |
| 229 | 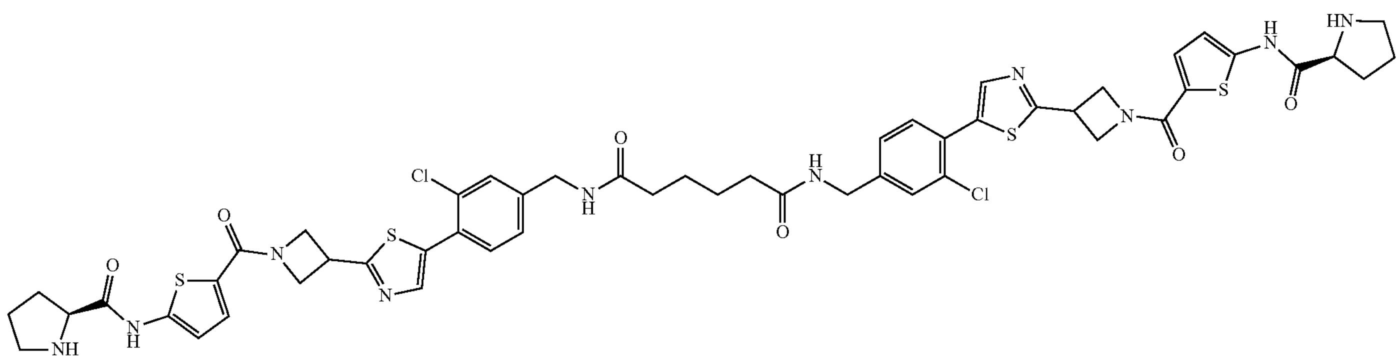 [SMILES: O=C(CCCCC(=O)NCc1ccc(-c2cnc(C3CN(C(=O)c4ccc(NC(=O)[C@@H]5CCCN5)s4)C3)s2)c(Cl)c1)NCc1ccc(-c2cnc(C3CN(C(=O)c4ccc(NC(=O)[C@@H]5CCCN5)s4)C3)s2)c(Cl)c1] | 1113.2560 | |

TABLE 2-continued

Exemplary Compounds

| Number | Structure | HRMS (M − H+), calc'd | HRMS (M − H+), found |
|---|---|---|---|
| 230 | 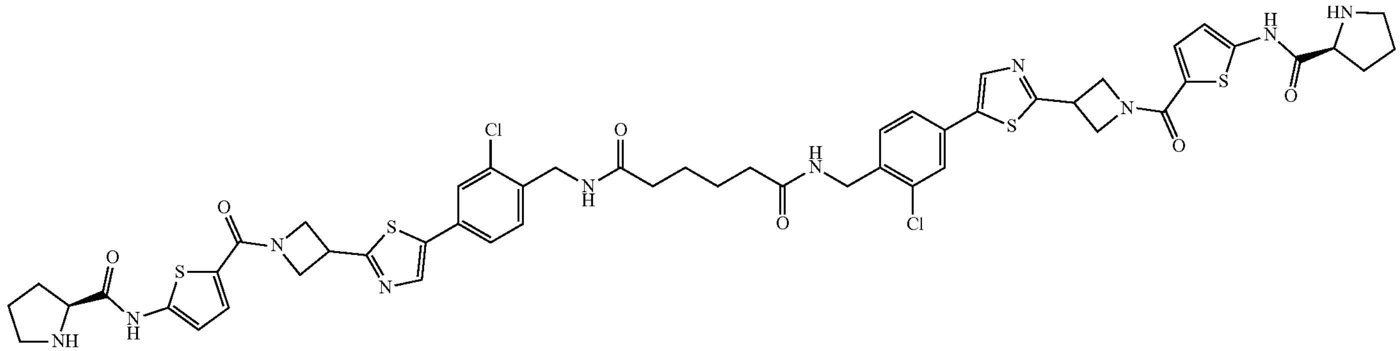 [SMILES: O=C(CCCCC(=O)NCc1ccc(-c2cnc(C3CN(C(=O)c4ccc(NC(=O)[C@@H]5CCCN5)s4)C3)s2)cc1Cl)NCc1ccc(-c2cnc(C3CN(C(=O)c4ccc(NC(=O)[C@@H]5CCCN5)s4)C3)s2)cc1Cl] | 1113.2560 | |
| 231 | 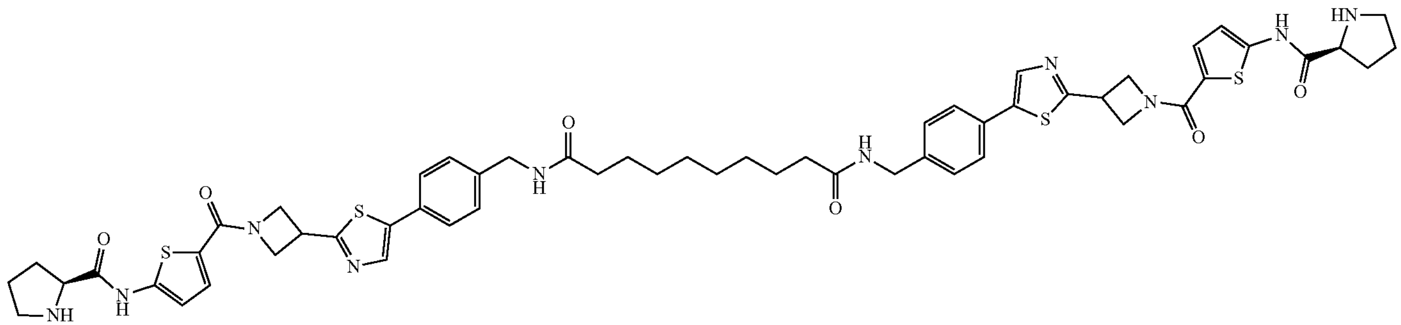 [SMILES: O=C(CCCCCCCCC(=O)NCc1ccc(-c2cnc(C3CN(C(=O)c4ccc(NC(=O)[C@@H]5CCCN5)s4)C3)s2)cc1)NCc1ccc(-c2cnc(C3CN(C(=O)c4ccc(NC(=O)[C@@H]5CCCN5)s4)C3)s2)cc1] | 1101.3966 | |

TABLE 2-continued

Exemplary Compounds

| Number | Structure | HRMS (M – H+), calc'd | HRMS (M – H+), found |
|---|---|---|---|
| 232 | 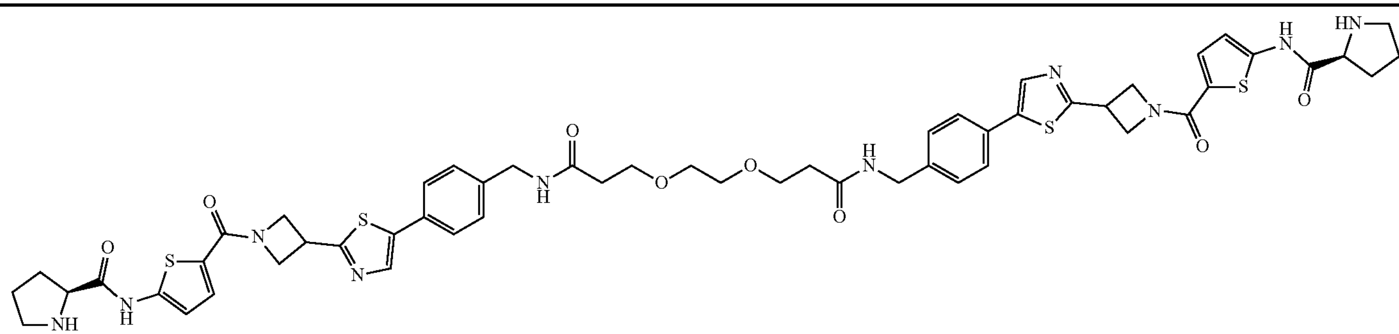 | 1105.3551 | |
| 233 | 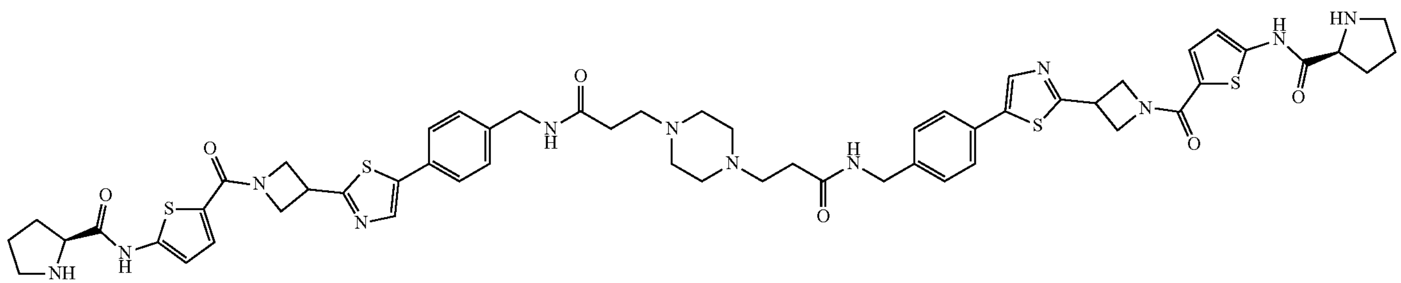 [SMILES: O=C(CCN1CCN(CCC(=O)NCc2ccc(-c3cnc(C4CN(C(=O)c5ccc(NC(=O)[C@@H]6CCCN6)s5)C4)s3)cc2)CC1)NCc1ccc(-c2cnc(C3CN(C(=O)c4ccc(NC(=O)[C@@H]5CCCN5)s4)C3)s2)cc1] | 1129.4027 | |

TABLE 2-continued
Exemplary Compounds
| Number | Structure | HRMS (M − H+), calc'd | HRMS (M − H+), found |
|---|---|---|---|
| 252 | 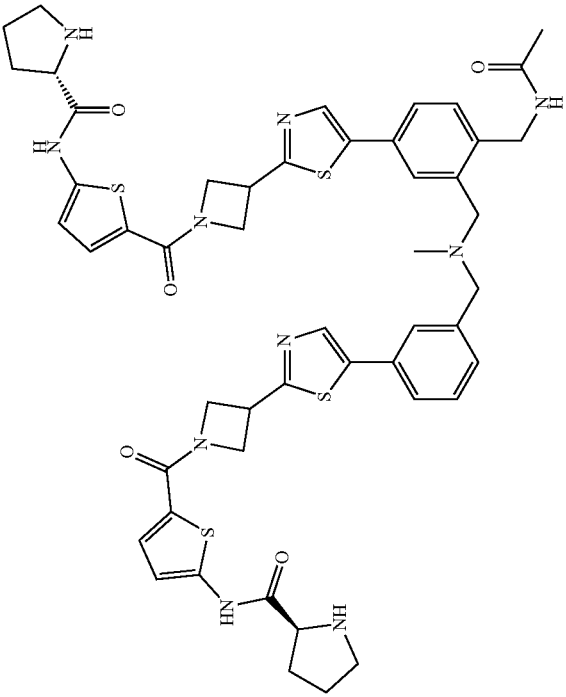 | 1003.3234 also M − H+2/ 2502.1654 | 1003.3239 also M − H+2/ 2502.1658 |

Example 3

Fluorescence Polarization Assay

A fluorescence polarization anisotropy (FP) assay was developed, employing di-crotonylated histone H3 derived peptide conjugated with a fluorophore (FAM-H3K23crK27cr), which binds to GST-fused GAS41 YEATS domain with sub-micromolar affinity ($K_D$=0.9 µM). 5' 6-Fluorescein (FAM)-labeled di-crotonylated Histone H3 peptide probe H3K23crK27cr was synthesized and used for competition experiments with 1 µM GST-GAS41(1-148) incubated with a competitor (e.g. compounds of the disclosure) at 1% DMSO in assay buffer containing 50 mM TRIS pH 7.5, 150 mM sodium chloride, 1 mM TCEP, 0.01% BSA, and 0.01% Tween-20 for 1 hour. 25 nM FAM-H3K23crK27cr peptide was added and the plate was incubated for an additional hour before fluorescence polarization data was measured at 525 nM on a Pherastar plate reader (BMG Labtech).

This assay was validated by testing competition with H3K27ac peptide and determined $IC_{50}$=243 µM, which is consistent with relatively weak affinity of mono-acetylated peptide (Cho 2018). In this assay, the Compound 134 ((5-(tert-butyl)thiophen-2-yl)(pyrrolidin-1-yl)methanone) exhibits comparable activity to H3K27ac, with $IC_{50}$=210 µM.

$IC_{50}$ values for selected compounds of the disclosure were determined using the fluorescence polarization assay with GAS41-YEATS and FAM-H3K23crK27cr. Table 3 shows biological activities ($IC_{50}$ values for inhibition of GAS41 YEATS) for selected compounds from Table 1 in a fluorescence polarization assay. Compound numbers correspond to the numbers and structures provided in Table 1.

TABLE 3

| | Less than 2 µM | 2 µM to less than 10 µM | 10 µM to less than 50 µM | Greater than 50 µM |
|---|---|---|---|---|
| GAS41 YEATS inhibitor $IC_{50}$ (µM) | 96, 98, 105, 106, 107, 109, 110, 111, 113, 116, 118, 119, 123, 124, 126, 129, 130, 131, 132, 133, 234, 235, 236, 241, 242, 243, 244, 245, 246 | 73, 76, 81, 85, 86, 87, 88, 89, 90, 91, 92, 93, 94, 95, 97, 99, 100, 108, 112, 114, 117, 120, 121, 122, 125, 127, 128, 237, 238, 239, 240 | 36, 37, 38, 40, 41, 42, 44, 46, 47, 49, 51, 52, 53, 54, 56, 58, 59, 60, 61, 62, 63, 64, 65, 67, 68, 69, 70, 71, 72, 75, 77, 78, 79, 80, 82, 84, 101, 102, 103, 104, 115, 208 | 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 39, 43, 45, 48, 50, 55, 57, 66, 74, 83, 134 |

Example 4

AlphaScreen Assay

An AlphaScreen competition assay was also developed using His$_6$-tagged full-length GAS41 and biotinylated-, di-crotonylated-H3 peptide (biotin-H3K23crK27cr). For full-length protein competition experiments, 100 nM MOCR-his$_6$-Gas41 protein was incubated with 100× competitor in 50 mM HEPES pH 7.5, 100 mM NaCl, 1 mM TCEP, 0.05% BSA, 0.01% Tween-20 for 1 hour at 1% DMSO in a 96-well ½-Area AlphaPlate. H3K23crK27cr-biotin was added to a final concentration of 25 nM and incubated for 1 hour. Nickel Chelate Acceptor AlphaScreen beads were added to a final concentration of 10 µg/mL and incubated for 1 hour. Streptavidin Donor AlphaScreen beads were added to a final concentration of 10 µg/mL and incubated for 2 hours. Alpha signal was measured on a Pherastar plate reader. We found $IC_{50}$=73 µM for the compound (5-(tert-butyl)thiophen-2-yl)(pyrrolidin-1-yl)methanone (Compound 134 from Table 1), and $IC_{50}$=24 µM for H3K27ac.

Table 4 shows biological activities ($IC_{50}$ values for inhibition of GAS41) for selected compounds from Table 2 in the AlphaScreen assay. Compound numbers correspond to the numbers and structures provided in Table 2.

TABLE 4

| | Less than 500 nM | 500 nM to less than 10 µM |
|---|---|---|
| GAS41 YEATS inhibitor $IC_{50}$ (µM) | 210, 211, 212, 213, 217, 218, 219, 220, 221, 222, 223 | 214, 215, 216 |

Example 5

Crystal Structure

The crystal structure of the complex of Compound 85 with GAS41 YEATS at 2.10 Å resolution was determined (FIG. 1). Compound 85 binds in a channel that constitutes a recognition site for acetyl-lysine (Cho 2018) and is comprised of side chains of H43, H71, S73, Y74, W93, and F96 and backbone of G92, G94 and E95 (FIG. 1).

Example 6

Dimeric Compounds Induce Dimerization of GAS41 YEATS Domain

An AlphaScreen assay based on His-tagged and biotin-labeled Avi-tagged GAS41 YEATS domain constructs was developed. For dimerization experiments, 500 nM his$_6$-Gas41(13-158) and 250 nM avi-Gas41-YEATS were incubated in 50 mM HEPES pH 7.5, 100 mM NaCl, 1 mM TCEP, 0.05% BSA, 0.01% Tween-20 in a 96-well ½-Area AlphaPlate incubated for 30 minutes. Compounds 221 and 223 were added to a final concentration of 250 nM at 1% DMSO. Nickel Chelate Acceptor AlphaScreen beads were added to a final concentration of 10 µg/mL and incubated for 1 hour. Streptavidin Donor AlphaScreen beads were added to a final concentration of 10 μg/mL and incubated for 2 hours. For competition experiments with the dimeric complex, 500 nM his-Gas41(13-158) and 250 nM avi-Gas41-YEATS were incubated in assay buffer with 250 nM dimeric inhibitor for 30 minutes before the addition of monomeric competitor. AlphaScreen beads were added as in previous experiments. Alpha signal was measured on a Pherastar plate reader.

Figure 2A:
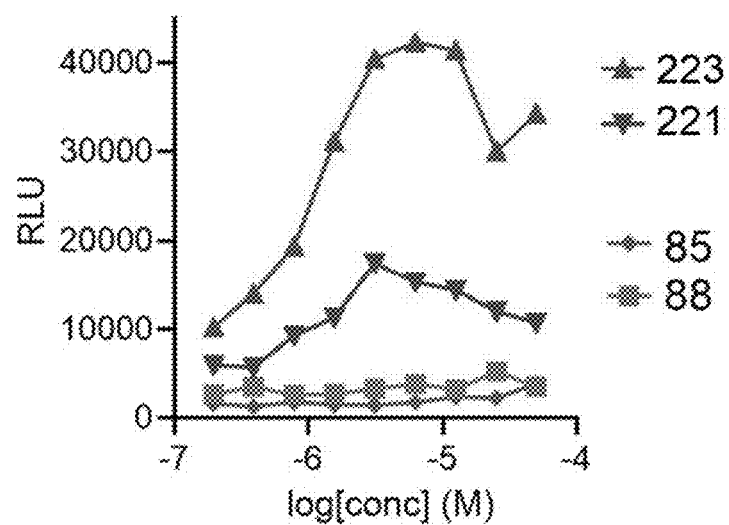
FIGS. 2A-2C show data for activities of compounds disclosed herein. A) Results of a dimerization assay to determine bivalent inhibitor-induced dimerization of GAS41 YEATS domain, as described in Example 6. B) $^1$H-$^{15}$N HSQC spectrum of 60 µM $^{15}$N-labeled GAS41 YEATS domain (black) and in presence of 60 µM Compound 85 (red). C) $^1$H-$^{15}$N HSQC spectrum of 60 µM $^{15}$N-labeled GAS41 YEATS domain in presence of 30 µM Compound 223 (red).
Figure 2B:
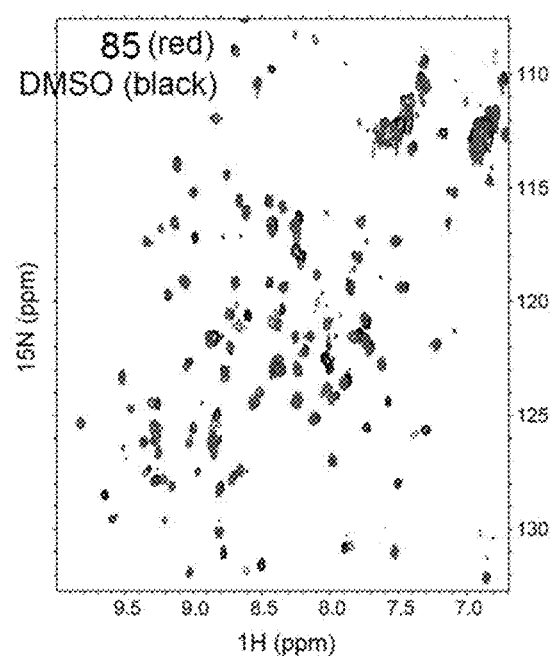
Figure 2C:
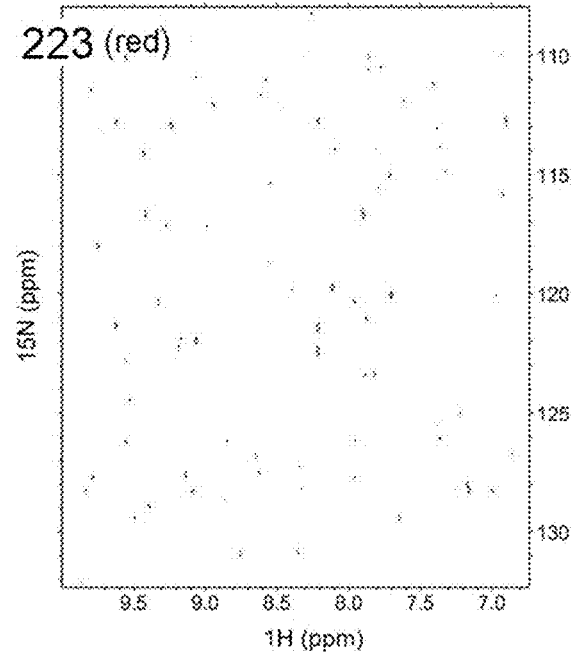

Titration of his$_6$-Gas41(13-158) and avi-Gas41-YEATS with either Compound 223 or 221 resulted in an increase of luminescence signal reflecting formation of the dimeric complex (FIG. 2A). The signal was further decreased at highest compound concentrations, and indicates saturation of YEATS domain via independent inhibitor molecules (Hook effect). Binding of Compound 85 and Compound 223 to $^{15}$N-labeled GAS41 YEATS domain were also compared by NMR; only dimeric Compound 223 but not monomeric Compound 85 induces very substantial broadening of signals, suggesting formation of a larger dimeric complex (FIGS. 2B,C).

Example 7

Inhibition of GAS41 Interactions in Cells

A NanoBiT assay (Promega Corporation, Madison, WI) was developed to detect inhibition of protein-protein interaction in HEK293T cells by compounds. GAS41-WT and GAS41-W93A mutant were cloned into pBiT1.1-C[TK/LgBiT] vector. SmBiT-H3.3 was purchased from Promega. HEK293T cells (4×10E5) were plated into 6-well plates (DMEM with 10% FBS) and incubated for 5 h. The LgBiT-GAS41 and SmBiT-H3.3 plasmids were co-transfected using FuGENE HD for 42 h. 5×104 cells were transferred into 96-well white plates (DMEM with 10% FBS and 1% Penicillin and Streptomycin) and treated with compounds for 24 h. After the Nano-Glo Live Cell Reagent was added to each well, the luminescence was measured immediately using PHERAstar FS instrument.

Figure 3:
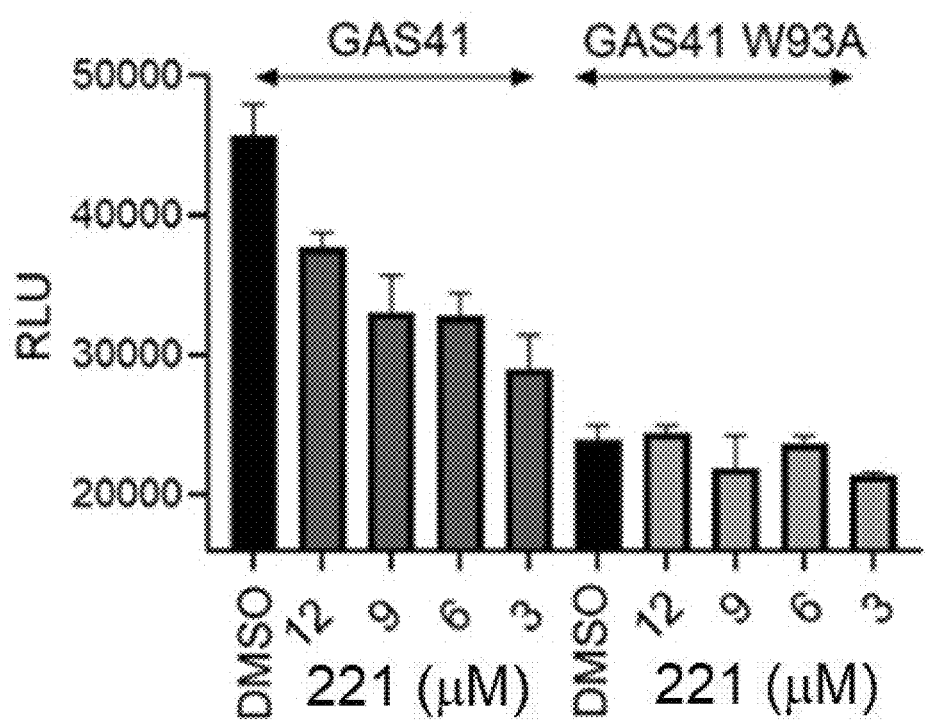
FIG. 3 shows activity of Compound 221 in a NanoBiT assay after 24 h treatment in 293T cells co-transfected with SmBiT-H3.3 and LgBiT-GAS41-WT or W93A mutant, as described in Example 7.

Co-expression of both proteins resulted in strong luciferase signal reflecting the interaction of GAS41 with acetylated H3.3 in cells. Introduction of a point mutation W93A in LgBit GAS41 abolishing histone recognition (Hsu 2018) largely diminished luminescence signal and validates the NanoBit assay. Subsequently, activity of dimeric Compound 221 was tested in the NanoBit assay and found dose-dependent inhibition of the luminescence signal and estimated IC$_{50}$=6 μM (FIG. 3). Importantly, treatment with Compound 221 did not reduce the signal for W93A GAS41 mutant, further supporting specific activity (FIG. 3).

Example 8

Activity in NSCLS Cells

Figure 4A:
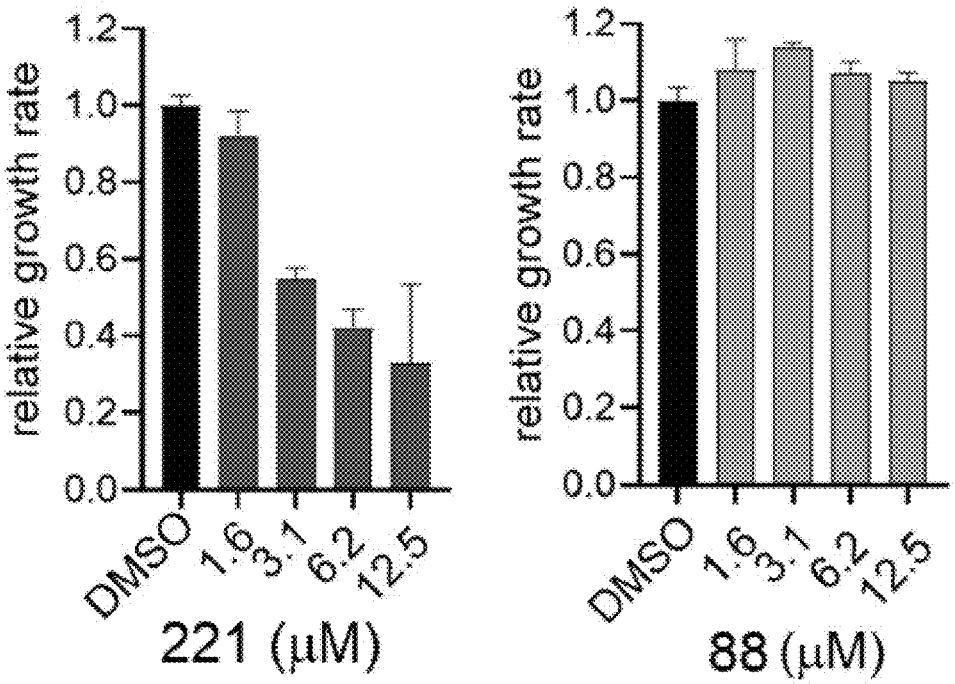
FIGS. 4A-4D show cellular activity of certain compounds, as described in Example 8. A) Inhibition of cell proliferation of H1299 cells by Compound 221 and Compound 88. B) Inhibition of growth in A549 or A549-KO cells by Compound 221. C) Inhibition of growth in H1299 or H1993 cells by Compound 221. D) Relative mRNA levels of E2F2, FOXM1, and MCM6 in H1299 cells after 7 days treatment with Compound 221.
Figure 4B:
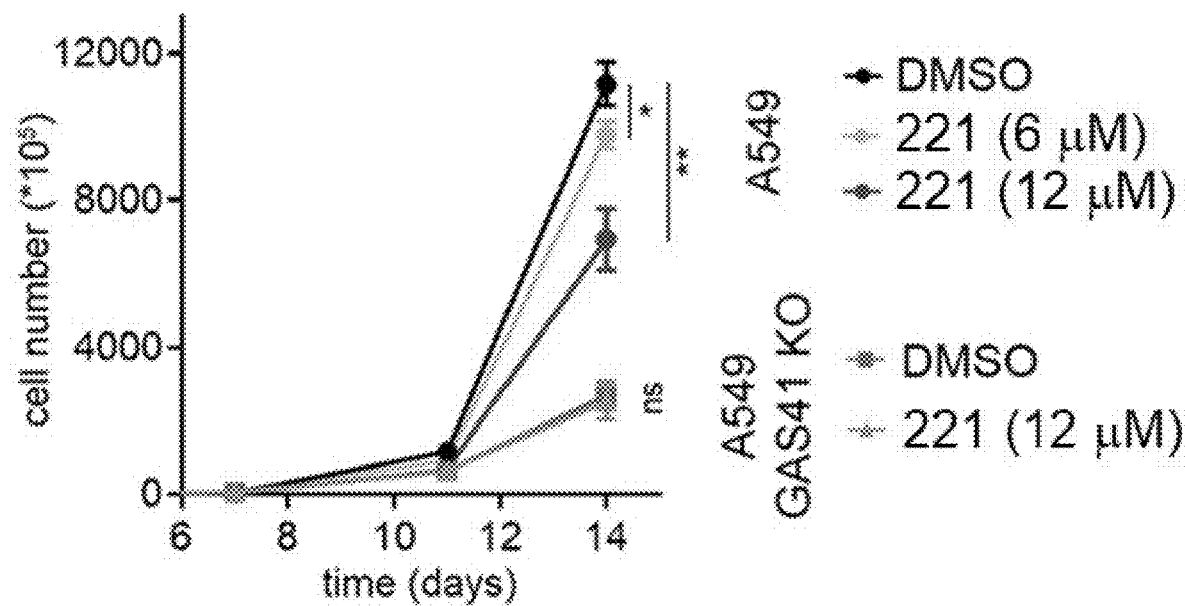
Figure 4C:
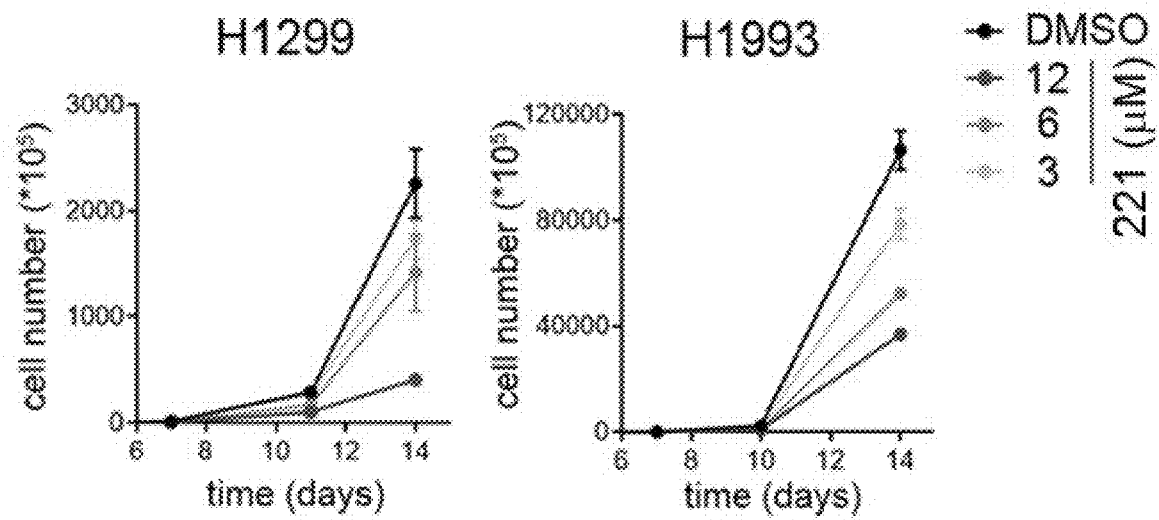
Figure 4D:
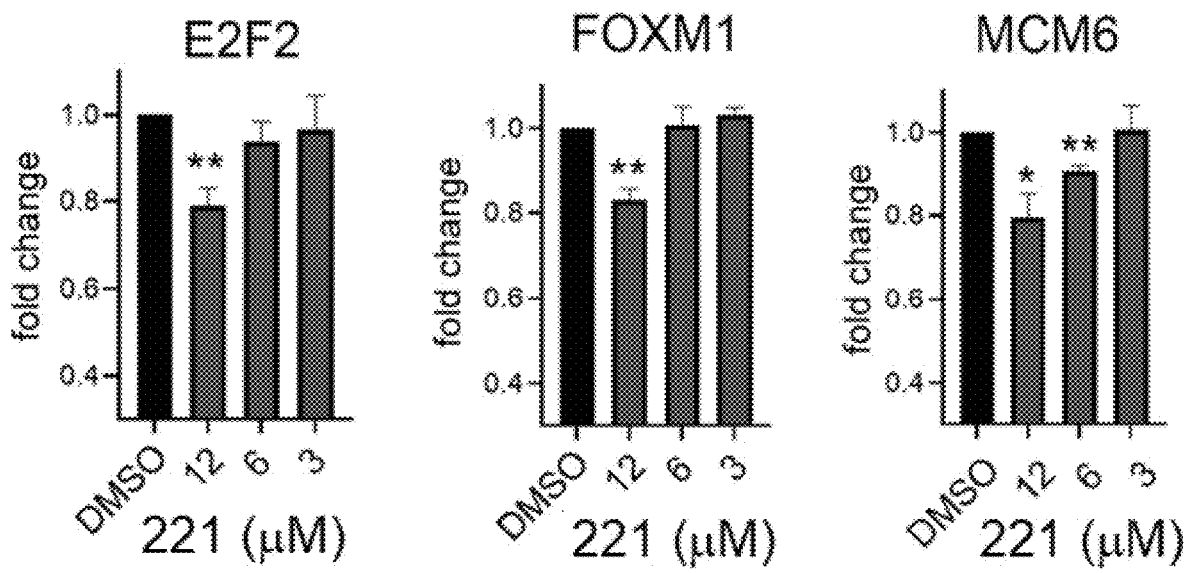

To investigate cellular activity of GAS41 inhibitors, H1299 cells were treated with monomeric Compound 88 and dimeric Compound 221 for 4 days. Only the dimer Compound 221 induces dose dependent growth inhibition with GI$_{50}$~3 μM (FIG. 4A). To determine whether growth inhibition is dependent on presence of GAS41 we developed A549 GAS41 knocked-out cells using the CRISPR/CAS9 system. We found GAS41-KO were viable but grew more slowly compare with parental A549 cells and had reduced growth by ~70% at day 14 (FIG. 4B). Treatment with Compound 221 partially inhibited growth of A549 cells by ~40% at 12 μM concentration, but had no effect on the GAS41-KO cells (FIG. 4B), validating specific growth inhibition. Next, we evaluated the effect of Compound 221 on growth of two NSCLC cell lines H1299 and H1933 with GAS41 amplification. Treatment with Compound 221 reduced growth of both cell lines with GI$_{50}$~6 μM at day 14 (FIG. 4C). Such effect correlates closely with activity of Compound 221 in NanoBit assay (FIG. 3). To further validate on-target activity of Compound 221, we tested expression of GAS41 target genes in H1299 (Hsu 2018). Treatment with Compound 221 resulted in statistically significant decrease in the expression of E2F2, FOXM1, and MCM6 (FIG. 4D). Altogether, dimeric inhibitor Compound 221 reduces binding of GAS41 to acetylated H3.3 in cells and induces on-target growth inhibition in NSCLCs lines.

The invention claimed is:
1. A compound of formula (I):

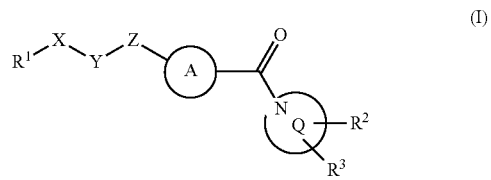

or a pharmaceutically acceptable salt thereof, wherein:
$R^1$ is selected from heterocyclyl, heterocyclylalkyl, heteroaryl, heteroarylalkyl, aryl, arylalkyl, cycloalkyl, cycloalkylalkyl, hydroxy, alkoxy, thioalkyl, halogen, haloalkyl, carboxy, acyl, amido, cyano, and sulfonyl;
X is —C(O)—, —C(S)—, —CH$_2$—, or —SO$_2$—, or is absent;
Y is —NR$^a$—;
$R^a$ is selected from hydrogen, alkyl, haloalkyl, heteroalkyl, cycloalkyl, hydroxyalkyl, and aminoalkyl, or $R^a$ is taken together with the nitrogen atom to which it is attached to form a fused ring with A, or $R^a$ and $R^1$ together with the atoms to which they are attached together form an optionally substituted heterocyclic ring;
Z is absent or is —CR$^b$R$^c$—;
$R^b$ and $R^c$ are each independently selected from hydrogen and alkyl;
A is a five-membered heteroaryl;
Q is a four-, five-, or six-membered heterocyclyl;
$R^2$ is selected from hydrogen, halo, alkyl, amino, and hydroxy; and
$R^3$ is a group of formula:

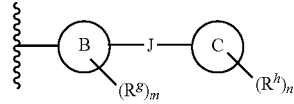

wherein: B is a 5-membered monocyclic heteroaryl having 1 or 2 heteroatoms independently selected from N and S; J is absent; C is selected from aryl, heteroaryl, and heterocyclyl; m is 0 or 1; n is 0, 1, 2, or 3; $R^g$ is $C_1$-$C_6$ alkyl; and each $R^h$ is independently selected from alkyl, halo, haloalkyl, amino, aminoalkyl, amido, amidoalkyl, sulfonamido, sulfonamidoalkyl, acyl, aryl, arylalkyl, heteroaryl, heteroarylalkyl, heterocyclyl, heterocyclylalkyl, cycloalkyl, and cycloalkylalkyl;

wherein each alkyl, alkenyl, alkynyl, aryl, arylalkyl, heteroalkyl, heteroaryl, heteroarylalkyl, cycloalkyl, heterocyclyl, and heterocyclylalkyl is independently optionally substituted with 1, 2, 3, 4, or 5 substituents, with the proviso that when Z is —CR$^b$R$^c$—, R$^1$ is not cycloalkyl.

2. The compound of claim 1, or a pharmaceutically acceptable salt thereof, wherein R$^1$ is a monocyclic heterocyclyl having 1 or 2 heteroatoms independently selected from N, O, and S.

3. The compound of claim 1, or a pharmaceutically acceptable salt thereof, wherein X is —C(O)—.

4. The compound of claim 1, or a pharmaceutically acceptable salt thereof, wherein R$^a$ is hydrogen.

5. The compound of claim 1, or a pharmaceutically acceptable salt thereof, wherein Z is absent.

6. The compound of claim 1, or a pharmaceutically acceptable salt thereof, wherein A is a five-membered heteroaryl having 1, 2, or 3 heteroatoms independently selected from N, O, and S.

7. The compound of claim 1, or a pharmaceutically acceptable salt thereof, wherein A is selected from thiophene and thiazole.

8. The compound of claim 1, or a pharmaceutically acceptable salt thereof, wherein Q is selected from azetidine, pyrrolidine, and piperidine.

9. The compound of claim 1, or a pharmaceutically acceptable salt thereof, wherein R$^2$ is hydrogen.

10. The compound of claim 1, or a pharmaceutically acceptable salt thereof, wherein the group

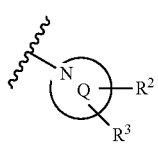

a formula selected from:

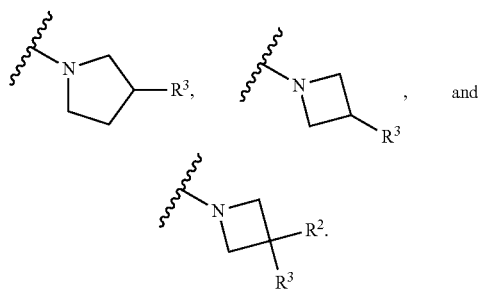

11. The compound of claim 1, or a pharmaceutically acceptable salt thereof, wherein the compound has formula (Ia):

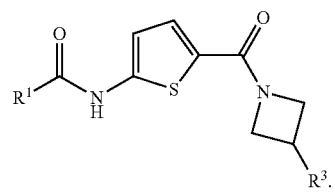

12. The compound of claim 1, or a pharmaceutically acceptable salt thereof, wherein the compound has formula (Ib):

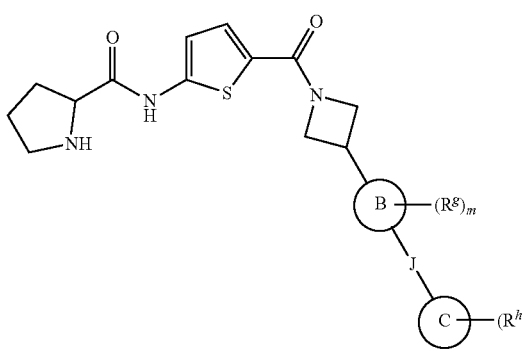

13. The compound of claim 1, or a pharmaceutically acceptable salt thereof, wherein the compound has formula (Ic):

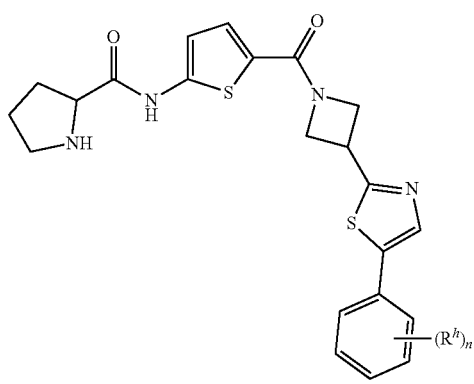

wherein:

n is 0, 1, 2 or 3; and each R$^h$ is independently selected from $C_1$-$C_6$ alkyl, halo, halo-$C_1$-$C_6$-alkyl, amino, amino-$C_1$-$C_6$-alkyl, hydroxy, hydroxy-$C_1$-$C_6$-alkyl, $C_1$-$C_6$ alkoxy, amido, amido-$C_1$-$C_6$-alkyl, acyl, aryl, aryl-$C_1$-$C_6$-alkyl, heteroaryl, heteroaryl-$C_1$-$C_6$-alkyl, heterocyclyl, heterocyclyl-$C_1$-$C_6$-alkyl, cycloalkyl, and cycloalkyl-$C_1$-$C_6$-alkyl.

14. A pharmaceutical composition comprising a compound of claim 1, or a pharmaceutically acceptable salt thereof, and a pharmaceutically acceptable carrier.

15. The compound of claim 1, wherein the compound is selected from the group consisting of:

287
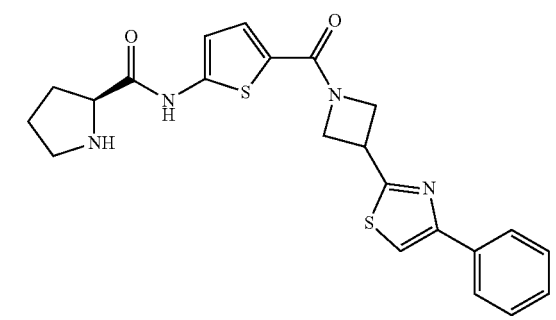
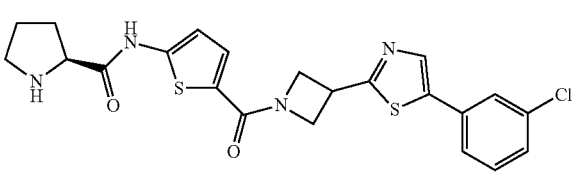
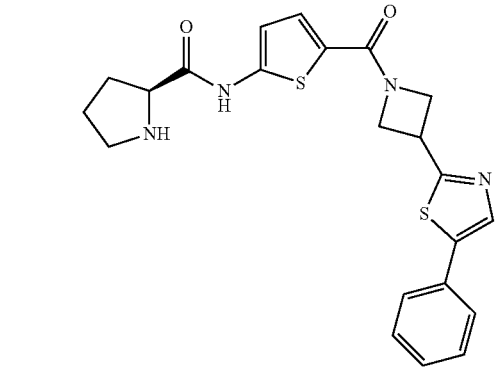
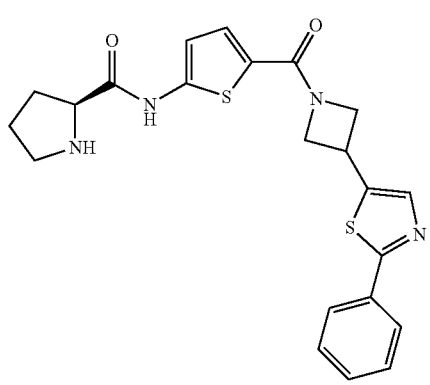
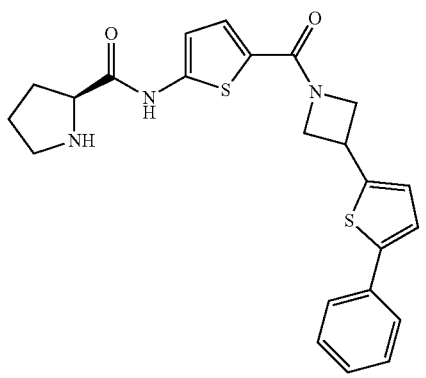
288
-continued
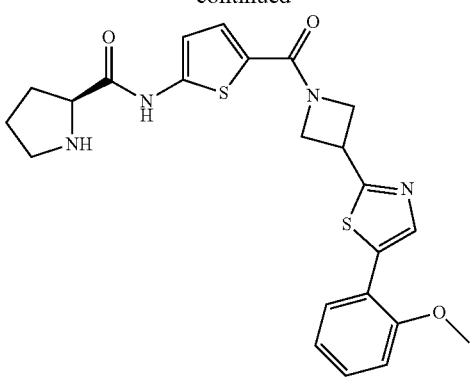
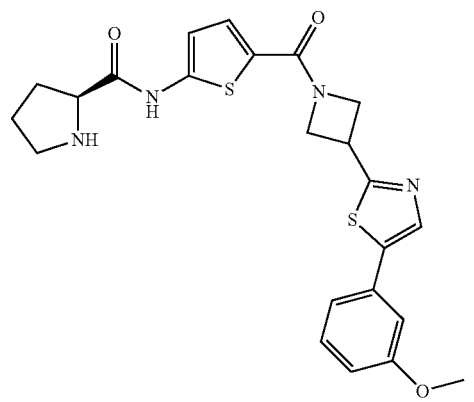
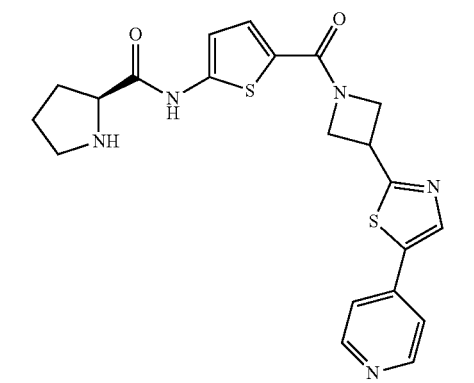
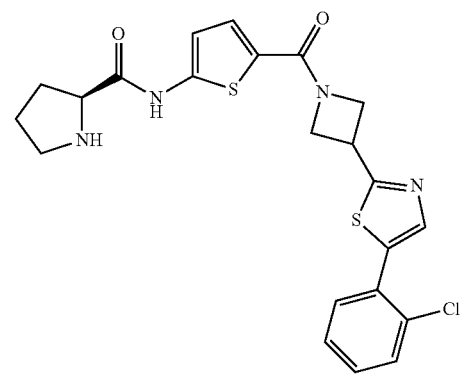

289
-continued
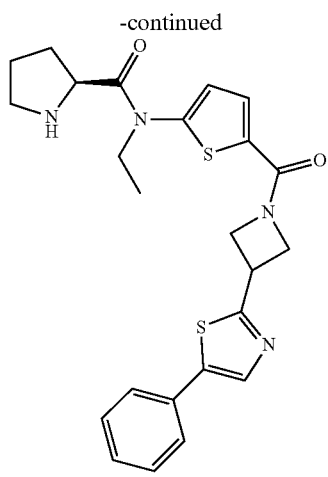
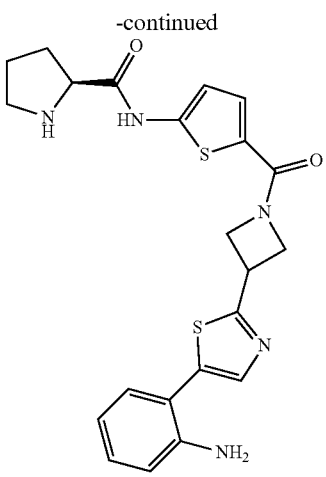
290
-continued
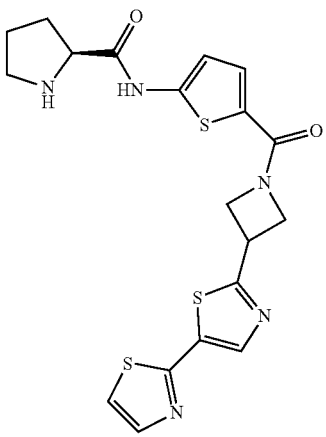
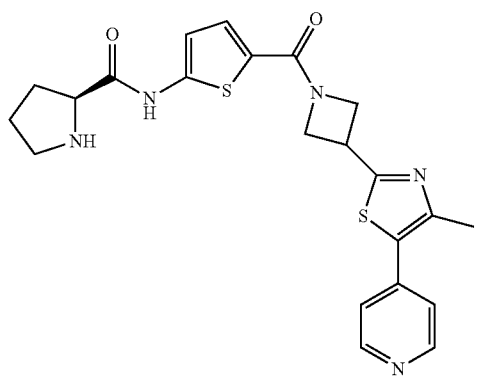
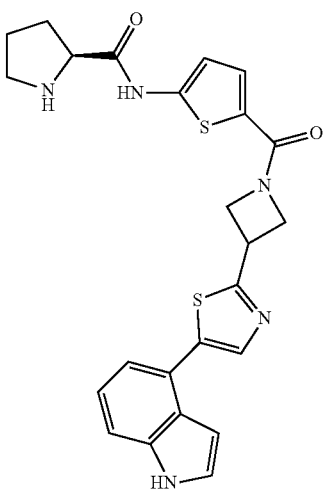

291
-continued
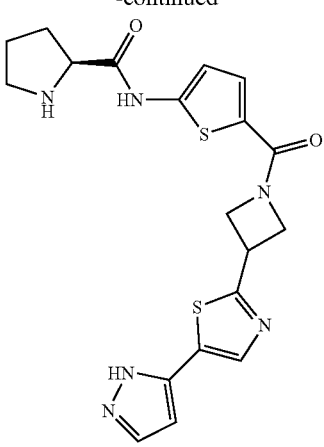
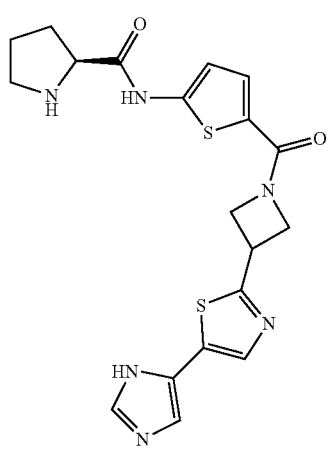
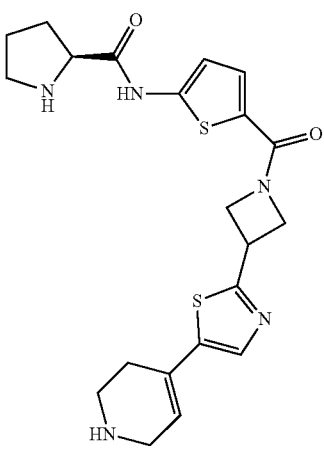
292
-continued
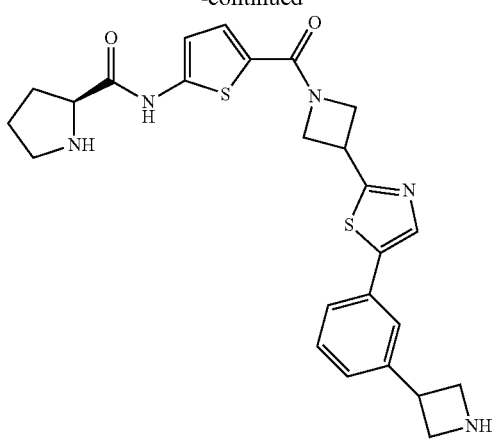
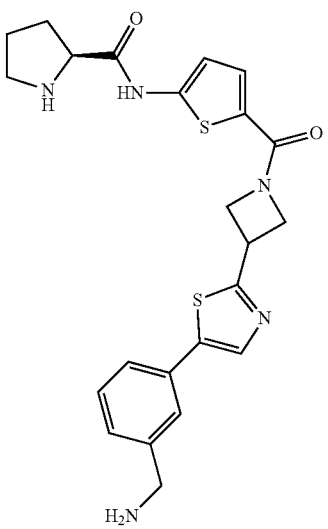
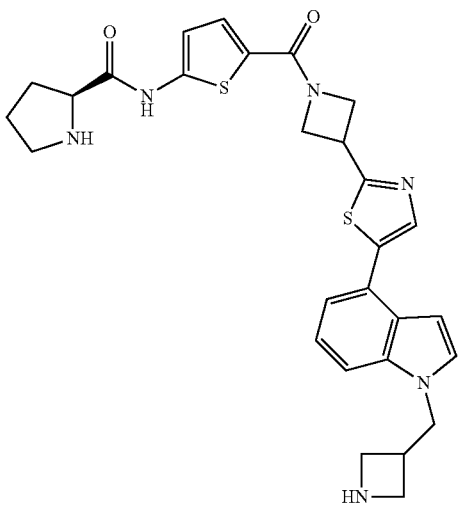

293
-continued
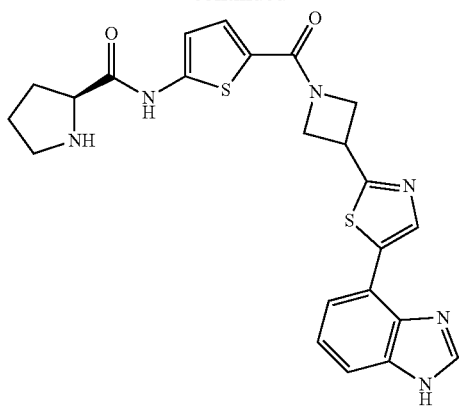
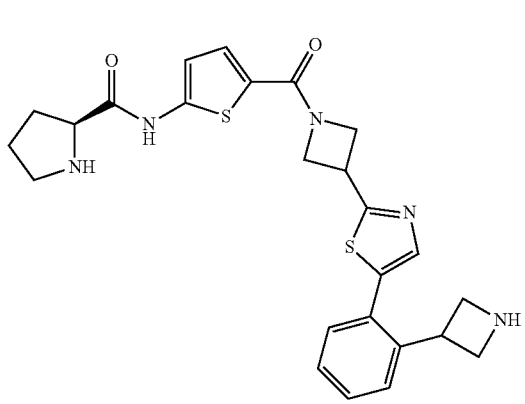
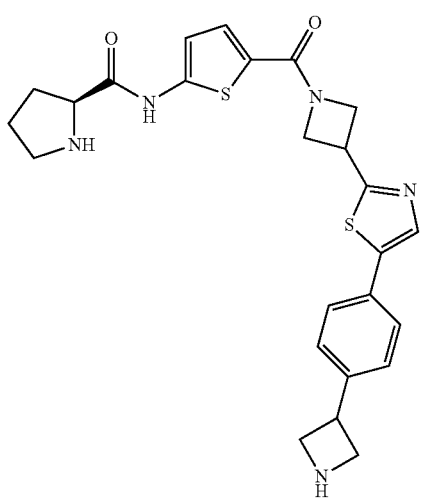
294
-continued
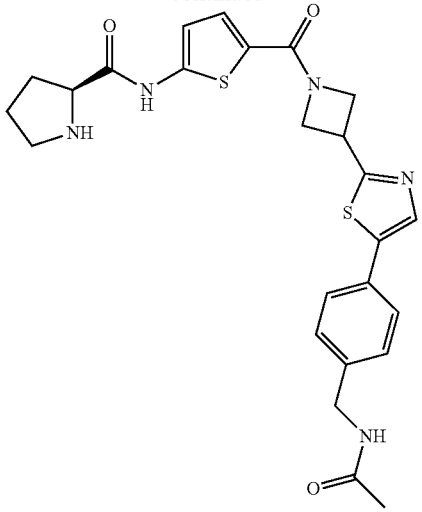
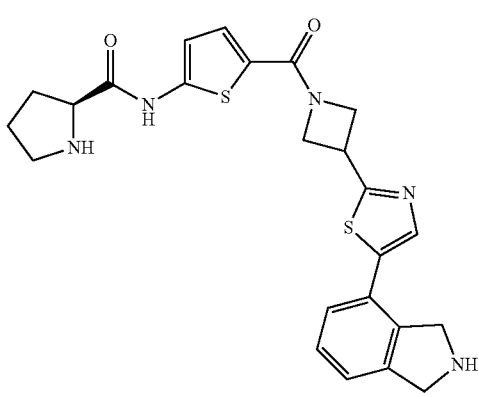
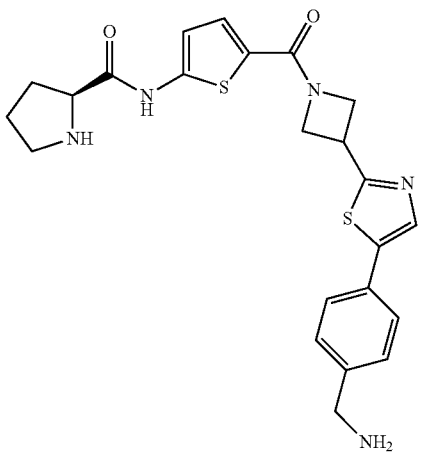

295
-continued
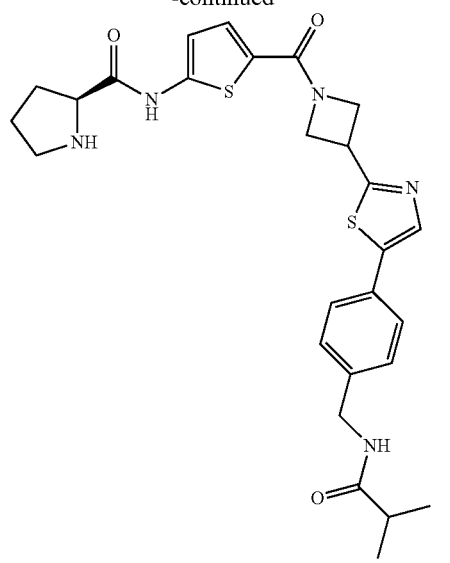
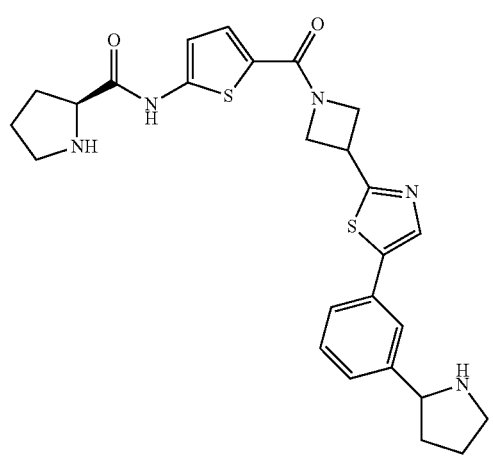
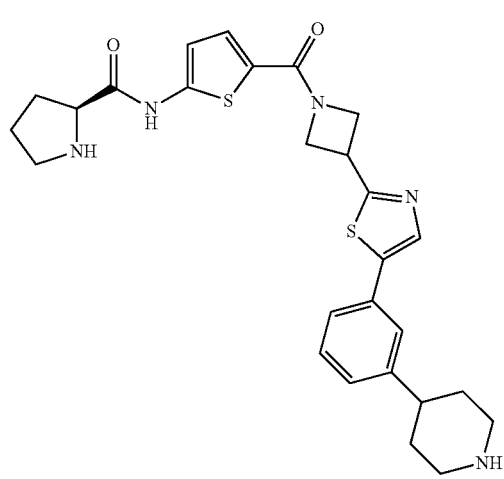
296
-continued
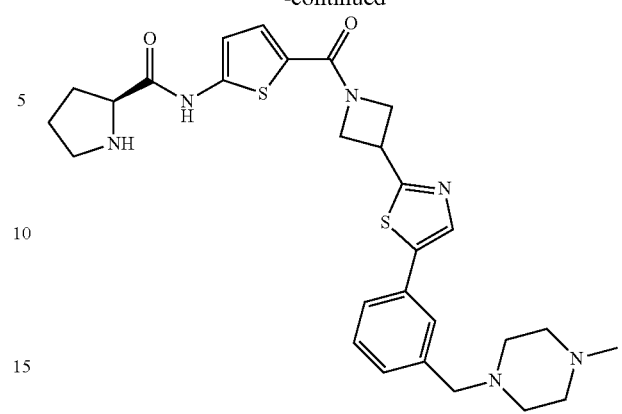
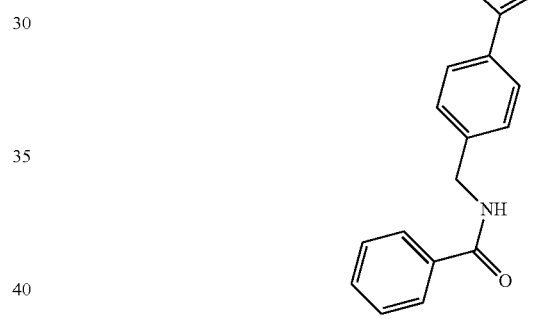
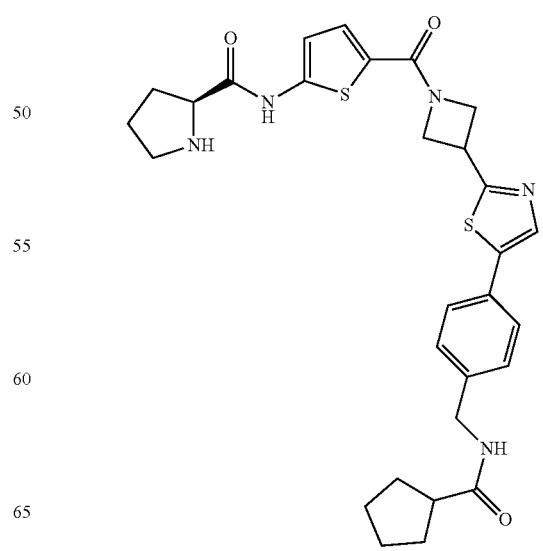

297
-continued
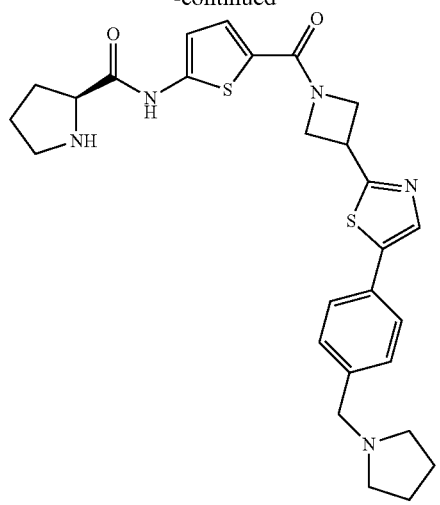
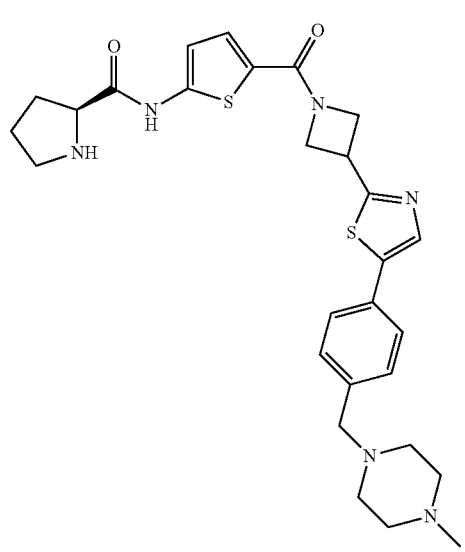
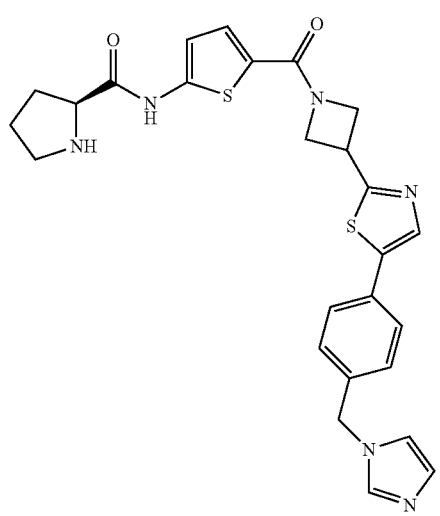
298
-continued
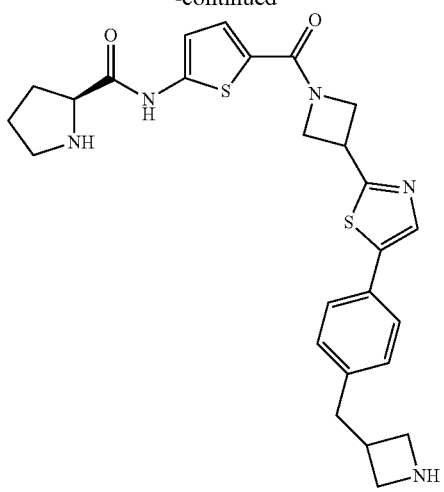
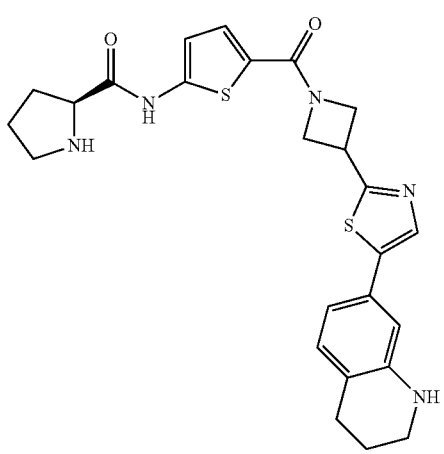
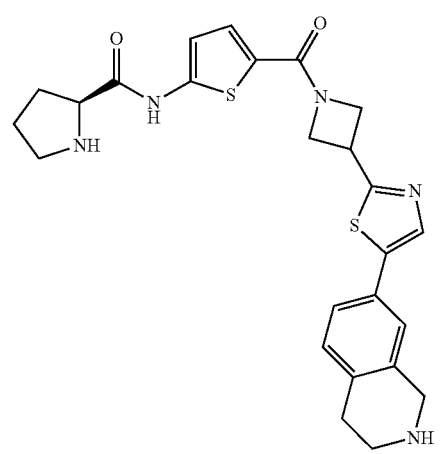

299
-continued
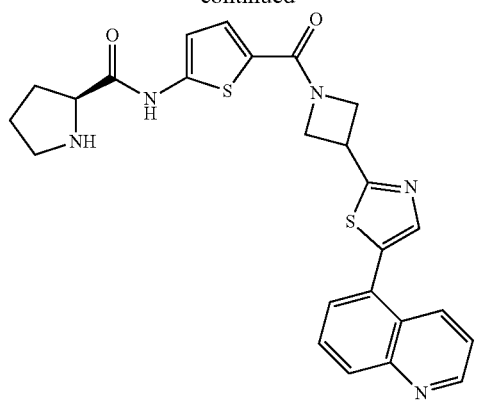
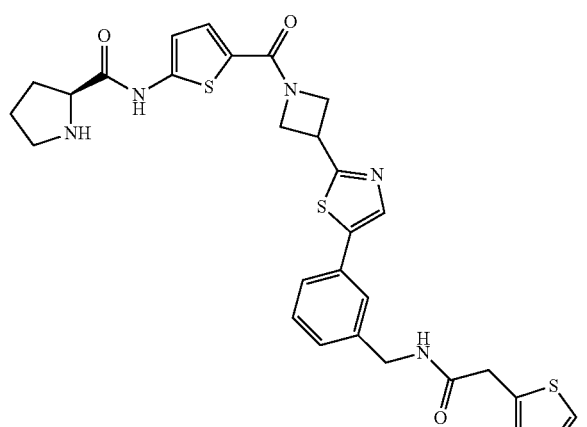
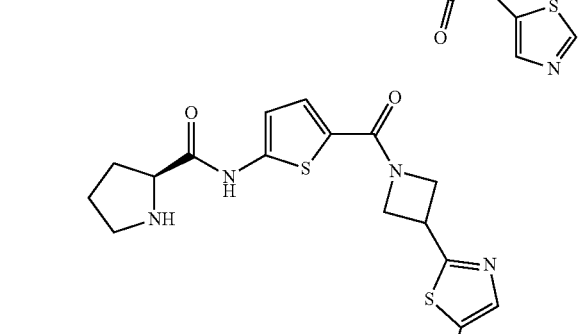
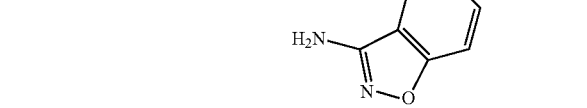
300
-continued
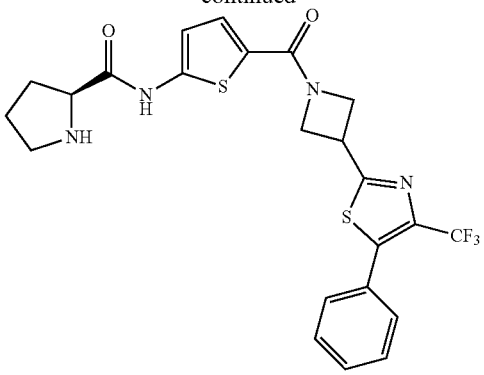
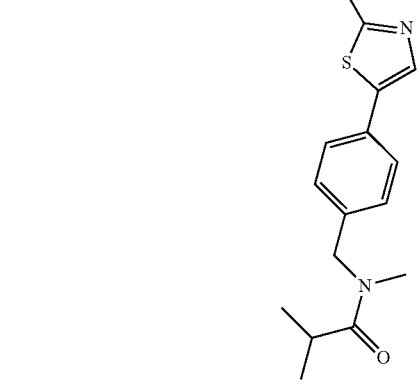
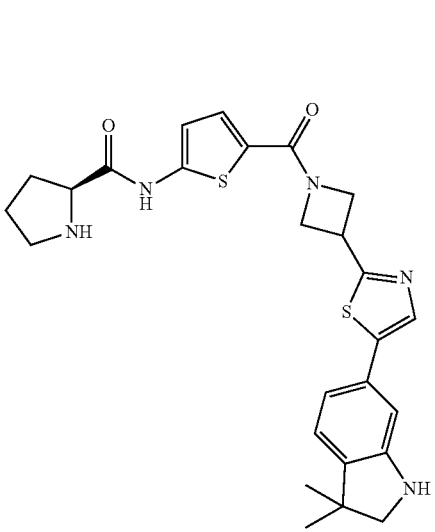

301
-continued
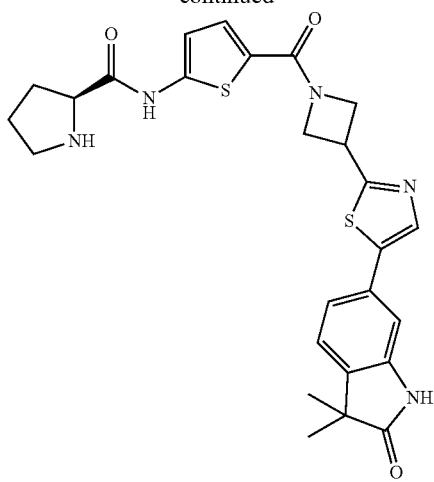
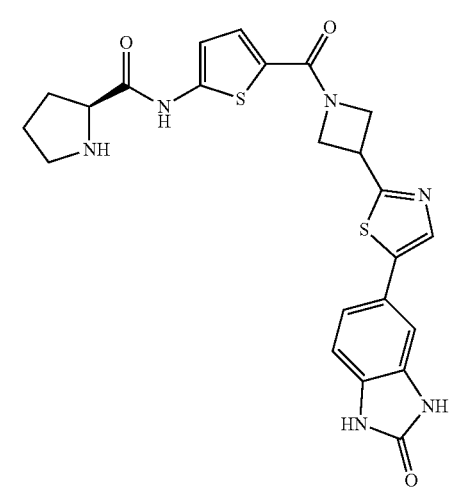
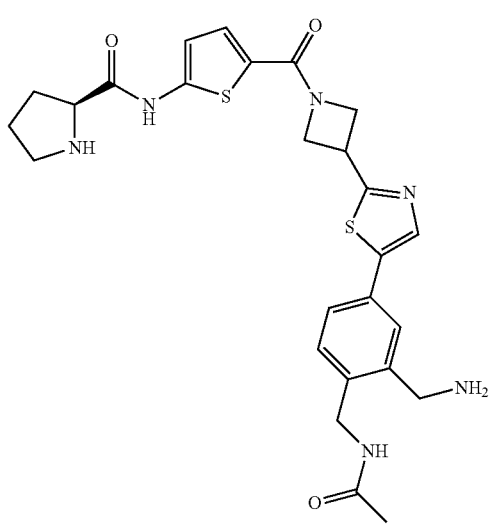
302
-continued
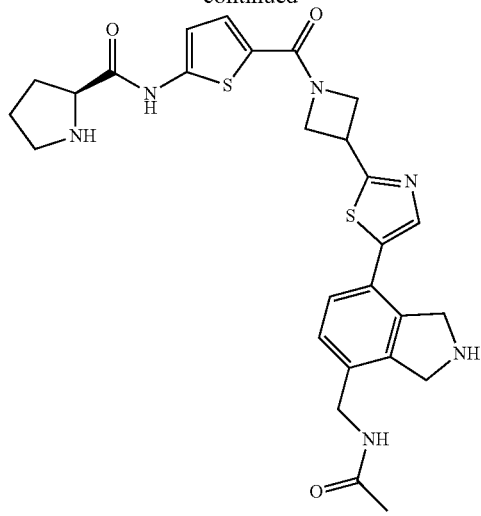
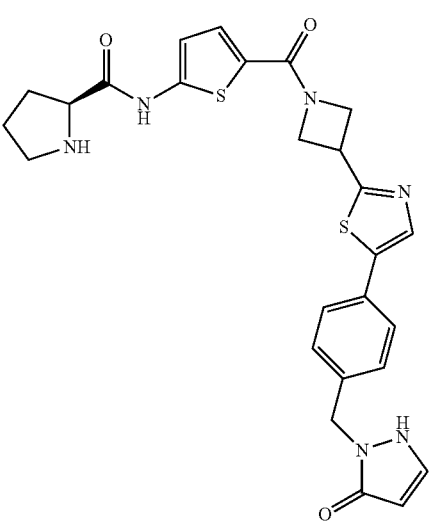
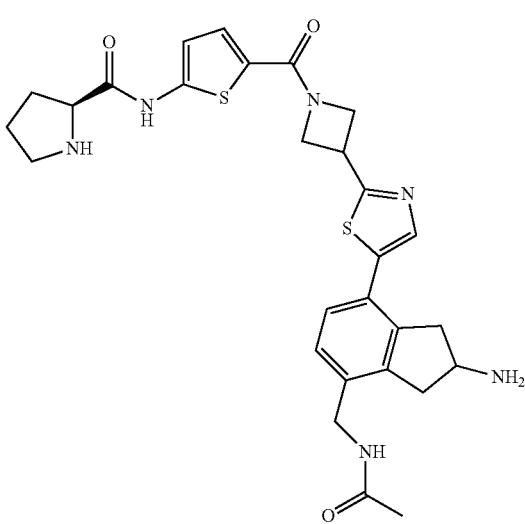

303
-continued
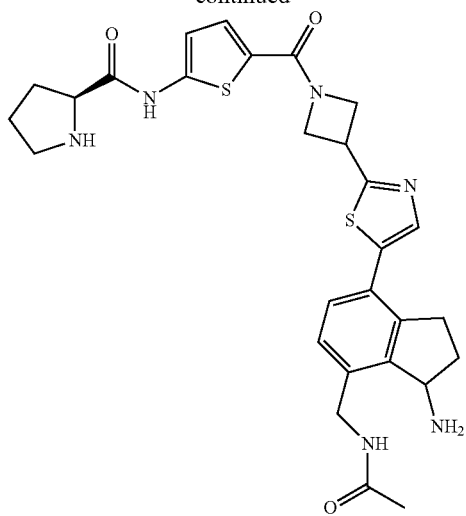
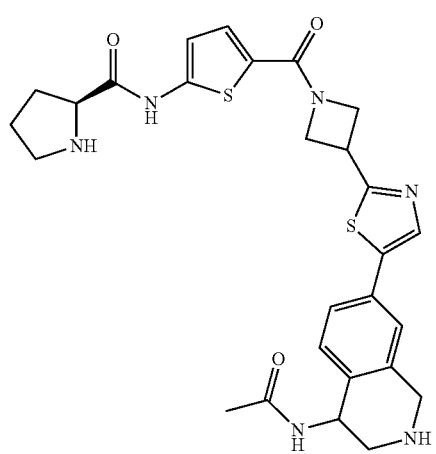
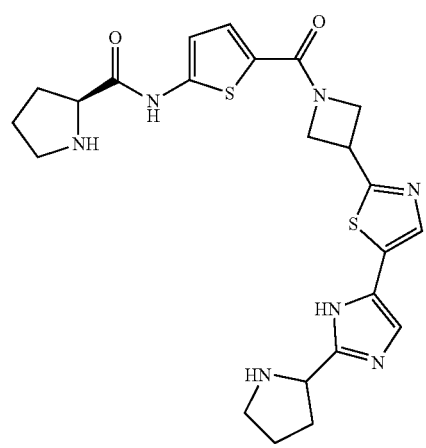
304
-continued
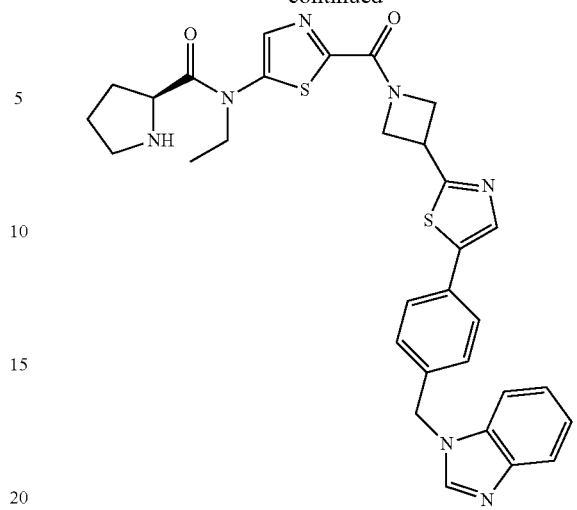
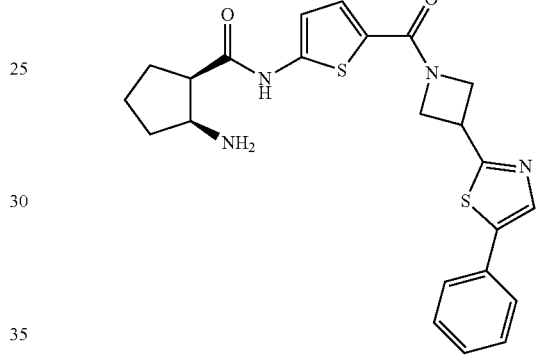
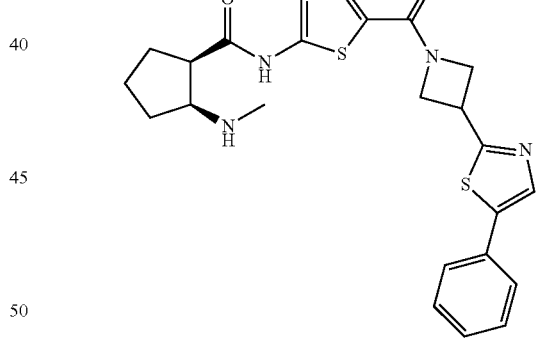
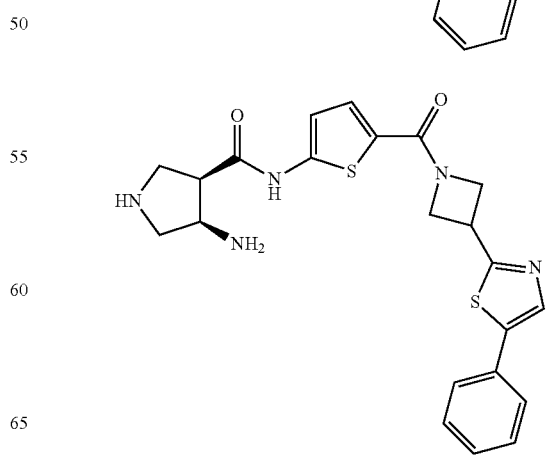

305
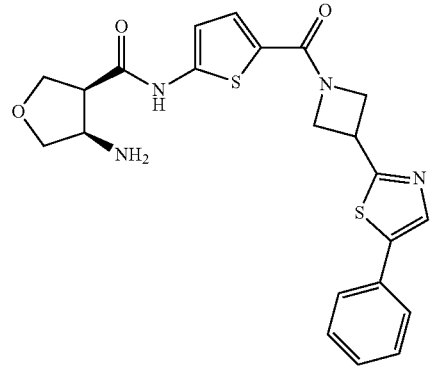
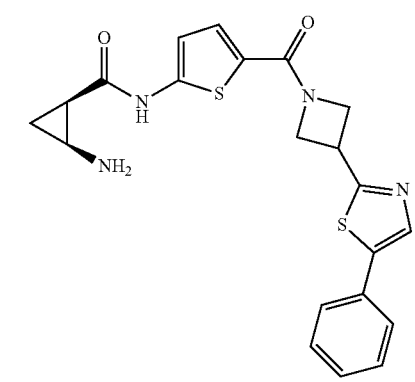
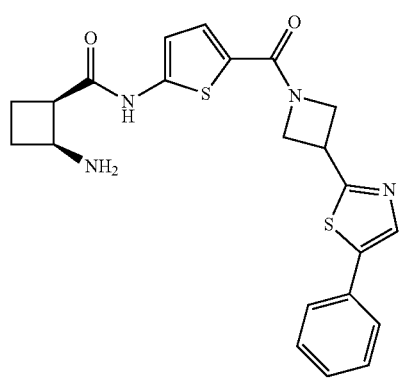
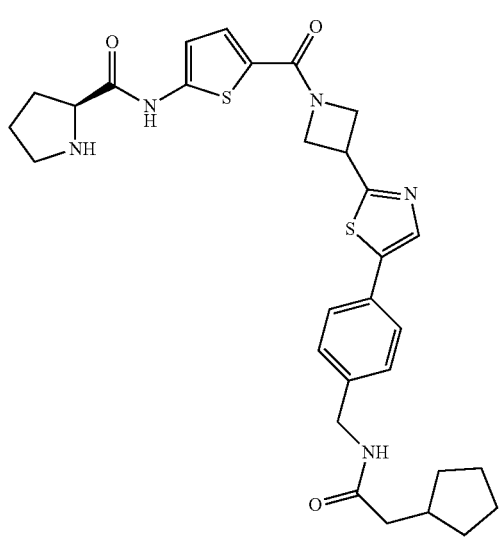
306
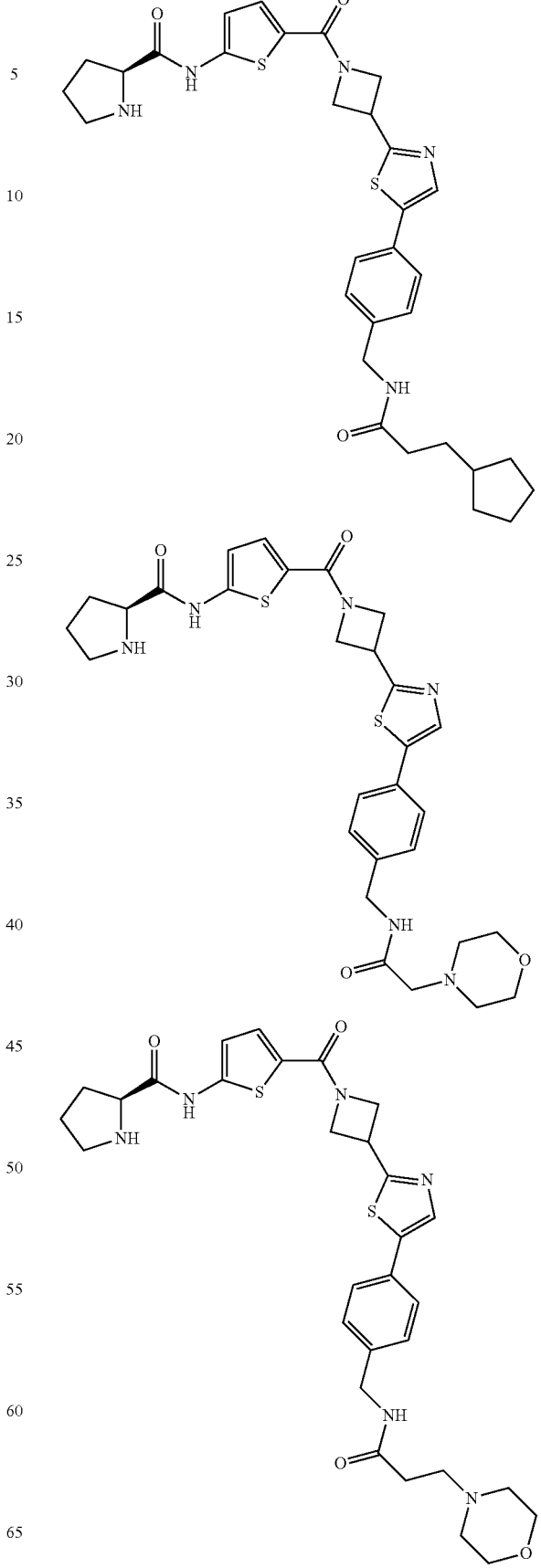

307

308

309
-continued
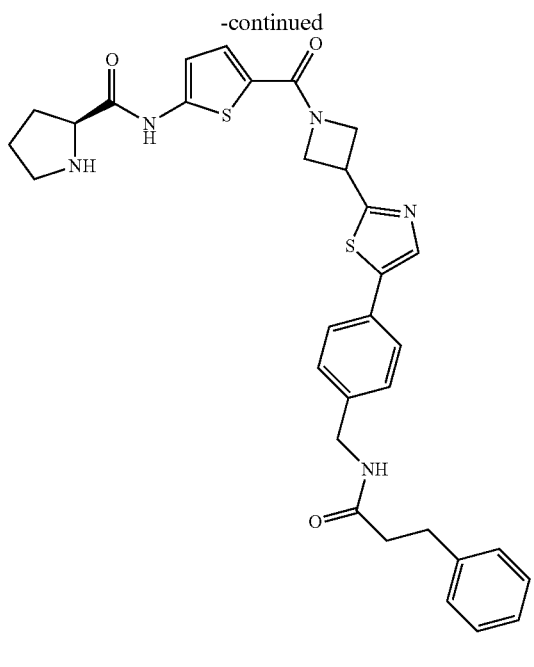
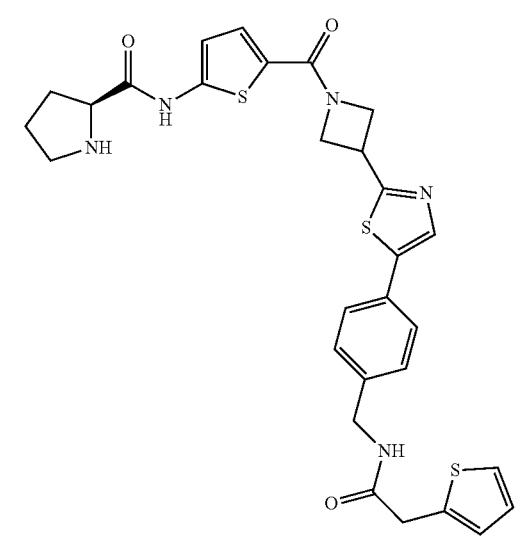
310
-continued
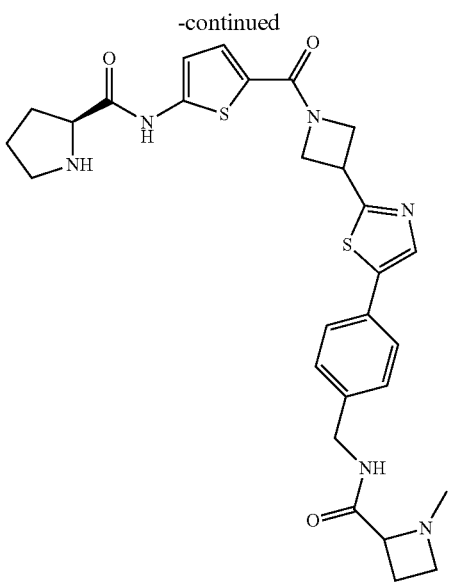
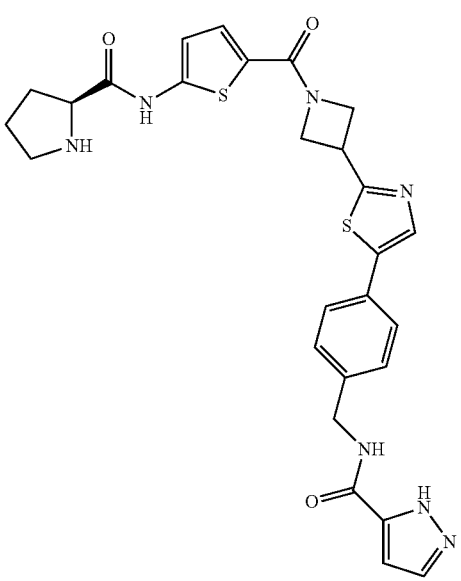

311
-continued
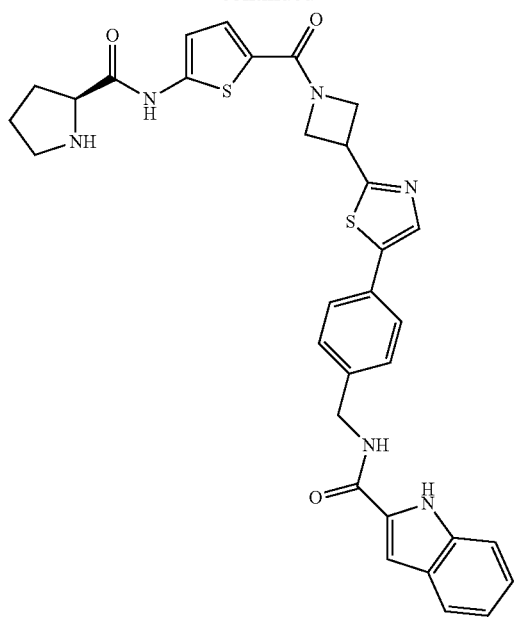
312
-continued
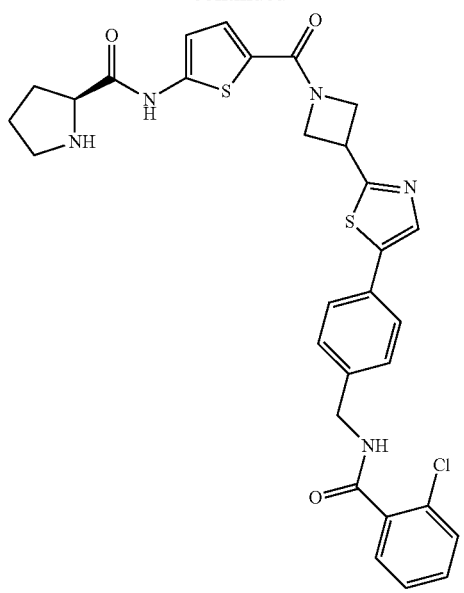
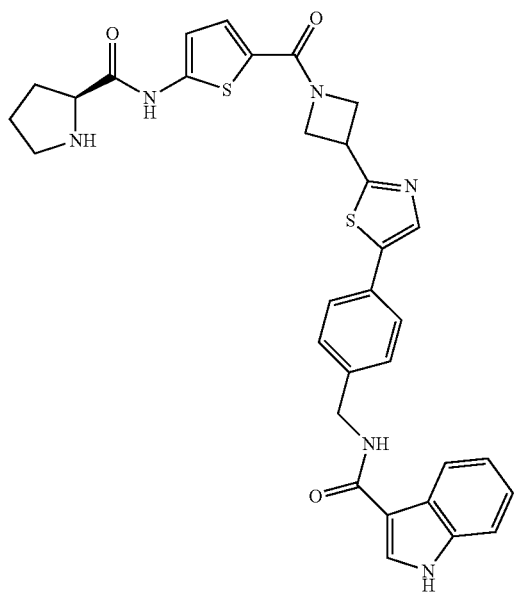
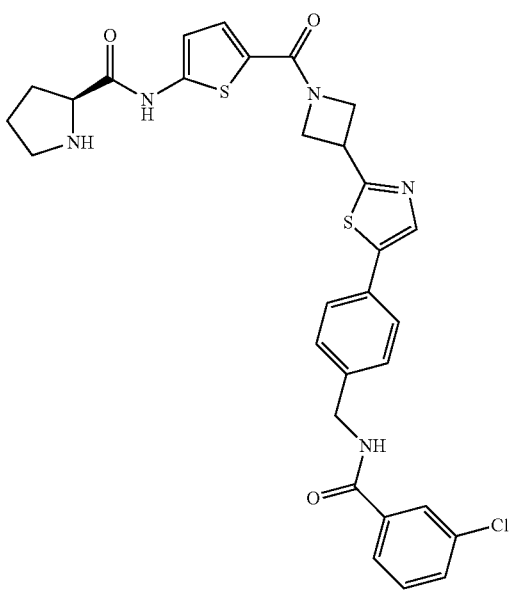

313
-continued
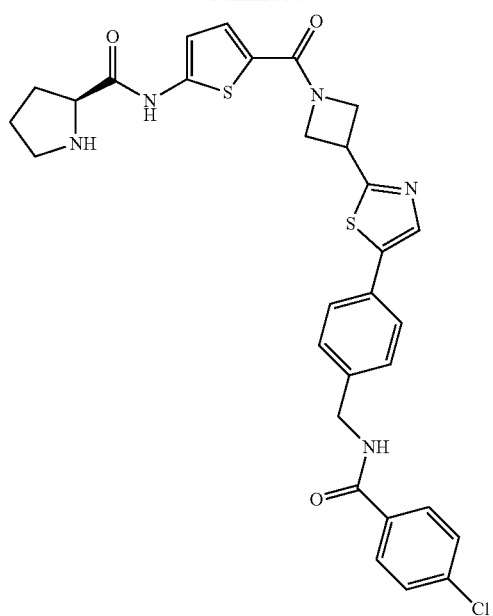
314
-continued
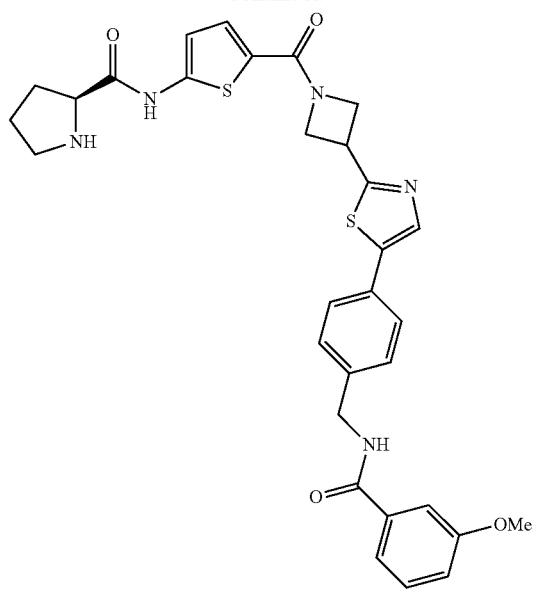
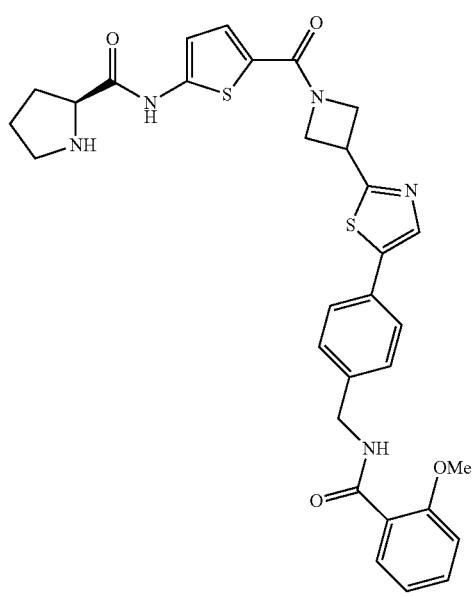
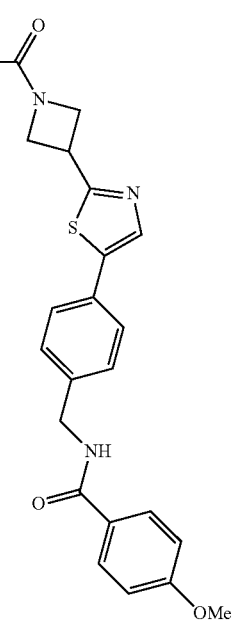

315
-continued
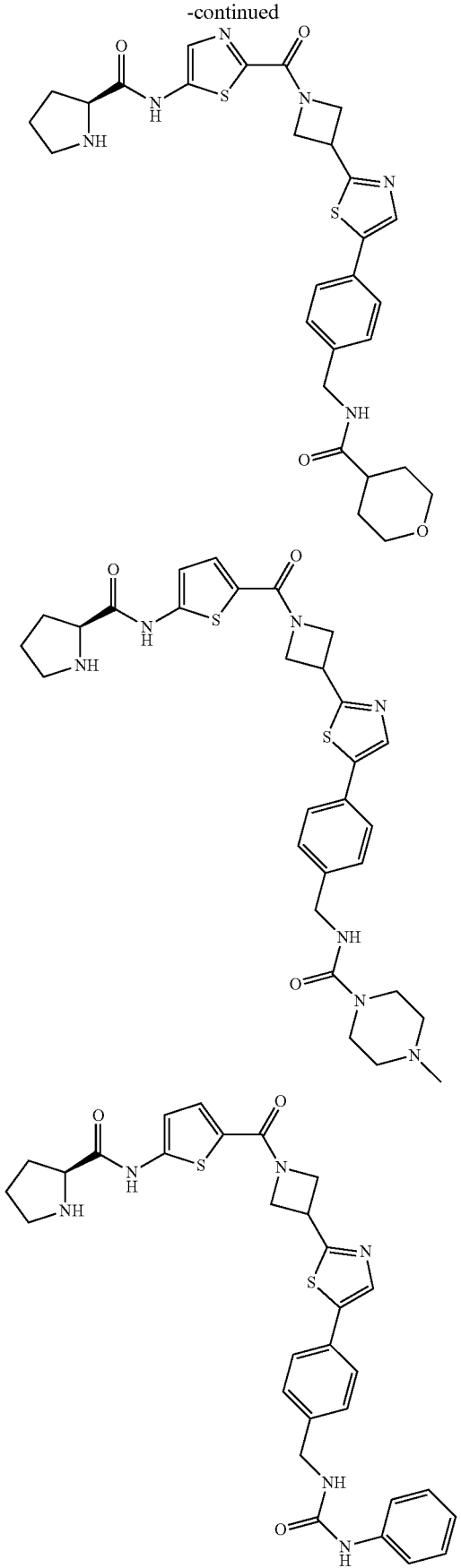
316
-continued

317
-continued
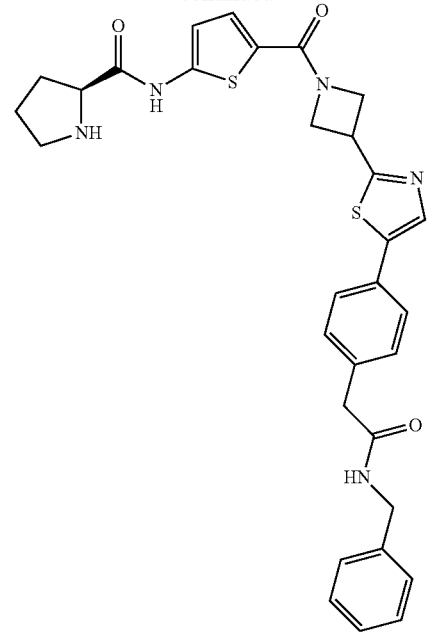
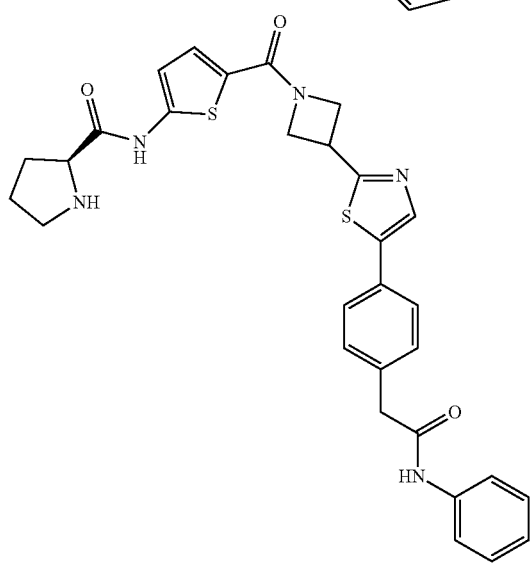
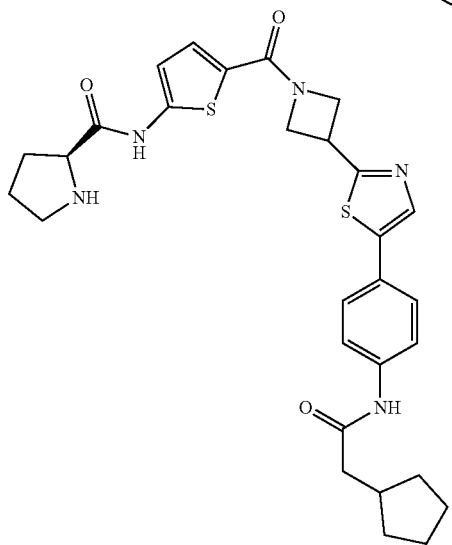
318
-continued
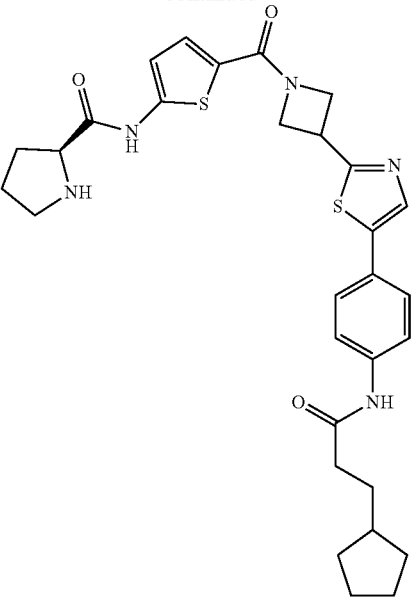
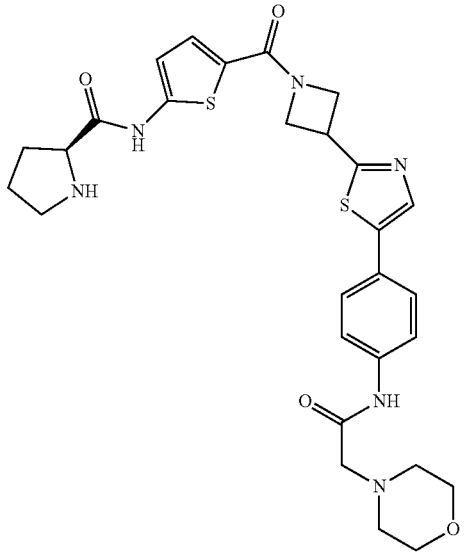

319
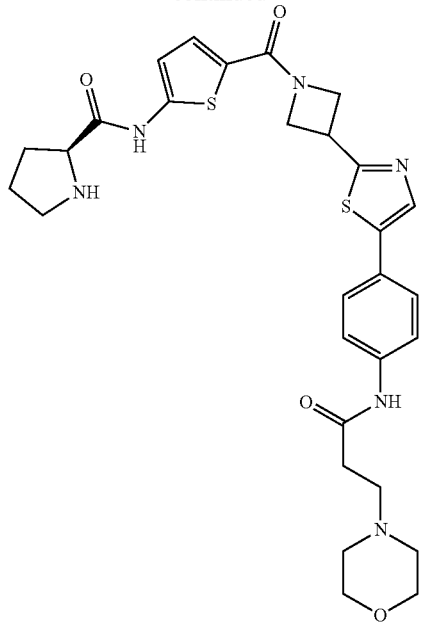
320
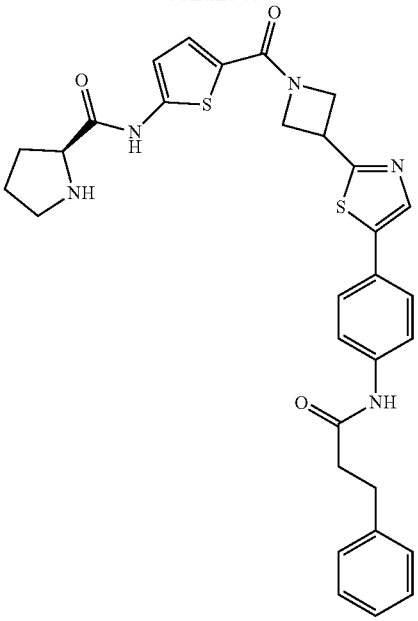
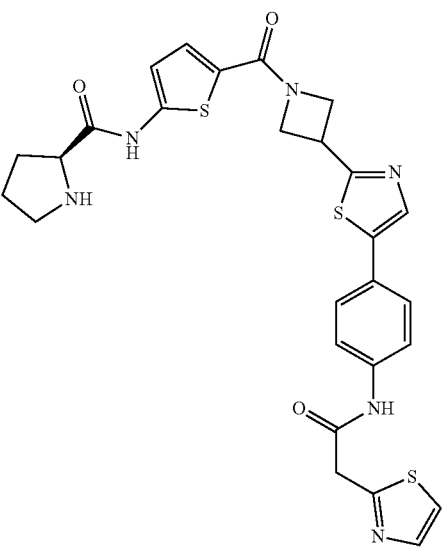
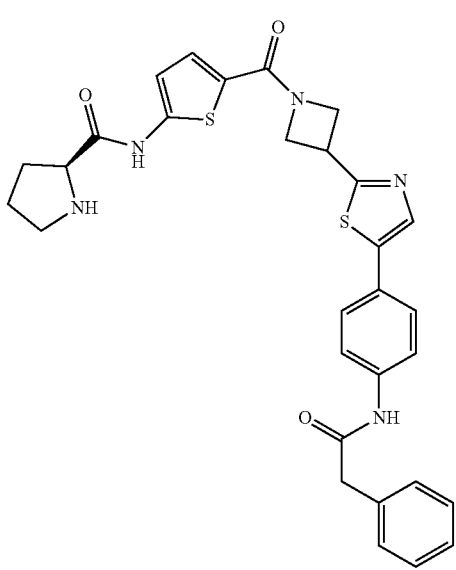
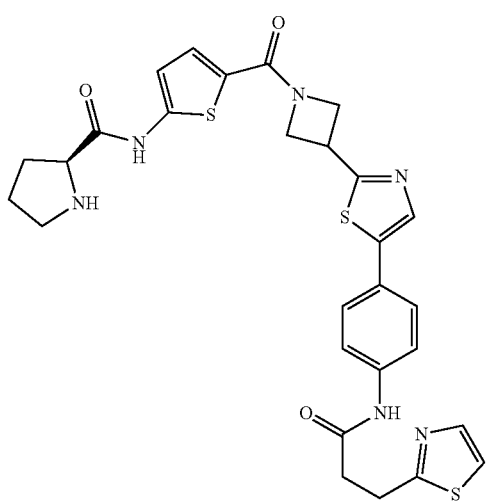

321
-continued
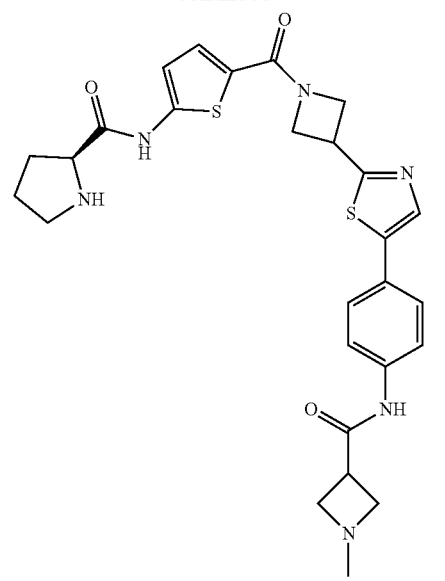
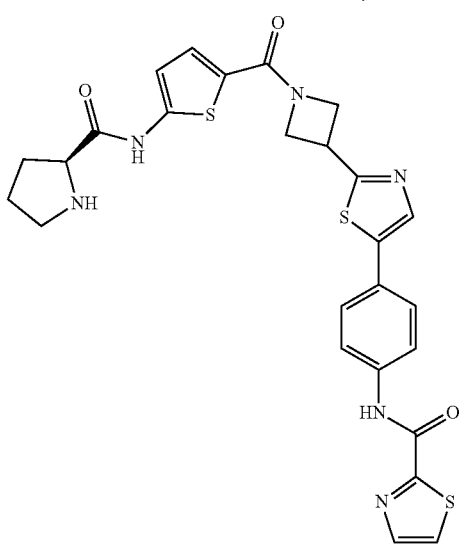
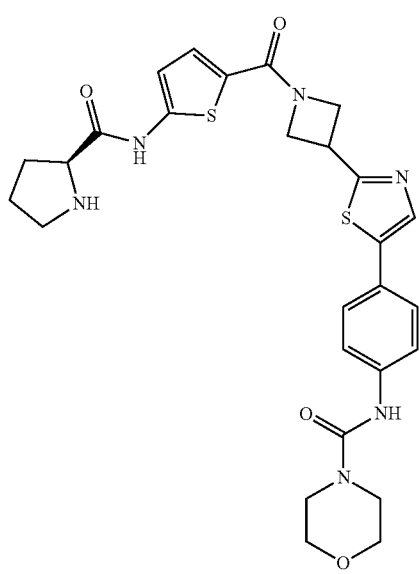
322
-continued
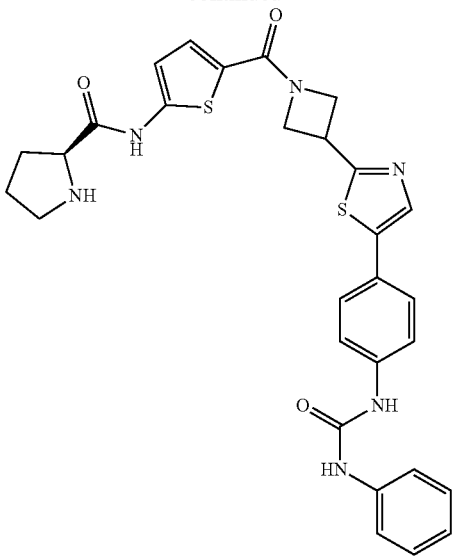
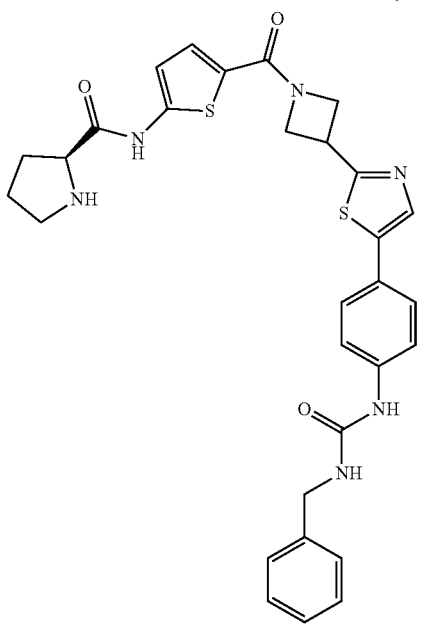
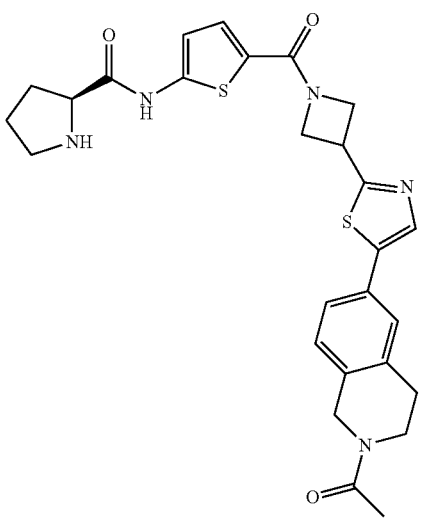

323
-continued
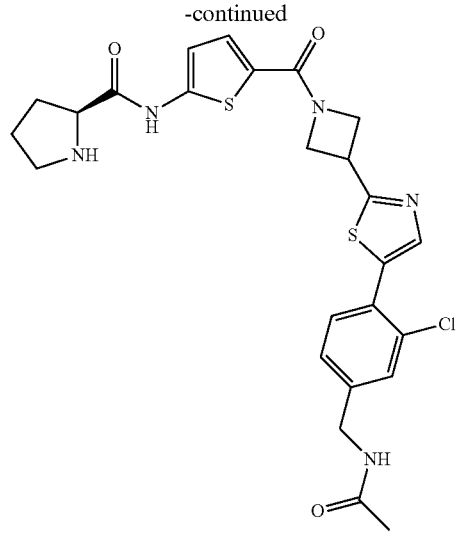
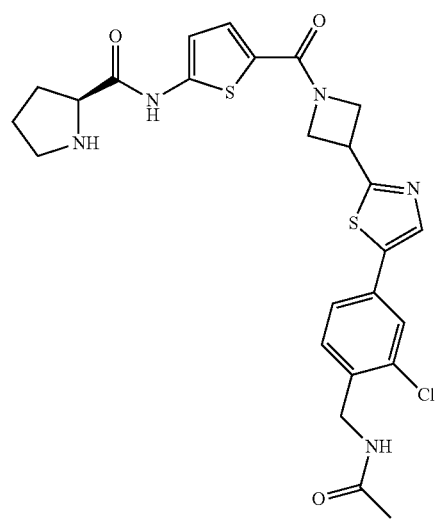
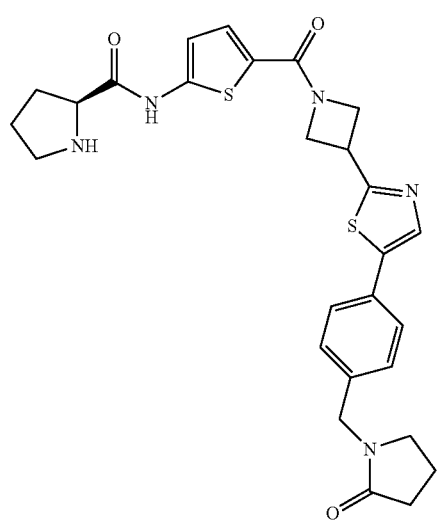
324
-continued
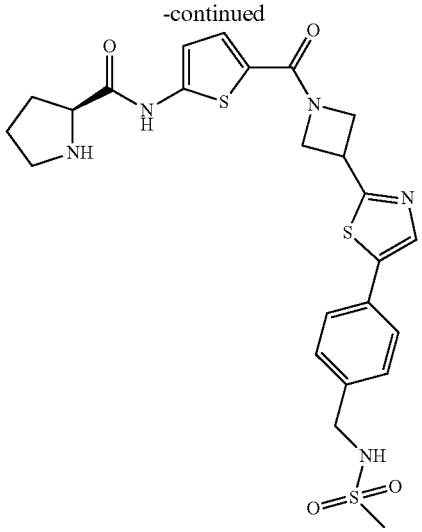
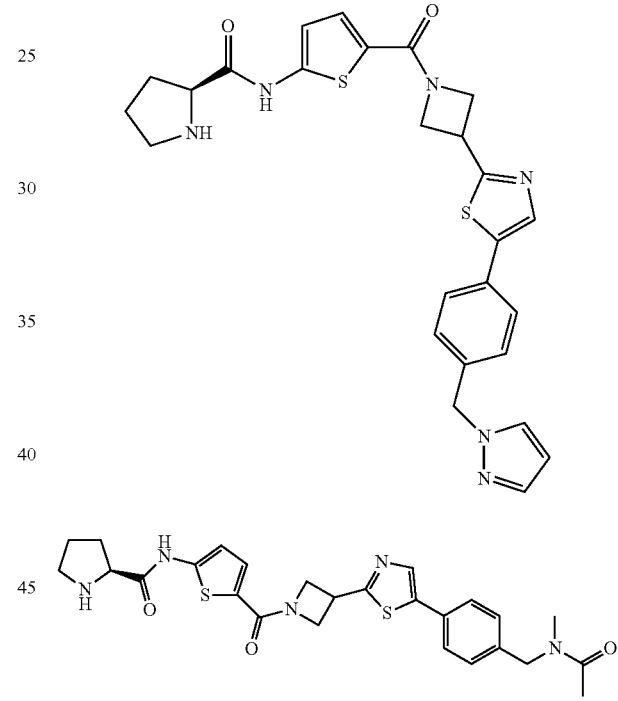
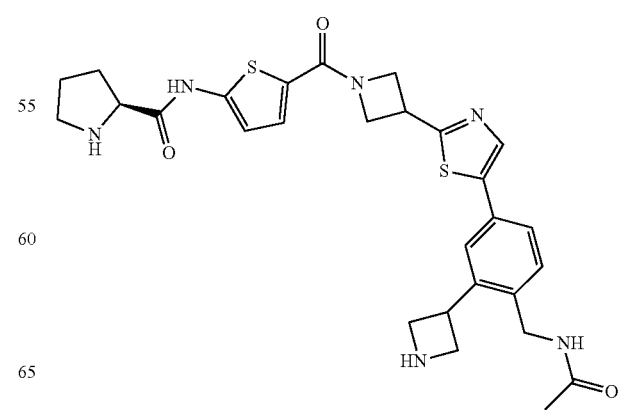

325
-continued
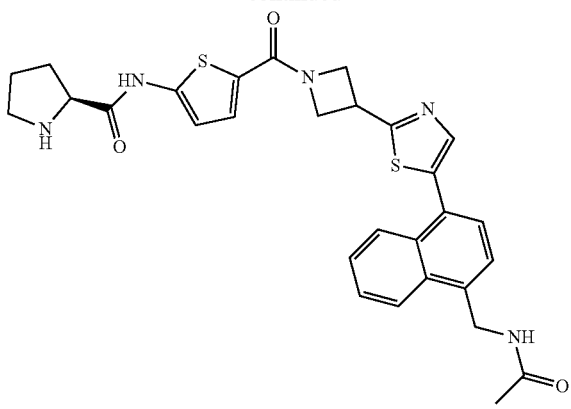
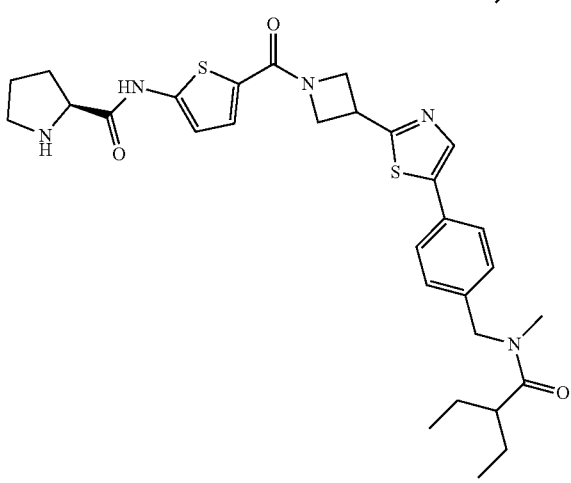
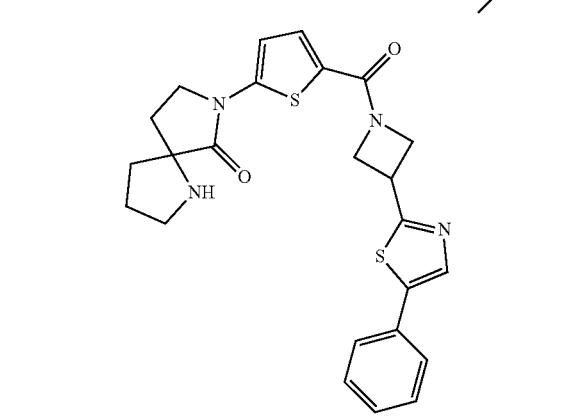
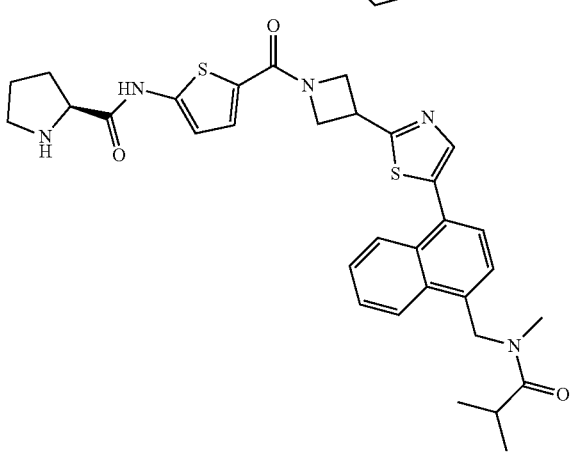
326
-continued
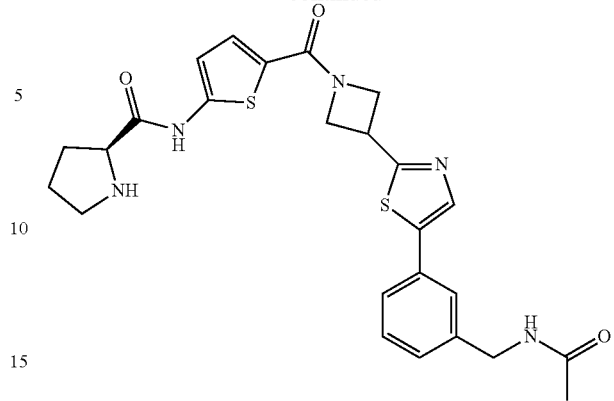
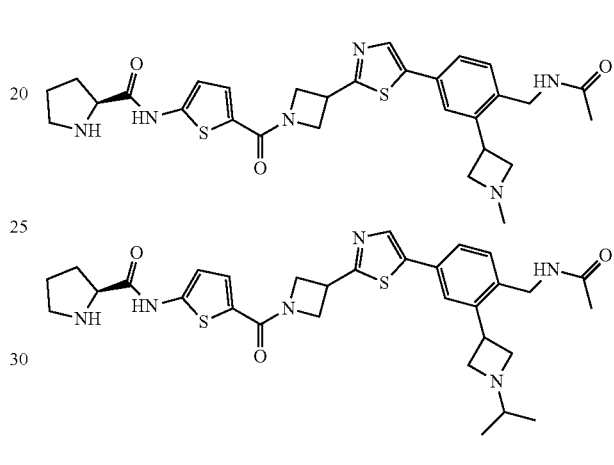
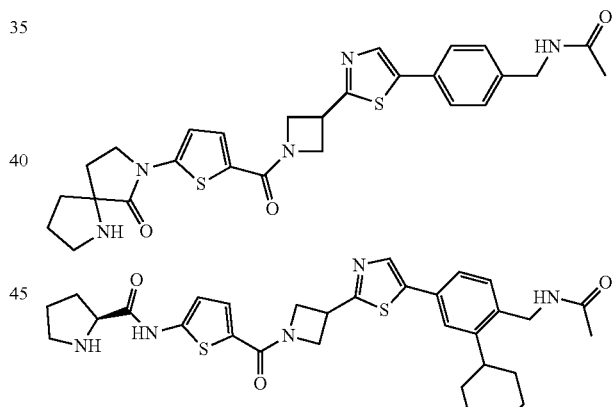
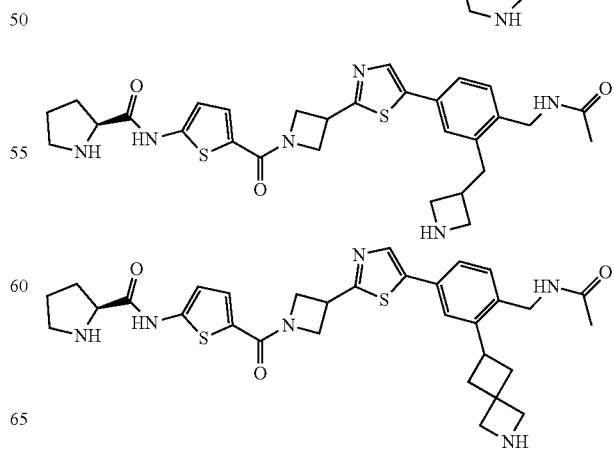

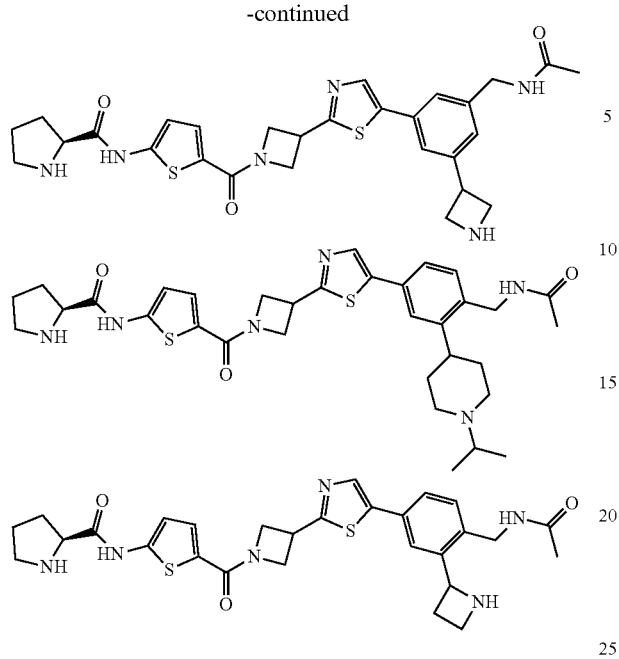
and pharmaceutically acceptable salts thereof.
* * * * *